United States Patent
Rawls-Meehan

(10) Patent No.: US 9,737,155 B2
(45) Date of Patent: *Aug. 22, 2017

(54) SYSTEM FOR TANDEM BED COMMUNICATION

(71) Applicant: Martin B. Rawls-Meehan, Franklin, MI (US)

(72) Inventor: Martin B. Rawls-Meehan, Franklin, MI (US)

(*) Notice: Subject to any disclaimer, the term of this patent is extended or adjusted under 35 U.S.C. 154(b) by 302 days.

This patent is subject to a terminal disclaimer.

(21) Appl. No.: 14/535,956

(22) Filed: Nov. 7, 2014

(65) Prior Publication Data

US 2015/0059096 A1    Mar. 5, 2015

Related U.S. Application Data

(63) Continuation of application No. 13/355,931, filed on Jan. 23, 2012, now Pat. No. 8,909,357, which is a
(Continued)

(51) Int. Cl.
*A47C 31/00* (2006.01)
*A47C 20/04* (2006.01)
(Continued)

(52) U.S. Cl.
CPC ............ *A47C 31/008* (2013.01); *A47C 17/86* (2013.01); *A47C 20/041* (2013.01);
(Continued)

(58) Field of Classification Search
CPC ..... A47C 31/008; A47C 17/86; A47C 21/003; A47C 21/04; A47C 21/006; A47C 20/041;
(Continued)

(56) References Cited

U.S. PATENT DOCUMENTS 1,259,650 A    3/1918   Mcintyre
1,371,098 A    3/1921   Jones
(Continued)

FOREIGN PATENT DOCUMENTS

| CN | 1466925 A | 1/2004 |
|---|---|---|
| CN | 1482881 A | 3/2004 |
| JP | 03068744 | 3/1991 |
| JP | 24105285 | 4/2004 |
| JP | 2004105285 A | 4/2004 |
| JP | 2005/118163 A | 5/2005 |
| KR | 2000/72802 Y1 | 2/1993 |

(Continued)

OTHER PUBLICATIONS

Chinese Application Serial No. 200780042298.0, First Office Action mailed Jul. 28, 2011 with accompanying English language translation, received on Oct. 17, 2011, 17 pages.

(Continued)

*Primary Examiner* — Nathan L Laughlin
(74) *Attorney, Agent, or Firm* — Marshall, Gerstein & Borun LLP

(57) ABSTRACT

This disclosure concerns a communication system adapted to communicate between a handheld remote control and a first adjustable bed controller of a first adjustable bed facility, and a second communication system adapted to communicate between the first adjustable bed controller of the first adjustable bed facility and a second adjustable bed controller of a second adjustable bed facility.

17 Claims, 59 Drawing Sheets

Related U.S. Application Data continuation of application No. 13/286,812, filed on Nov. 1, 2011, now abandoned, which is a continuation-in-part of application No. 12/704,117, filed on Feb. 11, 2010, now Pat. No. 8,926,535, and a continuation-in-part of application No. 12/256,029, filed on Oct. 22, 2008, now Pat. No. 8,909,378, and a continuation-in-part of application No. 12/269,987, filed on Nov. 13, 2008, now abandoned, and a continuation-in-part of application No. 11/855,255, filed on Sep. 14, 2007, now abandoned.

(60) Provisional application No. 61/508,958, filed on Jul. 18, 2011, provisional application No. 61/408,778, filed on Nov. 1, 2010.

(51) Int. Cl.
| | |
|---|---|
| *A47C 21/00* | (2006.01) |
| *A47C 21/04* | (2006.01) |
| *A61G 7/015* | (2006.01) |
| *A61G 7/018* | (2006.01) |
| *A61H 23/02* | (2006.01) |
| *G06F 19/00* | (2011.01) |
| *A47C 17/86* | (2006.01) |
| *A61G 7/05* | (2006.01) |
| *A61B 5/11* | (2006.01) |
| *A61B 5/00* | (2006.01) |

(52) U.S. Cl.
CPC .......... *A47C 21/003* (2013.01); *A47C 21/006* (2013.01); *A47C 21/04* (2013.01); *A61G 7/015* (2013.01); *A61G 7/018* (2013.01); *A61G 7/0514* (2016.11); *A61H 23/0254* (2013.01); *G06F 19/3406* (2013.01); *A61B 5/1115* (2013.01); *A61B 5/4815* (2013.01); *A61G 2203/16* (2013.01); *A61G 2203/36* (2013.01); *A61G 2203/726* (2013.01); *A61H 2201/0138* (2013.01); *A61H 2201/0142* (2013.01); *A61H 2201/0149* (2013.01); *A61H 2201/5002* (2013.01); *A61H 2201/5046* (2013.01); *A61H 2201/5097* (2013.01); *A61H 2203/0443* (2013.01)

(58) Field of Classification Search
CPC ...... A61G 7/0514; A61G 7/018; A61G 7/015; G06F 19/3406; A61H 23/0254
See application file for complete search history.

(56) References Cited

U.S. PATENT DOCUMENTS

| | | | |
|---|---|---|---|
| 2,147,538 A | 2/1939 | Maguire | |
| 3,113,567 A | 12/1963 | Russell | |
| 3,611,453 A | 10/1971 | Lokken | |
| 3,854,153 A | 12/1974 | Fadler | |
| 4,095,296 A | 6/1978 | Ferro | |
| 4,243,263 A | 1/1981 | Thiboutot | |
| 4,447,921 A | 5/1984 | Greenblatt | |
| 4,458,371 A | 7/1984 | Whitehead | |
| 4,589,620 A | 5/1986 | Sakamoto | |
| 4,699,038 A | 10/1987 | Wedge | |
| 4,764,881 A | 8/1988 | Gagnon | |
| 4,924,418 A | 5/1990 | Bachman et al. | |
| 4,992,784 A | 2/1991 | Ruttiger | |
| 5,073,999 A | 12/1991 | Thomas et al. | |
| 5,165,129 A | 11/1992 | Rohm | |
| 5,230,113 A | 7/1993 | Foster et al. | |
| 5,235,258 A | 8/1993 | Schuerch | |
| 5,257,428 A | 11/1993 | Carroll et al. | |
| 5,335,313 A | 8/1994 | Douglas | |
| 5,544,376 A | 8/1996 | Fromson | |
| 5,577,280 A | 11/1996 | Elliott | |
| 5,592,153 A | 1/1997 | Welling et al. | |
| 5,600,214 A | 2/1997 | Fromson | |
| 5,659,905 A | 8/1997 | Palmer, Jr. et al. | |
| 5,664,270 A | 9/1997 | Bell et al. | |
| 5,694,335 A | 12/1997 | Hollenberg | |
| 5,720,471 A | 2/1998 | Constantinescu et al. | |
| 5,771,511 A | 6/1998 | Kummer et al. | |
| 5,787,528 A | 8/1998 | Antinori | |
| 5,948,303 A | 9/1999 | Larson | |
| 5,969,488 A | 10/1999 | Fromson | |
| 6,008,598 A | 12/1999 | Luff et al. | |
| 6,075,575 A | 6/2000 | Schein et al. | |
| 6,079,065 A | 6/2000 | Luff et al. | |
| 6,098,222 A | 8/2000 | Hand et al. | |
| 6,101,647 A | 8/2000 | Stroud et al. | |
| 6,106,576 A | 8/2000 | Fromson | |
| 6,209,157 B1 | 4/2001 | Hensley | |
| 6,263,527 B1 | 7/2001 | Ross et al. | |
| 6,276,011 B1 | 8/2001 | Antinori | |
| 6,311,348 B1 | 11/2001 | Luff et al. | |
| 6,315,319 B1 | 11/2001 | Hanson et al. | |
| 6,327,727 B1 | 12/2001 | Bocharnikov | |
| 6,351,678 B1 | 2/2002 | Borders | |
| 6,374,436 B1 | 4/2002 | Foster et al. | |
| 6,378,152 B1 | 4/2002 | Washburn et al. | |
| 6,393,641 B1 | 5/2002 | Hensley | |
| 6,396,224 B1 | 5/2002 | Luff et al. | |
| 6,446,282 B1 | 9/2002 | Wu | |
| 6,486,792 B1 | 11/2002 | Moster et al. | |
| 6,499,161 B1 | 12/2002 | Godette | |
| 6,502,264 B1 | 1/2003 | Clothier et al. | |
| 6,502,284 B2 | 1/2003 | Juda et al. | |
| 6,560,492 B2 | 5/2003 | Borders | |
| 6,600,421 B2 | 7/2003 | Freeman | |
| 6,681,425 B2 | 1/2004 | Leventhal et al. | |
| 6,684,423 B2 | 2/2004 | Godette | |
| 6,704,962 B2 | 3/2004 | Choi | |
| 6,708,358 B2 | 3/2004 | Hensley | |
| 6,748,278 B1 | 6/2004 | Maymudes | |
| 6,772,462 B1* | 8/2004 | Harrell ................ | A47C 19/045 5/659 |
| 6,784,797 B2 | 8/2004 | Smith et al. | |
| 6,885,362 B2 | 4/2005 | Suomela | |
| 6,928,673 B2 | 8/2005 | Risk, Jr. | |
| 6,971,997 B1 | 12/2005 | Ryan et al. | |
| 7,000,269 B2 | 2/2006 | Borda | |
| 7,017,208 B2 | 3/2006 | Weismiller et al. | |
| 7,040,057 B2 | 5/2006 | Gallant et al. | |
| 7,089,612 B2 | 8/2006 | Rocher et al. | |
| 7,120,956 B1 | 10/2006 | Liao | |
| 7,154,397 B2 | 12/2006 | Zerhusen et al. | |
| 7,165,277 B2 | 1/2007 | Taguchi et al. | |
| 7,174,586 B2 | 2/2007 | Nagaoka | |
| 7,237,287 B2 | 7/2007 | Weismiller et al. | |
| 7,242,308 B2 | 7/2007 | Ulrich et al. | |
| 7,315,535 B2 | 1/2008 | Schuman | |
| 7,321,811 B1 | 1/2008 | Rawls-Meehan | |
| 7,322,058 B2 | 1/2008 | Long | |
| 7,346,944 B2 | 3/2008 | Shaw | |
| 7,353,550 B2 | 4/2008 | Antinori | |
| 7,364,539 B2 | 4/2008 | Mackin et al. | |
| 7,448,100 B1 | 11/2008 | Shih | |
| 7,465,280 B2 | 12/2008 | Rawls-Meehan | |
| 7,477,285 B1 | 1/2009 | Johnson | |
| 7,487,562 B2 | 2/2009 | Frondorf et al. | |
| 7,504,931 B2 | 3/2009 | Nguyen | |
| 7,669,261 B2 | 3/2010 | Fruh et al. | |
| 7,690,059 B2 | 4/2010 | Lemire et al. | |
| 7,698,756 B1 | 4/2010 | Chen | |
| 7,730,401 B2 | 6/2010 | Gillespie et al. | |
| 7,805,782 B2 | 10/2010 | Hakamiun et al. | |
| 7,805,785 B2 | 10/2010 | Rawls-Meehan | |
| 7,832,039 B2 | 11/2010 | Chambers et al. | |
| 7,869,824 B2 | 1/2011 | Min | |
| 7,886,379 B2 | 2/2011 | Benzo et al. | |
| 7,900,302 B2 | 3/2011 | Long | |
| 7,933,669 B2 | 4/2011 | Rawls-Meehan | |

(56) References Cited

U.S. PATENT DOCUMENTS

| | | | |
|---|---|---|---|
| 7,965,309 B2 | 6/2011 | Mattila et al. |
| 7,979,169 B2 | 7/2011 | Rawls-Meehan |
| 8,019,486 B2 | 9/2011 | Rawls-Meehan |
| 8,032,263 B2 | 10/2011 | Rawls-Meehan |
| 8,032,960 B2 | 10/2011 | Rawls-Meehan |
| 8,046,114 B2 | 10/2011 | Rawls-Meehan |
| 8,046,115 B2 | 10/2011 | Rawls-Meehan |
| 8,046,116 B2 | 10/2011 | Rawls-Meehan |
| 8,046,117 B2 | 10/2011 | Rawls-Meehan |
| 8,050,805 B2 | 11/2011 | Rawls-Meehan |
| 8,069,512 B2 | 12/2011 | Rawls-Meehan |
| 8,078,336 B2 | 12/2011 | Rawls-Meehan |
| 8,078,337 B2 | 12/2011 | Rawls-Meehan |
| 8,150,562 B2 | 4/2012 | Rawls-Meehan |
| 8,321,976 B1 | 12/2012 | Edgerton |
| 8,375,488 B2 | 2/2013 | Rawls-Meehan |
| 2002/0013518 A1 | 1/2002 | West et al. |
| 2002/0014951 A1 | 2/2002 | Kramer et al. |
| 2002/0067282 A1 | 6/2002 | Moskowitz et al. |
| 2002/0091340 A1 | 7/2002 | Robbins |
| 2003/0052787 A1 | 3/2003 | Zerhusen et al. |
| 2003/0115672 A1 | 6/2003 | Newkirk |
| 2003/0135604 A1 | 7/2003 | Harrison et al. |
| 2004/0117835 A1 | 6/2004 | Lorkovic |
| 2004/0139546 A1 | 7/2004 | Ferrand et al. |
| 2004/0143201 A1 | 7/2004 | Moriyasu |
| 2004/0183681 A1 | 9/2004 | Smith |
| 2004/0216235 A1 | 11/2004 | Rees |
| 2005/0000020 A1 | 1/2005 | Schermel |
| 2005/0011005 A1 | 1/2005 | Borda |
| 2005/0076020 A1 | 4/2005 | Huntley et al. |
| 2005/0102167 A1 | 5/2005 | Kapoor |
| 2005/0166324 A1 | 8/2005 | Dixon et al. |
| 2005/0172405 A1 | 8/2005 | Menkedick et al. |
| 2005/0219059 A1 | 10/2005 | Ulrich et al. |
| 2006/0037532 A1 | 2/2006 | Eidson |
| 2006/0056616 A1 | 3/2006 | Heimbrock |
| 2006/0058587 A1 | 3/2006 | Heimbrock et al. |
| 2006/0087097 A1 | 4/2006 | Kramer et al. |
| 2006/0117482 A1 | 6/2006 | Branson |
| 2006/0146017 A1 | 7/2006 | Leung et al. |
| 2006/0179571 A1 | 8/2006 | Newkirk |
| 2006/0230529 A1 | 10/2006 | Long |
| 2006/0260054 A1 | 11/2006 | Lubbers et al. |
| 2006/0271207 A1 | 11/2006 | Shaw |
| 2006/0277683 A1 | 12/2006 | Lamire et al. |
| 2006/0282945 A1 | 12/2006 | Gallawa et al. |
| 2007/0000057 A1 | 1/2007 | Ward |
| 2007/0026889 A1 | 2/2007 | Yamauchi et al. |
| 2007/0038334 A1 | 2/2007 | Chou et al. |
| 2007/0120689 A1 | 5/2007 | Zerhusen et al. |
| 2007/0133994 A1 | 6/2007 | Chi |
| 2007/0143920 A1 | 6/2007 | Frondorf et al. |
| 2007/0157385 A1 | 7/2007 | Lemire |
| 2007/0163045 A1 | 7/2007 | Becker et al. |
| 2007/0174964 A1 | 8/2007 | Lemire et al. |
| 2007/0174965 A1 | 8/2007 | Lemire et al. |
| 2007/0233051 A1 | 10/2007 | Hohl et al. |
| 2008/0024455 A1 | 1/2008 | Lee et al. |
| 2008/0028535 A1 | 2/2008 | Rodrigues Moreira |
| 2008/0052830 A1 | 3/2008 | Koughan et al. |
| 2008/0052831 A1 | 3/2008 | Weismiller et al. |
| 2008/0071200 A1 | 3/2008 | Rawls-Meehan |
| 2008/0076969 A1 | 3/2008 | Kraft et al. |
| 2008/0092291 A1 | 4/2008 | Rawls-Meehan |
| 2008/0092292 A1 | 4/2008 | Rawls-Meehan |
| 2008/0092293 A1 | 4/2008 | Rawls-Meehan |
| 2008/0092294 A1 | 4/2008 | Rawls-Meehan |
| 2008/0094207 A1 | 4/2008 | Collins et al. |
| 2008/0104750 A1 | 5/2008 | Rawls-Meehan |
| 2008/0104754 A1 | 5/2008 | Rawls-Meehan |
| 2008/0104755 A1 | 5/2008 | Rawls-Meehan |
| 2008/0104756 A1 | 5/2008 | Rawls-Meehan |
| 2008/0104757 A1 | 5/2008 | Rawls-Meehan |
| 2008/0104758 A1 | 5/2008 | Rawls-Meehan |
| 2008/0104759 A1 | 5/2008 | Rawls-Meehan |
| 2008/0104760 A1 | 5/2008 | Rawls-Meehan |
| 2008/0104761 A1 | 5/2008 | Rawls-Meehan |
| 2008/0109959 A1 | 5/2008 | Rawls-Meehan |
| 2008/0109965 A1 | 5/2008 | Mossbeck et al. |
| 2008/0115272 A1 | 5/2008 | Rawls-Meehan |
| 2008/0115273 A1 | 5/2008 | Rawls-Meehan |
| 2008/0115274 A1 | 5/2008 | Rawls-Meehan |
| 2008/0115275 A1 | 5/2008 | Rawls-Meehan |
| 2008/0115276 A1 | 5/2008 | Rawls-Meehan |
| 2008/0115277 A1 | 5/2008 | Rawls-Meehan |
| 2008/0115278 A1 | 5/2008 | Rawls-Meehan |
| 2008/0115279 A1 | 5/2008 | Rawls-Meehan |
| 2008/0115280 A1 | 5/2008 | Rawls-Meehan |
| 2008/0115281 A1 | 5/2008 | Rawls-Meehan |
| 2008/0115282 A1 | 5/2008 | Rawls-Meehan |
| 2008/0117085 A1 | 5/2008 | Garfio et al. |
| 2008/0120775 A1 | 5/2008 | Rawls-Meehan |
| 2008/0120776 A1 | 5/2008 | Rawls-Meehan |
| 2008/0120777 A1 | 5/2008 | Rawls-Meehan |
| 2008/0120778 A1 | 5/2008 | Rawls-Meehan |
| 2008/0120779 A1 | 5/2008 | Rawls-Meehan |
| 2008/0127418 A1 | 6/2008 | Rawls-Meehan |
| 2008/0178388 A1 | 7/2008 | Schermel |
| 2008/0180304 A1 | 7/2008 | McRae |
| 2008/0224861 A1 | 9/2008 | McNeely et al. |
| 2008/0235872 A1 | 10/2008 | Newkirk et al. |
| 2008/0262657 A1 | 10/2008 | Howell et al. |
| 2008/0316730 A1 | 12/2008 | Diederiks et al. |
| 2009/0038073 A1 | 2/2009 | Dippl et al. |
| 2009/0100599 A1 | 4/2009 | Rawls-Meehan |
| 2009/0121660 A1 | 5/2009 | Rawls-Meehan |
| 2009/0300844 A1 | 12/2009 | Taylor |
| 2010/0199432 A1 | 8/2010 | Rawls-Meehan |
| 2010/0212087 A1 | 8/2010 | Leib et al. |
| 2010/0231421 A1 | 9/2010 | Rawls-Meehan |
| 2010/0275376 A1 | 11/2010 | Benzo et al. |
| 2010/0287699 A1 | 11/2010 | Brune |
| 2010/0302044 A1 | 12/2010 | Chacon et al. |
| 2011/0001860 A1 | 1/2011 | Taruki et al. |
| 2011/0010860 A1 | 1/2011 | Grimes et al. |
| 2011/0191959 A1 | 8/2011 | Hornbach et al. |
| 2011/0219545 A1 | 9/2011 | Dorenbeck et al. |
| 2011/0291795 A1 | 12/2011 | Rawls-Meehan |
| 2012/0056729 A1 | 3/2012 | Rawls-Meehan |
| 2012/0057685 A1 | 3/2012 | Rawls-Meehan |
| 2012/0110738 A1 | 5/2012 | Rawls-Meehan |
| 2012/0110739 A1 | 5/2012 | Rawls-Meehan |
| 2012/0110740 A1 | 5/2012 | Rawls-Meehan |
| 2012/0112890 A1 | 5/2012 | Rawls-Meehan |
| 2012/0112891 A1 | 5/2012 | Rawls-Meehan |
| 2012/0112892 A1 | 5/2012 | Rawls-Meehan |
| 2012/0116591 A1 | 5/2012 | Rawls-Meehan |
| 2012/0119886 A1 | 5/2012 | Rawls-Meehan |
| 2012/0119887 A1 | 5/2012 | Rawls-Meehan |
| 2012/0137439 A1 | 6/2012 | Heimbrock |
| 2013/0276234 A1 | 10/2013 | Rawls-Meehan |
| 2013/0289770 A1 | 10/2013 | Rawls-Meehan |

FOREIGN PATENT DOCUMENTS

| | | |
|---|---|---|
| KR | 2002/14428 Y1 | 3/2001 |
| WO | WO-02/49509 | 6/2002 |
| WO | WO-03/079953 | 10/2003 |
| WO | WO-2008/034037 | 3/2008 |
| WO | WO-2009/055432 | 4/2009 |
| WO | WO-2009/120970 | 10/2009 |
| WO | WO-2011/100495 | 8/2011 |
| WO | WO-2012/061406 | 5/2012 |

OTHER PUBLICATIONS

Chinese Application Serial No. 200780042298.0, Second Office Action mailed Mar. 13, 2012 with ccompanying English language translation, 10 pages.

Chinese Application Serial No. 2008801223654, First Office Action mailed Feb. 23, 2012 (received Mar. 19, 2012) with accompanying English language translation, 67 pages.

(56) References Cited

OTHER PUBLICATIONS

Chinese Patent Application No. 2088011223654, Office Action, Mar. 19, 2012, all pages.
Chinese Patent Application No. 208801223654, English translation, Mar. 31, 2012, pp. 1-62.
European Application Serial No. 11006965.5, Office Action mailed Jul. 3, 2012, 3 pages.
Flaherty et al., Medical apparatus remote control and method, SIPO English Patent Detail, English translation, CN1482881, Mar. 17, 2004, 1 pg.
Hudak, Tom K., "Programmable Controllers", Process / Industrial Instruments and Controls Handbook, Gregory McMillan et al. Editor. Fifth Edition, McGraw-Hill, ISBN 0-07- 012582-1 NPL-244 1999, 1999, pp. 3.32-3.33.
International Application Serial No. PCT/US07/78462, International Search Report and Written Opinion, mailed Nov. 12, 2008.
International Application Serial No. PCT/US08/80729, International Preliminary Report on Patentability, mailed May 6, 2010, 3 pages.
International Application Serial No. PCT/US08/80729, International Search Report and Written Opinion, mailed on Apr. 29, 2009.
International Application Serial No. PCT/US09/38578, International Preliminary Report on Patentability mailed Oct. 7, 2010, 5 pages.
International Application Serial No. PCT/US09/38578, Search Report and Written Opinion mailed Nov. 17, 2009, 10 Pgs.
International Application Serial No. PCT/US11/24442, International Preliminary Report on Patentability mailed Aug. 23, 2012, 12 pages.
International Application Serial No. PCT/US11/24442, International Search Report and Written Opinion mailed May 9, 2011, 17 pages.
International Application Serial No. PCT/US11/58809, International Preliminary Report on Patentability mailed Jul. 4, 2013, 10 pages.
International Application Serial No. PCT/US11/58809, International Search Report and Written Opinion mailed Jun. 18, 2013, 14 pages.
Leggett & Platt, Prodigy Owners Manual, pp. 8 and 13 (Jul. 2009).
U.S. Appl. No. 10/985,834, Final Office Action mailed Apr. 27, 2010, 8 pgs.
U.S. Appl. No. 11/740,491, Notice of Allowance mailed Aug. 26, 2008, 6 pgs.
U.S. Appl. No. 11/855,255, Final Office Action mailed Jan. 18, 2011, 14 pages.
U.S. Appl. No. 11/855,255, Non-Final Office Action mailed Jun. 22, 2010, 23 pages.
U.S. Appl. No. 11/855,265, Final Office Action mailed Dec. 30, 2010, 18 pages.
U.S. Appl. No. 11/855,265, Non-Final Office Action mailed Jun. 21, 2010, 21 pages.
U.S. Appl. No. 11/855,272, Non-Final Office Action mailed Jun. 22, 2010, 15 pages.
U.S. Appl. No. 11/855,272, Notice of Allowance mailed Jan. 6, 2011, 13 pages.
U.S. Appl. No. 11/855,272, Notice of Allowance mailed May 13, 2011, 8 pages.
U.S. Appl. No. 11/855,278, Non-Final Office Action mailed Oct. 7, 2009, 13 pages.
U.S. Appl. No. 11/855,287, Final Office Action mailed Apr. 15, 2011, 16 pages.
U.S. Appl. No. 11/855,287, Final Office Action mailed Jun. 21, 2012, 23 pages.
U.S. Appl. No. 11/855,287, Non-Final Office Action mailed Jul. 21, 2010, 22 pages.
U.S. Appl. No. 11/855,287, Non-Final Office Action mailed Oct. 6, 2011, 24 pages.
U.S. Appl. No. 11/855,299, Final Office Action mailed Jun. 21, 2010, 11 pages.
U.S. Appl. No. 11/855,299, Final Office Action mailed Jul. 21, 2011, 12 pages.
U.S. Appl. No. 11/855,299, Non-Final Office Action mailed Feb. 18, 2011, 11 pages.
U.S. Appl. No. 11/855,299, Non-Final Office Action mailed Mar. 14, 2012, 7 pages.
U.S. Appl. No. 11/855,299, Non-Final Office Action mailed Dec. 23, 2009, 8 pages.
U.S. Appl. No. 11/855,300, Final Office Action mailed Mar. 25, 2011, 20 pages.
U.S. Appl. No. 11/855,300, Non-Final Office Action mailed Aug. 16, 2010, 24 pgs.
U.S. Appl. No. 11/855,305, Final Office Action mailed Mar. 28, 2011, 22 pages.
U.S. Appl. No. 11/855,305, Non-Final Office Action mailed Aug. 16, 2010, 16 pages.
U.S. Appl. No. 11/855,311, Final Office Action mailed Jan. 19, 2011, 8 pages.
U.S. Appl. No. 11/855,311, Non-Final Office Action mailed Apr. 26, 2010, 12 pages.
U.S. Appl. No. 11/855,311, Notice of Allowance mailed Jun. 10, 2011, 11 pages.
U.S. Appl. No. 11/855,351, Final Office Action mailed Apr. 21, 2011, 12 pages.
U.S. Appl. No. 11/855,351, Non-Final Office Action mailed Aug. 16, 2010, 26 pages.
U.S. Appl. No. 11/855,354, Final Office Action mailed Jul. 6, 2010, 11 Pgs.
U.S. Appl. No. 11/855,354, Non-Final Office Action mailed Dec. 16, 2009, 21 pages.
U.S. Appl. No. 11/875,842, Final Office Action mailed Jul. 8, 2010, 17 pgs.
U.S. Appl. No. 11/875,842, Non-Final Office Action mailed Dec. 16, 2009, 14 pages.
U.S. Appl. No. 11/875,843, Final Office Action mailed Jan. 19, 2011, 9 pages.
U.S. Appl. No. 11/875,843, Non-Final Office Action mailed Jun. 17, 2011, 7 pages.
U.S. Appl. No. 11/875,843, Non-Final Office Action mailed Jul. 8, 2010, 9 pages.
U.S. Appl. No. 11/875,843, Non-Final Office Action mailed Oct. 2, 2009, 9 pages.
U.S. Appl. No. 11/875,843, Notice of Allowance mailed Dec. 14, 2011, 9 pages.
U.S. Appl. No. 11/875,844, Final Office Action mailed Apr. 29, 2010, 9 pages.
U.S. Appl. No. 11/875,844, Non Final Office Action mailed Oct. 15, 2009, 8 pages.
U.S. Appl. No. 11/875,844, Non-Final Office Action mailed Mar. 14, 2011, 7 pages.
U.S. Appl. No. 11/875,844, Notice of Allowance mailed Jun. 23, 2011, 12 pages.
U.S. Appl. No. 11/875,845, Final Office Action mailed May 21, 2010, 16 pages.
U.S. Appl. No. 11/875,845, Non-Final Office Action mailed Sep. 2, 2009, 16 pgs.
U.S. Appl. No. 11/875,846, Final Office Action mailed Jan. 18, 2011, 7 pages.
U.S. Appl. No. 11/875,846, Non Final Office Action mailed Oct. 27, 2009, 8 pages.
U.S. Appl. No. 11/875,846, Non-Final Office Action mailed May 11, 2010, 8 pages.
U.S. Appl. No. 11/875,846, Notice of Allowance mailed Mar. 10, 2011, 7 pages.
U.S. Appl. No. 11/875,847, Final Office Action mailed Dec. 22, 2010, 15 Pgs.
U.S. Appl. No. 11/875,847, Non-Final Office Action mailed Apr. 13, 2010, 16 pages.
U.S. Appl. No. 11/875,848, Final Office Action mailed Apr. 27, 2011, 8 pages.
U.S. Appl. No. 11/875,848, Final Office Action mailed Jun. 27, 2012, 6 pages.

(56) References Cited

OTHER PUBLICATIONS

U.S. Appl. No. 11/875,848, Final Office Action mailed Jul. 7, 2010, 9 pages.
U.S. Appl. No. 11/875,848, Non-Final Office Action mailed Nov. 10, 2011, 11 pages.
U.S. Appl. No. 11/875,848, Non-Final Office Action mailed Dec. 30, 2010, 9 pages.
U.S. Appl. No. 11/875,848, Non-Final Office Action mailed Dec. 30, 2009, 9 pages.
U.S. Appl. No. 11/875,848, Non-Final Office Action mailed Sep. 30, 2009, 7 Pgs.
U.S. Appl. No. 11/875,849, Final Office Action mailed Dec. 22, 2010, 15 pages.
U.S. Appl. No. 11/875,849, Restriction Requirement mailed Dec. 14, 2009, 6 pages.
U.S. Appl. No. 11/875,850, Non Final Office Action mailed Oct. 28, 2009, 9 pages.
U.S. Appl. No. 11/875,850, Notice of Allowance mailed Jun. 23, 2011, 10 pages.
U.S. Appl. No. 11/875,851 Non-Final Office action mailed on Nov. 12, 2008.
U.S. Appl. No. 11/875,851, Final Office Action mailed Jul. 22, 2009, 8 pages.
U.S. Appl. No. 11/875,851, Non-Final Office Action mailed Apr. 22, 2010, 6 pages.
U.S. Appl. No. 11/875,851, Non-Final Office Action mailed on Nov. 12, 2008.
U.S. Appl. No. 11/875,851, Notice of Allowance mailed May 17, 2010, 5 pages.
U.S. Appl. No. 11/875,852, Final Office Action mailed Nov. 24, 2010, 15 pages.
U.S. Appl. No. 11/875,853, Final Office Action mailed Apr. 2, 2010, 9 pages.
U.S. Appl. No. 11/875,853, Non-Final Office Action mailed Mar. 16, 2011, 7 pages.
U.S. Appl. No. 11/875,853, Non-Final Office Action mailed Oct. 1, 2009, 8 pages.
U.S. Appl. No. 11/875,853, Notice of Allowance mailed Jun. 23, 2011, 10 pages.
U.S. Appl. No. 11/875,856, Final Office Action mailed Jul. 8, 2010, 9 pgs.
U.S. Appl. No. 11/875,856, Non Final Office Action mailed Sep. 29, 2009, 8 pages.
U.S. Appl. No. 11/875,856, Non-Final Office Action mailed Mar. 28, 2011, 8 pages.
U.S. Appl. No. 11/875,856, Notice of Allowance mailed Jun. 27, 2011, 10 pages.
U.S. Appl. No. 11/875,857, Final Office Action mailed Jun. 22, 2012, 12 pages.
U.S. Appl. No. 11/875,857, Final Office Action mailed Dec. 2, 2010, 16 pages.
U.S. Appl. No. 11/875,857, Non-Final Office Action mailed Apr. 1, 2010, 11 pages.
U.S. Appl. No. 11/875,857, Non-Final Office Action mailed Oct. 7, 2011, 15 pages.
U.S. Appl. No. 11/875,861, Final Office Action mailed Jun. 7, 2010, 15 pages.
U.S. Appl. No. 11/875,861, Non-Final Office Action mailed Sep. 16, 2009, 18 pages.
U.S. Appl. No. 11/875,861, Notice of Allowance mailed Jan. 20, 2011, 9 pages.
U.S. Appl. No. 11/875,863, Non-Final Office Action mailed Mar. 29, 2011, 8 pages.
U.S. Appl. No. 11/875,863, Non-Final Office Action mailed Sep. 15, 2009, 9 Pgs.
U.S. Appl. No. 11/875,864, Final Office Action mailed May 20, 2010, 9 pages.
U.S. Appl. No. 11/875,864, Non Final Office Action mailed Sep. 29, 2009, 9 pages.
U.S. Appl. No. 11/875,864, Non-Final Office Action mailed Mar. 29, 2011, 8 pages.
U.S. Appl. No. 11/875,864, Notice of Allowance mailed Aug. 8, 2011, 11 pages.
U.S. Appl. No. 11/875,865, Final Office Action mailed May 20, 2010, 14 pages.
U.S. Appl. No. 11/875,865, Non-Final Office Action mailed Sep. 1, 2009, 11 pages.
U.S. Appl. No. 11/875,865, Non-Final Office Action mailed Oct. 28, 2011, 24 pages.
U.S. Appl. No. 11/875,866, Final Office Action mailed Mar. 14, 2011, 6 pages.
U.S. Appl. No. 11/875,866, Final Office Action mailed Apr. 13, 2010, 10 pages.
U.S. Appl. No. 11/875,866, Non-Final Office Action mailed Sep. 27, 2010, 9 pgs.
U.S. Appl. No. 11/875,866, Notice of Allowance mailed Jun. 23, 2011, 12 pages.
U.S. Appl. No. 11/875,867, Final Office Action mailed May 20, 2010, 7 pages.
U.S. Appl. No. 11/875,867, Non-Final Office Action mailed Jan. 18, 2011, 6 pages.
U.S. Appl. No. 11/875,867, Non-Final Office Action mailed Sep. 15, 2009, 9 pages.
U.S. Appl. No. 11/875,867, Notice of Allowance mailed May 5, 2011, 7 pages.
U.S. Appl. No. 11/876,753, Notice of Allowance mailed Jul. 6, 2011, 7 pages.
U.S. Appl. No. 12/256,029, Final Office Action mailed Feb. 15, 2011, 10 pages.
U.S. Appl. No. 12/256,029, Final Office Action mailed Dec. 8, 2011, 17 pages.
U.S. Appl. No. 12/256,029, Non-Final Office Action mailed May 12, 2011, 10 pages.
U.S. Appl. No. 12/256,029, Non-Final Office Action mailed Oct. 14, 2010, 22 pages.
U.S. Appl. No. 12/269,987, Final Office Action mailed Jun. 6, 2012, 20 pages.
U.S. Appl. No. 12/269,987, Non-Final Office Action mailed Oct. 5, 2011, 17 pages.
U.S. Appl. No. 12/328,728, Final Office Action mailed Mar. 18, 2011, 15 pages.
U.S. Appl. No. 12/328,728, Final Office Action mailed Mar. 25, 2011, 13 pages.
U.S. Appl. No. 12/328,728, Final Office Action, Mar. 25, 2011.
U.S. Appl. No. 12/328,728, Non-Final Office Action mailed Jun. 23, 2010, 19 pages.
U.S. Appl. No. 12/328,728, Notice of Allowance and Fee(s) due mailed Jul. 1, 2011, 14 pages.
U.S. Appl. No. 12/328,728, Notice of Allowance, Jul. 1, 2011.
U.S. Appl. No. 12/702,405, Final Office Action mailed Jun. 1, 2012, 12 pages.
U.S. Appl. No. 12/702,405, Non-Final Office Action mailed Jun. 28, 2011, 16 pages.
U.S. Appl. No. 13/205,784, Non-Final Office Action mailed Feb. 1, 2012, 32 pages.
U.S. Appl. No. 13/233,373, Non-Final Office Action mailed Jun. 6, 2012, 36 pages.

* cited by examiner

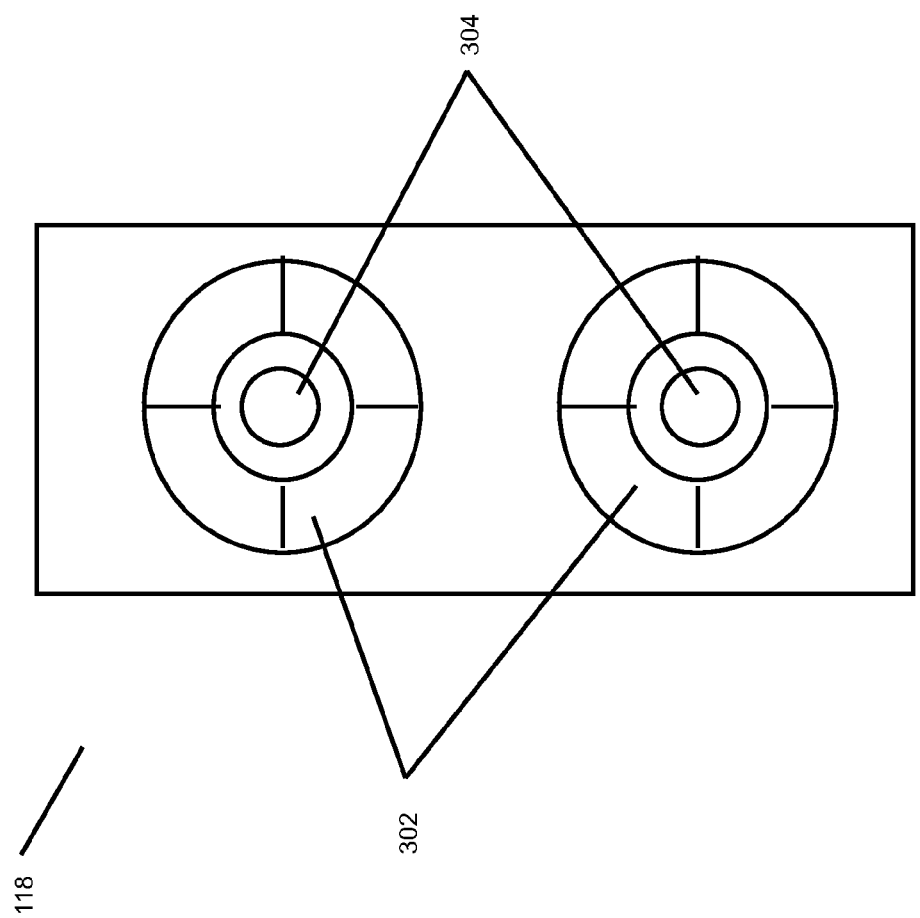

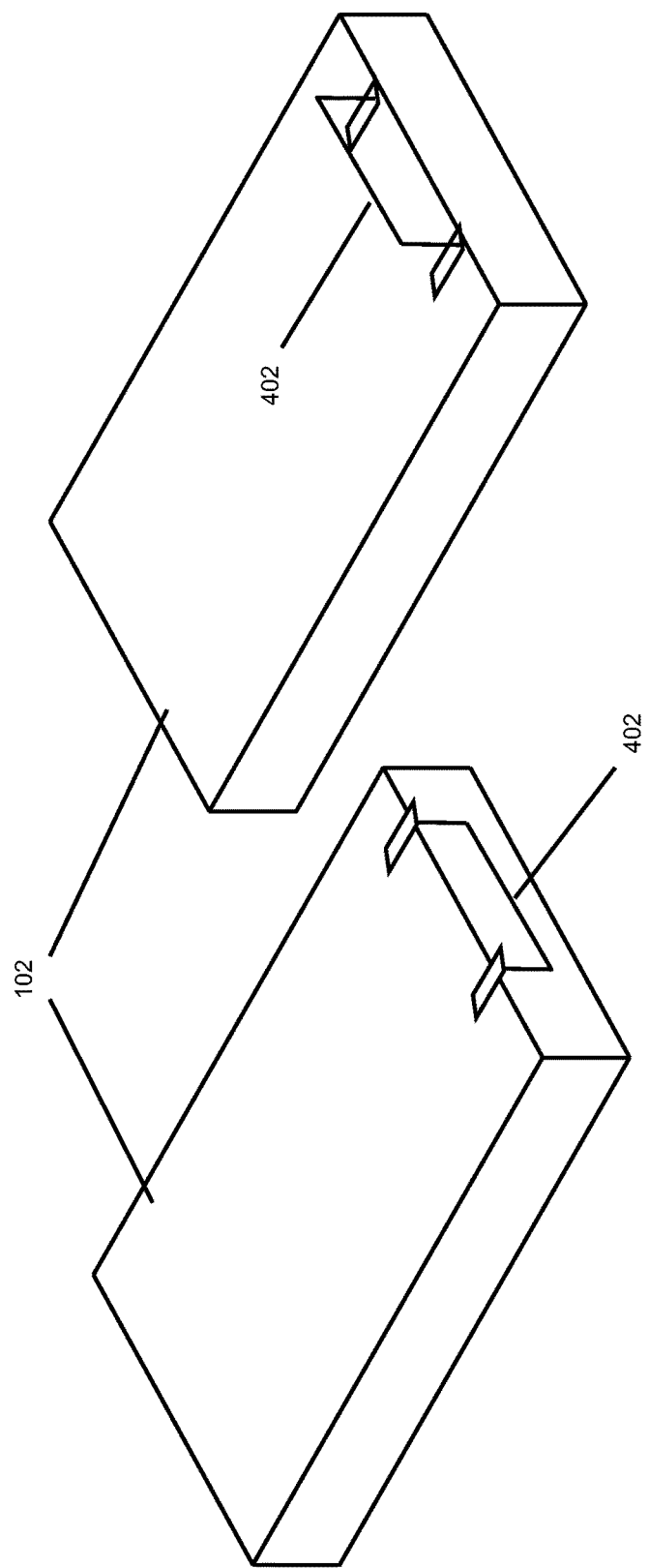

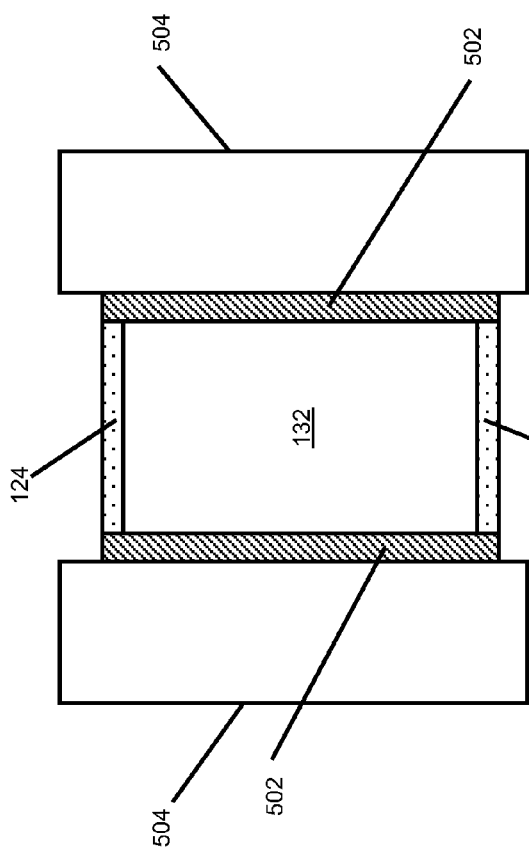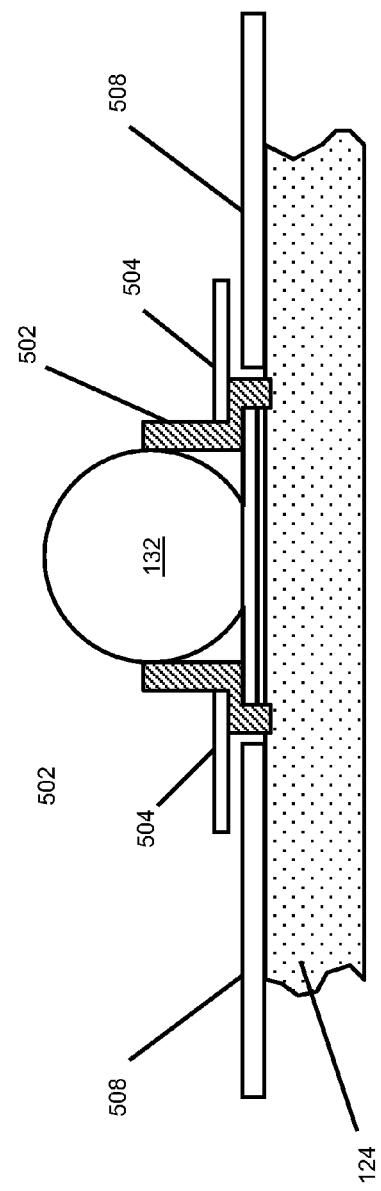

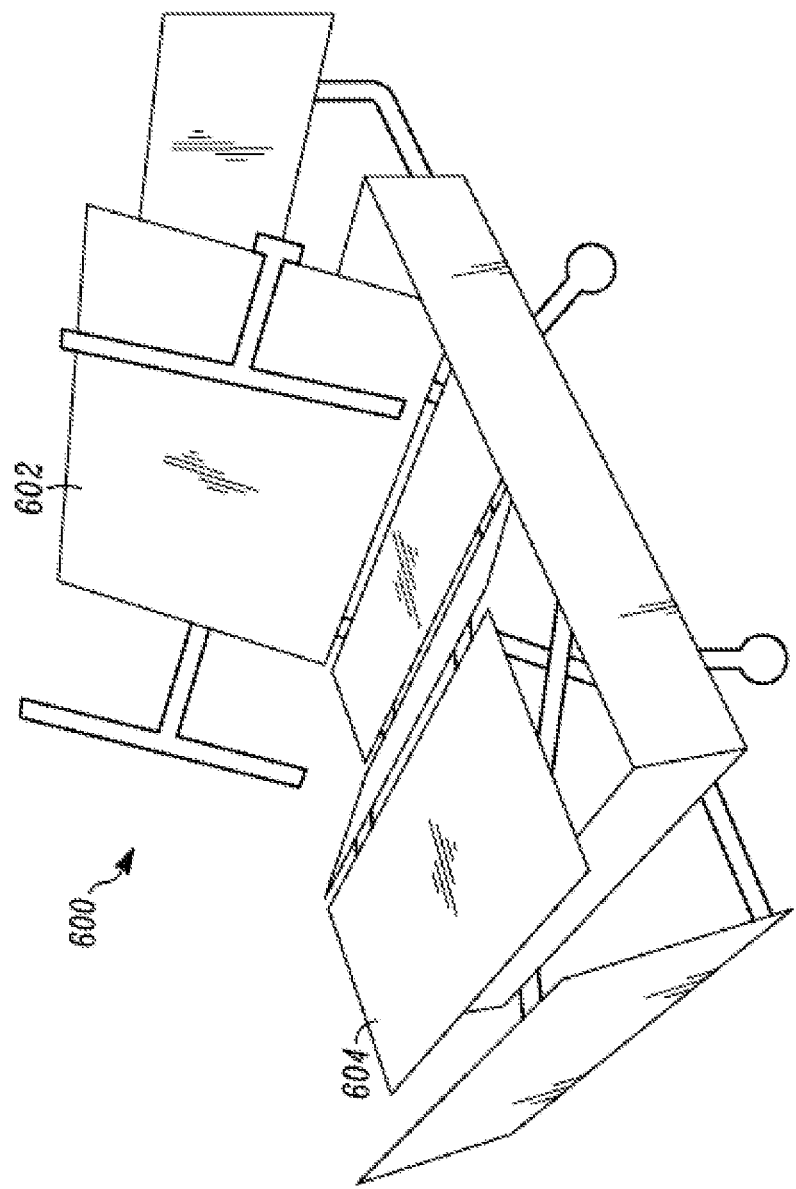

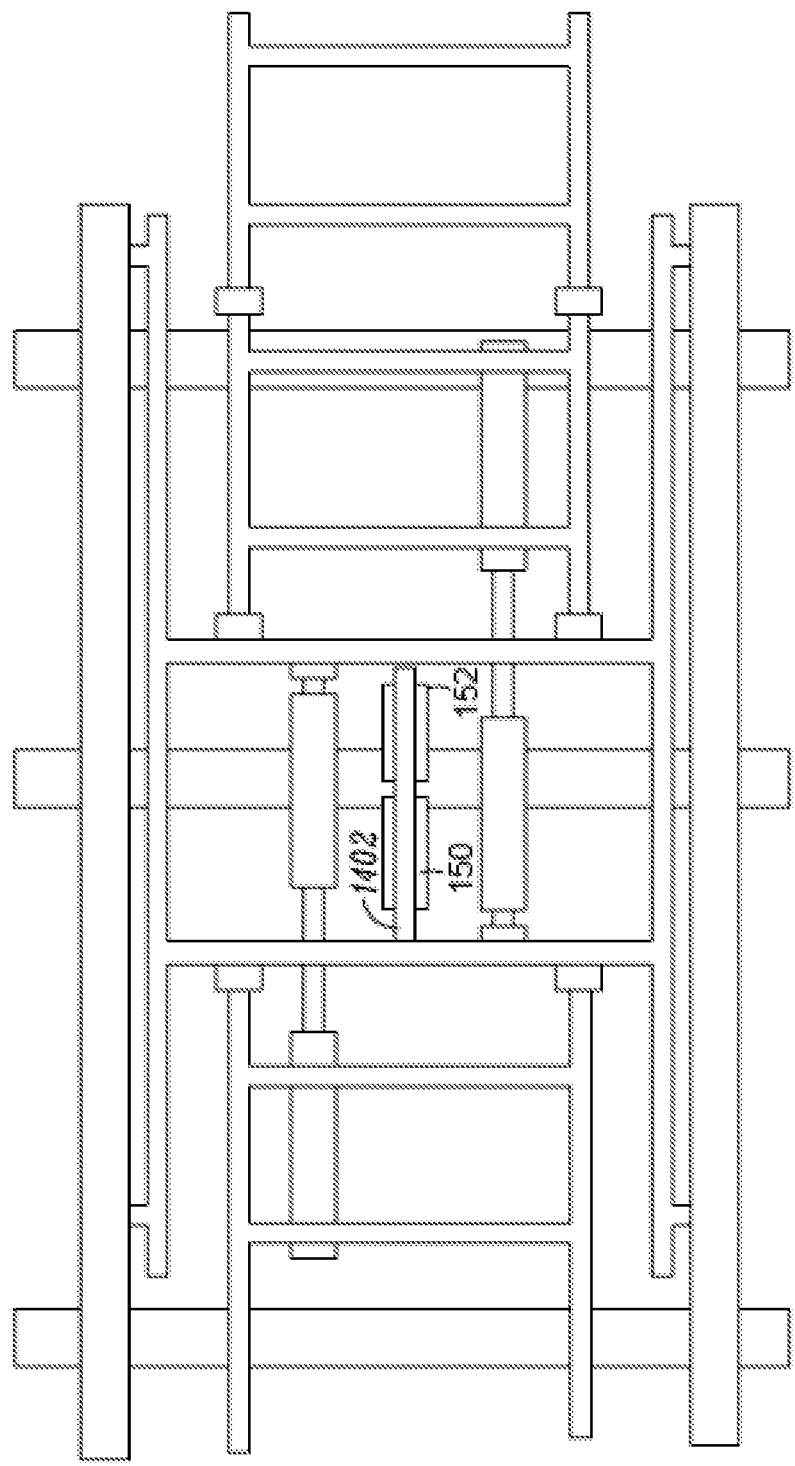

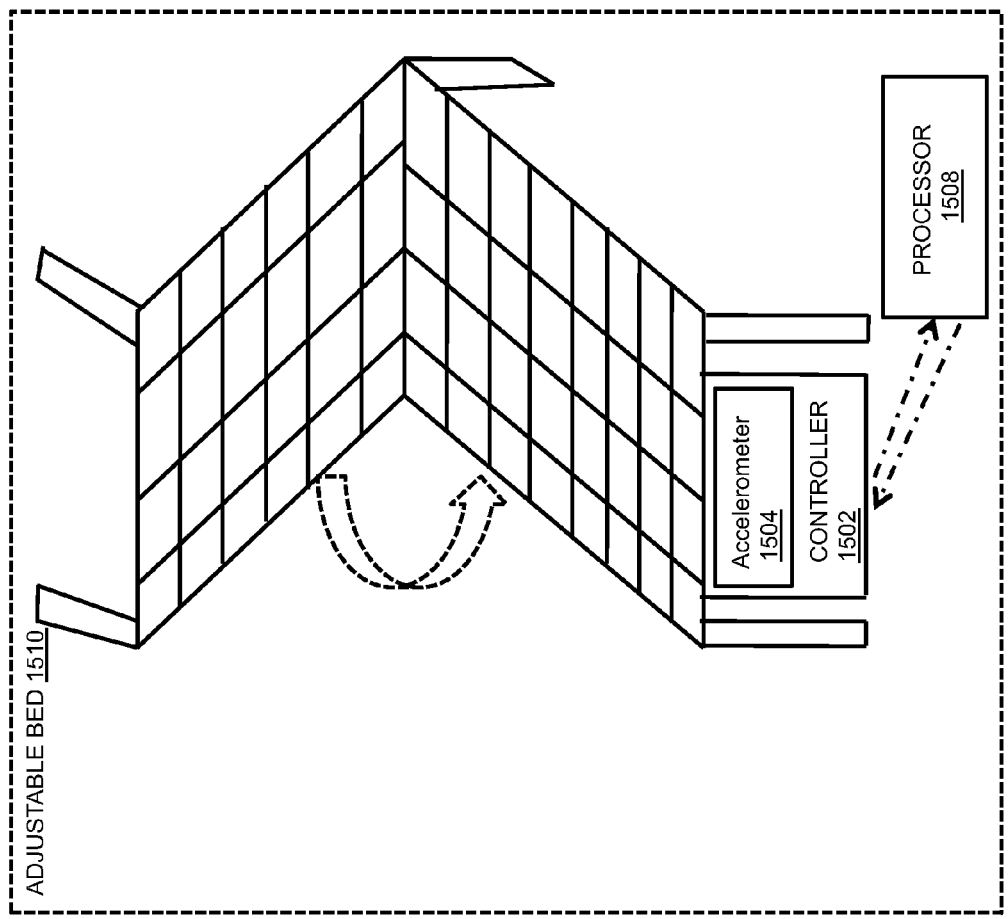

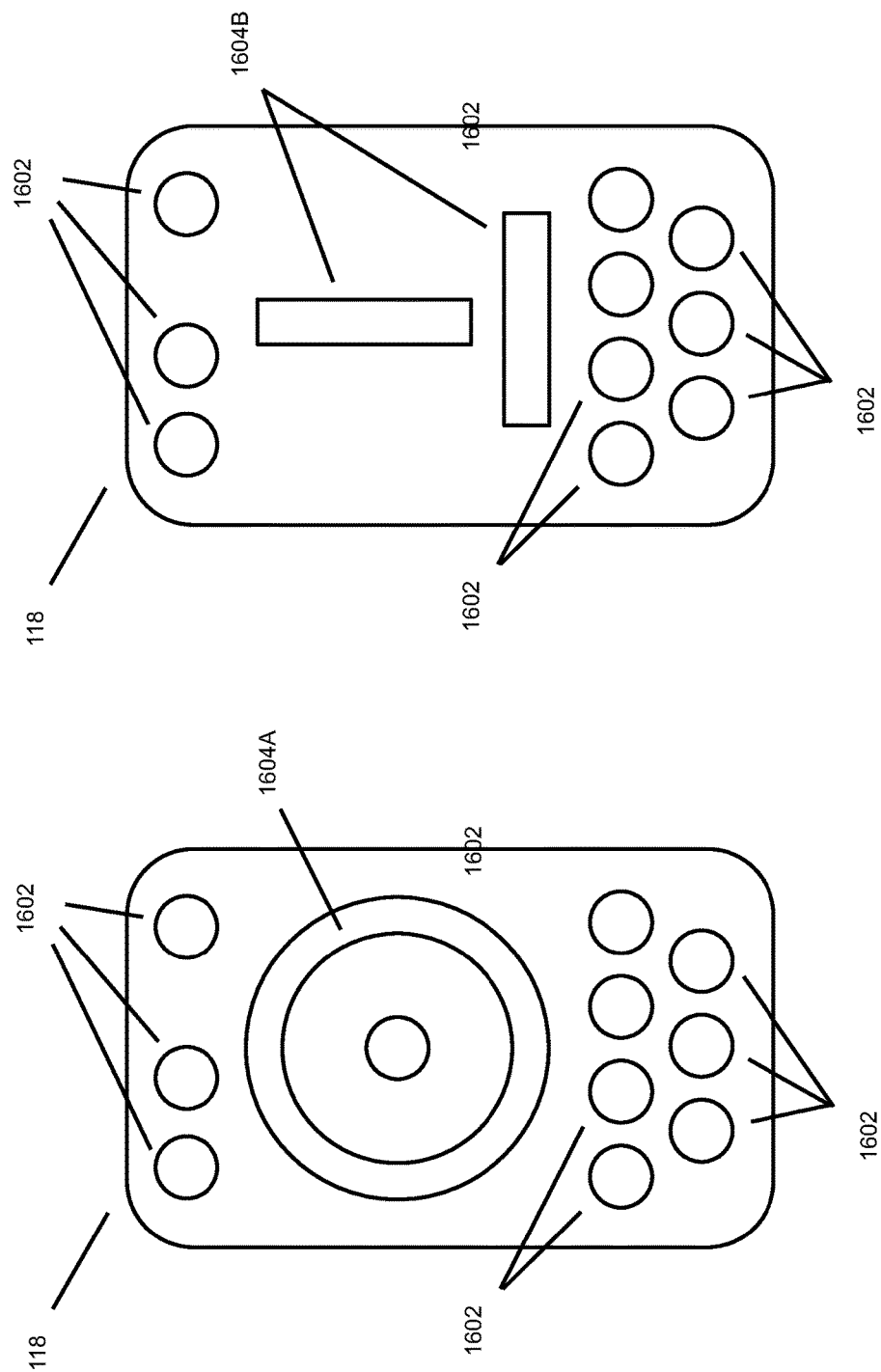

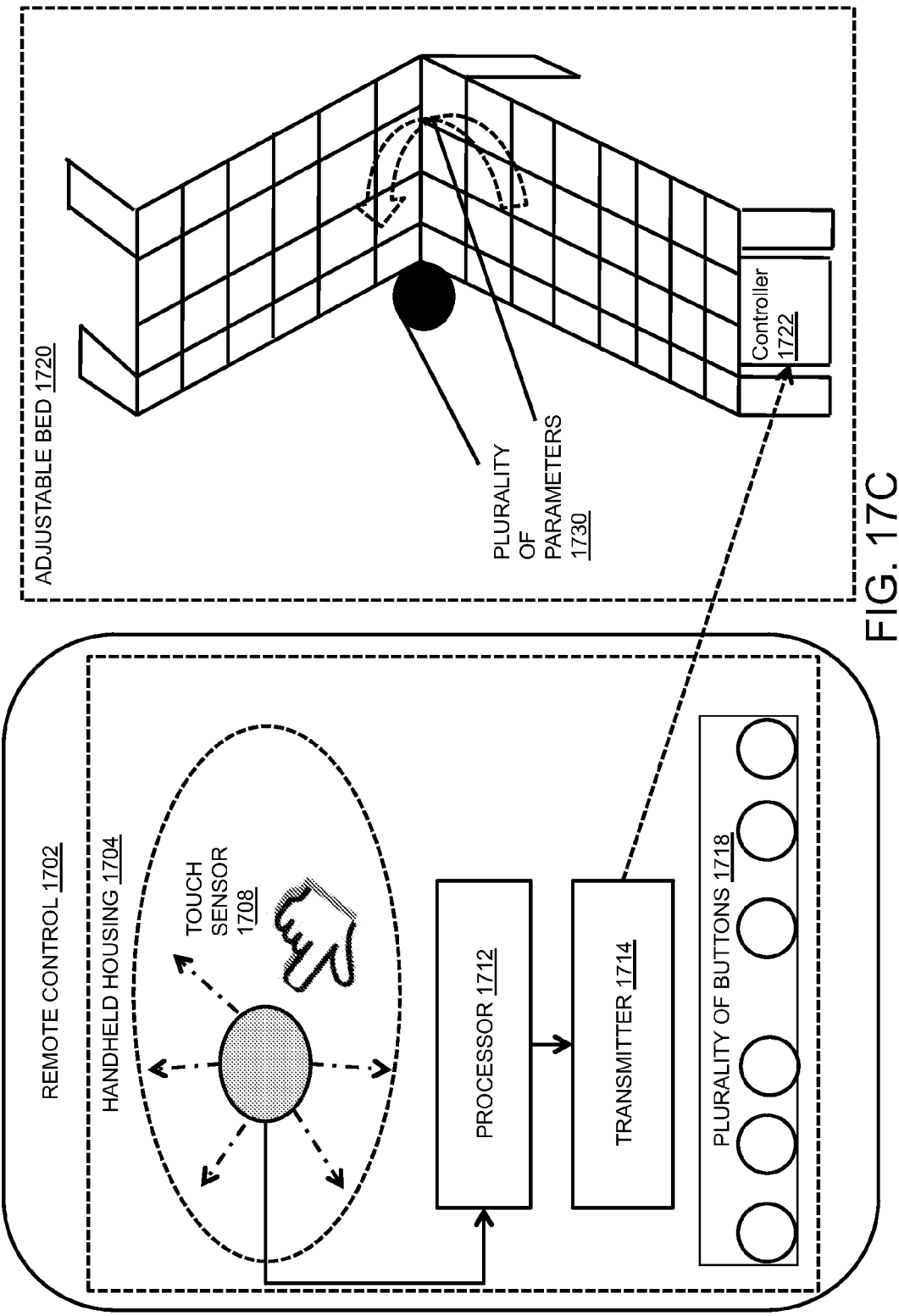

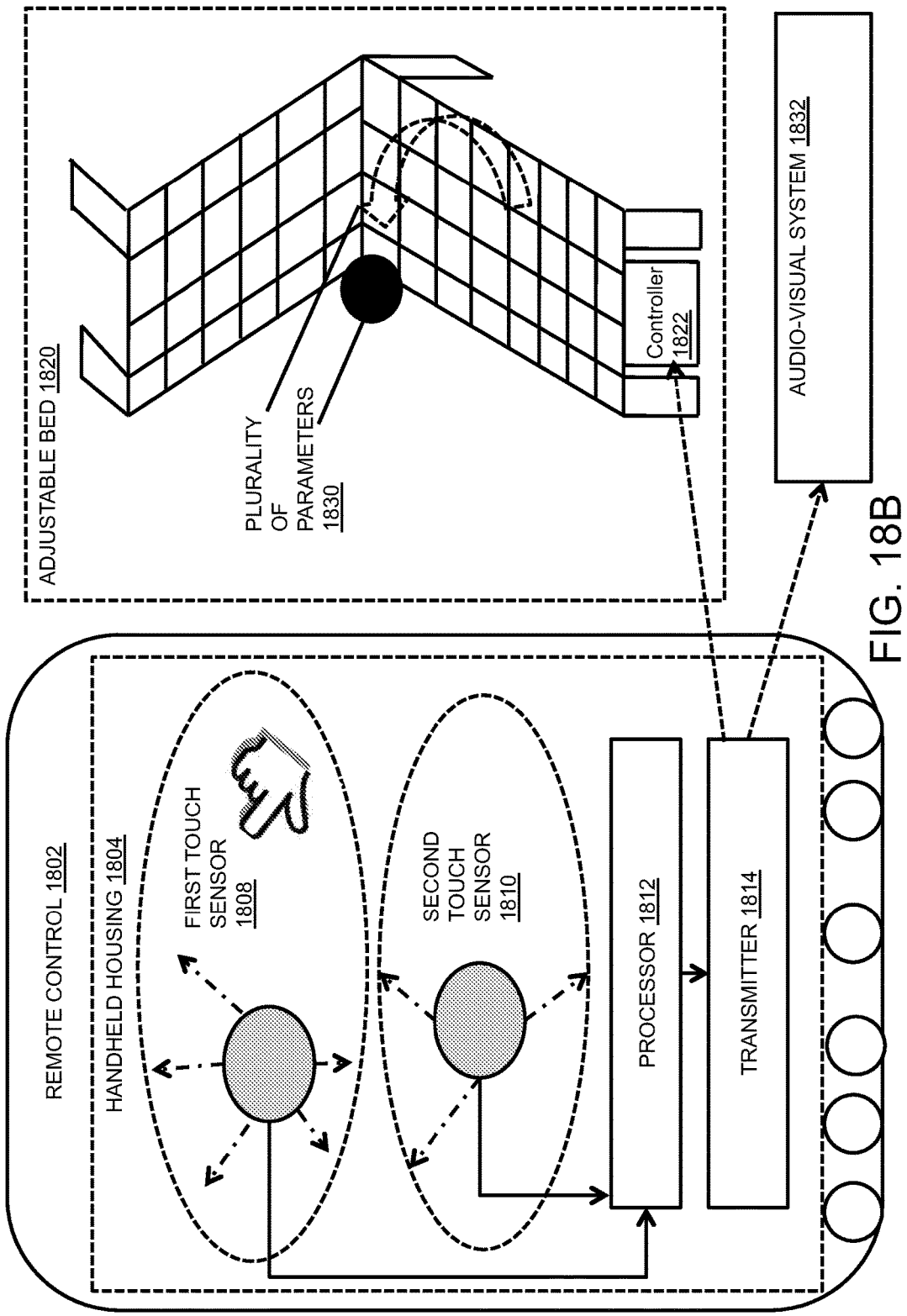

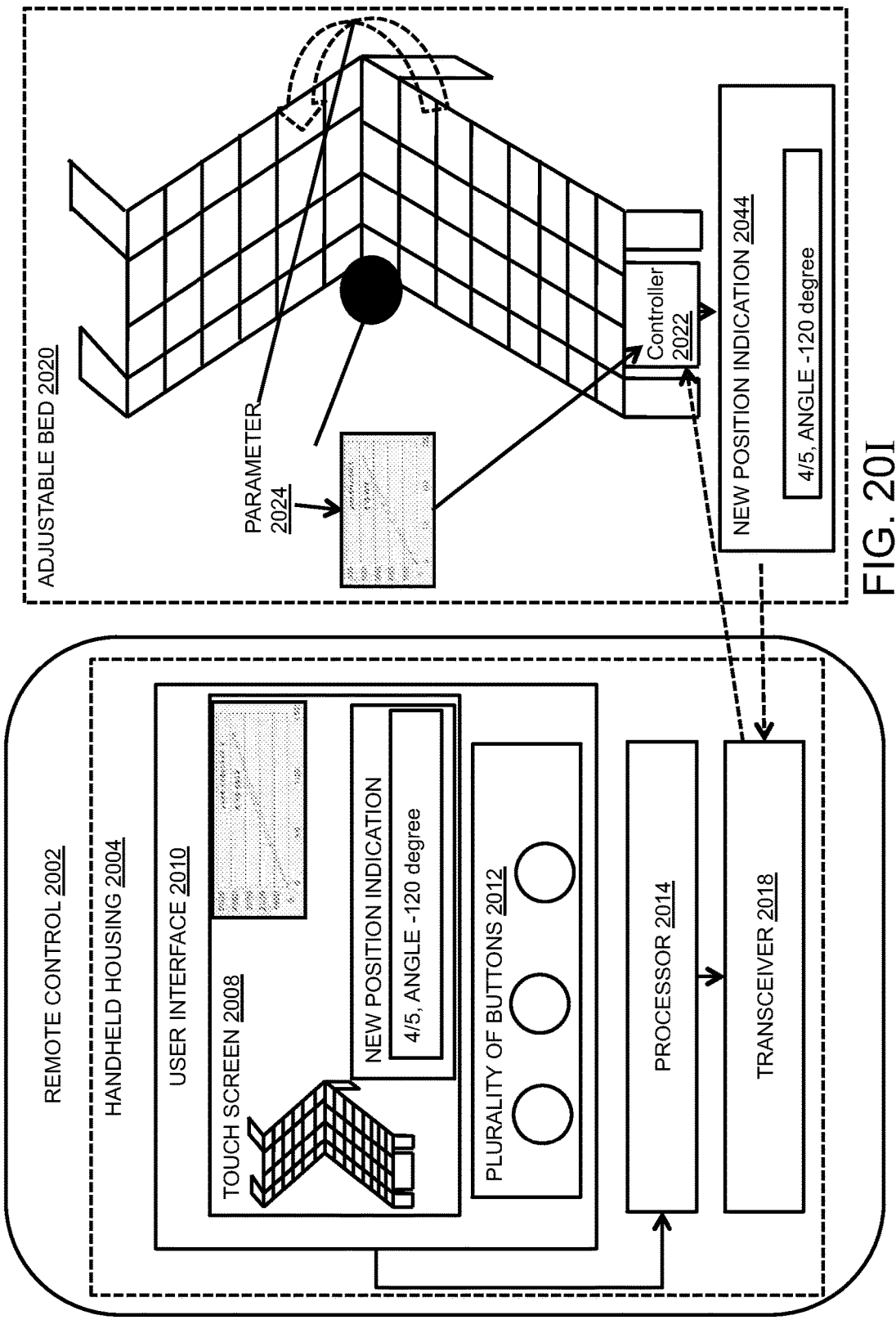

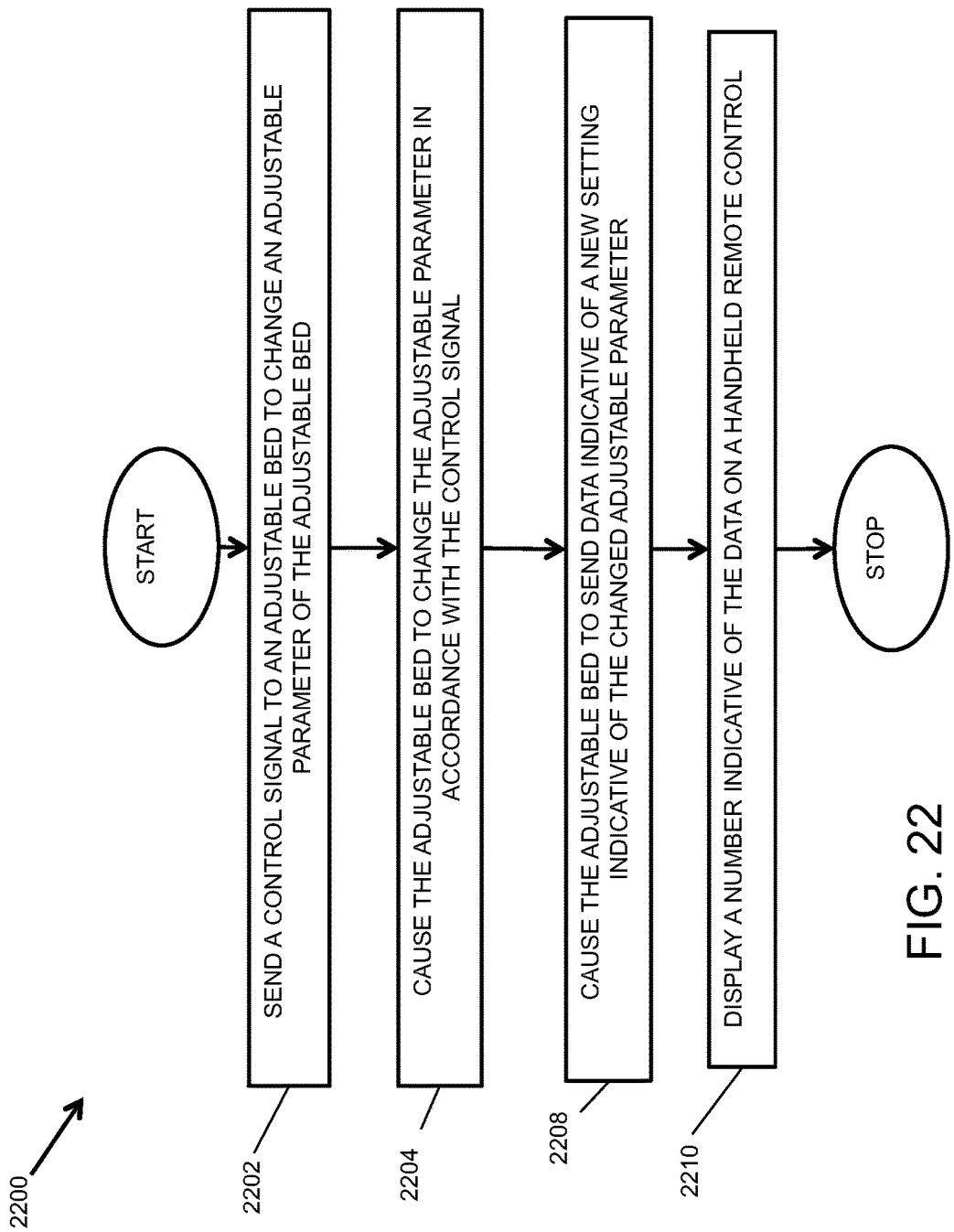

SYSTEM FOR TANDEM BED COMMUNICATION

CROSS-REFERENCE TO RELATED APPLICATIONS

This application is a continuation of U.S. patent application Ser. No. 13/355,931 filed Jan. 23, 2012, which is a continuation of U.S. patent application Ser. No. 13/286,812 filed Nov. 1, 2011, which claims the benefit of U.S. Provisional Patent Application No. 61/408,778, filed Nov. 1, 2010 and U.S. Provisional Patent Application No. 61/508,958, filed Jul. 18, 2011, each of which is hereby incorporated by reference in its entirety.

U.S. patent application Ser. No. 13/286,812 is a continuation-in-part of the following U.S. Patent Applications, each of which is hereby incorporated by reference in its entirety: U.S. patent application Ser. No. 12/704,117, filed Feb. 11, 2010; U.S. patent application Ser. No. 12/256,029, filed Oct. 22, 2008; and U.S. patent application Ser. No. 12/269,987 filed Nov. 13, 2008.

U.S. patent application Ser. No. 13/286,812 is also a continuation-in-part of U.S. patent application Ser. No. 11/855,255 filed Sep. 14, 2007, now abandoned, which is hereby incorporated by reference in its entirety.

BACKGROUND OF THE INVENTION

Field

This invention relates to the field of adjustable beds, and more specifically to information technology facilities associated with adjustable beds.

Description of the Related Art

Adjustable furniture, including chairs, couches, beds, and other furniture, may contain at least one section of component of which a user may control a feature or attribute, such as the position, vibration, motion, or the like of that section or component. The user may typically adjust the bed by using a control, which may be an on-furniture controller or a remote controller, to move an adjustable section in one or more directions of movement. Additionally, the adjustable furniture may include various types of mattresses, cushions, pillows, or similar elements to cushion the furniture for the user, and the furniture may allow for vibration, heating, cooling, or other action related to one or more of the sections.

A typical adjustable bed may consist of a wood decking for each of the sections of the bed connected together with hinges to allow the various positions between the sections. There are actuators connected between the bed frame and the wood decking for moving the adjustable sections into user-desired positions. The adjustable bed may have a "wall hugging" feature that maintains a consistent distance between the mattress and the wall as the bed is adjusted. Some adjustable beds may use wooden or plastic slats to support the mattress instead of a solid wood platform.

The adjustable bed may have at least one actuator to position the adjustable bed sections. In some cases, there is one actuator to position more than one, such as positioning both the thigh and foot sections with one actuator. There may also be more than one actuator for each adjustable section.

Hospitals have used adjustable beds for many years to provide comfortable and medically required positions, and many home users have adjustable furniture because of a medical issue and therefore require certain positions, movements, or settings (such as vibration, heating, cooling or the like) to aid recovery, positioning to relieve discomfort as a result of pain, or the like. These users, whether at home or in a medical environment such as a hospital, nursing home, assisted living facility, or long-term care facility, may, because of these issues, spend significant amounts of time in bed, and some users may be confined to spending long periods of time in or on furniture. With aging populations in many countries, such as the United States, more and more users face such confinement.

Associated with the trend for users to spend more time in sedentary positions, such as in bed, is a trend toward increasing use of technology in home and medical environments, including in rooms where users have adjustable furniture. Such technology includes increasingly sophisticated computer and networking technology, entertainment technology, information technology, and the like. While many existing adjustable beds provide the basic requirements of moving sections to positions that are required by a user, a need exists for adjustable furniture that works in better association with other technologies that are capable of being deployed in the environments in which the furniture is used.

SUMMARY OF THE INVENTION

Methods and systems are disclosed herein for improved integration of adjustable furniture, such as beds, with the technologies associated with the environments in which the beds are used. Such methods and systems include facilitating using control systems for the adjustable furniture to control a wide range of other technologies; actuating a wide range of actions as a result of events, states or attributes associated with the adjustable furniture, use of the adjustable furniture, or users of the furniture; and controlling the adjustable bed as result of events, states or attributes of the environment of the adjustable bed.

It should be understood that where context permits as would be understood by one of ordinary skill in the art references herein to adjustable beds should be understood to be capable of encompassing a range of adjustable furniture facilities, including beds, couches, chairs, love seats, and the like.

The methods and systems disclosed herein may include storing preferences associated with an adjustable furniture facility and at least one second system in a plurality of memory locations, wherein the second system is any of the devices or systems disclosed in this disclosure, such as a lighting system, an air purification system, an audio system, a CD player, an MP3 player, a DVD player, a lamp, an alarm clock, a music player, a telephone, a video system, or an entertainment technology system, computer system, information technology system, networking system or other device or system, such as described in any of the embodiments disclosed herein.

The methods and systems disclosed herein may include providing a modular controller for controlling an adjustable furniture facility and at least one second system associated with the adjustable furniture facility in a plurality of memory locations, wherein the second system is any of the devices or systems disclosed in this disclosure, such as a lighting system, an air purification system, an audio system, a CD player, an MP3 player, a DVD player, a lamp, an alarm clock, a music player, a telephone, a video system, or an entertainment technology system, computer system, information technology system, networking system or other device or system, such as described in any of the embodiments disclosed herein.

The methods and systems disclosed herein may include using a global command input to command more than one facility associated with an adjustable furniture facility using a single input, wherein the global command input is enabled by a modular controller capable of controlling an adjustable furniture facility and an second system associated with the adjustable furniture facility, wherein the second system is any of the devices or systems disclosed in this disclosure, such as a lighting system, an air purification system, an audio system, a CD player, an MP3 player, a DVD player, a lamp, an alarm clock, a music player, a telephone, a video system, or an entertainment technology system, computer system, information technology system, networking system or other device or system, such as described in any of the embodiments disclosed herein.

The methods and systems disclosed herein may include using a global command input to command more than one facility associated with an adjustable furniture facility using a single input, wherein the global command input is enabled by a modular controller capable of controlling an adjustable furniture facility and an second system associated with the adjustable furniture facility, wherein the second system is any of the devices or systems disclosed in this disclosure, such as a lighting system, an air purification system, an audio system, a CD player, an MP3 player, a DVD player, a lamp, an alarm clock, a music player, a telephone, a video system, or an entertainment technology system, computer system, information technology system, networking system or other device or system, such as described in any of the embodiments disclosed herein, wherein the modular controller has a touch screen for accepting user input.

The methods and systems disclosed herein may include using a programmable logic controller in a control facility for an adjustable furniture facility. The programmable logic controller may control the bed or any of the devices or systems disclosed herein that are associated with the environment of the furniture.

The methods and systems disclosed herein may include using a programmable logic controller in a control facility for an adjustable furniture facility and an second system, wherein the second system is any of the devices or systems disclosed in this disclosure, such as a lighting system, an air purification system, an audio system, a CD player, an MP3 player, a DVD player, a lamp, an alarm clock, a music player, a telephone, a video system, or an entertainment technology system, computer system, information technology system, networking system or other device or system, such as described in any of the embodiments disclosed herein.

The methods and systems disclosed herein may include storing memory for controlling an adjustable furniture facility, wherein at least a portion of the memory is stored remotely from the bed.

The methods and systems disclosed herein may include storing memory used to store data used for controlling an adjustable furniture facility and an second system, wherein at least a portion of the memory is stored remotely from the bed, wherein the second system is any of the devices or systems disclosed in this disclosure, such as a lighting system, an air purification system, an audio system, a CD player, an MP3 player, a DVD player, a lamp, an alarm clock, a music player, a telephone, a video system, or an entertainment technology system, computer system, information technology system, networking system or other device or system, such as described in any of the embodiments disclosed herein.

The methods and systems disclosed herein may include providing memory to store data for controlling an adjustable furniture facility, wherein the memory is removable and replaceable.

The methods and systems disclosed herein may include providing memory to store data for controlling an adjustable furniture facility and an second system, wherein the memory is removable and replaceable, wherein the second system is any of the devices or systems disclosed in this disclosure, such as a lighting system, an air purification system, an audio system, a CD player, an MP3 player, a DVD player, a lamp, an alarm clock, a music player, a telephone, a video system, or an entertainment technology system, computer system, information technology system, networking system or other device or system, such as described in any of the embodiments disclosed herein.

The methods and systems disclosed herein may include providing a remote controller for an adjustable furniture facility that has at least one bed position command set and at least one command set enabling a user to at least one of play, adjust volume, fast forward, and rewind using a device associated with the bed.

The methods and systems disclosed herein may include using two-way communications between a remote control facility and a controller for an adjustable furniture facility.

The methods and systems disclosed herein may include using two-way communications between a remote control facility and a controller for an adjustable furniture facility and an second system, wherein the second system is any of the devices or systems disclosed in this disclosure, such as a lighting system, an air purification system, an audio system, a CD player, an MP3 player, a DVD player, a lamp, an alarm clock, a music player, a telephone, a video system, or an entertainment technology system, computer system, information technology system, networking system or other device or system, such as described in any of the embodiments disclosed herein.

The methods and systems disclosed herein may include using a cellular phone to provide communication with the control box for an adjustable furniture facility, wherein entering a command on the phone controls a function of the adjustable furniture facility.

The methods and systems disclosed herein may include using a cellular phone to provide communication with the control box for an adjustable furniture facility and an second system, wherein entering a command on the phone controls a function of the adjustable furniture facility, wherein the second system is any of the devices or systems disclosed in this disclosure, such as a lighting system, an air purification system, an audio system, a CD player, an MP3 player, a DVD player, a lamp, an alarm clock, a music player, a telephone, a video system, or an entertainment technology system, computer system, information technology system, networking system or other device or system, such as described in any of the embodiments disclosed herein.

The methods and systems disclosed herein may include using a touch screen interface to allow a user to provide a control command to adjust a bed position of an adjustable furniture facility.

The methods and systems disclosed herein may include using a touch screen to provide a control command to adjust a bed position and to provide a control function to a second system associated with the adjustable furniture facility wherein the second system is any of the devices or systems disclosed in this disclosure, such as a lighting system, an air purification system, an audio system, a CD player, an MP3 player, a DVD player, a lamp, an alarm clock, a music player, a telephone, a video system, or an entertainment technology system, computer system, information technology system, networking system or other device or system, such as described in any of the embodiments disclosed herein.

The methods and systems disclosed herein may include providing a controller for an adjustable furniture facility, the controller capable of controlling a function of the bed and controlling an MP3 player.

The methods and systems disclosed herein may include providing a controller for an adjustable furniture facility, the controller capable of managing at least one wireless communication function, the wireless communication function a BLUETOOTH communication, an 802.11 communication, a WIFI communication, and a peer-to-peer communication.

The methods and systems disclosed herein may include providing a controller for an adjustable furniture facility and a second system, the controller capable of managing at least one wireless communication function, the wireless communication function a BLUETOOTH communication, an 802.11 communication, a WIFI, and a peer-to-peer communication, wherein the second system is any of the devices or systems disclosed in this disclosure, such as a lighting system, an air purification system, an audio system, a CD player, an MP3 player, a DVD player, a lamp, an alarm clock, a music player, a telephone, a video system, or an entertainment technology system, computer system, information technology system, networking system or other device or system, such as described in any of the embodiments disclosed herein.

The methods and systems disclosed herein may include providing a control system for an adjustable furniture facility, the control system accepting spoken commands to control a function of the adjustable furniture facility.

The methods and systems disclosed herein may include providing a control system for an adjustable furniture facility and a second system, the control system accepting spoken commands to control a function of the adjustable furniture facility, wherein the second system is any of the devices or systems disclosed in this disclosure, such as a lighting system, an air purification system, an audio system, a CD player, an MP3 player, a DVD player, a lamp, an alarm clock, a music player, a telephone, a video system, or an entertainment technology system, computer system, information technology system, networking system or other device or system, such as described in any of the embodiments disclosed herein.

An apparatus disclosed herein includes an adjustable bed handheld remote control that may include a handheld housing, a touch sensor on a front face of the handheld housing, a transmitter and the like. The touch sensor may be presented in a slider form and may be adapted to facilitate a user in adjusting a frame position of an adjustable bed. The transmitter may be electrically coupled to a processor that may receive input from the touch sensor, for communication control signals to the adjustable bed in accordance with the input received from the touch sensor.

In embodiments, the touch sensor may be a capacitive touch sensor. In embodiments, the slider may be in the form of a dial, a linear strip, a curvilinear strip, a curve, and the like.

In embodiments, the transmitter may be a transceiver and may be adapted to transmit control signals from the adjustable bed handheld remote control to the adjustable bed and receive data from the adjustable bed.

An apparatus disclosed herein includes an adjustable bed handheld remote control that may include a handheld housing, a touch sensor on a front face of the handheld housing, a transmitter and the like. The touch sensor may be presented in a slider form and may be adapted to facilitate a user in adjusting a massage motor setting of an adjustable bed. The transmitter may be electrically coupled to a processor that may receive input from the touch sensor, for communication control signals to the adjustable bed in accordance with the input received from the touch sensor.

An apparatus disclosed herein includes an adjustable bed handheld remote control that may include a handheld housing, a touch sensor on a front face of the handheld housing, a transmitter and the like. The touch sensor may be presented in a slider form and may be adapted to facilitate a user in adjusting a parameter of an adjustable bed. The transmitter may be electrically coupled to a processor that may receive input from the touch sensor, for communication control signals to the adjustable bed in accordance with the input received from the touch sensor.

An apparatus disclosed herein includes an adjustable bed handheld remote control that may include a handheld housing, a first touch sensor on a front face of the handheld housing, a second sensor on a front face of the handheld housing, a transmitter, and the like. The first touch sensor may be presented in a slider form and may be adapted to facilitate a user in adjusting a parameter of an adjustable bed. The second touch sensor may be adapted to facilitate the user in adjusting a parameter of an audiovisual system. The transmitter may be electrically coupled to a processor that may receive input from the first and second touch sensors, for communicating control signals to the adjustable bed in accordance with the input received from the first touch sensor.

An apparatus disclosed herein includes an adjustable bed handheld remote control that may include a handheld housing, a first touch sensor on a front face of the handheld housing, a second sensor on a front face of the handheld housing, a transmitter, and the like. The first touch sensor may be presented in a slider form and may be adapted to facilitate a user in adjusting a parameter of an adjustable bed. The second touch sensor may be adapted to facilitate the user in adjusting a parameter of an audio system. The transmitter may be electrically coupled to a processor that may receive input from the first and second touch sensors, for communicating control signals to the adjustable bed in accordance with the input received from the first touch sensor.

An apparatus disclosed herein includes an adjustable bed handheld remote control that may include a handheld housing, a first touch sensor on a front face of the handheld housing, a second sensor on a front face of the handheld housing, a transmitter, and the like. The first touch sensor may be presented in a slider form and may be adapted to facilitate a user in adjusting a parameter of an adjustable bed. The second touch sensor may be adapted to facilitate the user in adjusting a parameter of a remote computer facility. The transmitter may be electrically coupled to a processor that may receive input from the first and second touch sensors, for communicating control signals to the adjustable bed in accordance with the input received from the first touch sensor.

An apparatus disclosed herein includes an adjustable bed handheld remote control that may include a handheld housing, a first touch sensor on a front face of the handheld housing, a second sensor on a front face of the handheld housing, a transmitter, and the like. The first touch sensor may be presented in a slider form and may be adapted to facilitate a user in adjusting a parameter of an adjustable bed. The second touch sensor may be adapted to facilitate the user in adjusting a parameter of a HVAC system. The transmitter may be electrically coupled to a processor that may receive input from the first and second touch sensors, for communicating control signals to the adjustable bed in accordance with the input received from the first touch sensor.

An apparatus disclosed herein includes an adjustable bed handheld remote control that may include a handheld housing, a first touch sensor on a front face of the handheld housing, a second sensor on a front face of the handheld housing, a transmitter, and the like. The first touch sensor may be presented in a slider form and may be adapted to facilitate a user in adjusting a parameter of an adjustable bed. The second touch sensor may be adapted to facilitate the user in adjusting a parameter of a kitchen appliance. The transmitter may be electrically coupled to a processor that may receive input from the first and second touch sensors, for communicating control signals to the adjustable bed in accordance with the input received from the first touch sensor.

An apparatus disclosed herein includes an adjustable bed handheld remote control that may include a handheld housing, a first touch sensor on a front face of the handheld housing, a second sensor on a front face of the handheld housing, a transmitter, and the like. The first touch sensor may be presented in a slider form and may be adapted to facilitate a user in adjusting a parameter of an adjustable bed. The second touch sensor may be adapted to facilitate the user in adjusting a parameter of an alarm system. The transmitter may be electrically coupled to a processor that may receive input from the first and second touch sensors, for communicating control signals to the adjustable bed in accordance with the input received from the first touch sensor.

An apparatus disclosed herein includes an adjustable bed handheld remote control that may include a handheld housing, a first touch sensor on a front face of the handheld housing, a second sensor on a front face of the handheld housing, a transmitter, and the like. The first touch sensor may be presented in a slider form and may be adapted to facilitate a user in adjusting a parameter of an adjustable bed. The second touch sensor may be adapted to facilitate the user in adjusting a parameter of a vehicle system. The transmitter may be electrically coupled to a processor that may receive input from the first and second touch sensors, for communicating control signals to the adjustable bed in accordance with the input received from the first touch sensor.

An apparatus disclosed herein includes an adjustable bed handheld remote control that may include a handheld housing, a first touch sensor on a front face of the handheld housing, a second sensor on a front face of the handheld housing, a transmitter, and the like. The first touch sensor may be presented in a slider form and may be adapted to facilitate a user in adjusting a parameter of an adjustable bed. The second touch sensor may be adapted to facilitate the user in adjusting a second parameter of the adjustable bed facility. The transmitter may be electrically coupled to a processor that may receive input from the first and second touch sensors, for communicating control signals to the adjustable bed in accordance with the input received from the first touch sensor.

An apparatus disclosed herein includes an adjustable bed handheld remote control that may include a handheld housing, a touch screen on a front face of the handheld housing, a plurality of images presented on the touch screen each representative of a different function associated with an adjustable bed, a transmitter for the communication of the control signal to the adjustable bed, and the like. Each of the plurality of images may be coded to generate a control signal in response to an interaction with the image.

In embodiments, at least one of the images may be adapted to produce a control signal when touched and may produce an additional control signal when touched for a predetermined period of time. In embodiments, at least one of the images may be configured to accept an interaction by sliding across the image.

In embodiments, the adjustable bed handheld remote control may include an auxiliary image presented on the touch screen, which may be representative of a function associated with an auxiliary system. The auxiliary system may include an audiovisual system, an audio system, a computer system, an HVAC system, a kitchen appliance, an alarm system, a vehicle system, and the like.

An apparatus disclosed herein includes an adjustable bed handheld remote control that may include a handheld housing, a user interface on a front face of the handheld housing, a transceiver, and the like. The user interface may be adapted to facilitate a user in adjusting a parameter of an adjustable bed. The transceiver may be electronically coupled to a processor that may receive input from the user interface. The transceiver may transmit control signals from the adjustable bed handheld remote control to the adjustable bed in accordance with the input received from the user interface, and may receive data indicative of a receipt of the control signals from the adjustable bed.

In embodiments, the transceiver may operate following BLUETOOTH protocol. In embodiments, the transceiver may be an RF transceiver.

An apparatus disclosed herein includes an adjustable bed handheld remote control that may include a handheld housing, a user interface on a front face of the handheld housing, a transceiver, and the like. The user interface may be adapted to facilitate a user in adjusting a frame position of an adjustable bed. The transceiver may be electronically coupled to a processor that may receive input from the user interface. The transceiver may transmit control signals from the adjustable bed handheld remote control to the adjustable bed in accordance with the input received from the user interface, and may receive data indicating that the frame position has been achieved by the adjustable bed.

An apparatus disclosed herein includes an adjustable bed handheld remote control that may include a handheld housing, a user interface on a front face of the handheld housing, a transceiver, and the like. The user interface may be adapted to facilitate a user in adjusting a massage motor setting of an adjustable bed. The transceiver may be electronically coupled to a processor that may receive input from the user interface. The transceiver may transmit control signals from the adjustable bed handheld remote control to the adjustable bed in accordance with the input received from the user interface, and may receive data indicating that the massage motor setting has been achieved by the adjustable bed.

An apparatus disclosed herein includes an adjustable bed handheld remote control that may include a handheld housing, a user interface on a front face of the handheld housing, a transmitter, a receiver and the like. The user interface may be adapted to facilitate a user in adjusting a parameter of an adjustable bed. The transmitter may be electronically coupled to a processor that may receive input from the user interface. The transmitter may transmit control signals from the adjustable bed handheld remote control to the adjustable bed in accordance with the input received from the user interface. The receiver may receive data indicative of a receipt of the control signals from the adjustable bed.

In embodiments, the transmitter and receiver may operate at different frequencies.

An apparatus disclosed herein includes an adjustable bed handheld remote control that may include a handheld housing, a user interface on a front face of the handheld housing, a transceiver, a receiver and the like. The user interface may be adapted to facilitate a user in adjusting a frame position of an adjustable bed. The transceiver may be electronically coupled to a processor that may receive input from the user interface. The transceiver may transmit control signals from the adjustable bed handheld remote control to the adjustable bed in accordance with the input received from the user interface. The receiver may receive data indicating that the frame position has been achieved by the adjustable bed.

In embodiments, the transmitter and receiver may operate at different frequencies.

An apparatus disclosed herein includes an adjustable bed handheld remote control that may include a handheld housing, a user interface on a front face of the handheld housing, a transceiver, a receiver and the like. The user interface may be adapted to facilitate a user in adjusting a massage motor setting of an adjustable bed. The transceiver may be electronically coupled to a processor that may receive input from the user interface. The transceiver may transmit control signals from the adjustable bed handheld remote control to the adjustable bed in accordance with the input received from the user interface. The receiver may receive data indicating that the massage motor setting has been achieved by the adjustable bed.

In embodiments, the transmitter and receiver may operate at different frequencies.

An apparatus disclosed herein includes an adjustable bed handheld remote control that may include a handheld housing, a user interface on a front face of the handheld housing, a transceiver, and the like. The user interface may be adapted to facilitate a user in adjusting a parameter of an adjustable bed. The transceiver may be electronically coupled to a processor that may receive input from the user interface. The transceiver may transmit control signals from the adjustable bed handheld remote control to the adjustable bed in accordance with the input received from the user interface and may receive data indicative of an error encountered in a control system of the adjustable bed.

An apparatus disclosed herein includes an adjustable bed handheld remote control that may include a handheld housing, a user interface on a front face of the handheld housing, a transceiver, and the like. The user interface may be adapted to facilitate a user in adjusting a parameter of an adjustable bed. The transceiver may be electronically coupled to a processor that may receive input from the user interface. The transceiver may transmit control signals from the adjustable bed handheld remote control to the adjustable bed in accordance with the input received from the user interface. The transceiver may transmit diagnostic control signals from the adjustable bed handheld remote control to the adjustable bed to cause a controller of the adjustable bed to go into a diagnostic mode and may receive data indicative receive data indicative of the diagnostic mode from the adjustable bed.

An apparatus disclosed herein includes an adjustable bed handheld remote control that may include a handheld housing, a user interface on a front face of the handheld housing, a transceiver, and the like. The user interface may be adapted to facilitate a user in adjusting a frame position of an adjustable bed. The transceiver may be electronically coupled to a processor that may receive input from the user interface. The transceiver may transmit control signals from the adjustable bed handheld remote control to the adjustable bed in accordance with the input received from the user interface. The transceiver may receive data indicative of a new setting of the adjustable bed and may display information on the adjustable bed remote control indicative of the new setting.

An apparatus disclosed herein includes an adjustable bed handheld remote control that may include a handheld housing, a user interface on a front face of the handheld housing, a transceiver, and the like. The user interface may be adapted to facilitate a user in adjusting a parameter of an adjustable bed. The transceiver may be electronically coupled to a processor that may receive input from the user interface. The transceiver may transmit control signals from the adjustable bed handheld remote control to the adjustable bed in accordance with the input received from the user interface. The transceiver may receive data indicating that the frame position has been achieved and may display information on the adjustable bed remote control indicative of the frame position.

In embodiments, the information displayed on the adjustable bed remote control may be a position number associated with the frame position.

An apparatus disclosed herein includes an adjustable bed handheld remote control that may include a handheld housing, a user interface on a front face of the handheld housing, a transceiver, and the like. The user interface may be adapted to facilitate a user in adjusting a massage setting of an adjustable bed. The transceiver may be electronically coupled to a processor that may receive input from the user interface. The transceiver may transmit control signals from the adjustable bed handheld remote control to the adjustable bed in accordance with the input received from the user interface. The transceiver may receive data indicating that the massage setting has been achieved and may display information on the adjustable bed remote control indicative of the massage setting.

In embodiments, the information displayed on the adjustable bed remote control may be a position number associated with the massage setting.

In embodiments, a method for displaying a number indicative of the data on a handheld remote control may be provided. The method may include sending a control signal to an adjustable bed to change an adjustable parameter of the adjustable bed, causing the adjustable bed to change the adjustable parameter in accordance with the control signal, causing the adjustable bed to send data indicative of a new setting indicative of the changed adjustable parameter and displaying a number indicative of the data on a handheld remote control.

An apparatus disclosed herein includes an adjustable bed handheld remote control that may include a handheld housing, a user interface on a front face of the handheld housing, a transceiver, and the like. The user interface may be adapted to facilitate a user in adjusting a parameter of an adjustable bed. The transceiver may be electronically coupled to a processor that may receive input from the user interface. The transceiver may transmit control signals from the adjustable bed handheld remote control to the adjustable bed in accordance with the input received from the user interface. The transceiver may receive data indicating a new setting of the adjustable bed and may display graphical information on the adjustable bed remote control indicative of the new setting.

An apparatus disclosed herein includes an adjustable bed handheld remote control that may include a handheld housing, and a user interface on a front face of the handheld housing. The user interface may be adapted to facilitate a user in adjusting a parameter of an adjustable bed and displaying a graphical representation of the adjustable bed parameter.

In embodiments, the graphical representation of the adjustable bed parameter may indicate a current status of the parameter as indicated by the adjustable bed.

An apparatus disclosed herein includes an adjustable bed handheld remote control that may include a handheld housing, and a user interface on a front face of the handheld housing. The user interface may be adapted to facilitate in adjusting a parameter of an adjustable bed, adjusting a parameter of an auxiliary system, displaying a graphical representation of the adjustable bed parameter and displaying a graphical representation of the auxiliary system parameter.

In embodiments, the graphical representation of the adjustable bed parameter may indicate a current status of the parameter as indicated by the adjustable bed.

In embodiments, the graphical representation of the auxiliary system parameter may indicate a current status of the parameter as indicated by the auxiliary system.

An apparatus disclosed herein includes an adjustable bed handheld remote control that may include a handheld housing, a user interface on a front face of the handheld housing, a transmitter, a receiver, and the like. The user interface may be adapted to facilitate a user in adjusting a parameter of an adjustable bed. The transmitter may be electronically coupled to a processor that may receive input from the user interface. The transmitter may be adapted to transmit control signals from the adjustable bed handheld remote control to the adjustable bed in accordance with the input received from the user interface. The receiver may be electronically coupled to the processor and may be adapted to receive data from the adjustable bed indicative of a new setting of the adjustable bed. The user interface may display graphical information on the adjustable bed remote control indicative of the new setting.

In embodiments, the transmitter and receiver may operate at different frequencies.

In embodiments, a method for displaying a graphical representation of the adjusted parameter may be provided. The method may include sending a control signal to an adjustable bed from a handheld remote control to adjust a parameter of the adjustable bed, and displaying a graphical representation on the handheld remote control in response to receiving information from the adjustable bed indicating that the parameter has been adjusted. The graphical representation may be illustrative of the adjusted parameter.

In embodiments, a method for displaying a graphical representation of the adjusted parameter may be provided. The method may include sending a control signal at a first frequency to an adjustable bed from a handheld remote control to adjust a parameter of the adjustable bed and displaying a graphical representation on the handheld remote control in response to receiving information at a second frequency from the adjustable bed indicating that the parameter has been adjusted. The graphical representation may be illustrative of the adjusted parameter.

An apparatus disclosed herein includes an adjustable bed handheld remote control that may include a handheld housing, a touch screen user interface on a front face of the handheld housing, a transceiver, and the like. The user interface may be adapted to facilitate a user in adjusting a parameter of an adjustable bed. The transceiver may be adapted to transmit control signals from the adjustable bed handheld remote control to the adjustable bed in accordance with the input received from the user interface and may be adapted to receive data from the adjustable bed indicative of a new setting of the adjustable bed. The graphical information indicative of the new setting may be displayed on the touch screen user interface and the user may adjust the parameter by interacting with the graphical information displayed on the touch screen.

An apparatus disclosed herein includes an adjustable bed handheld remote control that may include a handheld housing, a touch screen user interface on a front face of the handheld housing, a transmitter, a receiver, and the like. The user interface may be adapted to facilitate a user in adjusting a parameter of an adjustable bed. The transceiver may be adapted to transmit control signals from the adjustable bed handheld remote control to the adjustable bed in accordance with the input received from the user interface. The receiver may be adapted to receive data from the adjustable bed indicative of a new setting of the adjustable bed. The graphical information indicative of the new setting may be displayed on the touch screen user interface and the user may adjust the parameter by interacting with the graphical information displayed on the touch screen.

In embodiments, a method for adjusting a parameter associated with the adjustable bed may be provided. The method may include presenting an interactive graphical representation illustrative of an adjustable parameter of an adjustable bed, manipulating the interactive graphical representation, sending a control signal to the adjustable bed in accordance with the manipulation and causing the adjustable bed to respond to the control signal.

In embodiments, a method for causing the bed massage motor to be set according to a user selected setting may be provided. The method may include storing multiple values that may define a range of available settings for a bed massage motor, receiving a request to set the bed massage motor as the user selected setting, determining a value amongst the multiple values which may represent the user selected setting and causing the bed massage motor to be set to the user selected setting by using the value that represents the user selected setting. Storing of the multiple values may include storing a table having multiple entries. Each one of the multiple entries may specify one of the ranges of available settings for the bed massage motor.

In embodiments, the user selected setting may be an intensity setting, a mode setting, a frequency setting, or some other type of setting.

In embodiments, a method for storing an association of a current setting value with a user-selected position of the bed massage motor may be provided. The method may include storing multiple values that may define a range of available settings for a bed massage motor, receiving a request to save a setting of the bed massage motor as a user selected setting, determining which of the multiple values represents a current setting of the bed massage motor to provide a current setting value and storing an association of the current setting value with the user-selected position. Storing multiple values may include storing a table having multiple entries. The multiple entries may specify one of the ranges of available settings for the bed massage motor. Storing the association of the current setting value with the user-selected setting may include adding a store indication to each one of the multiple entries of the table except for the one of the multiple entries representing the current setting value.

In embodiments, a method for storing an association of a current setting value with a user-selected position of the bed massage motor may be provided. The method may include storing a plurality of values that may define a range of available settings for a bed massage motor, receiving a request to save a setting of the bed massage motor as a user selected setting, determining which of the multiple values may represent a current setting of the bed massage motor to provide a current setting value and storing the association of the current setting value with the user-selected position. Storing multiple values may include storing a table having multiple entries. The multiple entries may specify one of the ranges of available settings for the bed massage motor. Storing the association of the current setting value with the user-selected setting may include adding a store indication to the table entry representing the current setting value.

In embodiments, a method for storing an association of a current setting value with a user-selected position of a bed function may be provided. The method may include storing a plurality of values that may define a range of available settings for a bed function, receiving a request to save a setting of the bed function as a user selected setting, determining which of the multiple values may represent a current setting of the bed function to provide a current setting value and storing the association of the current setting value with the user-selected position. Storing multiple values may include storing a table having multiple entries. The multiple entries may specify one of the ranges of available settings for the bed function. Storing the association of the current setting value with the user-selected setting may include adding a store indication to the table entry representing the current setting value.

In an aspect of the invention, an adjustable bed handheld remote control may include a handheld housing; a user interface on a front face of the handheld housing, wherein the user interface is adapted to facilitate a user adjusting a parameter of an adjustable bed; a transmitter, electronically coupled to a processor that receives input from the user interface, adapted to transmit control signals from the adjustable bed handheld remote control to the adjustable bed in accordance with the input received from the user interface; a receiver, electronically coupled to the processor, adapted to receive data from the adjustable bed indicative of a new setting of the adjustable bed; and a piezoelectric circuit disposed inside the handheld housing, wherein the piezoelectric circuit is adapted to indicate accomplishment of the new setting of the adjustable bed, the indication being marked with vibration of the handheld remote control.

In an aspect, a method for operating an adjustable bed may include receiving information about a first wireless interface of a remote control at a first wireless communication module from the remote control, configuring a second wireless communication module using the information, the second wireless communication module adapted for communications with an adjustable bed and the second wireless communication module employing a second wireless interface incompatible with the first wireless interface, receiving a command for controlling the adjustable bed from the remote control through the first wireless interface, processing the command to produce a control signal suitable for communication over the second wireless interface that causes the adjustable bed to physically respond to the command, and transmitting the control signal through the second wireless interface. The incompatible wireless communications modules may be incompatible at a physical layer. The information may include a MAC address. Establishing communications may include establishing communications via a connection-based protocol. The command may be a lay-flat command, and wherein the control signal activates an actuator to move the adjustable bed toward a laying-flat position limit. The method where the command is a lay-flat command may further include detecting a motion of the adjustable bed caused by the actuator, detecting a halt in the motion, starting a timeout period in response to the halt, and deactivating the actuator in response to expiration of the timeout period. Receiving information may be done via Bluetooth and receiving a command may be done via WiFi.

In an aspect, a device may include a first wireless interface controlled by a first wireless communication module adapted for communications with a remote control, a second wireless interface controlled by a second wireless communication module adapted for communications with an adjustable bed, wherein the first wireless interface is incompatible with the second wireless interface, and a processor programmed to receive a first signal from the remote control through the first wireless communication module, to identify an adjustable bed command in the first signal, to generate a second signal suitable for communication to the adjustable bed through the second wireless communication module, and to communicate the second signal to the adjustable bed. The incompatible wireless communication modules may be incompatible at a physical layer. The information may include a MAC address. The computer program code, when run by the processor, may further perform a step of establishing connection-based communications between the second hardware wireless communication module and the remote wireless interface. The device may further include the adjustable bed, and an actuator disposed with the adjustable bed, the actuator that responds to the control signal by moving the adjustable bed into a lay-flat position, wherein the command is a lay-flat command, and wherein the computer program code, when run by the processor, may further perform the following steps: detecting a motion of the adjustable bed caused by the actuator, detecting a halt in the motion, starting a timeout period in response to the halt, and deactivating the actuator in response to expiration of the timeout period. The first wireless interface may be a Bluetooth interface and the second wireless interface may be a WiFi interface.

In an aspect, a computer program product may be embodied in a non-transitory computer readable medium that, when run by a processor, may perform the following steps: receiving, via a first hardware wireless communication module, information about a remote wireless interface, configuring a second hardware wireless communication module using the information, receiving, via the second hardware wireless communication module, a command for controlling an adjustable bed, and producing, in response to the command, a control signal that causes the adjustable bed to physically respond to the command. The computer code, when run by the processor, may further perform the following steps: detecting a motion of the adjustable bed caused by an actuator, detecting a halt in the motion, starting a timeout period in response to the halt, and deactivating the actuator in response to expiration of the timeout period. Receiving information may be done via Bluetooth and receiving a command may be done via WiFi.

In an aspect, a computer program product may be embodied in a non-transitory computer readable medium, the computer program product including computer code that, when run by at least one computing device, may perform the steps of: receiving, via a first communication channel, a first command for controlling an adjustable bed, this step of receiving causing a timeout period to begin, controlling the adjustable bed in response to the first command, failing to receive, via the first communication channel and prior to expiration of the timeout period, a second command for controlling the adjustable bed, attempting, after expiration of the timeout period, to receive the second command by alternating between tuning to the first communication channel and tuning to a second communication channel, receiving the second command while tuned to one of the first and the second communication channels, and after receiving the second command, attempting to receive a third command by remaining tuned to one of the first and the second communication channels.

In an aspect, a method of synchronously controlling a plurality of adjustable beds using a single remote control may include receiving an input for controlling an adjustable bed, transmitting, responsive to the input, a bed-control command to a first adjustable bed, starting a first timeout period in response to the act of transmitting to the first adjustable bed, failing to receive a first acknowledgement from the first adjustable bed prior to expiration of the first timeout period, transmitting, responsive to expiration of the first timeout period, the bed-control command to a second adjustable bed, starting a second timeout period in response to the act of transmitting to the second adjustable bed and retransmitting, responsive to an earlier expiration of the second timeout period and receipt of an acknowledgement from the second adjustable bed, the bed-control command to the first adjustable bed.

In an aspect, a method in an adjustable bed may include activating an actuator to move the adjustable bed toward a laying-flat position limit, detecting a motion of the adjustable bed caused by the actuator, detecting a halt in the motion, starting a timeout period in response to the halt, deactivating the actuator in response to expiration of the timeout period.

In an aspect, a system may include a communication module including both hardware and a protocol stack capable of communicating at least at 1 Mbps via a broadcast network, a peer-to-peer network, a secure authenticated network, a star network, a shared uni-directional network, a shared bi-directional network, an ad-hoc automatically shared network, a scanning mode network, a practical mesh network, and a shared cluster network, a programmable logic controller operatively coupled to the communication module, a bed-lift motor operatively coupled to the programmable logic controller, and a computer program product embodied in a non-transitory computer readable medium and operatively coupled to the programmable logic controller, the computer program product including computer code that, when run by the programmable logic controller, may perform the steps of: receiving, via the communication module, a command for controlling an adjustable bed, and producing, in response to the command, a control signal that causes the bed-lift motor to move a part of the adjustable bed. The computer code, when run by the programmable logic controller, may further perform the steps of: detecting movement of the part of the adjustable bed caused by the bed-lift motor, detecting a halt in the movement, starting a timeout period in response to the halt, and deactivating the bed-lift motor in response to expiration of the timeout period.

In an aspect, a method in an adjustable bed may include monitoring a sensor for a first reading indicative of a snoring user, activating an actuator to move the adjustable bed into an anti-snore position, monitoring the adjustable bed to confirm that it achieves the anti-snore position, monitoring the sensor for a second reading indicative of a non-snoring user, and after failing to receive the second reading, activating the actuator to move the adjustable bed into a second anti-snore position. Monitoring the sensor for the first reading may include monitoring the sensor in response to receipt of an anti-snore-mode activation signal from a remote control.

In an aspect, a system may include an adjustable bed including an actuator that moves an adjustable portion of the adjustable bed between a plurality of positions, a sensor that produces a reading indicative of a snoring user, a handheld remote control including a touchscreen graphical user interface, the remote control adapted to transmit an anti-snore-mode activation signal in response to user selection of an icon via the interface, and a controller operatively coupled to the actuator and the sensor, the controller adapted to carry out the following steps: receiving the activation signal, monitoring, in response to receipt of the activation signal, a sensor for a first reading indicative of a snoring user, activating the actuator to move the adjustable bed into an anti-snore position, and monitoring the adjustable bed to confirm that it achieves the anti-snore position. The controller may be further adapted to carry out the following steps: monitoring the sensor for a second reading indicative of a non-snoring user, and after failing to receive the second reading, activating the actuator to move the adjustable bed into a second anti-snore position.

In an aspect, a method of controlling an adjustable bed may include in response to an indication by a user that the user would like the adjustable bed in a position to mitigate snoring, causing a bed frame position controller to move a mechanical component of the adjustable bed to a pre-selected position and causing the controller to confirm that the pre-selected position has been achieved by monitoring the position of the mechanical component and comparing the position of the mechanical component with the pre-selected position. The bed frame position controller may maintain the pre-selected position in a table of positions along with an indication that the pre-selected position is the position to mitigate snoring. The user may initiate the indication by making a selection on a hand held remote control. The hand held remote control may include a touch screen graphical user interface and the selection is made by touching a selectable icon indicative of the position to mitigate snoring. The hand held remote control may include a telephone feature. The hand held remote control may include a cell phone feature. The hand held remote control may include a VoIP feature.

In an aspect, a method of controlling a plurality of adjustable beds may include using a remote control of a first adjustable bed to command the first adjustable bed to perform a function, adapting the first adjustable bed to communicate with a second adjustable bed, causing the first adjustable bed to communicate at least one of the command and a current setting of the adjustable bed to the second adjustable bed, and causing the second adjustable bed to interpret the communication. The communication may be interpreted as a command.

In an aspect, a method of wireless communication between adjustable beds may include adapting a first adjustable bed to wirelessly communicate with a second adjustable bed, causing the first adjustable bed to wirelessly communicate at least one of a command, a setting, a preference, a software update, and a report to the second adjustable bed, and adapting the second adjustable bed to receive the wireless communication. The wireless communication protocol may be one of radio frequency (RF), infrared (IR), BLUETOOTH, and WIFI.

These and other systems, methods, objects, features, and advantages of the present invention will be apparent to those skilled in the art from the following detailed description of the preferred embodiment and the drawings. All documents mentioned herein are hereby incorporated in their entirety by reference.

BRIEF DESCRIPTION OF FIGURES

The systems and methods described herein may be understood by reference to the following figures:

FIG. 3 shows an embodiment of a remote control used to command the adjustable bed facility.

FIG. 4A shows an embodiment of the shipping of a mattress retainer bracket in the upside down position.

FIG. 4B shows an embodiment of the shipping of a mattress retainer bracket in the upright position FIG. 5A shows a top view of a vibration motor within an opening of an adjustable bed facility section lateral surface.

FIG. 5B shows a side view of a vibration motor within an opening of an adjustable bed facility lateral surface.

FIG. 6 shows a typical hospital adjustable bed.

FIG. 14 shows mounting of a control box, a receiver, and a power supply on an adjustable bed facility according to an embodiment of the present invention.

FIG. 15 shows an accelerometer, a control box, and a processor of an adjustable bed facility according to an embodiment of the present invention.

FIG. 16 depicts remote control devices with slider controls in circular and linear configurations.

FIG. 17C depicts a remote control to control an adjustable parameter of an adjustable bed.

FIG. 18B depicts a remote control for controlling an adjustable bed and an audio system.

FIGS. 20A-L depict a remote control for controlling the parameters of an adjustable bed 1824 in accordance with various embodiments of the present invention.

FIG. 22 depicts a flow chart for changing an adjustable parameter associated with an adjustable bed.

DETAILED DESCRIPTION OF THE PREFERRED EMBODIMENTS

Figure 1A:
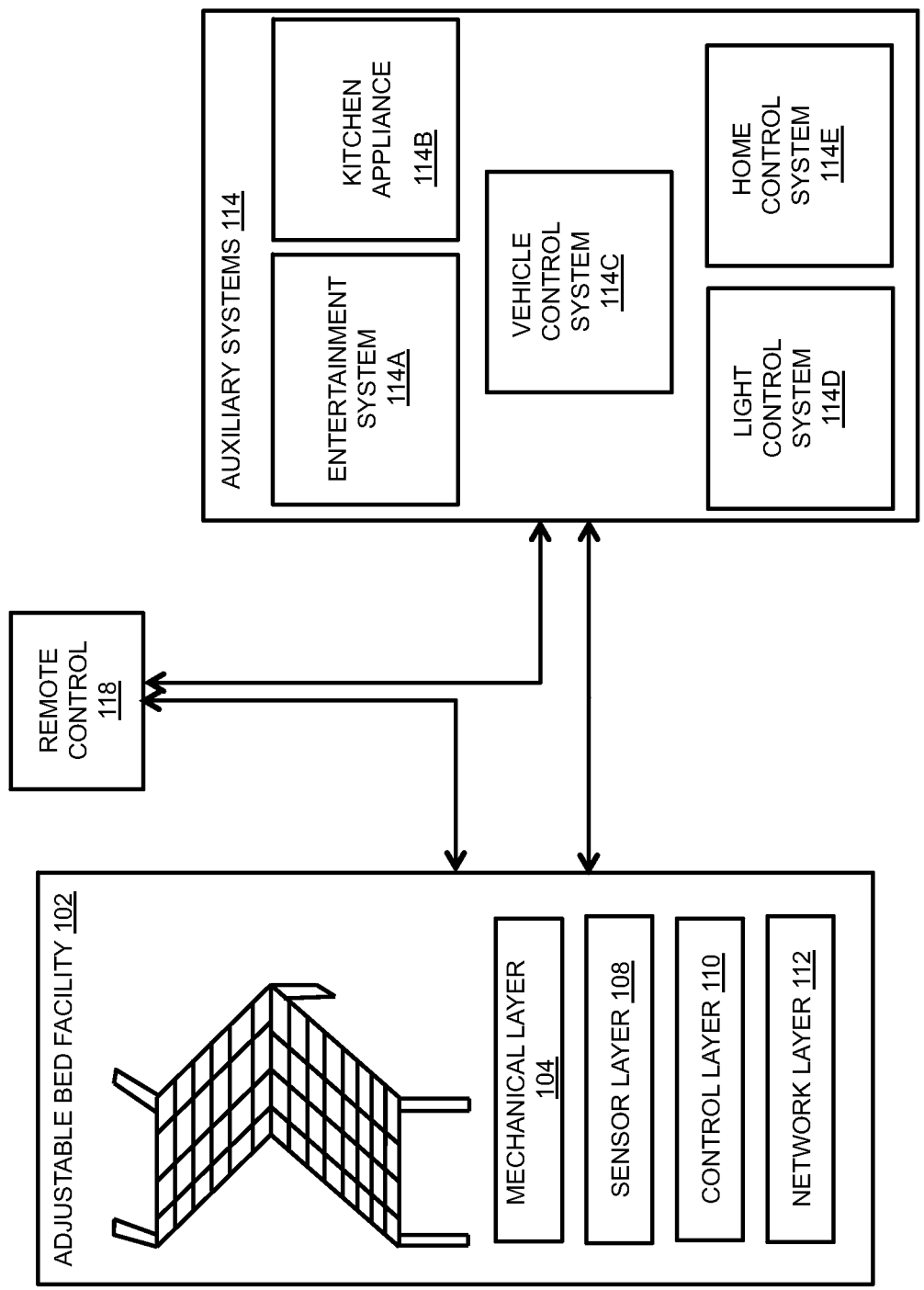
FIG. 1A shows a block diagram of an adjustable bed facility and associated components.

In the following description, terms such as 'adjustable mattress', 'adjustable bed', 'adjustable bed facility' and the like are used interchangeably to refer generally to an apparatus including a sleeping or resting surface with one or more adjustable or moveable sub-surfaces that can be positioned for user comfort and/or convenience, unless a specific meaning is explicitly provided or otherwise clear from the context.

As users spend more and more time in adjustable beds they may desire to have a level of independence by controlling devices that may be in the room from the adjustable bed. The devices and facilities that users may wish to control may include audio equipment, video equipment, lamps, air purification facilities, power outlets, and the like. It may be desirable for the user to control these devices and facilities from the adjustable bed without having to leave the bed or ask for aid from someone else. For example, the user may be confined to the bed and may want the simple ability to control the lights around the adjustable bed.

In an embodiment, an adjustable bed may not be the only rest facility to benefit from position and additional function control. Users may also use beds, adjustable beds, adjustable chairs, adjustable couches, and the like to provide comfortable positions when the user may have limited mobility. For example, a user that has had hip replacement surgery may not be confined to bed but may require a chair or couch to be adjustable to provide a comfortable sitting position while providing control of other devices within the room to limit the number of times the user must get up and adjust the devices. In an embodiment, while recovering from a surgery, an injury, an illness, or the like, the user may use more than one type of rest facility. The user may require confinement to an adjustable bed for a time and then, with health improvement, be able to move to either an adjustable chair or adjustable couch.

Aspects of the invention may be described as an adjustable bed, but it may be understood that the same aspects may be applied to other rest facilities that may include a bed, a couch, a chair, or the like. Such rest facilities may be in a home, a car, a recreational vehicle, a cruise ship, an airline, a train, or anywhere that a user required them, and they may be fixed or mobile.

One aspect of this invention may be to provide the adjustable bed with more than one power option to move the adjustable bed sections. The adjustable bed may use electric motors with gearboxes, pneumatic springs, hydraulic springs, or the like to actuate the adjustable bed sections. There may be both pricing and durability reasons to have the different actuation types.

Another aspect of this invention may be to provide the ability to provide additional functionality to the adjustable bed by using modular controls that may be able to communicate with the user's interface control. The modular controls may be designed to control a number of additional devices and facilities that may include audio devices, video devices, lamps, air purification facilities, power outlets, and the like.

Another aspect of the adjustable bed may be to provide a support structure to support the bed materials (e.g. mattress), motors, actuators, hinges between bed sections, and the like. The support structure may be a frame structure to provide the support yet remain lightweight.

Another aspect may be the use of replaceable memory to maintain the bed memory and software applications. The replaceable memory may allow user specific information to be moved from one adjustable bed to another adjustable bed. This may be useful in care facilities where a user may move from one bed to another bed during the stay in the care facility. If the user has saved a preferred positioning of the adjustable bed, when the user moves to another bed, the preferred positioning settings may be moved to the other bed with the user.

Another aspect of the adjustable bed may be to provide safety features that may control the refraction of the adjustable bed sections to reduce the risk of crushing an object that may be under the adjustable bed. Many other aspects of the present invention will become apparent by reading the disclosure herein.

FIG. 1A illustrates a block diagram of the various components of an adjustable bed facility 102. In an embodiment, the adjustable bed facility 102 may be made up of a plurality of layers that may include a mechanical layer 104, a sensor layer 108, a control layer 110, and a network layer 112, and one or more auxiliary systems 114. In addition, the adjustable bed facility 102 may interact with a remote control 118 and the like. In an embodiment, the auxiliary systems 114 may include an entertainment system 114a, a kitchen appliance 114b, a vehicle control system 114c, a light control system 114d, a home control system 114e, and the like. In an embodiment, the auxiliary systems 114 may be combined with the adjustable bed facility 102, stand-alone devices, or the like.

In an embodiment, the mechanical layer 104 may include physical aspects of the adjustable bed facility 102 that provide support for the user. The mechanical layer 104 may include actuators, springs, mattresses, a sub-frame, a skeleton structure, vibration motors, supports, and safety brackets of the adjustable bed facility 102. These support and connection members may have any shape or configuration required to provide the support and connections needed by the various other components.

In an embodiment, the sensor layer 108 may include a plurality of sensors of various types. The sensor layer 108 may be interchangeably referred as sensor 108 within this disclosure. The sensors may be mechanical sensors, electrical sensors, bio-sensors, and so on. In embodiments, the sensor(s) may be associated with the various mechanical and electrical components that make up the mechanical layer 104. For example, the sensor(s) may be associated with an actuator to assess the position of the actuator or the mechanical pressure being exerted on the actuator or some other mechanical component. The sensor(s) may also be associated with an electrical component to assess the electrical component's condition. In other embodiments, the sensors may be associated with the mattress such that sleeping, resting, sitting, and other user conditions can be assessed. The information from the sensor lay may be fed back into a processor (e.g. within the electrical layer) for processing and response control. The response control may alter a condition of the adjustable bed, the mattress, an auxiliary system, or the like. The information from the sensor layer may also be processed and communicated to a remote control.

In an embodiment, the control layer 110 may coordinate the electronic requirements of the adjustable bed facility 102. The control layer 110 may interface with the sensor layer 108, the network layer 112, the remote control 118, the auxiliary systems 114, and the like. In an embodiment, the control layer 110 may receive control requests from a user for controlling the adjustable bed facility 102 functions by interfacing with the remote control 118. In an embodiment, the remote control 118 may communicate with the sensor layer 108 so that the latter may transmit the received requests to the control layer 110. In an embodiment, the control layer 110 may be combined with the adjustable bed facility 102, or it may be attached to the adjustable bed facility 102, or it may be a modular stand-alone device, or the like. In an embodiment, the control layer 110 and the sensor layer 108 may be individual devices or a combined device.

In an embodiment, the control layer 110 may also control functions of the adjustable bed facility 102 using a wired or wireless technology. In an embodiment, the wireless technology may include WIFI, BLUETOOTH, ultra-wideband (UWB), wireless USB (WUSB), IEEE 802.11, cellular, or the like. The various controlled functions may be able to communicate using the wireless technology, and may use an intermediate wireless receiver, a router, or the like to communicate with the control layer 110.

In an embodiment, the remote control 118 may be a user controlled device to provide control commands to the control layer 110 relating to certain functions of the adjustable bed facility 102. These functions may be adjustable bed facility section movement (e.g., up or down), vibration control, functions of modular devices, or the like. In an embodiment, the remote control 118 may communicate with the control box using wired communication, wireless communication, or the like. In an embodiment, the wireless communication may use a radio frequency (RF), infrared (IR), BLUETOOTH, WIFI network, or the like. If the remote communicates using a wireless technology, the communication may be with the sensor layer 108, and the sensor layer 108 may pass the command request to the control layer 110.

In embodiments, the remote control may include a cellular phone or smart phone, such as and without limitation an IPHONE, or the like. The remote control 118 may be used to direct any and all functions of the adjustable bed facility 102, for example by receiving user input, converting the input into control signals, and transmitting the control signals to the adjustable bed facility 102. Receiving user input may include receiving touch screen inputs, voice inputs, picture or video inputs, acceleration inputs (e.g., rotating the remote control 118 relative to the acceleration of gravity, shaking the remote control 118, and so on), magnetic inputs (e.g., orienting the remote control 118 relative to Earth's magnetic field), and so on. For example, an IPHONE app may be used to control any of the functions of the adjustable bed and/or associated devices.

In an embodiment, the network layer 112 may be used to connect the control layer 110 to a network connection. In an embodiment, the network connection may be a LAN, a WAN, an Internet, an intranet, peer-to-peer network, or the like. Using the network connection 112, the control layer 110 may be able to communicate with computer devices on the network. In an embodiment, the network layer 112 may facilitate wired or wireless connection. In an embodiment, the network layer 112 may be combined with the adjustable bed facility 102, or it may be attached to the network layer 112, or it may be a modular stand-alone device, or the like.

In an embodiment, the auxiliary systems 114 may provide additional functionality to the adjustable bed facility 102 or the user of the adjustable bed facility 102 that may include a plurality of functional devices, for example, entertainment system 114a, kitchen appliance 114b, vehicle control system 114c, light control system 114d, home control system 114e, child monitoring system, or the like. This additional functionality may be considered optional equipment that may be offered with the adjustable bed facility 102 or used in the environment associated with the adjustable bed facility 102. In an exemplary scenario, the user may be able to control the audio-visual system via the remote control 118. The user may control the volume of the audio-visual system of the entertainment system 114a using an interface provided on the remote control 118. The remote control 118 may send the signals to the sensor layer 108. The sensor layer 108 may transmit the signals to the control layer 110. The control layer 110 may generate the control signals and transmit to the audio-visual system. In another exemplary scenario, the user may be able to control the light control system 114d, for example, to turn the light on/off, and dim the light or the like. The control signals may be generated and transmitted to the light control system 114d. Similarly, the remote control 118 may provide the input to control the kitchen appliance 114b, the vehicle system 114c (e.g., a remote starter for the vehicle), or other auxiliary systems as shown in FIG. 1.

In an embodiment, the auxiliary systems 114 and the remote control 118 may have wired or wireless communication. In an embodiment, the wireless communication may be by radio frequency (RF), infrared (IR), BLUETOOTH, WIFI network, or the like.

A remote control may be configured to support more than one bed, such as to allow a parent who uses a remote controlled adjustable bed to also monitor and/or control a child's adjustable bed. Multi-bed remote monitoring and control may allow a parent to monitor status and activity associated with a child's bed even when the parent is in another room, such as a master bedroom while the child is in his/her own bedroom. In an environment with more than two adjustable beds, the remote may be paired with one or more of the beds to allow access to certain features, such as monitoring and control features on the remote for the paired beds. In an example, a parent may have an infant and a nine-year old each sleeping in separate rooms in an adjustable bed. The parent may pair a remote control (that may also be used by the parent to control a master bedroom adjustable bed) with the infant's bed for certain features and with the nine-year old child's bed for other features.

Figure 1B:
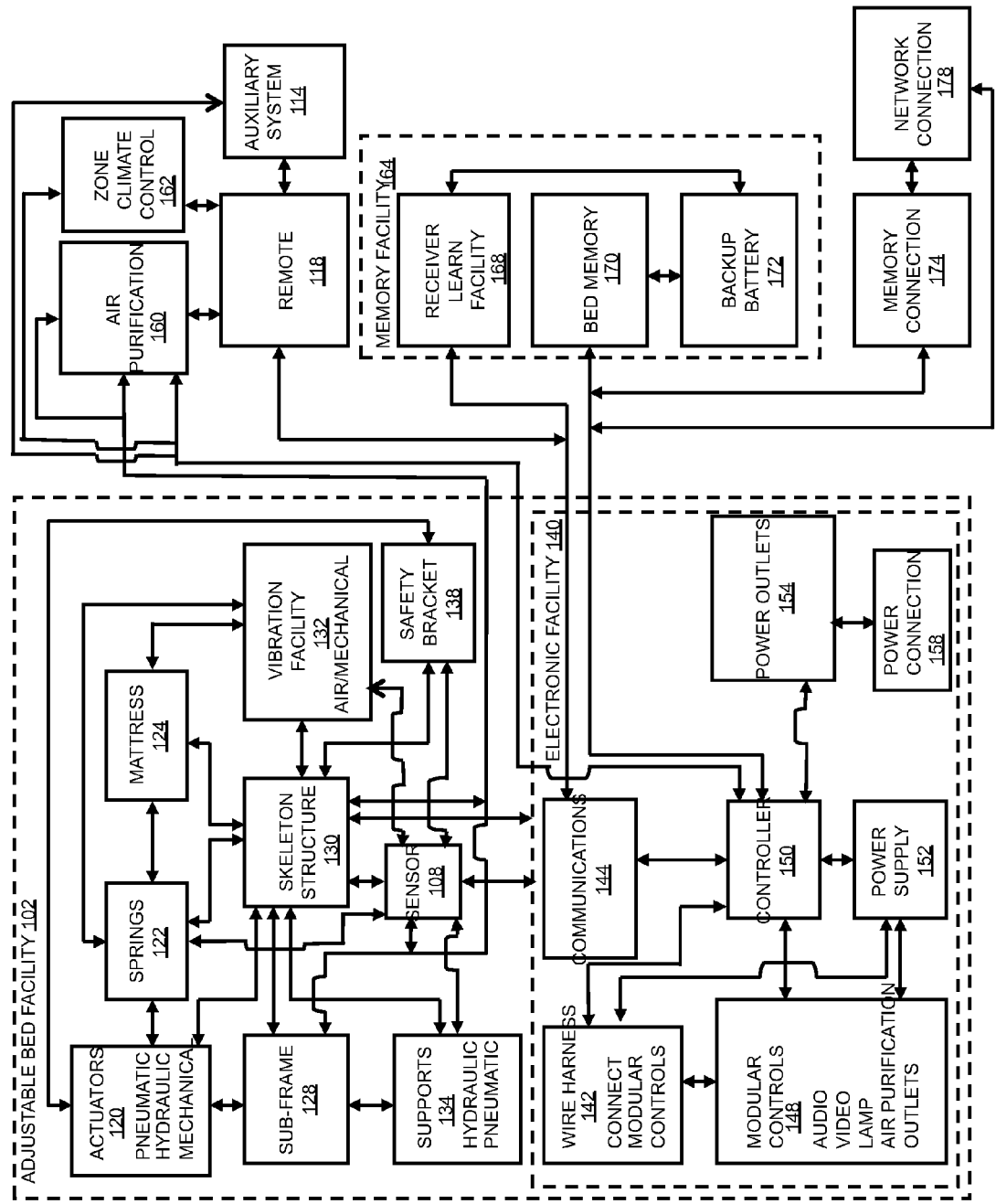
FIG. 1B shows a block diagram of an adjustable bed facility and associated components.

Now referring to FIG. 1B, a block diagram of the various components of the adjustable bed facility 102 is shown. In an embodiment, an adjustable bed facility 102 may be made up of a number of devices and facilities that may include a sensor 108, actuators 120, springs 122, mattresses 124, a sub-frame 128, a skeleton structure 130, vibration motors 132, supports 134, safety brackets 138, an electronic facility 140, an air purification facility 160, a zone climate control system 162, a remote control 118, a memory facility 164, a memory connection 174, a network connection 178, and the like. In an embodiment, the electronic facility 140 may include a wire harness 142, communications module 144, modular controls 148, a controller 150, power outlets 154, a power connection 158, and the like. In an embodiment, the memory facility 164 may include a receiver learn facility 168, bed memory 170, a backup battery 172, and the like. In an embodiment, the receiver learn facility 168, bed memory 170, and backup battery 172 may not be part of the memory facility 164, but may be combined into other facilities or devices, be stand-alone devices, or the like.

In an embodiment, the physical aspects of the adjustable bed facility 102 that provide support for the user may include the actuators 120, springs 122, mattresses 124, a sub-frame 128, a skeleton structure 130, vibration motors 132, supports 134, and safety brackets 138.

In an embodiment, the skeleton structure 130 may provide the central structure that the other physical aspects may interact with. In an embodiment, the skeleton structure 130 may provide direct support to the mattress 124, springs 122, and the like. In an embodiment, the skeleton structure 130 may be a lightweight frame structure that may provide both the strength and rigidity required to properly support the mattress 124 and springs 122. In embodiments, the skeleton structure 130 may use materials that include metal, plastic, wood, or the like; the materials may be used individually or in combination.

In an embodiment, springs 122 may be used with a mattress 124, instead of a mattress 124, or the like. In an embodiment, the springs 122 may be a standard bed spring system (e.g. coils within a wire framework), individual coil springs, individual foam springs, air springs, or the like. In an embodiment, the individual springs (e.g. coil, foam, or air) may be used to provide variable firmness to provide comfort to the user. For example, the springs 122 may be less firm or firmer in a local area to provide the user with the support that may be required for a body location that is experiencing discomfort (e.g. a hip, shoulder, back, neck). Springs that may have local firmnesses will be described in more detail below.

In an embodiment, the mattress 124 may include foam, feathers, springs 122, material, or the like. In an embodiment, the different materials may be used individually or in combination. The mattress may be intended to provide the user with a firmness that provides for the comfort requirements of the user.

In an embodiment, the mattress 124 may be an air mattress 124. In an embodiment, the air mattress 124 may be constructed using a single chamber, a plurality of chambers, a plurality of individual chambers, a combination of chamber shapes, or the like. In an embodiment, the air mattress 124 may be inflated to various pressures that may provide the user with the desired comfort level. In an embodiment, there may be separate air mattresses 124 for each of the adjustable bed facility 102 sections. For example, there may be separate air mattresses 124 for the head, torso, and foot sections of the adjustable bed facility 102. In an embodiment, the inflation pressure of the individual air mattresses 124 may be different from each other depending on user settings.

In an embodiment, the adjustable bed facility 102 sections may each contain individual air mattresses 124. For example, the head, torso, and foot sections may each have individual air mattresses that may be individually controlled for air pressures and therefore firmness. In an embodiment, the user may be able to control the firmness of the individual air mattresses 124 using a remote control 118. In an embodiment, the remote control 118 may have indicators for each of the firmness adjustable air mattresses 124. For example, the remote control 118 may have keys for increasing or decreasing the pressures of the individual air mattresses. Using the remote control 118, the user may be able to adjust the firmness of the adjustable bed facility sections.

In an embodiment, the air mattress 124 may use a common air supply source facility as an air actuator 120. In an embodiment, a controller 150 may control both the air mattress 124 and air actuator 120. The controller 150 may provide controlling commands to both the air mattress 124 and air actuators 120.

In an embodiment, the skeleton structure 130 may have structural members that support the mattress 124 and springs 122 and may also provide support and connections for the actuators 120, sub-frame 128, supports 134, vibrator motors 118, safety bracket 138, and the like. In an embodiment, the structural members may be positioned on the peripheral edges of the mattress 124 and springs 122 to provide overall support and rigidity to the mattress 124 and springs 122 and may form the base of the individual adjustable bed facility 102 sections. Additionally, there may other structural members as support, cross pieces, or the like that may provide additional support to the mattress 124 and springs 122 as may be required. A person knowledgeable in the art may understand that the frame structure may have many different construction configurations to provide support and rigidity to the mattress 124 and springs 122.

In an embodiment, the skeleton structure 130 may form the base of the adjustable bed facility 102 sections that may be moved relative to each other to provide the various bed positions required by the user. The adjustable bed facility 102 may include more than one section; a section may be fixed or may be adjustable. For example, the typical adjustable bed may have adjustable sections for the head, leg, and foot while the torso section may remain fixed and horizontal. There may be different combinations of movable and fixed sections with one or all of the sections being movable. In an embodiment, the sections may include the skeleton structure 130, mattress 124, springs 122, and the like, and may individually be small mattress structures of the entire adjustable bed facility 102 mattress.

In an embodiment, the adjustable bed sections may be connected together using hinges or like devices that allow a freedom of motion between two adjacent adjustable bed facility 102 sections. In an embodiment, one section of the adjustable bed may remain fixed, such as the torso section, and act as the foundation for the other movable sections to be positions. In an embodiment, any or none of the sections may be a fixed foundation section in the adjustable bed facility 102. In embodiments, there may be more than one adjustable bed facility 102 configuration depending on the requirements of a user, cost requirements, medical needs, or the like. For example, there may be a configuration where only the head section is adjustable to provide the user with the ability to have an elevated upper body position. This configuration may be a single purpose bed but may also provide the user with a less expensive adjustable bed facility 102 that meets the user's needs. One skilled in the art may understand that there may be many different adjustable bed facility configurations containing fixed and moveable sections.

This moveable section may also provide support and connection members for the components that may be used In an embodiment, the skeleton structure 130, as part of each adjustable bed facility 102 section, may also provide support and connection members for the components that may be used to move the various adjustable bed facility 102 sections. There may be skeleton structure 130 members that provide connection support to the actuators 120, supports 134, safety brackets 138, vibration motors 132, and the like. These support and connection members may have any shape or configuration required to provide the support and connections needed by the various other components. For example, in addition to the skeleton structure 130 that is used to provide support to the mattress 124 and springs 122 there may be at least one cross member that may provide a connection to the actuator 120 and safety bracket 138.

In an embodiment, the skeleton structure 130 and the sub-frame 128 may interface with each other; the sub-frame 128 may provide structural support and a rigid foundation base to the skeleton structure 130. In an embodiment, the sub-frame 130 may be the rigid structure that is in contact to the floor and may provide a base for any fixed adjustable bed facility 102 sections and an interface for any movable adjustable bed facility 102 sections. In an embodiment, the sub-frame 128 legs may be connected to the sub-frame 128 using a threaded stud into threads of the sub-frame 128. In an embodiment, to prevent the threaded stud from pulling out of the legs during tightening, the head of the threaded stud may be fixed between two or more layers of leg material. This construction may trap the threaded stud head to prevent it from moving away from the end of the leg and may also prevent the threaded stud head from being pulled through the end of the leg during the tightening of the leg to the sub-frame. In addition, the two or more layers of leg material may provide for added strength to the sub-frame 128 legs to prevent distortion at the sub-frame 128 and leg interface. In an example of a fixed torso section, the sub-frame 128 may provide a base to solidly connect the torso section to provide a fixed non-moving section. The other moveable sections may be moveably connected to the fixed torso section and additionally supported by the sub-frame 128 using a moveable interface connection.

In an embodiment, the sub-frame 128 may have structural members that may run along the length of the adjustable bed facility 102, run along the width of the adjustable bed facility 102, run diagonally across the adjustable bed facility 102, or other orientation in relation to the adjustable bed facility 102 that may be required for support or connection to components.

In an embodiment, the skeleton structure 130 may be used as an RF antenna for receiving communication from the remote control 118. In embodiment, the entire skeleton structure 130 may be used as an antenna; a portion of the skeleton structure 130 may be used as an antenna, or the like.

In one embodiment, the sub-frame 128 may provide solid connections for any fixed section and skeleton structure 130 by rigidly connecting the skeleton structure 130 directly to the sub-frame 128. In this manner, any fixed section and skeleton structure 130 may be rigidly connected to the sub-frame 128, and through the sub-frame 128, rigidly connected to the floor.

In another embodiment, the sub-frame 128 may provide an interface for the fixed adjustable bed facility 102 section and skeleton structure 130 where the fixed section may be able to move or slide in relation to the sub-frame 128. By providing a non-rigid interface connection between the sub-frame 128 and the skeleton structure 130, the fixed adjustable bed facility 102 section may have freedom of motion but still may be supported by the sub-frame in a solid foundation manner. For example, the fixed adjustable bed facility 102 section may have wheels that run in a track, groove, "C" channel, or the like of the sub-frame 128 and may be able to move horizontally during the motion of one or more of the movable adjustable bed facility 102 sections. In an embodiment, the horizontal freedom of motion may provide for a "wall hugger" feature where, as the head section is adjusted up or down, the fixed torso section may move, along with the head section, horizontally forward and away from an adjacent wall to maintain a fixed distance between the head section and the wall, therefore "hugging" the wall. It may be understood by one skilled in the art that the moveable interface between the skeleton structure 130 and sub-frame 128 may be any type of interface that may allow freedom of motion between the sub-frame 128 and skeleton structure 130.

In an embodiment, the sub-frame 128 may provide an interface for the fixed adjustable bed facility 102 section and skeleton structure 130 where the fixed section may be able to move or slide in relation to the sub-frame 128.

In an embodiment, the sub-frame 128 may provide an interface for the fixed adjustable bed facility 102 section and the skeleton structure 130 where the fixed section may move away or towards in relation to the sub-frame 128.

In an embodiment, any adjustable sections may have two connections: a first connection provided by a hinge type connection and a second connection provided by the connection with the actuator 120 and safety bracket 138 that provide the force to rotate the adjustable bed facility 102 section up or down. In an embodiment, the hinge type connection between the skeleton structure 130 of a first section and a second section may provide the point of rotation for the section motion. In an embodiment, the adjustable bed facility 102 may contain more than one section and any or all of the sections may be connected by a hinge type connection.

In an embodiment, there may be a support gusset for connection between the actuator 120 and the adjustable bed facility 102 section. In embodiments, the gusset may be an I beam, a T beam, an L beam, a box beam, or any other beam design that may provide the strength to lift the combined weight of the adjustable bed facility 102 section and the user without bending. In an embodiment, to resist bending forces at the connections to the actuator 120 and the adjustable bed facility 102 section, the ends of the gusset may be reinforced. In embodiments, the reinforcement may be an additional bracket added to the ends of the gusset, such as a U bracket or any other bracket shape, to provide for increased material thickness and strength of the gusset ends. The thickness of the additional bracket may be determined by the amount of force and torque that may need to be resisted during the adjustable bed facility 102 section movements.

With the adjustable bed facility 102 sections interconnected by using hinge type connections, there may be at least one actuator 120 that may provide a connection between a fixed adjustable bed facility 102 section and a moveable section. In an embodiment, the hinge connection between the adjustable bed facility 102 sections may be a pivot point bracket that may include additional strengthening to resist bending forces. Similar to the gusset described above, the pivot point connections may have additional reinforcement, such as a U bracket or any other shaped bracket, to provide for increased material thickness and strength to resist bending forces. The thickness of the additional bracket may be determined by the amount of force and torque that may need to be resisted during movement of the adjustable bed facility 102 section. In an embodiment, the actuation 120 connection may be between two of the skeleton structures 114. For example, a first end of the actuator 120 may be connected to the fixed torso section of the adjustable bed facility 102 and a second end of the actuator 120 may be connected to the section that is to be moved (e.g. head, leg, or foot sections). In an embodiment, the actuator 120 may use electric motors and mechanical gears, pneumatic pressure, hydraulic pressure, pneumatic spring, air spring, hydraulic spring or the like to provide the force to extend and retract the actuator 120. The action of extending and retracting the actuator 120 may move the various movable bed sections up or down. By the actuator 120 pushing against the section, the section may rotate upward around the pivot point provided by the hinge type connection. In the same manner, by the actuator 120 pulling against the section, the section may rotate downwards and around the pivot point provided by the hinge type connection. In an embodiment, there may be at least one actuator 120 for every moveable adjustable bed facility 102 section.

In an embodiment, the combination of actuator 120, safety bracket 138, and supports 134 may provide a safety feature to prevent an object that may be under the adjustable bed facility 102 from being damaged, impinged, crushed, or the like during the decent of the adjustable bed facility 102 section. During the downward motion of one adjustable bed facility 102 sections, the section may come in contact with an object that is under the adjustable bed facility 102. If the actuator 120 is allowed continuing to pull the section in the downward direction, the object may be crushed under the force the actuator 120 may apply. In an embodiment, the safety bracket 138 may have a slot that may provide time to determine that there is an object under the section that is moving downward.

In an embodiment, the slot may have a first side that is on the opposite side of the slot from the actuator 120 and a second side that is on the same side as the actuator 120. In an embodiment, the slot that is between the first side and the second side may be of any length. In an embodiment, the actuator may push against the first side to move the adjustable bed facility 102 section in an upward direction. In an embodiment, during the downward motion of the section, the actuator 120 may move at the same speed as the adjustable bed facility 102 section and therefore the actuator connection to the safety bracket 138 may remain within the safety bracket 138 slot without contacting either the first or second sides of the slot. In an embodiment, the section may move in the downward direction under the weight of the section without the actuator 120 pulling on the second side of the safety bracket 138.

In an embodiment, the adjustable bed facility 102 section downward speeds may be further controlled by supports 134 that may provide resistance to the section motion to control the rate of decent. In an embodiment, the support 134 may be a pressurized device using pneumatic pressure, hydraulic pressure, or the like to provide a resistive force to slow the decent of the adjustable bed facility 102 section. In an embodiment, the supports may provide enough resistance to control the rate of decent of the section as the actuator 120 is retracted.

In an embodiment, as the actuator 120 retracts, the adjustable bed facility 102 section, with the aid of the support 134, may descend at the same rate as the as the actuator 120 is retracting. By matching the rates of the actuator 120 retraction and the adjustable bed facility 102 section descending, the actuator 120 connection within the safety bracket 138 slot may remain within the slot area and not contact either the first or second side of the slot. In an embodiment, as the section descends, if an object is encountered, the adjustable bed facility 102 sections may stop its decent and the actuator 120 connection will move within the safety bracket 138 slot without pulling the section downward. In an embodiment, the amount of time that the actuator 120 connection is moving within the safety bracket 138 slot while the adjustable bed facility 102 section is stopped may provide time to the user to realize that an object has been contacted and to stop the downward motion of the section.

In an embodiment, an additional safety feature may be the addition of a shut off sensor, shut off switch, or the like on the first side of the safety bracket 138 slot to stop the retraction of the actuator 120 if the actuator 120 connection comes in contact with the first side of the slot. In this manner, if the actuator 120 connection with the safety bracket 138 slots reaches the first side of the slot, the actuator 120 retraction may be stopped and the adjustable bed facility 102 section will not be forcibly pulled down into the object that may be under the section. In an embodiment, there may be an indication to the user that the actuator 120 connection has come in contact with the first side of the slot and the adjustable bed facility 102 sections downward motion has been stopped. In an embodiment, the indication may be an audio indication, a visual indication, a motion indication (e.g. vibration), or the like to indicate to the user that the motion has been stopped and there may be an obstruction with the adjustable bed facility 102 section.

In an embodiment, an additional safety feature may be the dual motion of one or more moveable section of the adjustable bed facility 102 to stop the side-to-side movement of a user. In such an arrangement, when the head portion of the individual moves, the head section may be restricted from movement by nestling in a groove or the like, around the head portion of the user. In a similar manner, the fixed torso portion of the user may also move side-to-side along with the head portion. The fixed torso section of the adjustable bed facility 102 may form a groove around the moving torso portion of the individual, allowing the user to rest its torso portion inside the formed groove. Also, the foot section may be moved to form a groove around the foot portion of the user.

In an embodiment, there may be at least one vibration motor 132 that may provide vibration and massage functions to the adjustable bed facility 102 sections and mattresses 124. In an embodiment, there may be vibration motors 132 associated with any of the adjustable bed facility 102 sections. In an embodiment, there may be more than one vibration motor 132 for each adjustable bed facility 102 section that may have vibration motors 132. In an embodiment, using the remote control 118, the user may be able to control the vibration mode of the various vibration motors 132; the mode may include the vibration setting for a particular bed section, the vibration frequency of at least one of the vibration motors, stopping the vibration of at least one of the vibration motors, or the like. The user may vary the vibration frequency for the particular bed section that has been positioned for a long duration. For example, the user may require different vibration frequencies for a body location that is experiencing discomfort (e.g. a hip, shoulder, back, neck). Such an arrangement may allow the user to vary the vibration frequency settings of various sections of the adjustable bed facility 102 in case of inflexibility, pain or the like of any body portion.

In an embodiment, the vibration motors 118 may be operated independently or in combination. In an embodiment, the user may select a vibration mode on the remote control 118 and the controller 150 may use a software application to control the various vibration motors 118 to the user's request.

In an embodiment, the vibration motor 132 may be an electric/mechanical device, a pneumatic device, a hydraulic device, or the like. The mechanical device may use an electric motor to rotate an offset mass to create a vibration; the vibration motor may be controlled for vibration frequency and amplitude by the speed of rotation of the electric motor. Referring to FIG. 5A and FIG. 5B, an embodiment of a vibration motor 132 is shown within an opening of a adjustable bed facility 102 support lateral surface 508. The adjustable bed facility 102 section may have a lateral surface 508 and the lateral surface 508 may include an opening in which the vibration motor 132 may be located; the vibration motor 132 may fit within the opening such that the vibration motor 132 may not contact the lateral surface 508.

In an embodiment, the vibration motor 132 may be secured to the adjustable bed facility 102 section using at least one bracket 504. In an embodiment, when more than one bracket 504 is used, at least one of the brackets 504 may be separable and removable. In an embodiment, the at least one bracket 504 may be shaped to secure the vibration motor 132 within the section opening such as a straight bracket, a U shaped bracket, an L shaped bracket, or the like; in FIG. 5A and FIG. 5B the bracket 504 is shown as a straight bracket 504. In an embodiment, the removal of one of the brackets 504 may facilitate securing the vibration motor 132 to the bed section, facilitating the servicing of the vibration motor 132, or the like. The bracket 504 may be positioned such that at least one portion of the bracket 504 is within the opening of the lateral surface 508 and may also be positioned such that the bracket 504 may overlap the vibration motor 132 flange. The bracket 504 may provide support to the vibration motor 132 flange along a majority of the perimeter of the mattress support opening. The bracket 504 may be coupled to the mattress support 508 using a removable coupling. Removing the bracket 504 may facilitate removing and servicing the vibration motor 132. The vibration motor 132 flange may extend beyond the perimeter of the opening of the mattress support 508 and the resilient material 502 may provide positional support for the motor so that the flange may impart vibration to the mattress without contacting the mattress support. The resilient material 502 may provide mechanical insulation between the flange and the perimeter of the opening in the mattress support 508. The resilient material 502 disposed between the flange and the lateral support 508 surface of the bracket 504 may further provide positional support for the vibration motor 132 housing.

The bracket 504 may be constructed using material such as plastic, metal, or the like, and may be constructed using the materials individually or in combination. In an embodiment, there may be a resilient material 502 associated with the brackets 504, the resilient material may provide for dampening the vibration between the vibration motor 132 and the adjustable bed facility 102, may contact the vibration motor 132 to secure the vibration motor 132 to the bed section, may provide for dampening of vibration to the adjustable bed facility 102 and hold the vibration motor 132 in place, or the like. The resilient material 502 may include latex foam, polyurethane foam, polypropylene foam, polyethylene foam, or the like and may be used individually or in combination.

In an embodiment, either of the pneumatic or hydraulic devices may act as a vibration motor 132 increasing and decreasing the pressure within a cylinder, bladder, or the like at certain frequencies to provide the vibration required by the user. In an embodiment, a device to provide the pressure frequency may be part of the vibration motor 132, a separate device from the vibration motor 132, or the like.

In an embodiment, the vibration facility 132 may be connected to the skeleton structure 130, the mattress 124, the lateral surface 508, or the like where the vibration may be imparted into the adjustable bed facility 102 mattress 124 as desired by the user. In an embodiment, the vibration motor 132 flange may provide surface area that may impart a vibration into the mattress 124. In another embodiment, the vibration motor 132 may be in proximity to a vibration distribution facility (not shown) that may aid in the propagation of vibration energy to the adjustable bed facility 102 sections. In an embodiment, the vibration motor 132 may be operatively connected to the vibration distribution facility, may be in contact with the vibration distribution facility, may not be in contact with the vibration distribution facility, or the like. The vibration distribution facility may be constructed using materials such as plastic, rubber, metal, or the like and may be constructed using these materials individually or in combination. In an embodiment, the vibration distribution facility may provide for a more uniform distribution of the vibration characteristics of the vibration motor 132 and may have a size and shape relative to the size and shape of the adjustable bed facility 102 section.

Referring again to FIG. 1, in an embodiment, the adjustable bed facility 102 may have an electronic facility 140 that may contain components that provide control of the physical aspects of the adjustable bed facility 102 (e.g. actuator, vibration motors), interface with the remote control 118, interface with networks, interface with bed memory 170, control electronic devices of the adjustable bed facility 102, and the like.

In an embodiment, the adjustable bed facility 102 may have the sensor 108 that may be combined with the adjustable bed facility 102; or it may be attached to the adjustable bed facility 102; or it may be a modular, stand-alone facility; or the like. In an embodiment, the sensor 108 may be connected to the electronic facility 140 and may interface with the controller 150.

In an embodiment, the controller 150 may coordinate the electronic requirements of the electronic facility 140. In an embodiment, the controller 150 may interface with the communications module 144, remote control 118, air purification facility 160, power outlets 154, power supply 152, power connection 158, modular controls 148, wire harness 142, and the like. In an embodiment, the controller 150, communications module 144, and power supply 152 may be mounted directly to the skeleton structure 130.

In an embodiment, the controller 150 may receive its command request from the user requesting adjustable bed facility 102 functions using the remote control 118. In an embodiment, the remote may communicate to the communications module 144 and the receiver may transmit the received user command request to the controller 150. Therefore, communications module 144 may be bi-directional. In an embodiment, the communications module 144 and controller 150 may be individual devices or may be combined into a single device.

In an embodiment, the remote control 118 and communications module 144 may have wired or wireless communication. In an embodiment, the wireless communication may be by radio frequency (RF), infrared (IR), BLUETOOTH, WIFI network, or the like. In an embodiment, the communications module 144 may receive the user commands from the remote control 118 and transmit the same command to the controller 150; the communications module 144 may not provide any interpretation of the remote control 118 commands. In an embodiment, the remote control 118 and communications module 144 may be communication matched by the use of a code key. The code key may be any indicator that may be interpreted by the remote control 118 and communications module 144 that commands may be received and executed between the remote control 118 and communications module 144. In embodiments, the code key may be a number, a word, a serial number, a bed identification, a remote identification, a user identification, or any other identification known to both the remote control 118 and communications module 144, all an indication that communications should be received. The code key may be transmitted as the beginning of the communication, the end of the communication, as part of the communication or the like. Additional aspects of the communications module 144 between the adjustable bed facility 102 and the remote control 118 are described hereinafter with reference to FIG. 28 et seq.

In an embodiment, the skeleton structure 130 may be used as an RF antenna for receiving communication from the remote control 118 to the communications module 144. In embodiment, the entire skeleton structure 130 may be used as an antenna; a portion of the skeleton structure 130 may be used as an antenna, or the like.

In an embodiment, the controller 150 may also control the functions of the adjustable bed facility 102 using a wireless technology in place of, or in coordination with, the wire harness 142. In an embodiment, the wireless technology may include BLUETOOTH, ultra-wideband (UWB), wireless USB (WUSB), WIFI, IEEE 802.11, cellular, or the like. The various controlled functions (e.g. actuators 120 or external devices) may be able to communicate using the wireless technology, may use an intermediate wireless receiver, router, or the like to communicate with the controller 150.

In an embodiment, the controller 150 wireless communication may use a wireless network protocol that may include peer-to-peer communication, master/slave communication, as a hub, as a server, or the like. In an embodiment, the wireless communication may be used to control more than one adjustable bed facility. For example, the user may be able to control his/her adjustable bed facility and may additionally be able to control another adjustable bed that may be within the range of the communication method.

In an embodiment, the cellular communication may utilize a cell phone, a smart phone, or the like to provide the communication method with the controller 150, modular controls 148, or the like. In an embodiment, the controller 150 may be a programmable control controller (PLC) and may be configured from programmable logic circuits. In an embodiment, the user may use a menu on the cell phone for adjustable bed functions that may be controlled by the cell phone. For example, the cell phone technology may be able to control the bed position and vibration characteristics of the adjustable bed facility 102 and therefore the cell phone menu may present the user with options for controlling the bed position and vibration.

In an embodiment, if the communication between the remote control 118 and communications module 144 is wireless, the receiver learn facility 168 may be used to establish the communication between them. In an embodiment, a learn protocol between the remote control 118 and communications module 144 may be user initiated by pressing a button on the receiver learn facility 168, powering up the receiver learn facility 168, bringing the receiver learn facility 168 within a certain proximity of the communications module 144, indicating on the remote control 118 to begin the learn protocol, or the like. In an embodiment, the learn protocol may be fully automatic, semi-automatic with user intervention, manual, or the like. In an embodiment, a user may select a channel, frequency, or the like during learn protocol or after the learn protocol. The changing of the channel, frequency, or the like may prevent two different remote control 118 and communications module 144 combinations from interfering with other wireless communication devices. In an embodiment, each time the learn protocol is executed, a new unique communication link may be established; there may be a plurality of unique communication links available for each remote control 118 and communications module 144 combination.

In an embodiment, the remote control 118 may be a user controlled device to provide control commands to the controller 150 to command certain functions of the adjustable bed facility 102. In an embodiment, the certain functions may be adjustable bed facility section movement (e.g. up or down), vibration control, modular controlled 132 devices, or the like. In an embodiment, the remote control 118 may communicate with the control box using wired communication, wireless communication, or the like. In an embodiment, the wireless communication may use a radio frequency (RF), infrared (IR), BLUETOOTH, WIFI network, or the like. If the remote communicates using a wireless technology, the communication may be with the communications module 144 and the communications module 144 may pass the command request to the controller 150.

In embodiments, the communications module 144 of one bed may be adapted to communicate with the communications module 144 of another bed, such as by a wireless communication protocol including a radio frequency (RF), infrared (IR), BLUETOOTH, WIFI network, or the like. For example, a king size adjustable bed may comprise two side-by-side twin size adjustable beds. Each of the twin size beds may have a communications module 144. A single remote control may be used to adjust each of the twin size beds simultaneously, and in some embodiments, each of the twin size beds may be separately adjustable with individual remote controls. In any event, the communications modules 144 may be adapted to signal to the other bed. The signal may be related to synchronizing a motion of the beds, implementing a safety feature, communicating an error, communicating a software update, communicating a preference, communicating a setting, communicating a report, and the like. In some embodiments, upon receiving the signal from the other bed, the signaled bed may interpret the signal as a command.

In an embodiment, the inputs of the remote control 118 may be organized into groups of common function control; the remote control 118 groups may be arranged in a circular orientation. As shown in FIG. 3, the remote control 118 may include more than one group 302 and may include at least one positioning control group and one vibration control group. In one embodiment, the remote control 118 groups 302 may be organized into a circular pattern where the circular pattern may provide for inputs that control increasing a function, decreasing a function, storing a function, global command functions 304, or the like. For example, a circular group 302 may be divided up into a number of segments to control certain functions of the adjustable bed facility 102. FIG. 3 shows four sections for each of the circular groups 302, but it should be understood that there may be any number of sections to provide the required adjustable bed facility 102 control.

In one example, one of the circular groups 302 may be used to control movements of the adjustable bed facility 102 sections. The movement circular group 302 may have inputs for moving the head section up/down, moving the foot section up/down, inputs for storing a user preferred positions to the controller 150, or the like. Additionally, there may be a global command input 304 that may provide for commanding more than one adjustable bed facility 102 function using a single input such as commanding the adjustable bed facility 102 to go to a flat position. For example, the user may be able to select the flat button and the adjustable bed facility 102 may move all of the adjustable sections to the flat position.

A vibration circular group 302 may have inputs for controlling the vibration of the head section up/down, controlling the foot section vibration up/down, inputs for storing a user preferred vibration characteristics to the controller 150, or the like. Additionally, there may be a global command input 304 that may provide for commanding more than one adjustable bed facility 102 vibration characteristic using a single input such as commanding the adjustable bed facility 102 to stop all vibration. For example, the user may be able to select the stop vibration input and the adjustable bed facility 102 may stop all of the adjustable sections from vibrating. In an embodiment, the user may select the all stop global 304 input to stop the adjustable bed facility 102 vibration before selecting a different vibration characteristic for one of the adjustable bed facility 102 sections.

In an embodiment, the user may be able to determine the control functions that the global command 304 may control. For example, the user may be able to input a command sequence to indicate the global command that should be applied to the global command 304 input. In an embodiment, the global command may be stored in the adjustable bed facility 102 memory 164 for later recall. In an embodiment, after the global command 304 has been stored, the user may select the global command 304 input for the command sequence execution.

The function of the remote control 118 has been described with controlling adjustable bed facility 102 movement and vibration, but it should be understood that the remote may have control inputs for any function of the adjustable bed facility 102. Additionally, the control inputs have been described as having a circular pattern, but it should be understood that other embodiments of the control input organization may be used for controlling the function of the adjustable bed facility 102.

The remote control 118 may include a timer that has a user defined setting that may allow the user to determine when the remote control 118 communicates a control command to the adjustable bed facility. For example, the user may be able to set a timer on the remote control 118 to indicate a time when the adjustable bed facility 102 is to go to a flat position. The user may use this function in the evening where the user may want to read for a half hour and then go to sleep, the user could set the timer for a half hour and the adjustable bed facility 102 may go to the flat position after the half hour. In another embodiment, the timer may be a clock where the user may be able to set a time when the adjustable bed facility 102 is to complete a certain function. In an embodiment, the user may be able to indicate the command that the remote control 118 is to transmit to the adjustable bed facility 102 when the timer or clock setting indication has been reached.

In an embodiment, the remote control 118 may be able to directly control the settings of external power outlets associated with the adjustable bed facility 102. The power outlet may be an RF controlled power outlet and the remote control 118 may be able to transmit an RF command directly to the RF power outlet. In an embodiment, the power outlet may include settings of at least on, off, a percentage of power, or the like. The power outlet control power setting may be controlled by a hardware setting, a software setting, or the like. The power outlet may be an AC powered power outlet or a DC powered power outlet.

The remote control 118 may include a timer that has a user defined setting that may allow the user to determine when the remote control 118 communicates a control command to the RF power outlet. For example, the user may be able to set a timer on the remote control 118 to indicate a time when the RF power outlet is to turn on or off. For example, the user may use this function in the evening where the user may want to read for a half hour and then go to sleep, the user could set the timer for a half hour to turn off a power outlet that controls a light fixture, after the half hour the remote control 118 may command the RF power outlet to turn off and therefore turn the light fixture off. In another embodiment, the timer may be a clock where the user may be able to set a time when the RF power outlet may turn on or off. In an embodiment, the user may be able to indicate the command, such as on or off, that the remote control 118 is to transmit to the RF power outlet when the timer or clock setting indication has been reached.

In an embodiment, the user may indicate adjustable bed facility 102 functions using the remote control 118 by pressing a button, touching a screen, entering a code, speaking a command, or the like. In an embodiment, the controller 150, using the communications module 144, may receive and interpret the command provided by the remote control 118. The remote may control devices with commands that may include on, off, high power, medium power, low power, volume, play, fast forward, rewind, skip, modular device to control, or the like. For example, the remote control 118 may transmit a command to move the head section up and the controller 150 may command the actuator 120 to extend a certain amount in response to the command. In another example, the remote control 118 may command that a modular control 148 connected lamp be turned off. The controller 150 may command the controller 150 to turn off the lamp.

Referring again to FIG. 1, in an embodiment, the controller 150 may use the bed memory 170 to store adjustable bed facility 102 settings, application software, demonstration software, and the like. In an embodiment, the user may determine that certain adjustable bed locations are preferred and should be saved for future recall. The controller 150 may save the user preferred settings in the bed memory 170 in order to recall the preferred settings at the use request. In an embodiment, the controller 150 may also store non-user requested information to the bed memory 170 as needed for the control of the various adjustable bed facility 102 components. For example, when the user requests an adjustable bed facility 102 sections to move, the controller 150 may store the last position into bed memory 170 to be used as a last position recall, an undo command, the last settings for the entire adjustable bed facility 102 component at shutdown, or the like.

In an embodiment, the controller 150 application software may be stored in the bed memory 170. In an embodiment, the software may be downloaded to the controller 150, may be run from the bed memory 170, or the like. In an embodiment, the application software may be an interrupt type application, a polling type application, or the like for sensing what command the user may have indicated on the remote control 118. For example, in an interrupt application, each command requested by the remote control 118 may send an interrupt code to the controller 150. The controller 150 may then request from the application software the command sequence that is associated with the received interrupt. In another example, the polling application may continually poll the remote control 118 for requested user commands and when a user command is detected, then request the command sequences for the requested user command.

In another embodiment, the controller 150 may use a programmable logic controller (PLC) or the like to store application programs for control of the adjustable bed facility components. The controller 150 may include programmable logic circuits for facilitating application program store and execution. In an embodiment, the PLC may be part of the controller 150, part of a bed memory 170, in a separate control box, or the like. In an embodiment, the controller 150 may include a microcomputer, a microprocessor, volatile memory, non-volatile memory, IO connection to components, or the like. The controller 150 may provide an interface to permit software application updates to the controller memory; controller memory may be over written. In an embodiment, this may provide a method and system for providing software application upgrades to the adjustable bed facility 102.

In an embodiment, the controller may have a connection to an external interface that may allow updates to be downloaded to the controller 150. The connection may be a serial connection, a USB connection, a USB device, a parallel connection, a wireless connection, a bed memory 170, or the like. The capability to download information to the controller 150 may allow for controller updates including software updates, remote control 118 interface updates, memory updates, or the like. For example, if the user was supplied with a new or upgraded remote control 118, the user may also be supplied with updated software for the controller 150. The user may be able to connect the device containing the new software to the external interface and download the new software to the controller 150.

In an embodiment, the controller 150 may have a connection interface with the modular controls 148 to provide the user with control over other devices that may be connected to the adjustable bed facility 102. The controller 150 may receive commands from the remote control 118 for the modular controls 148 and may pass the command through to the modular control 148, may interpret the remote control 118 command and command the modular control 148, or the like.

In an embodiment, the controller 150 may interface with a modular control 148 that is associated with external power outlets. In this embodiment, the user may be able to control the setting of the external power outlet by selecting a setting on the remote control 118. The setting on the remote control 118 may be received by the communications module 144 and/or the PLC (e.g. within the controller 150) to set the power outlet setting. For example, the user may be able to turn on the external power outlet by selecting an external outlet on input on the remote. This may result in the external outlet power being turned on to power an attached device such as a lamp.

In an embodiment, the bed memory 170 may be part of the controller 150, external from the controller 150, a combination of internal and external memory from the controller 150, or the like.

In an embodiment, the bed memory 170 may be separate from the controller 150. In an embodiment, the bed memory 170 may be removable memory, the bed memory 170 may be moved from a first adjustable bed facility 102 to a second bed facility 102 to move user settings from the first adjustable bed facility 102 to the second bed facility 102. For example, a user in a care facility may be moved from a first adjustable bed facility 102 to a second adjustable bed facility 102 but the user may have already determined and saved at least one preferred setting to the bed memory 170. The bed memory 170 may be removed from the first adjustable bed facility 102 and moved to the second adjustable bed facility 102 with the user and therefore the user may keep the same preferred adjustable bed 102 settings.

In this manner, the bed memory 170 may be considered portable memory. In an embodiment, the removable bed memory 170 may be flash memory, programmable logic circuits, secure digital (SD) memory, mini SD memory, Compact Flash type I memory, Compact Flash type II memory, Memory Stick, Multimedia Card, xD Picture card, Smartmedia, eXtreme Digital, Microdrive, or the like.

In an embodiment, the bed memory 170 may be part of the remote control 118. As part of the communication between the remote control 118, communications module 144, and controller 150 memory information may be exchanged between the remote control 118 and controller 150. For example, the user may indicate that a certain adjustable bed facility 102 position should be maintained for future recall. The controller 150 may receive the save position request from the remote control 118 and transmit the position information back to the remote control 118 for storage within the bed storage 154. In a like manner, when the user requests the recall of a previously saved position, the controller 150 may request the position information from the remote control 118 to the bed memory 170.

In an embodiment, if the remote control 118 is wireless, the remote control 118 may contain both a transmitter and receiver, or a transceiver, to transmit and receive information with the controller 150. In an embodiment, the remote control 118 may communicate with the communications module 144 using a connection key. The connection key may be a code that indicates that a certain remote is associated with a certain adjustable bed facility 102. When the remote control 118 transmits information to the receiver, the remote may first send a key code to indicate that the remote control 118 is associated with the adjustable bed facility 102. If the key code matches the key that the communications module 144 is listening for, the communications module 144 may receive the command from the remote.

Figure 2:
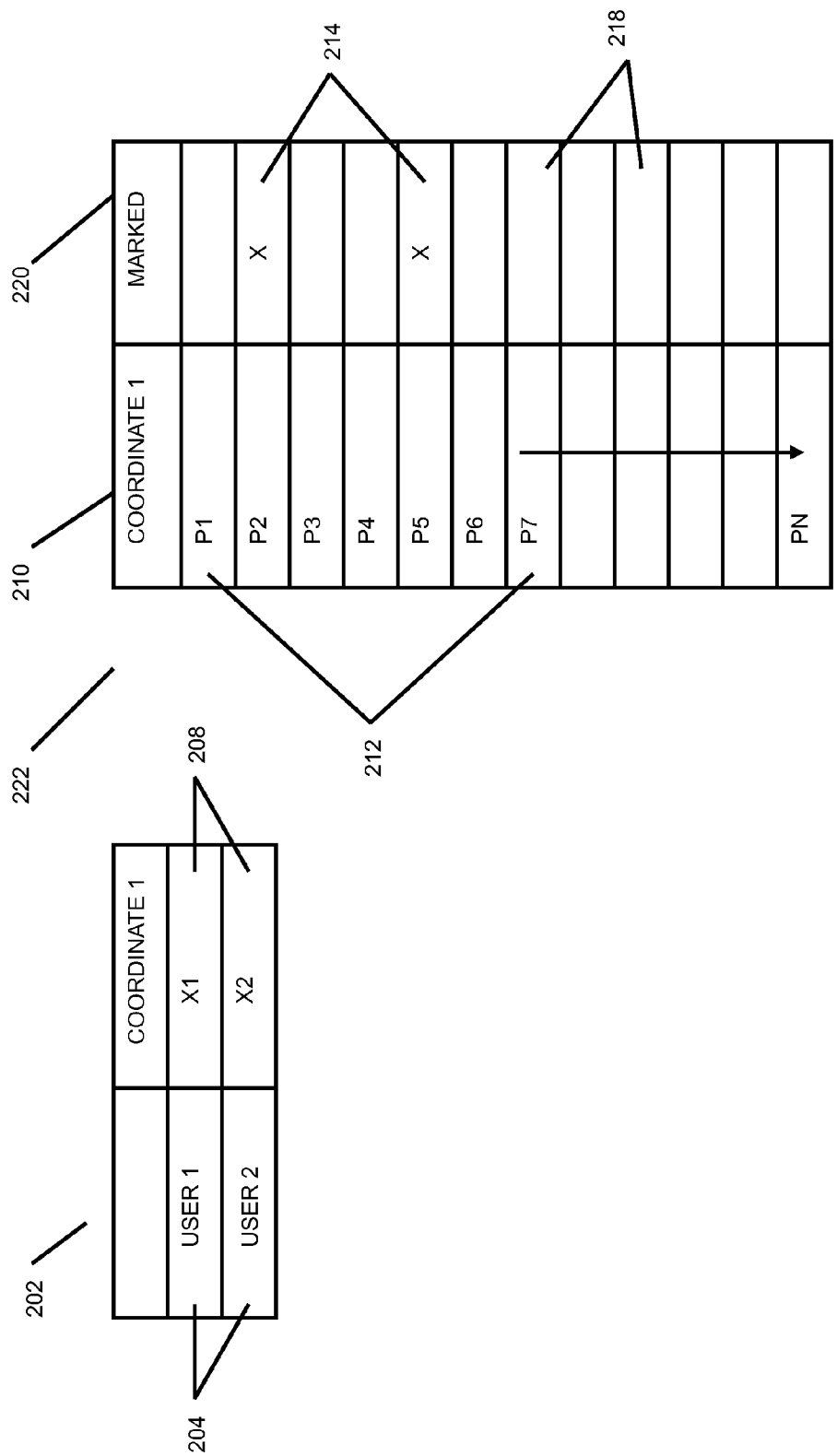
FIG. 2 shows an embodiment of two methods of maintaining user memory for storing user preferred adjustable bed positions.

In an embodiment, the bed memory 170 may maintain the position information for the user preferred positions of the adjustable bed facility 102 sections. In an embodiment, the bed memory 170 may be implemented as programmable logic circuits, a logic circuit (LC), or the like. FIG. 2 shows an embodiment of two methods of maintaining the user preferred positions in memory. In an embodiment, a first method may be to have discreet memory table 202 for each preferred user bed position 204. There may be the same number of preferred bed positions 204 and memory locations 208 as indicators on the user remote control 118. For example, the remote may have two buttons for the user to set the preferred positions that may be used for later recall; the two buttons may be associated with two discreet memory locations 208. In an embodiment, each time the user indicates a new preferred position for a button on the remote control 118 the memory location 208 may be over written with the new position information. In an embodiment, this method may only allow the user to set one user preferred position for every button on the remote control 118.

In an embodiment, a second method of memory storage for user preferred adjustable bed positions may be a table 222 that may have a plurality of possible positions 212 the user may select. In an embodiment, as shown, the possible positions 212 may be P1 through Pn. In an embodiment, the possible positions 212 may be a plurality of values that may define the range of available positions for the adjustable bed facility 12; the plurality of values may be a set of values that define the range of available positions for one or more adjustable bed facility 102 functions. For example, the available positions 212 may be a set of increments of section positions that may include a set of actuator 120 positions, a set of actuator 120 activation times, bed section rotation angles, or the like. The set of increments may be determined from a base value for the section. For example, the increments may start at zero from the flat position for the adjustable bed facility 102 sections. In an embodiment, the user may be able to select the increment set to be used as possible positions 212 for the section. For example, the user may be able to select the type of graduations by selecting from a set of possible graduation methods such as distance, angle of rotation, actuation time, or the like.

In FIG. 2, the table 222 is shown with an increment column 210 and an indication column 220. In an embodiment, the table 222 may have a plurality of columns 220 to store position information for any of the adjustable aspects of the adjustable bed facility 102. For example, there may be an indication column 220 for the head section angle, the foot angle section, the vibration characteristics for the various vibration motors of the adjustable bed facility 102, or the like. In another embodiment, the adjustable aspects of the adjustable bed facility 102 may be represented by a plurality of individual tables 210 for storing indication information for each of the individual adjustable attributes for the adjustable bed facility 102. The individual tables 210 may be substantially the same as the table 222 shown in FIG. 2 where there may be one column 210 for increments 212 and another column 220 for indication information (214 and 218). For example, there may be individual tables 210 for the head section angle, foot section angle, vibration motor characteristics, or the like. In an embodiment, the controller 150 may be able to access the adjustable bed facility 102 settings by accessing large tables 210 that contain many columns, small tables 210 that contain a few columns, a combination of large and small tables 210, or the like.

In an embodiment, the controller 150 may store the tables 210 within the controller 150 memory for accessing the settings of the adjustable bed facility 102. In another embodiment, the table 222 may be stored in memory outside of the controller 150 and the controller 150 may access the table 222 through an interface connection. The table 222 increment column 210 may represent a plurality of available positions associated with adjustable bed facility functions. In an embodiment, the increment values may be a measurement scale (e.g. inches or angle), may be the number of rotations of the actuator, the vibration frequency of the vibration motor, or other increment scale. In response to a user input, the indication column 220 may be marked with the indication 214 to represent the position intended by the user. When the user makes a request to save a position, the controller 150 may search the increment column 210 to determine which of the plurality of increments 212 represents the current position value of the adjustable bed facility 102 section. Once the current position value increment 212 within the table 222 is determined, an indication 214 may be stored to the indication column 220 associated to the current position value increment 212. In an embodiment, the indication 214 may be any character that may represent a position being selected such as a letter, a number, special character, or the like. In embodiments, the indication column 220 may include all indications, no indications, one indication, more than one indication, or the like to indicate the user's intended position. The storing of the indication association of the current position value with the user selected position may include adding a store indication to the table 222 entry representing the current position value, removing the current position value from the table 222 of values, removing a plurality of the table 222 values where the removal does not include removing the current position value, adding a store indication to every table 222 entry except a table 222 entry representing the current position value, or the like.

In an embodiment, when a user indicates on the remote control 118 that a position is to be saved in the table 222, the controller 150 may select the increment value 212 from within the increment column 210 set of values that represents the current position of the adjustable bed facility 102. The controller 150 may store an indication 214 associated with the increment value 212; the stored indication associated with the current position value may be a recall value that may be recalled at a later time to reposition the adjustable bed facility 102.

In an embodiment, in response to the user requesting to return to a recall value, the controller 150 may scan the table 222 indication column 220 for an indication 214 that may represent the user's recall value. Upon locating the recall value indication 214, the controller 150 may command the adjustable bed function to the recall value indicated 214 location, position, vibration, or the like.

In an embodiment, the indication column 220 of the table 222 may initially contain indications 214 in all to the available discrete locations 212. As a user indicates that current position value is the position to be stored within the table 222, the indication 214 for the current position value may be removed from the table 222. This may result in one increment location 212 being empty of an indication. In this case, when a user requests to return to the recall position, the controller 150 may scan the table 222 indication column 220 for the empty increment location 212. Once the empty increment location is found, the controller 150 may command the adjustable bed function to the recall position, vibration, or other adjustable bed facility 102 function. In an embodiment, if the user stores a different current position value, the empty discrete location 212 may be filled with an indication and the new indication associated to the current position value may have the indication 214 removed. In an embodiment, the user may be able to clear the stored position by indicating a clear command and all of the increment locations 212 may be filled with indications 214.

In an embodiment, the available increment locations 212 in the indication column 220 of the table 222 may initially contain no indications 214 so that the indication column 220 may be empty. As a user indicates that a current position value is the position to be stored within the table 222, the indication 214 associated to the current position value may be added to the table 222. This may result in one increment location 212 having an indication. In this case, when a user requests to return to recall value position, the controller 150 may scan the table 222 indication column 220 for the increment location 212 containing the indication 214 associated with the recall value. Once the increment location is found, the controller 150 may command the adjustable bed function to the recall value position, position, vibration, or other adjustable bed facility 102 function. In an embodiment, if the user stores a different position, the increment location 212 indication 214 may be removed and the new current position value may have the indication 214 added. In an embodiment, the user may be able to clear the stored position by indicating a clear command and all of the discrete locations 212 may have the indication 214 removed.

In an embodiment, when a user indicates a current position value is to be indicated in the table 222, the indication may represent the user's preferred adjustable bed facility 102 position. In an embodiment, the user's indicated current position value may be rounded to the closest table 222 increment location 214. For example, if the user selects a current position value that is between two increment positions on the table 222, an algorithm may be used to determine which of the increment positions are to be indicated in the indication column 220.

Embodiments of the present invention involve setting a recall bed position in response to a user making a storage selection. The user's storage selection may send a command to the adjustable bed facility's 102 controller (e.g. the PLC) indicating that the user would like the present position of the adjustable bed facility 102 stored such that the user can later have the adjustable bed facility 102 return to the stored position. The user may use a user interface (e.g. the remote control 118) and make such a storage selection once the adjustable bed facility 102 is in a desired position. As described herein elsewhere, a plurality of position values that define a range of available positions for the adjustable bed facility 102 may be stored in memory accessible by the adjustable bed facility's controller 150. The available positions may be stored in a table 222 or other structure for example. Once the user initiates such a storage request, the controller may receive the request to save the current adjustable bed facility 102 position as a user selected position. The controller may then make a determination of which of the plurality of position values represent the current position of the adjustable bed facility 102 to provide a current position value. In determining which of the plurality of position values represents the current position, the controller may use an algorithm to decide which of the plurality of values best represents the current adjustable bed facility 102 positions. For example, the actual adjustable bed facility 102 position may match one of the values and the algorithm may then select the matching value as the one that best represents the current position. In another situation, the actual adjustable bed facility 102 position may not match any of the plurality of values. In this case, an algorithm may be used to determine which value best represents the position of the adjustable bed facility 102. The algorithm may run an averaging calculation, interpolation calculation or other form of prediction algorithm to select between two positions representing positions on either side of the actual adjustable bed facility 102 position, for example. Once the controller has made the determination as to which value represents the current adjustable bed facility 102 position, the controller may then store an association of the current position value with the user-selected position (e.g. as described elsewhere herein).

The embodiment of unmarking 218 preferred positions will be used in the following illustrations, but it should be understood that marking a current position value may also be used as a method of indicating a preferred position 212.

In an embodiment, the user may indicate the current position value by indicating a set position on the remote control 118; this indication may result in all of the possible increment locations 212 having an indication 214 except for the one increment the user has selected which may be non-marked 218. For example, if the user selected the P3 position 212 as a preferred position, all of the positions 212 may receive a mark 214 except the one position P3, which may receive a non-mark 218.

In an embodiment, the positioning recall position logic of the adjustable bed may seek possible positions 212 that do not have a mark 218 when determining what user positions to select.

In an embodiment, the user may be able to set more than one increment position 212 in the table 222 for a single button on the remote control 118. For example, the user may be able to press a button on the remote control 118 in a certain way to set a non-mark 218 at different preferred positions 212. In another example, when the user presses a button on the remote control 118, the current position value may be unmarked 218 as a preferred position and an algorithm may be executed to unmark 218 other preferred positions 212 at certain increments from the user selected position. In one example of the algorithm, every third position may be selected to be unmarked 218 as a preferred position 212. The additional non-markings 218 may be by actuation time, section rotation angle, or the like. A person skilled in the art may understand that there may be any number of different methods of unmarking more than one position 212 using a single button on the remote control 118.

In an embodiment, with user preferred positions 212 unmarked 218 on the table 222, the user may indicate on the remote control 118 to recall the user preferred position 212. In an embodiment, there may be an algorithm to search the table 222 for an unmarked 218 user preferred position 212 to position the bed to the recall value. Once the preferred position 212 is determined, the command logic may command the actuator or actuators to move the adjustable bed sections into the preferred position 212 recall value. In an embodiment, there may be more than one preferred position 212 unmarked 218 on the table 222. In this case, the algorithm may seek the first unmarked 218 position 212 and move the adjustable bed section to that position. In an embodiment, if this is not the user desired position, the user may indicate again on the remote to recall a preferred position and the algorithm may seek the next unmarked 218 position 212. A person skilled in the art may understand that there may be a number of different methods of recalling a plurality of marked 214 or unmarked 218 positions 212 from the table 222.

Referring again to FIG. 1B, in an embodiment, the removable bed memory 170 may be used to upgrade the adjustable bed facility 102 memory and software. For example, if new controller 150 software was developed to provide better control over one of the adjustable bed facility 102 components, the software may be saved to a new replaceable memory that may replace the existing replaceable memory. In this manner, the software of the adjustable bed facility 102 could be upgraded just by providing the user with a new replaceable memory.

In an embodiment, the removable memory may be used to provide a sales enterprise with the adjustable bed facility 102 demonstration software where the enterprise may be able to indicate at least one of a plurality of demonstrations for a user. For example, the user may be interested in how the adjustable bed facility 102 sections may be adjusted and the enterprise may select a demonstration to shows all the section motion available. In an embodiment, before an adjustable bed facility 102 is shipped to a user, the enterprise may remove the demonstration removable memory and replace it with a standard adjustable bed facility 102 bed memory 170.

In an embodiment, the memory connection 174 may be any connection type that provides a connection between the bed memory 170, controller 150, and the like. In an embodiment, the memory connection 174 may be a wired or wireless connection. The wired connection may be a USB connection, a serial connection, parallel connection, or the like. The wireless connection may be by radio frequency (RF), infrared (IR), BLUETOOTH, WIFI network, or the like. In an embodiment, the memory connection 174 may be in a location that is easy for the user to access the bed memory 170, may be attached to the memory facility 164, may be attached to the controller 150, or the like. In an embodiment, the easy access memory connection may be on the side of the adjustable bed facility 102, on a rail of the adjustable bed facility 102, under the adjustable bed facility 102, or the like.

In an embodiment, the controller 150 may also access a network using a network connection 178. In an embodiment, the network may be a LAN, WAN, Internet, intranet, peer-to-peer, or other network with computer devices that the controller 150 may communicate with. In an embodiment, the network connection 178 may be a wired or wireless connection.

In an embodiment, using the network connection 178, the controller 150 may be able to communicate with the network to periodically check for application software updates. In an embodiment, if an application software update is located, the controller 150 may send the user an email, instant messenger message, phone message, phone call, cell phone message, cell phone call, fax, pager message, or the like to indicate that software updates are available. The user, using the device that received the notice of software update, may send a reply to the control box that the software upgrade should be downloaded, should not be downloaded, or the like.

In an embodiment, an adjustable bed facility 102 enterprises, an adjustable bed facility 102 manufacturers, an adjustable bed facility 102 service enterprises, or the like may send the controller 150 software updates using the network connection 178. In an embodiment, an adjustable bed facility 102 enterprise, an adjustable bed facility 102 manufacturer, an adjustable bed facility 102 service enterprise, or the like may notify the user of available software upgrades for the adjustable bed facility 102 by email, instant messenger message, phone message, phone call, cell phone message, cell phone call, fax, pager message, or the like. The user, using the device that received the notice of software upgrade, may send a reply to the adjustable bed facility 102 enterprise, the adjustable bed facility 102 manufacturer, the adjustable bed facility 102 service enterprise, or the like that the software upgrade should be downloaded, should not be downloaded, or the like.

In an embodiment, an adjustable bed facility 102 enterprise, an adjustable bed facility 102 manufacturer, an adjustable bed facility 102 service enterprise, or the like may notify the user of one or more identified problems or errors in the adjustable bed facility 102 by email, instant messenger message, phone message, phone call, cell phone message, cell phone call, fax, pager message, or the like. The user, using the device that received the notice of the identified problems or errors, may trouble shoot the problem, may not trouble shoot the problem or the like.

In an embodiment, the user may access the network connection 162 with the user's own computer device.

In an embodiment, the remote control 118 and controller 150 may be able to control other devices that may be connected to modular controls 148. In an embodiment, the modular controls 148 may be similar to the control box by interpreting commands to control a device, but may be unique to the device that is connected to it. In an embodiment, the modular controls 148 may control audio equipment, video equipment, lamps, air purification facilities, outlets, and the like. For example, the modular control 148 may be connected to audio equipment and may contain the command sequences to control the audio equipment based on commands that may be received from the remote control 118. It may be obvious to someone in the art that any of the devices that are connected to modular controls 148 may be controlled in the same manner.

In an embodiment, the user may indicate a function to be accessed for a certain device connected to a modular control 148, the controller 150 may receive the request from the remote control 118 and pass the command onto the appropriate modular control 148. In an embodiment, the remote control 118 may have modular control 148 device functions that the user may select to control a modular control 148 device. For example, the remote control 118 may have functions such as play, fast-forward, rewind, skip, pause, and the like for an audio device connected to the modular control 148.

In an embodiment, the modular controls 148 may be connected to the controller 150 and power supply 152 using a wire harness 142. The wire harness 142 may contain power and data connections for all of the possible connection locations for the modular controls 148. For example, if there are six locations on the adjustable bed facility 102 for attaching modular controls 148, the wire harness 142 may have six sets of power and data connections available.

In another embodiment, the wire harness may provide only power to the modular controls 148 and the communication between the modular controls 148 and controller 150 may be wireless that may include radio frequency (RF), infrared (IR), BLUETOOTH, and the like.

In an embodiment, using the remote control 118, the controller 150 may be able to control power outlets 142 to which external devices may be connected; the power outlets 142 may be associated with the adjustable bed facility 102, remote from the adjustable bed facility 102, or the like. In an embodiment, the controller 150 may communicate with the power outlet 142 using wired or wireless communications. In this embodiment, the power outlets 154 may receive power directly from a household outlet, fuse box, circuit box, or the like but the function of the power outlets 154 (e.g. on or off) may be controlled by the controller 150. For example, an external lamp may be connected to the power outlets 154, there may be a selectable control on the remote control 118 for the user to turn the power outlet 154 on and off and therefore to turn the lamp on and off. In an embodiment, the power outlets 154 may include a control circuit that is able to control if the power outlet 154 receives power from the household current. In an embodiment, there may be more than one power outlet 154 controlled by the controller 150 and there may be a selection for each of the power outlets 154 on the remote control 118.

In an embodiment, the power outlets 154 may be directly controlled by the remote control 118 using radio frequency (RF). The remote control and power outlets 154 may be RF capable for communication within the adjustable bed facility 102. The remote control 118 may be able to directly control the power outlets 152 to turn the power outlets 154 on and off using RF without interfacing with the controller 150.

In an embodiment, the controller 150 may be able to control an external air purification 160 facility; the air purification 160 facility may be directly controlled by the control box using a wired or wireless connection. In an embodiment, the wireless connection may be radio frequency (RF), infrared (IR), BLUETOOTH, or the like. In an embodiment, the air purification facility 160 may be any type of device or facility that may be capable of improving that air environment in the area of the adjustable bed facility 102. In an embodiment, the air purification facility 160 may be an absorbent type (e.g. carbon), electro-static, HEPA filter, or the like. In an embodiment, absorbent materials may be used in a filter, in the adjustable bed facility 102, in the mattress 124, or the like to absorbed odor, dust, contaminants, or the like from the air environment around the bed, within the bed, or the like. In an embodiment, electro-static or iconic air filters may use negative ions to attract dust, contaminants, and the like from the air. In an embodiment, electro-static materials (e.g. tourmaline) may be used in a filter, in the adjustable bed facility 102, in the mattress 124, or the like to absorbed odor, dust, contaminants, or the like from the air environment around the bed, within the bed, or the like. In an embodiment, HEPA filters are composed of a mat of randomly arranged fibers that are designed to trap at least 99.97% of dust, pollen, mold, bacteria, and any airborne particles with a size of 0.3 micrometers (μm) at 85 liters per minute (Lpm). The HEPA filter may be used in a device, facility, or the like for filtering the air in the area of the adjustable bed facility 102.

In an embodiment, the air purification facility 160 may be part of the adjustable bed facility 102, a freestanding device or facility, or the like. In an embodiment, if the air purification facility 160 is part of the adjustable bed facility 102 the air purification facility 160 may be attached to any part of the adjustable bed facility 102 such as the mattress 124, sub-frame 128, skeleton structure 130, or the like. In an embodiment, the air purification facility 160 that is attached to the adjustable bed facility 102 may be controlled direct control of the air purification facility 160 device, control using the remote control 118, or the like.

In an embodiment, the air purification facility 160 may be a free standing device that may be plugged into a adjustable bed facility 102 power outlet 154 and therefore may be controlled with the remote control 118 controlling the on/off condition of the power outlet 154.

In an embodiment, the air purification facility 160 may be a freestanding device that may be connected to an adjustable bed facility 102 modular control 148. The modular control may provide power (AC or DC), control communication, and the like to the air purification facility 160. In an embodiment, the user may be able to control the air purification facility 160 using the remote control 118 to control the modular controls 148.

In an embodiment, the controller 150 may be able to control an external zone climate control system 162; the zone climate control system 162 may be directly controlled by the control box using a wired or wireless connection. In an embodiment, the wireless connection may be radio frequency (RF), infrared (IR), BLUETOOTH, or the like. In an embodiment, the zone climate control system 162 may be any type of device or facility that may be capable of controlling the environment within one or more zones of the adjustable bed facility 102. In an embodiment, the zone may be a single room or may be two different sides of the adjustable bed facility 102. In an embodiment, two different users may sleep in different environments or two users may sleep in a single environment controlled by the zone climate control system 162. In an embodiment, the user may request the provision of different environments in the different sides of the adjustable bed facility 102. Accordingly, the zone climate control system 162 may decide on which side the zone vents are to be closed and which side they are to be kept open. Additionally, the zone climate control system 162 may heat or cool the zones of the bed, circulate air to heat or cool a zone by mixing air with air from another zone, circulate air to reduce excessive conditioning of a zone, or circulate air to maintain air quality. In an embodiment, the zone climate control system 162 may determine and develop parameters such as airflow, thermal capacity, heating or cooling requirements, and the like by measurement and/or derivation.

In an embodiment, the zone climate control system 162 may be a free standing device that may be plugged into an adjustable bed facility 102 power outlet 140 and therefore may be controlled with the remote control 118 controlling the on/off condition of the power outlet 140.

In an embodiment, the zone climate control system 162 may be a freestanding device that may be connected to an adjustable bed facility 102 modular control 148. The modular control 148 may provide power (AC or DC), control communication, and the like to the zone climate control system 162. In an embodiment, the user may be able to control the zone climate control system 162 using the remote control 118 to control the modular controls 148.

In an embodiment, an adjustable bed facility 102 may be any bed that is capable of adjusting at least one aspect of the bed such as a head section, a foot section, a leg section, a torso section, or the like. In an embodiment, the adjustment may include moving the sections up, down, higher, lower, longer, shorter, and the like. In an embodiment, the section adjustments may also include vibration, massage, and the like. In an embodiment, the adjustable bed facility 102 may include components such as actuators 120, springs 122, a mattress 124, a sub-frame 128, a skeleton structure 130, vibration motors 132, supports 134, safety brackets 138, wire harness 142, communications module 144, modular controls 148, controller 150, power outlets 154, power supply 152, power connection 158, air purification facility 160, zone climate control system 162, remote control 118, receiver learn facility 168, bed memory 170, backup battery 172, memory connection 174, network connection 178, and the like.

Applications

In an embodiment, the adjustable bed facility 102 sections may be adjustable by a user, a care giver, a medical person, or the like to provide a comfortable position, a medically required position, a working position, a resting position, or the like. For example, a medical position may be required to elevate a user's legs to aid in the reduction of swelling and therefore the leg or foot sections may be elevated. In another example, a user with a back condition may need to rest his or her back and may still wish to work; the user may be able to position the adjustable bed facility 102 to provide a comfortable back position that may allow the user to work on papers or a computer device. The user may be able to tilt the adjustable bed facility 102 in the shape of a chair in order to rest his or her back and may sit on the horizontal section of the adjustable bed facility 102. Such an arrangement may be used for watching TV, eating, reading or the like, thereby providing the user a comfortable position.

In an embodiment, the adjustable bed facility 102 may be used in a home, a hospital, a long-term care facility, a hotel, or the like. The adjustable bed facility 102 may be used by users that may have limited mobility, are restricted to bed rest, require a non-flat sleeping position, and the like.

In an embodiment, actuators 120 may be used to move the adjustable bed facility 102 sections. The actuator 120 may typically be a cylinder device where a first component, under a force, is extendable from second component that may result in the action of moving an object. In an embodiment, there may be more than one actuator 120 per adjustable bed facility 102. There may be an actuator 120 to move any of the adjustable bed facility 102 sections or other aspects of the adjustable bed facility 102. For example, there may be individual actuators for the head section, leg section, foot section, torso section, or the like. In an embodiment, a single actuator may be used to move more than one adjustable bed facility 102 section. For example, one actuator may be used to move the leg and foot sections; the leg and foot sections may be connected by a mechanical structure that may control the orientation of the leg and foot sections during movement. In an embodiment, the actuators 120 may be connected between the adjustable bed facility 102 section to be moved and the sub-frame 128, skeleton structure 114, or the like.

In an embodiment, the actuator 120 may have different driving means to extend and retract the actuator 120 such as an electric motor, pneumatic pressure, hydraulic pressure, or the like.

In an embodiment, the electric motor driven actuator 120 may use a DC or AC motor and gear assembly to extend and retract the actuator 120.

In an embodiment, the pneumatic pressure actuator 120 may use an air source to extend and retract the actuator 120. The air source may be part of the pneumatic actuator 120, may be a separate device, or the like. In an embodiment, the separate air source device may be part of the adjustable bed facility 102 or may be external to the adjustable bed facility 102.

In an embodiment, the hydraulic pressure actuator 120 may use a fluid source to extend and retract the actuator 120.

The fluid source may be part of the hydraulic actuator 120, may be a separate device, or the like. In an embodiment, the separate fluid source device may be part of the adjustable bed facility 102 or may be external to the adjustable bed facility 102.

In an embodiment, springs 122 may be used with a mattress 124, instead of a mattress 124, or the like. In an embodiment, the springs may be a standard bed spring system (e.g. coils within a wire framework), individual coil springs, individual foam springs, air springs, or the like. In an embodiment, the individual springs (e.g. coil, foam, or air) may be used to provide variable firmness to provide comfort to the user. For example, the springs 122 may be less firm or firmer in a local area to provide the user with the support that may be required for a body location that is experiencing discomfort (e.g. a hip, shoulder, back, neck).

In an embodiment, the mattress 124 may include foam, feathers, springs 122, material, or the like. In an embodiment, the different materials may be used individually or in combination. The mattress may be intended to provide the user with a firmness that provides for the comfort requirements of the user.

In an embodiment, the mattress 124 may be an air mattress. In an embodiment, the air mattress may be constructed using a single chamber, a plurality of chambers, a plurality of individual chambers, a combination of chamber shapes, or the like. In an embodiment, the air mattress 124 may be inflated to various pressures that may provide the user with the desired comfort level. In an embodiment, there may be separate air mattresses 124 for each of the adjustable bed facility 102 sections. For example, there may be separate air mattresses 124 for the head, torso, and foot sections of the adjustable bed facility 102. In an embodiment, the inflation pressure of the individual air mattresses 124 may be different from each other depending on user settings.

In another embodiment of an air mattress 124 with individual chambers, local firmness control may provide local firmness comfort to a user to provide comfort. For example, a user may be recovering from surgery and may require the air mattress 124 to be fewer firms in a certain area, the user may be able to indicate the area to be less firm and the individual chamber pressures may be adjusted to provide the less firm area. Additionally, while a local area may be provided with less firm pressures, the remainder of the mattress 124 may have a consistent firmness pressure.

In an embodiment, the sub-frame 128 may be a structural support frame in contact with the floor and may include the floor legs, connections for the actuators 120, connections for the supports 134, support for the skeleton structure 130, and the like. In an embodiment, the sub-frame 128 materials may include wood, metal, plastic, and the like. In an embodiment, the sub-frame 128 may provide a support interface to the skeleton structure 130 and may support the freedom of motion for the skeleton structure 114. For example, the sub-frame 128 may include an interface such as a track, surface, groove, slot, or the like in which the skeleton structure 130 may interface and use as a guide while providing motion support for the various adjustable bed facility 102 sections. In an embodiment, the sub-frame 128 interface may be a "C" channel in which the skeleton structure 130 may have interfacing wheels to move within the "C" channel during the adjustable bed facility 102 section movements.

In an embodiment, the sub-frame 128 may be substantially the same shape as the adjustable bed facility 102 and may have structural members along the length and width of the sub-frame 128. In an embodiment, the structural members may be assembled in any configuration that meets the requirements of supporting the adjustable bed facility 102 and the various devices such as the actuators 120, supports 134, skeleton structure 128, and the like.

In an embodiment, the skeleton structure 130 may be a mechanical structure that may provide support to the springs 122, provide support to the mattress 124, interface with the sub-frame 128, provide a connection to the actuators 120, provide a connection to the supports 134, support the vibration motors 132, and the like. In an embodiment, there may be more than one skeleton structure 130 within the adjustable bed facility 102; there may be a skeleton structure 130 for each adjustable bed facility 102 section. For example, there may be a skeleton structure 130 for the head section, foot section, leg section, torso section, and the like.

In an embodiment, the skeleton structure 130 may be a frame type structure to support at least one mattress 124, provide connectivity between more than one mattress 124, contain a hinge mechanism to allow the motion of a first mattress 124 in relation to a second mattress 124, and the like. The frame structure may be substantially the same shape as the mattress 124 that the skeleton structure 130 is supporting and may have individual structure members at the peripheral edges of the mattress 124 in addition to other individual structural members that may be required for support of mechanical connections, support of the mattress 124, or the like. In an embodiment, the skeleton structure 130 may include materials such as metal, wood, plastic, and the like. The skeleton structure 130 materials may be used individually or in combination.

In an embodiment, the skeleton structure 130 may have an interface facility such as wheels, slides, skids, rails, pivot points, and the like that may interface with the sub-frame 128 support interface. The skeleton structure 130 interface facility may provide for smooth interaction with the sub-frame 128 support interface when the skeleton structure 130 is in motion as a result of actuation from the actuators 120.

In an embodiment, a vibration facility 132 may provide vibration input to the adjustable bed facility 102 sections such as the head section, foot section, leg section, torso section, and the like; there may be vibration facilities in any or all of the adjustable bed facility 102 sections. In an embodiment, the vibration facilities 132 may be operated independently, at the same time, at alternate times, in coordination, or the like. For example, the vibration facilities 132 in the head section and foot section may be operated at the same time to provide a full body massage or the vibration frequencies may operate at alternating times to provide a wave effect of the vibration moving from the head to foot of the adjustable bed facility 102. In another example, the different vibration facilities 132 may be used in concert where the vibration facilities 132 may be vibrated in sequences to create a massaging effect. It may be understood by one knowledgeable in the art that different effects may be created with more than one vibration facility 132.

In an embodiment, using the remote control 118, the user may be able to control the vibration mode of the various vibration motors 132; the mode may include the vibration setting for a particular bed section, the vibration frequency of at least one of the vibration motors 132, stopping the vibration of at least one of the vibration motors, or the like. The remote control 118 may provide vibration motor 132 control information to the adjustable bed facility 102 controller 150 for control of the vibration characteristics of the adjustable bed facility 102. In an embodiment, the remote control 118 may include user inputs that include at least one of head vibration increase, head vibration decrease, foot vibration increase, foot vibration decrease, user preferred vibration settings, vibration stop, or the like.

In an embodiment, the vibration motor 132 may be capable of a plurality of vibration frequencies. For example, the vibration motor 132 may be able to operate on frequencies such as high, medium, low, settings 1-10, or the like. In an embodiment, a first vibration frequency may be stopped before a second vibration frequency is started. In embodiments, the stopping between the first vibration and the second vibration may be automatic and controlled by the logic within the controller 150, may be manually indicated by the user using the remote control 118, or the like. As an example of manual input, the vibration motor 132 may be operating on a medium frequency and the user may provide a stop vibration input on the remote control 118 to stop the first vibration motor 132 vibration before pressing the low vibration frequency input.

Referring to FIG. 5A and FIG. 5B, an embodiment of a vibration motor 132 is shown within an opening of an adjustable bed facility 102 support lateral surface 508. The adjustable bed facility 102 section may have a lateral surface 508 and the lateral surface 508 may include an opening in which the vibration motor 132 may be located; the vibration motor 132 may fit within the opening such that the vibration motor 132 may not contact the lateral surface 508. In an embodiment, the vibration motor 132 may be secured to the adjustable bed facility 102 section using at least one bracket 504. In an embodiment, when more than one bracket 504 is used, at least one of the brackets 504 may be separable and removable. In an embodiment, the at least one bracket 504 may be shaped to secure the vibration motor 132 within the section opening such as a straight bracket, a U shaped bracket, an L shaped bracket, or the like; in FIG. 5A and FIG. 5B the bracket 504 is shown as a straight bracket 504. In an embodiment, the removal of one of the brackets 504 may facilitate securing the vibration motor 132 to the bed section, facilitating the servicing of the vibration motor 132, or the like. The bracket 504 may be positioned such that at least one portion of the bracket 504 is within the opening of the lateral surface 508 and may also be positioned such that the bracket 504 may overlap the vibration motor 132 flange. The vibration motor 132 flange may extend beyond the perimeter of the opening of the mattress support and the resilient material 502 may provide positional support for the vibration motor 132 so that the flange imparts vibration to the mattress 124 without contacting the mattress support. The at least one bracket 504 may be coupled to the mattress support 508 using a removable coupling. Removing the at least one bracket may facilitate removing and servicing the motor. The resilient material 502 may provide mechanical insulation between the flange and the perimeter of the opening in the mattress support 508. The resilient material 502 disposed between the flange and the lateral support 508 surface of the at least one bracket 504 may further provide positional support for the vibration motor 132 housing. The bracket 504 may be constructed using material such as plastic, metal, or the like and may be constructed using the materials individually or in combination. In an embodiment, there may be a resilient material 502 associated with the brackets 504, the resilient material may provide for dampening the vibration between the vibration motor 132 and the adjustable bed facility 102, may contact the vibration motor 132 to secure the vibration motor 132 to the bed section, may provide for dampening of vibration to the adjustable bed facility 102 and hold the vibration motor 132 in place, or the like. The resilient material 502 may include latex foam, polyurethane foam, polypropylene foam, polyethylene foam, or the like and may be used individually or in combination.

In an embodiment, the vibration facility 132 may be connected to the skeleton structure 114, the mattress 124, the lateral surface 508, or the like where the vibration may be imparted into the adjustable bed facility 102 mattress 124 as desired by the user. In an embodiment, the vibration motor 132 flange may provide surface area that may impart a vibration into the mattress 124. In an embodiment, the vibration motor 132 may be secured to the adjustable bed facility 102 section using two separable brackets; at least one of the two separable brackets may be removable. In an embodiment, the removal of one of the brackets may facilitate securing the vibration motor 132 to the bed section, facilitating the servicing of the vibration motor 132, or the like. The bracket may be constructed using a material such as plastic, metal, or the like and may be constructed using the materials individually or in combination. In an embodiment, there may be a resilient material attached to the brackets, the resilient material may provide for a dampening the vibration between the vibration motor 132 and the adjustable bed facility 102, may contact the vibration motor 132 to secure the vibration motor 132 to the bed section, or the like. For example, the brackets may be attached to the adjustable bed facility 102 section with the resilient material making contact with the vibration motor 132 that may be in an opening of the section. The resilient material may provide the force required to hold the vibration motor in place within the section opening and may provide dampening of the vibration to the adjustable bed facility. The resilient material may include latex foam, polyurethane foam, polypropylene foam, polyethylene foam, or the like and may be used individually or in combination.

In an embodiment, the electric motor vibration facility 132 may use DC or AC current to power the motor. In an embodiment, to provide the vibration, the motor may rotate an offset mass on the motor shaft that may cause the vibration facility 132, mattress 124, skeleton structure 130, or the like to vibrate. The user may feel the vibration through the mattress 124, springs 122, or the like.

In an embodiment, an air bladder or air spring may be used to provide a vibration to the adjustable bed facility 102. In an embodiment, the air bladder or air spring air pressure may be varied at a frequency to create a vibration within the vibration facility 132, mattress 124, skeleton structure 130, or the like. In an embodiment, there may be an air supply unit that supplies the frequency varied air pressure to the air bladder or air spring.

In an embodiment, the vibration motor 132 may be in proximity to a vibration distribution facility that may aid in the propagation of vibration energy to the adjustable bed facility 102 section. In an embodiment, the vibration motor 132 may be operatively connected to the vibration distribution facility, may be in contact with the vibration distribution facility, may not be in contact with the vibration distribution facility, or the like. In an embodiment, the vibration distribution facility may provide for a more uniform distribution of the vibration characteristics of the vibration motor 132 and may have a size and shape relative to the size and shape of the adjustable bed facility 102 section. The vibration distribution facility may be constructed using materials such as plastic, rubber, metal, or the like and may be constructed using these materials individually or in combination. In an embodiment, the user may be able to control the speed, amplitude, pulse, and the like of the vibration facility 132 using an interface such as the remote control 118.

In an embodiment, the vibrator facility 132 may be mounted to the mattress 124 using the vibration distribution facility, resilient material 502, strong fabric, or the like. In an embodiment, each adjustable bed facility 102 section that includes a vibrator facility 118 may have an opening in the section to accept the vibrator facility 118. In an embodiment, over the opening in the section, a layer of resilient material 502, strong fabric, or the like may be placed. The layer of resilient material 502, strong fabric, or the like may be placed between the vibrator facility 132 and the mattress 124. In an embodiment, the vibrator facility 132 may impart vibrations to a mattress 124 through the resilient material 502 disposed over an opening in an adjustable bed facility 102 section. In an embodiment, a fabric cover may be disposed over the resilient material 502 and/or an adjustable bed facility 102 section, between the vibrator facility 132 and the mattress 124. In embodiments, a plurality of fabric covers may be disposed over the resilient material 502 and/or an adjustable bed facility 102 section to provide stabilization. In an embodiment, the vibrator facility 132 may impart vibrations to a mattress 124 through a resilient material 502 and a fabric or plurality of fabrics covering the resilient material 502 and/or adjustable bed facility 102 section.

In an embodiment, the resilient material 502 may be foam, cotton matting, or the like. In an embodiment, the vibration distribution facility may be plastic, wood, rubber, metal, or the like and may be any size and/or shape that supports the required vibration characteristics. The vibration distribution facility may have a plurality of barbs or other anchoring devices that may be pushed into the resilient material, strong fabric, or the like to secure the vibration distribution facility in place on top of the resilient material, strong fabric, or the like. In an embodiment, the barbs or other anchoring devices may have a number of gripping edges, points, or the like to provide a connection with the resilient material and strong fabric.

In an embodiment, the vibrator facility 132 may be mounted to the vibration distribution facility through the opening of the adjustable bed facility 102 section lateral surface 508. In an embodiment, the vibration motor 132 may be operatively connected to the vibration distribution facility, may be in contact with the vibration distribution facility, may not be in contact with the vibration distribution facility, or the like. In an embodiment, there may be a layer of resilient material, strong fabric, or the like between the vibrator motor 118 and the vibration distribution facility.

In an embodiment, any space between the vibration facility 132 and the opening of the adjustable bed facility 102 section may be filled with a vibration absorbent material such as foam, cotton matting, rubber, or the like. The absorbent material may provide a layer of vibration insulation between the vibration facility 132 and the adjustable bed facility 102 section opening.

In an embodiment, the combination of the vibration distribution facility and vibration facility 132 may be a vibration facility assembly. In an embodiment, the vibration facility 132 assembly may be attached to the adjustable bed facility 118 sections with the plurality of barbs or anchoring devices.

Referring again to FIG. 1, in an embodiment, the supports 134 may be hydraulic pressurized cylinders that may provide additional control of the decent of the adjustable bed facility 102 sections. The pressurized supports 134 may be designed to support a certain amount of weight that may include the skeleton structure 130, mattress 124, springs 122, user, and the like. In an embodiment, the pressurized cylinders may be similar to the type of supports that are used in automobile trunks to support the trunk open while the user access the trunk area.

In an embodiment, the supports 134 may provide a safety feature when combined with the safety bracket 138. The safety bracket 138 may prevent the actuators from forcibly pulling the adjustable bed facility 102 sections down; the safety bracket is described in more detail below. The supports 134 may be positioned on the sections that are actuated and may provide a controlled speed at which the sections will return to a horizontal position. In an embodiment, the support 134 may provide support of a weight that is less than the weight of the section, therefore the section will provide enough force (e.g. weight) on the support 134 to compress the cylinder and move the section down. In an embodiment, there may be more than one support 134 for each actuated adjustable bed facility 102 section. In an embodiment, the support 134 may be connected between the skeleton structure 130 and the sub-frame 128.

In an embodiment, the safety bracket 138 may be a slotted bracket that provides the connection between the actuators 120 and the skeleton structure 130 for the purpose of moving the adjustable bed facility 102 sections. A side of the slot that is farthest from the actuator 120 may be the slot first side and may be the side that the actuator 120 pushes on to move the adjustable bed 102 section up. A side of the slot that is nearest to the actuator 120 may be the slot second side and may be the side the actuator 120 pulls on to move the adjustable bed 102 section down. In an embodiment, when the actuator 120 is expanding and moving an adjustable bed facility 102 section it may apply a force on the first side of the slot and move the section in an upward direction. When the actuator 120 is retracted to move the section in a downward direction, the actuator 120 connection may move into the middle area (e.g. not in contact with the first or second side of the slot) of the safety bracket 138 slot. As the actuator 120 connection moves into the slot middle area, the adjustable bed facility 102 section may move in a downward motion under the force of section weight. In an embodiment, the actuator 120 may retract at the same speed as the safety bracket 138 moves; therefore the actuator 120 connection may stay in the safety bracket 138 slot middle areas and not make contact with the second side of the safety bracket 138 slot. In this manner, the actuator 120 connection may not contact the second side of the slot and therefore the adjustable bed 102 section may not move in the downward direction by the force of the actuator 120.

In an embodiment, if the actuator 120 connection comes in contact with the second side of the safety bracket 138 slot, there may be a shutoff switch, shutoff indicator, or the like that may stop the retraction of the actuator 104.

In an embodiment, the adjustable bed facility 102 may include an electronic facility 140. In an embodiment, the electronic facility 140 may include a wire harness 142, a communications module 144, power outlets 154, modular controls 148, a power supply 152, a power connection 158, and the like. In an embodiment, different components of the electronic facility 140 may be individual components, combined components, individual and combined components, or the like. For example, the communications module 144, controller 150, and power supplied may be individual components, may be combined into a single component, may be a combination of individual and combined components, or the like. In an embodiment, the various electronic facility 140 components may be mounted on the sub-frame 128, skeleton structure 114, or the like as required for the particular component.

In an embodiment, the wire harness 142 may provide power and data connections to a plurality of modular controls 148. Depending on the power supply 152, the wire harness 142 may provide either DC or AC power to the modular controls 148. In an embodiment, the data connections may be serial, parallel, or the like. In an embodiment, the wire harness may have the same number of power/data connections as there are possible modular controls 148. In an embodiment, the wire harness may be a unit of power/data connections that may be bound together into a single wire harness. In another embodiment, the wire harness may be a group of individual power/data connections. In an embodiment, for each individual wire in the bundle, group, or the like, a first end may have connections for the controller 150 and power supply 152. A second end of the wire harness 142 may be a power and data connection for each individual modular control 148.

In an embodiment, a communications module 144 may receive user commands from a remote control 118. In an embodiment, the communications module 144 may have a wireless or wired connection to the remote control 118. In an embodiment, the wireless remote control 118 to communications module 144 communications may be a radio frequency (RF) communication, infrared (IR) communication, BLUETOOTH communication, or the like. In an embodiment, the communications module 144 may receive the communication command from the remote control 118 and transmit the remote control 118 command to the controller 150. The communication with the controller 150 may be wireless or wired. In an embodiment, the wireless communication between the communications module 144 and the controller 150 may be a radio frequency (RF) communication, infrared (IR) communication, BLUETOOTH communication, or the like. In an embodiment, the communications module 144 may be combined with the controller 150 into a single component. In an embodiment, the skeleton structure 130 may be used as an RF antenna for receiving communication from the remote control 118 to the communications module 144. In embodiment, the entire skeleton structure 130 may be used as an antenna; a portion of the skeleton structure 130 may be used as an antenna, or the like.

In an embodiment, the modular controls 148 may provide additional functionality to the adjustable bed facility 102 that may include a headboard, a footboard, a table, a cabinet, a book shelf, a refrigerator, a freezer, a space for personal waste accommodation that may include a stereo, a CD player, an MP3 player, a DVD player, a lamp, a digital recorder, one or more speakers with a surround sound system, a printer machine, a fax machine, a display system, power outlets 154, an air purification facility 160, a zoned climate control system 150 or the like. The additional functionality that the modular controls 148 provide may be considered optional equipment that may be offered with the adjustable bed facility 102. For example, a user may be able to purchase an adjustable bed facility 102 without any modular controls 148 and may add modular controls as he or she desires. In another example, the user may purchase the adjustable bed facility 102 with modular controls already installed.

In an embodiment, the modular controls 148 may have predetermined mounting locations on the sub-frame 128, skeleton structure 130, or the like. Such locations may have a widespread pivot to couple the modular controls with the adjustable bed facility 102. For example, the refrigerator can be removed and replaced by another refrigerator without any modification in the pivot connecting the refrigerator and the adjustable bed facility 102. In a similar manner, additional devices and facilities may be coupled to the adjustable bed facility 102 using the widespread pivot. In an embodiment, these devices and facilities coupled via the pivot may be removed for various functions. For example, a user may remove a device for repairing, for upgrading the devices with new and additional functionalities and the like. Also, the user may remove the device to perform some other function. For example, a foot section may be removed to create a chair in the adjustable bed facility 102. Therefore, the modular controls 148 may be compact, ready to use, provide a plurality of additional functionalities and may be mounted in accordance with the user's requirements.

In an embodiment, these devices and facilities may receive power from power outlets 154 controlled by the modular control 148. The modular control 148 may directly or indirectly control the facilities that are connected to the modular control 148. Further, the user may control the power outlet 140 to turn the device on or off but the user may not be able to control the individual device (e.g. raising or lowering of the foot board). In an embodiment, the user may control the additional functional devices by using the remote control 118 that may have an interface for each of the modular controls 148. For example, there may be an interface on the remote control 118 for raising the footboard, lowering the footboard, placing the foot board inside its cabinet or the like. Also, the user may open/close the book shelf, turn on/off the refrigerator by the interface of the remote control 118. In a similar manner, the user may be able to control if a power outlet 140 provided by a modular control 148 is on or off.

In an embodiment, the modular controls 148 may directly control devices, indirectly control devices, or the like such as a stereo, CD player, DVD player, a digital recorder, one or more speakers with a surround sound system, air purification facilities, a printer machine, a fax machine or the like. These devices and facilities may receive power from power outlets 154 that are controlled by the modular control 148. In an example, the modular control 148 may directly control a lamp that is connected to the modular control 148 but may indirectly control a device or facility that is plugged into a power outlet 154 controlled by the modular control 148. Further, the user may control the power outlet 154 to turn the device on or off but the user may not be able to control the individual device (e.g. the volume or functions of a stereo system). In an embodiment, the user may control the additional functional devices by using the remote control 118 that may have an interface for each of the modular controls 148. For example, there may be an interface on the remote control 118 for selecting the function of the stereo system, increasing or decreasing the volume of the system, as well as turning on a lamp, turning off a lamp, dimming a lamp, and the like. In a similar manner, the user may be able to control if a power outlet 154 provided by a modular control 148 is on or off.

In an embodiment, the user may install one or more display systems. The display system may be an LCD mounted on a swivel arm, a projector system, a footboard integrated flat screen, and the like. The user may control the display systems by using the remote control 118 that may have an interface for the display systems. For example, turning the display system on/off, adjusting the resolution of the screen, fine tuning the contrast and brightness of the display, and the like. In an exemplary scenario, the swivel arm may be mounted on the sub-frame 128, skeleton structure 130, or the like. In another exemplary scenario, the footboard integrated flat screen may be placed inside or outside a compartment. Further, the integrated flat screen may be raised or lowered, into the stored compartment or may be fixed in a single position. The user may be able to turn the power outlet 154 on/off using the remote control 118.

In an embodiment, the user may control additional functional devices by using communication ports. The communication ports may enable the use of additional devices such as a printer machine, a fax machine, and the like. The additional device connection may be a serial connection, a USB connection, a USB device, a parallel connection, a wireless connection, or the like. The user may control the printer machine by using the remote control 118 that may have an interface for the printer machine. For example, there may be an interface on the remote control 118 for turning on a printer machine, turning off the printer machine, executing one or more print commands, canceling the print commands, and the like. In a similar manner, the user may also control the fax machine by using the remote control 118 that may have an interface for the fax machine. The user may furnish one or more fax commands, receive incoming fax commands, turn the fax machine on/off with the use of the fax machine interface on the remote control 118. In an exemplary scenario, the user may be able to turn the power outlet 154 provided by the modular control 148 on/off using the remote control 118.

In an embodiment, the modular controls 148 may be connected to the controller 150, power supply 152, or the like; the connection may be the wire harness 142. In an embodiment, the modular controls 148 may communicate with the controller 150 by a wireless means that may include radio frequency (RF), infrared (IR), BLUETOOTH, or other wireless communication type.

In an embodiment, the controller 150 may interpret commands received from the communications module 144 into commands for the various adjustable bed facility 102 components such as the actuators 120, the vibration facility 132, the modular controls 148, power outlets 154, and the like. In an embodiment, the controller 150 may contain a microprocessor, microcontroller, or the like to run a software application to interpret the commands received from the remote control 118 through the communications module 144. In an embodiment, the software application may be interrupt based, polling based, or other application method for determining when a user has selected a command on the remote control 118. In an embodiment, the software application may be stored in the controller 150, stored in bed memory 170, or the like and may be stored as software, as firmware, as hardware, or the like.

In an embodiment, the controller 150 may receive information from the communications module 144 by wired communication, wireless communication, or the like. In an embodiment, the wireless communication may be by radio frequency (RF), infrared (IR), BLUETOOTH, or other wireless communication type.

In an embodiment, after the controller 150 has interpreted the received user commands, the controller 150 may transmit the interpreted commands to the various controllers for the adjustable bed facility 102 components such as the actuators 120, vibrator facility 132, modular controls 148, power outlets 154, and the like. The controller 150 may transmit information that may be further interpreted by the components into commands for the individual components. For example, the controller 150 may receive a command to move the head section up. The controller 150 may interpret the remote control 118 command into a command the actuator may understand and may transmit the command to extend the head section actuator to move the head section up.

In an embodiment, the power supply 152 may receive power from a standard wall outlet, fuse box, circuit box, or the like and may provide power to all the powered components of the adjustable bed facility 102. In an embodiment, the power supply 152 may provide DC power or AC power to the components. In an embodiment, if the power supply 152 provides DC power, the power supply 152 may convert the incoming AC power into DC power for the adjustable bed facility 102.

In an embodiment, the power outlets 154 may provide standard household AC current using a standard outlet for use by external devices using a standard plug. In an embodiment, the power outlets 154 may receive power directly from a standard wall outlet, a fuse box, a circuit box, or the like, but the controller 150 may control whether the power outlet 154 on or off. In an embodiment, the power outlet 154 may have a control circuit that may determine if the power outlet 154 is active (on) or inactive (off). In an embodiment, the command to indicate if the power outlet 154 is active or inactive may be received from the controller 150. In an embodiment, the controller 150 may receive commands for the power outlet 154 control from the remote control 118.

In an embodiment, the power connection 158 may receive standard power for the adjustable bed facility 102 from a standard outlet, fuse box, circuit box, or the like. In an embodiment, the power connection 158 may provide standard AC power to the power outlets 154, the power supply 152, or the like.

In an embodiment, the air purification facility 160 may be any type of device or facility that may be capable of improving that air environment in the area of the adjustable bed facility 102. In an embodiment, the air purification facility 160 may be an absorbent type (e.g. carbon), electro-static, HEPA filter, or the like. In an embodiment, absorbent materials may be used in a filter, in the adjustable bed facility 102, in the mattress 124, or the like to absorbed odor, dust, contaminants, or the like from the air environment around the bed, within the bed, or the like. In an embodiment, electro-static or iconic air filters may use negative ions to attract dust, contaminants, and the like from the air. In an embodiment, electro-static materials (e.g. tourmaline) may be used in a filter, in the adjustable bed facility 102, in the mattress 124, or the like to absorbed odor, dust, contaminants, or the like from the air environment around the bed, within the bed, or the like. In an embodiment, HEPA filters are composed of a mat of randomly arranged fibers that are designed to trap at least 99.97% of dust, pollen, mold, bacteria, and any airborne particles with a size of 0.3 micrometers ($\mu$m) at 85 liters per minute (Lpm). The HEPA filter may be used in a device, facility, or the like for filtering the air in the area of the adjustable bed facility 102.

In an embodiment, the air purification facility 160 may be part of the adjustable bed facility 102, a freestanding device or facility, or the like. In an embodiment, if the air purification facility 160 is part of the adjustable bed facility 102 the air purification facility 160 may be attached to any part of the adjustable bed facility 102 such as the mattress 124, sub-frame 128, skeleton structure 130, or the like. In an embodiment, the air purification facility 160 that is attached to the adjustable bed facility 102 may be controlled direct control of the air purification facility 160, control using the remote control 118, or the like.

In an embodiment, the air purification facility 160 may be a free standing device that may be plugged into an adjustable bed facility 102, power outlet 154 and therefore may be controlled with the remote control 118 controlling the on/off condition of the power outlet 154.

In an embodiment, the air purification facility 160 may be a freestanding device that may be connected to an adjustable bed facility 102 modular control 148. The modular control 148 may provide power (AC or DC), control communication, and the like to the air purification facility 160. In an embodiment, the user may be able to control the air purification facility 160 using the remote control 118 to control the modular controls 148.

In an embodiment, the zone climate control system 162 may be any type of device or facility that may be capable of controlling the environment within one or more zones of the adjustable bed facility 102. In an embodiment, the zone may be a single room or may be two different sides of the adjustable bed facility 102. In an embodiment, two different users may sleep in different environments or two users may sleep in a single environment controlled by the zone climate control system 162. In an embodiment, the user may request the provision of different environments in the different sides of the adjustable bed facility 102. Accordingly, the zone climate control system 162 may decide on which side the zone vents are to be closed and which side they are to be kept open. Additionally, the zone climate control system 162 may heat or cool the zones of the bed, circulate air to heat or cool a zone by mixing air with air from another zone, circulate air to reduce excessive conditioning of a zone, or circulate air to maintain air quality. In an embodiment, the zone climate control system 162 may determine and develop parameters such as airflow, thermal capacity, heating or cooling requirements, and the like by measurement and/or derivation.

In an embodiment, the zone climate control system 162 may be a free standing device that may be plugged into an adjustable bed facility 102 power outlet 140 and therefore may be controlled with the remote control 118 controlling the on/off condition of the power outlet 140.

In an embodiment, the zone climate control system 162 may be a freestanding device that may be connected to an adjustable bed facility 102 modular control 148. The modular control 148 may provide power (AC or DC), control communication, and the like to the zone climate control system 162. In an embodiment, the user may be able to control the zone climate control system 162 using the remote control 118 to control the modular controls 148.

In an embodiment, the remote control 118 may be a user controlled device to provide control commands to the controller 150 to command certain functions of the adjustable bed facility 102. In an embodiment, the certain functions may be adjustable bed facility section movement (e.g. up or down), vibration control, modular controlled 132 devices, or the like. In an embodiment, the remote control 118 may communicate with the control box using wired communication, wireless communication, or the like. In an embodiment, the wireless communication may be using a radio frequency (RF), infrared (IR), BLUETOOTH, or the like. If the remote communicates using a wireless technology, the communication may be with the communications module 144 and the communications module 144 may pass the command request to the controller 150.

In an embodiment, the user may indicate the certain adjustable bed facility 102 function using the remote control 118 by pressing a button, touching a screen, entering a code, speaking a command, or the like. In an embodiment, the controller 150, using the communications module 144, may receive and interpret the command provided by the remote control 118. In an embodiment, the certain functions available on the remote may instruct the controller 150 to directly control a device (e.g. actuator 104), control a modular control 148 connected device, or the like. The remote may control devices with commands that may include on, off, high power, medium power, low power, volume, play, fast forward, rewind, skip, modular device to control, or the like. For example, the remote control 118 may transmit a command to move the head section up and the controller 150 may command the actuator 120 to extend a certain amount in response to the command. In another example, the remote control 118 may command that a modular control 148 connected lamp be turned off.

In an embodiment, the remote control 118 may save adjustable bed facility 102 user preferred settings to a plurality of memory locations that may be used to maintain the user determined bed position, an adjustable bed facility 102 historical setting, or the like. For example, the user may have a certain preferred adjustable bed facility 102 position that may be stored in at least one of the memory locations that the user may be able to later recall to move the adjustable bed facility into the user preferred position. By indicating the recall of the at least one memory locations, the adjustable bed facility 102 controller 150 may command the various components to move to the stored memory location position to achieve the recalled position. In an embodiment, for a remote control 118 that may contain buttons, the user may press a single button, a combination of buttons, or the like to recall the memory position desired.

In an embodiment, the remote control 118 may have buttons, an LCD screen, a plasma screen, or the like to allow the user to indicate the desired command. In an embodiment, the user may press a button to indicate a command to the controller 150. In an embodiment, the LCD or plasma screens may be touch screen sensitive. In an embodiment, the remote control 118 screen may present the available controls to the user and the user may touch the screen to indicate the command desired. For example, the remote control 118 screen may only present controls that are available in the adjustable bed facility 102; therefore, if a modular control 148 is not available, the remote control 118 may not display a selection for that modular control 148. In an embodiment, the remote control 118 screen may present content sensitive selections to the user. For example, if the user selected to control a CD player, the user may be presented with CD player controls that may include play, fast forward, rewind, skip, stop, repeat, or the like. Also, the LCD touch screen may provide information relating to temperature, humidity, weather information, calendar, and contact personnel's lists, to-do lists, navigating maps or the like.

In an embodiment, the remote control 118 may provide feedback to the user to indicate the success of the certain command. In an embodiment, the feedback may be an audio feedback, a visual feedback, a forced feedback, or the like. In an embodiment, the feedback types may be used individually or in combination. In an embodiment, the audio feedback may be a sound that indicates that the command was successful, failed, is in progress, in conflict with a command in progress, failed for safety reasons, or the like. In an embodiment, the visual feedback may be an indication of the remote control 118 screen that indicates that the command was successful, failed, is in progress, in conflict with a command in progress, failed for safety reasons, or the like. In an embodiment, the forced feedback may be a vibration that indicates that the command was successful, failed, is in progress, in conflict with a command in progress, failed for safety reasons, or the like.

In an embodiment, a memory facility 164 may contain components that are intended to maintain certain memory locations for the control box to access, receiver to access, and the like. In an embodiment, the memory facility 164 may include a receiver learn facility 168, a bed memory 170, a backup battery 172, and the like. In an embodiment, the receiver learn facility 168, bed memory 170, and backup battery 172 may be in a single memory facility 164 or may be in more than one memory facilities 154. In an embodiment, the memory facility 164 may be part of the adjustable bed facility 102, part of the electronic facility 140, a separate facility, or the like. In an embodiment, the receiver learn facility 168, bed memory 170, and backup battery 172 may not be part of the memory facility 164, but may be combined into other facilities or devices, be stand-alone devices, or the like.

In an embodiment, the receiver learn facility 168 may act to establish the communication link between the remote control 118 and the communications module 144 where the communication between the remote control 118 and communications module 144 is a wireless connection. In an embodiment, the communication link between the remote control 118 and the communications module 144 may need to be a unique connection to assure that the remote control 118 communicates with only one communications module 144 within one adjustable bed facility 102. In an embodiment, the receiver learns facility 152 may be used to provide a unique communication between any remote control 118 and any adjustable bed facility 102. For example, a remote control 118 may be used to communicate with a first adjustable bed facility 102 and may be used to establish communication between the same remote and a second adjustable bed facility 102. The remote control 118 may only be able to communicate with one adjustable bed facility 102 at a time.

In an embodiment, a learn protocol between the remote control 118 and communications module 144 may be user initiated by pressing a button on the receiver learn facility 168, powering up the receiver learn facility 168, bringing the receiver learn facility 168 within a certain proximity of the communications module 144, indicating on the remote control 118 to begin the learn protocol, or the like. In an embodiment, the learn protocol may be fully automatic, semi-automatic with user intervention, manual, or the like. In an embodiment, a user may select a channel, frequency, or the like during learn protocol or after the learn protocol. The changing of the channel, frequency, or the like may prevent two different remote control 118 and communications module 144 combinations from interfering with other wireless communication devices. In an embodiment, each time the learn protocol is executed, a new unique communication link may be established; there may be a plurality of unique communication links available for each remote control 118 and communications module 144 combination.

In an embodiment, the bed memory 170 may be the memory location where the controller 150 stores user desired preset information, software for interpreting remote control 118 commands, demonstration software, and the like. In an embodiment, the bed memory 170 may be removable memory. For example, the bed memory 170 may be moved from a first adjustable bed facility 102 to a second bed facility 102 to move user settings from the first adjustable bed facility 102 to the second bed facility 102. In this manner, the bed memory 170 may be considered portable memory. In an embodiment, the removable bed memory 170 may be flash memory, programmable logic circuit memory, secure digital (SD) memory, mini SD memory, Compact Flash type I memory, Compact Flash type II memory, Memory Stick, Multimedia Card, xD Picture card, Smartmedia, eXtreme Digital, Microdrive, or the like.

In an embodiment, the removable bed memory 170 may be used to upgrade the adjustable bed facility 102 memory and software. For example, if new controller 150 software was developed to provide better control over one of the adjustable bed facility 102 components, the software may be saved to a new replaceable memory that may be used in the place of the existing replaceable memory. In this manner, the software of the adjustable bed facility 102 could be upgraded just by providing the user with a new replaceable memory.

In an embodiment, the removable memory may be used to provide a sales enterprise with adjustable bed facility 102 demonstration software where the enterprise may be able to indicate at least one of a plurality of demonstrations for a user. For example, the user may be interested in how the adjustable bed facility 102 sections may be adjusted and the enterprise may select a demonstration to shows all the section motion available. In an embodiment, before an adjustable bed facility 102 is shipped to a user, the enterprise may remove the demonstration removable memory and replace it with a standard adjustable bed facility 102 bed memory 170.

In an embodiment, the backup battery 172 may be used to provide power to volatile memory, provide power to the receiver learn facility 168; provide power to the programmable logic circuit memory, or the like.

In an embodiment, the memory connection 174 may be any connection type that provides a connection between the bed memory 170, controller 150, and the like. In an embodiment, the memory connection 174 may be a wired or wireless connection. The wired connection may be a USB connection, a serial connection, parallel connection, or the like. The wireless connection may be by radio frequency (RF), infrared (IR), BLUETOOTH, or the like. In an embodiment, the memory connection 174 may be in a location that is easy for the user to access the bed memory 170, may be attached to the memory facility 164, may be attached to the controller 150, or the like. In an embodiment, the easy access memory connection may be on the side of the adjustable bed facility 102, on a rail of the adjustable bed facility 102, under the adjustable bed facility 102, or the like.

In an embodiment, the network connection 178 may be used to connect the controller 150 to a network connection. In an embodiment, the network connection may be a LAN, a WAN, an Internet, an intranet, peer-to-peer network, or the like. Using the network connection 178, the controller 150 may be able to communicate with computer devices on the network. In an embodiment, the network connection 178 may be a wired or wireless connection.

In an embodiment, using the network connection 178, the controller 150 may be able to communicate with the network to periodically check for software updates. In an embodiment, if a software update is located, the controller 150 may send the user an email, instant messenger message, phone message, phone call, cell phone message, cell phone call, fax, pager message, or the like to indicate that software updates are available. The user, using the device that received the notice of software, may send a reply to the control box that the software upgrade should be downloaded, should not be downloaded, or the like.

In an embodiment, an adjustable bed facility 102 enterprises, an adjustable bed facility 102 manufacturers, an adjustable bed facility 102 service enterprises, or the like may send the controller 150 software updates using the network connection 178. In an embodiment, an adjustable bed facility 102 enterprise, an adjustable bed facility 102 manufacturer, an adjustable bed facility 102 service enterprise, or the like may notify the user of available software upgrades for the adjustable bed facility 102 by email, instant messenger message, phone message, phone call, message, cell phone call, fax, pager message, or the like. The user, using the device that received the notice of software, may send a reply to the adjustable bed facility 102 enterprise, the adjustable bed facility 102 manufacturer, the adjustable bed facility 102 service enterprise, or the like that the software upgrade should be downloaded, should not be downloaded, or the like.

Referring now to FIGS. 4A and 4B, an embodiment of shipping and assembling a mattress retaining bracket 402 is shown. The mattress retaining bracket 402 may be used to hold the mattress 124 (not shown) in place on the adjustable bed facility 102 as the adjustable bed facility 102 sections are adjusted. For example, as the head section is adjusted up, the mattress 124 may tend to slide down towards the foot of the bed, the mattress retaining bracket 402 may stop the mattress from sliding and may maintain the mattress 124 in the proper position on the adjustable bed facility 102. In an embodiment, there may be a mattress retaining 402 bracket at the head section and/or the foot section of the adjustable bed facility 102.

In an embodiment, the mattress retaining bracket 402 may be made of materials that include metal, plastic, rubber, wood, or the like. In an embodiment, the materials may be used individually or in combination.

In an embodiment, as shown in FIG. 4A, when the adjustable bed facility 102 is shipped to the user, the mattress retaining bracket 402 may be mounted upside down at the final location of the mattress retaining bracket 402. This mounting method may provide benefits that may include mattress retaining bracket 402 breakage prevention, mattress retaining bracket 402 bending prevention, clear user understanding of the final mattress retaining bracket 402 location, prevention of the mattress retaining bracket 402 becoming lost, and the like. In an embodiment, as shown in FIG. 4B, once the user receives the adjustable bed facility 102 with the upside down mounted mattress retaining bracket 402, the user may rotate the mattress retaining bracket 402 into the upright position and re-secure it to the adjustable bed facility 102.

Referring to FIG. 6, an example of an adjustable bed 600 (without the mattress) is shown with the head 602 and foot 604 sections raised to an elevated position. This adjustable bed 600 shows that sections, in this case the foot 604 section, may be divided into more than one section to provide contouring of bed sections.

Figure 7:
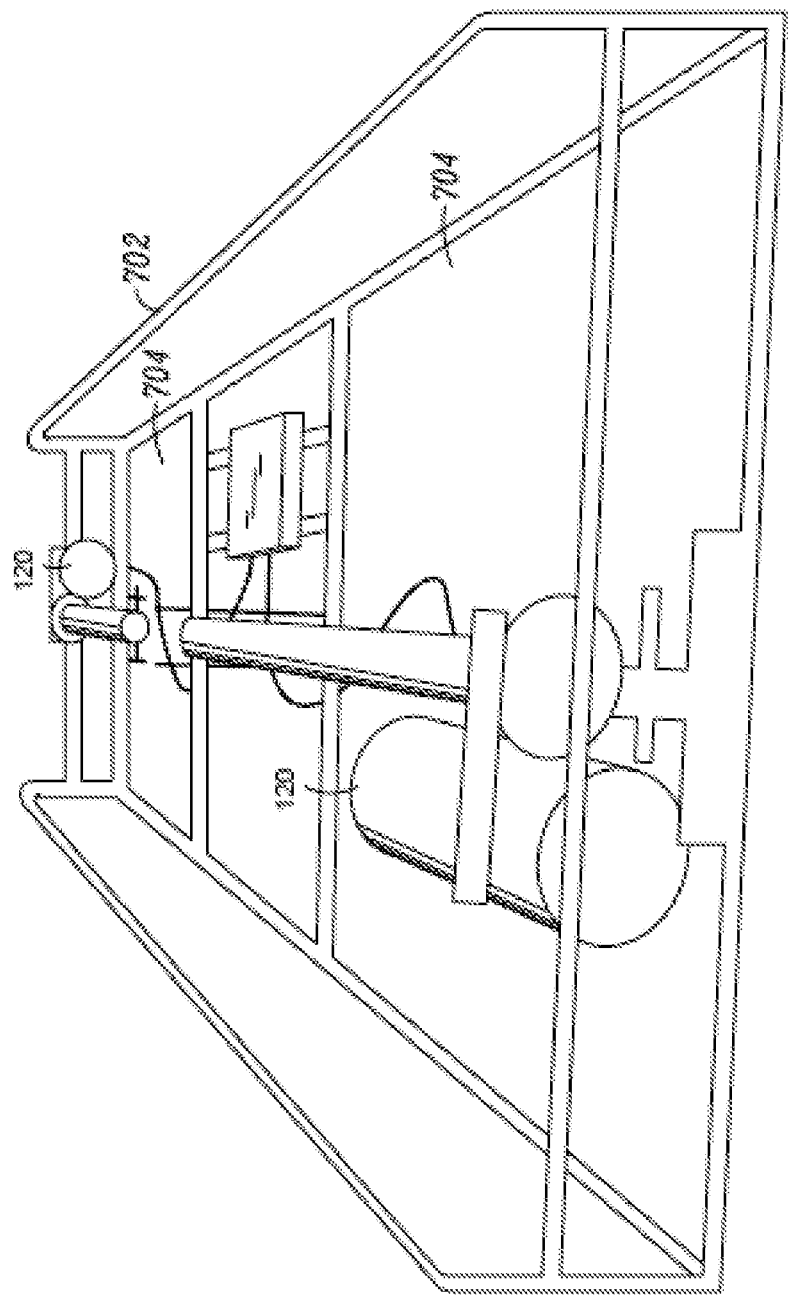
FIG. 7 shows one use of actuators connected to the bed frame and the adjustable sections.

Referring to FIG. 7, an example of actuators 120 connected to the bed frame 702 and the adjustable sections 704 is shown. In this case, two actuators 120 are used, one for each adjustable bed section 704.

Figure 8:
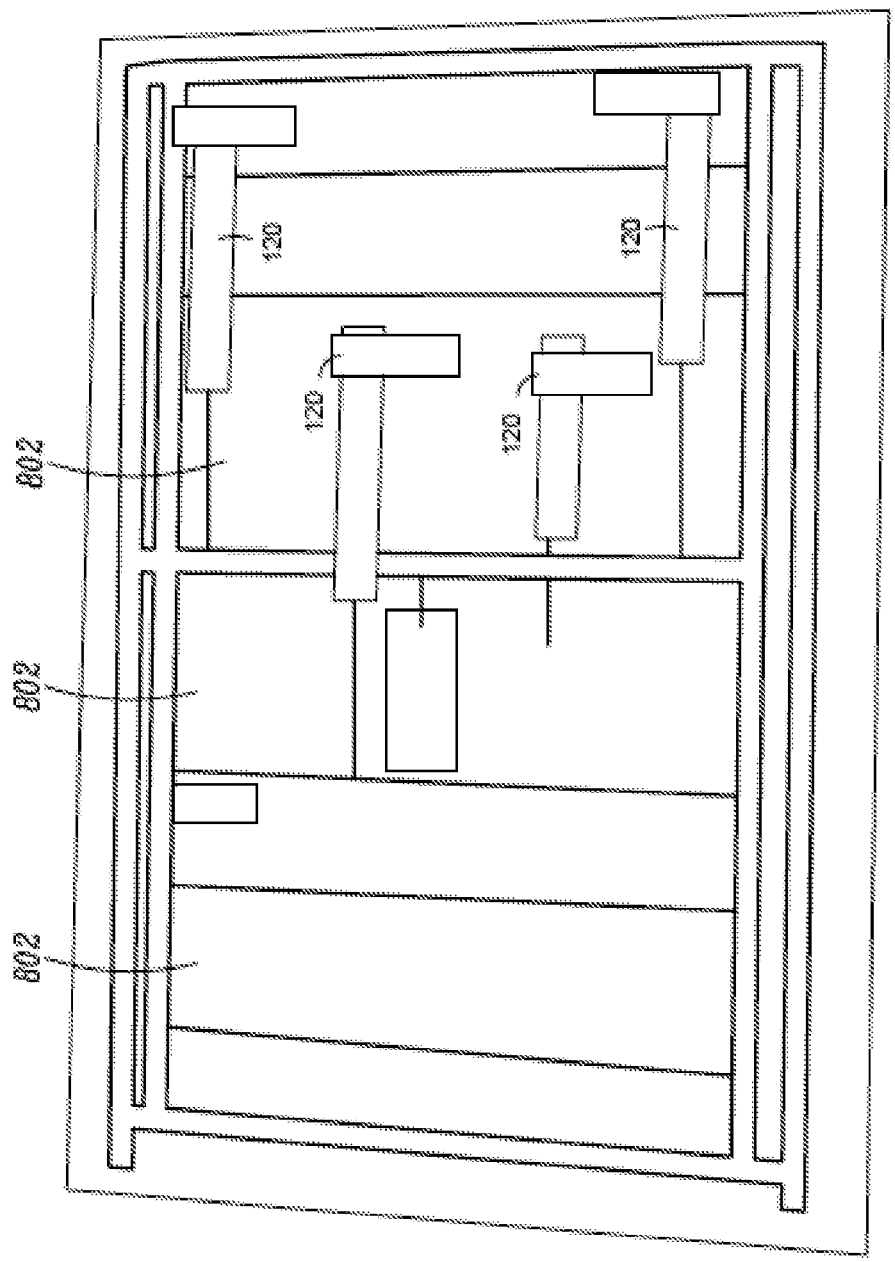
FIG. 8 shows more than one actuator for each adjustable bed section; in this case, there are two actuators for each adjustable section.

Referring to FIG. 8, an example of more than one actuator 120 for each adjustable bed section 802 is shown; in this case, there are two actuators 120 for each adjustable section 802. In embodiments, more than one actuator 120 per section 802 may be used if the bed sections 802 are heavy, smaller actuators 120 are used, if the bed is a wide bed (e.g. king bed), or the like.

Figure 9:
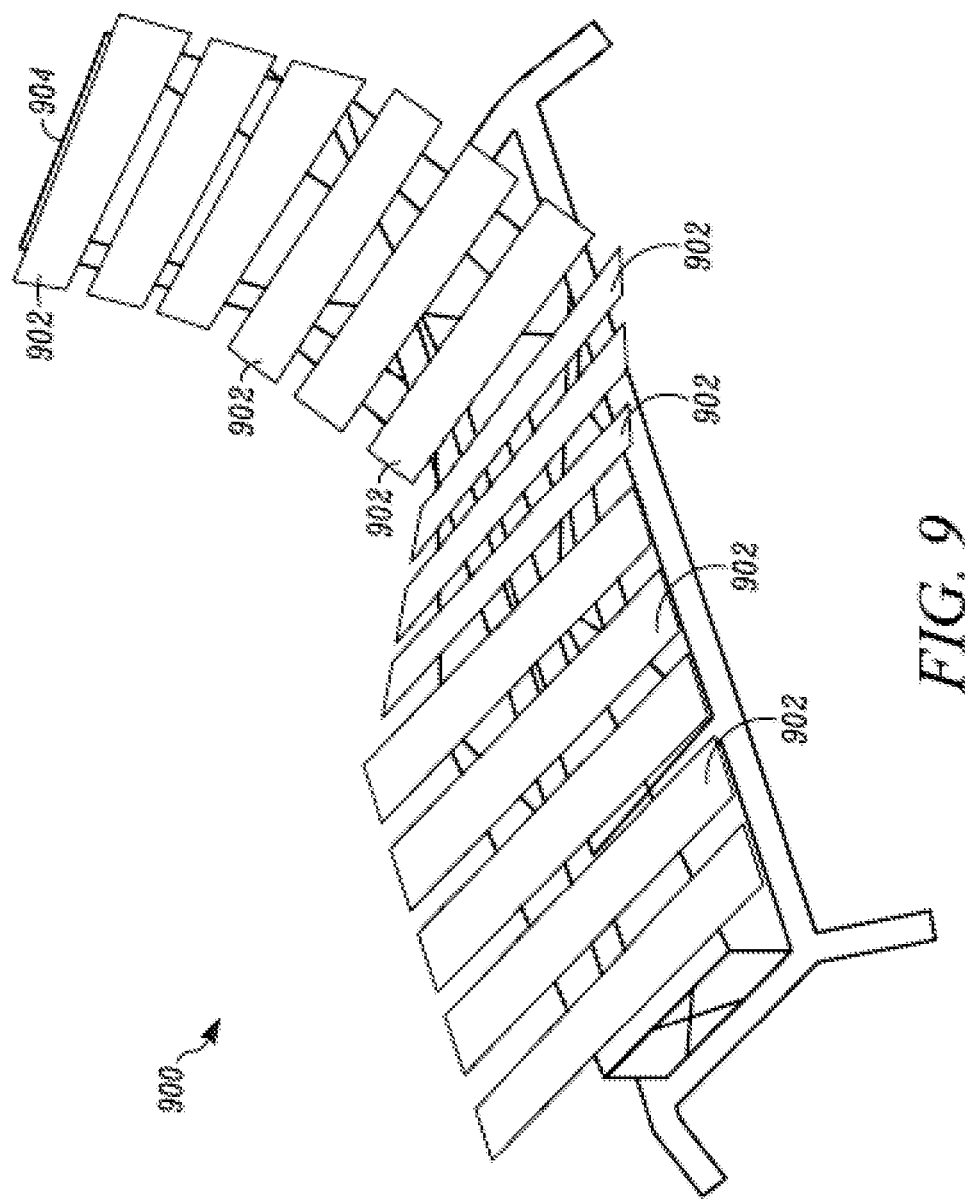
FIG. 9 shows an adjustable bed using slats instead of wood decking for the foundation of the adjustable sections.

Referring to FIG. 9, an example of an adjustable bed 900 using slats 902 instead of wood decking for the foundation of the adjustable sections is shown. In embodiments, the slats 902 may be wood, plastic, rubber, cloth, elastic material, or the like. Using this design, the adjustable bed 900 may be provided with curved contours has shown in the head section 904. In an embodiment, the curved sections may be constructed of a number of small connected individual sections.

Figure 10A:
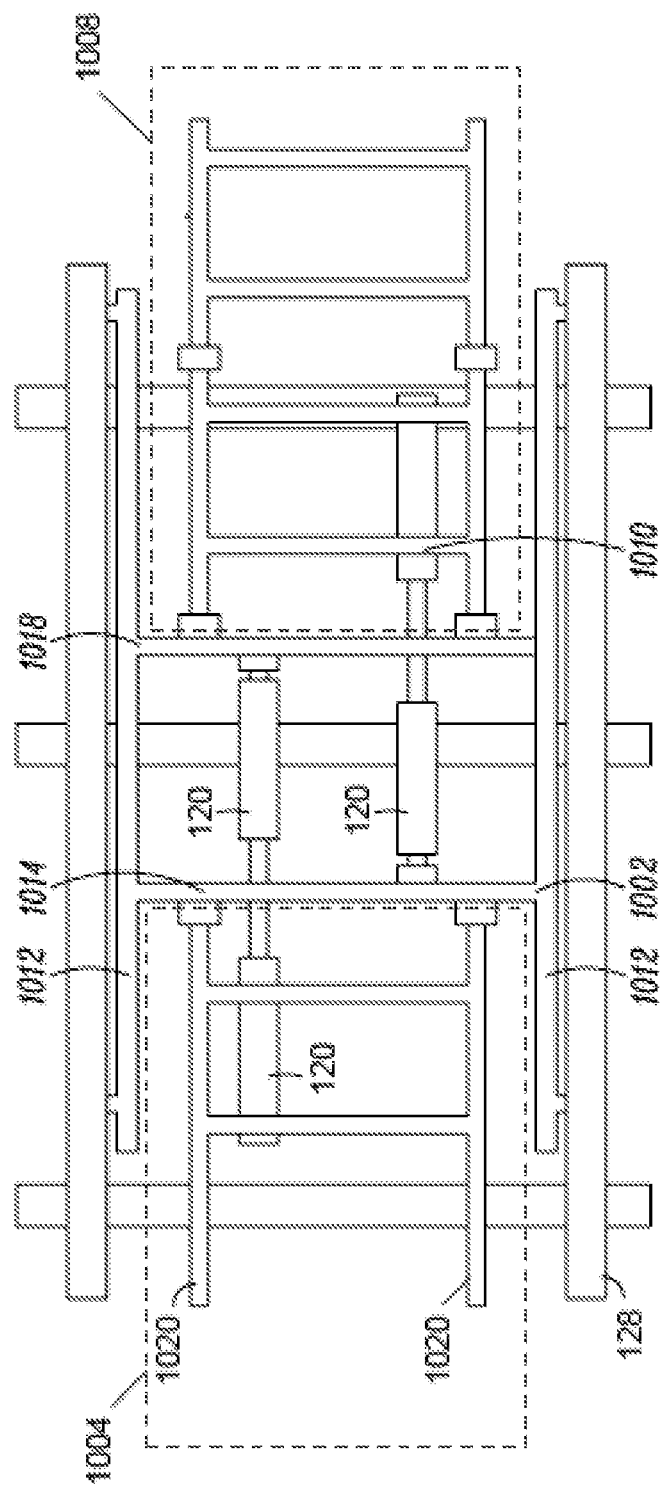
FIGS. 10A and 10B show an adjustable bed facility according to an embodiment of the present invention.
Figure 10B:
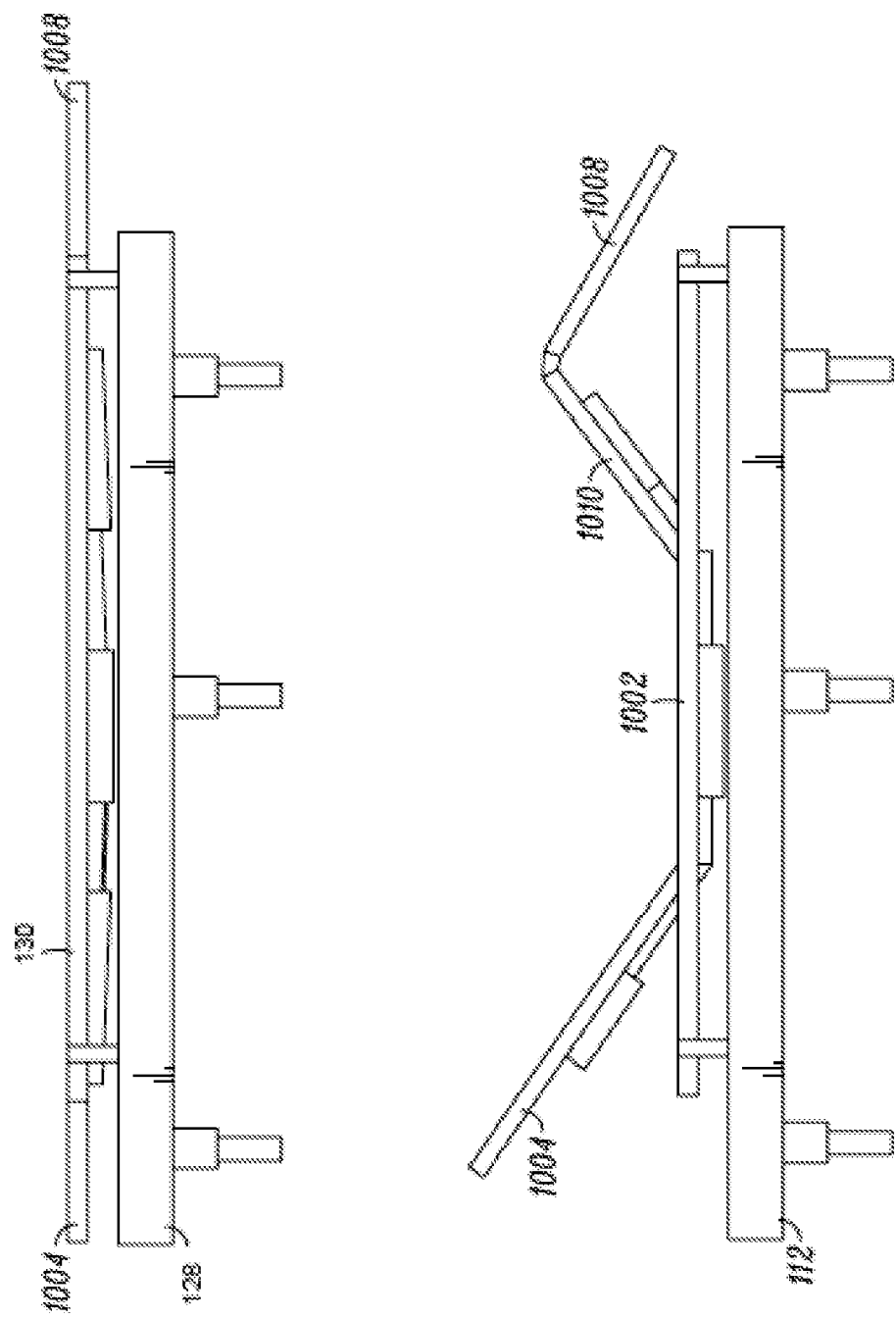
Figure 35:
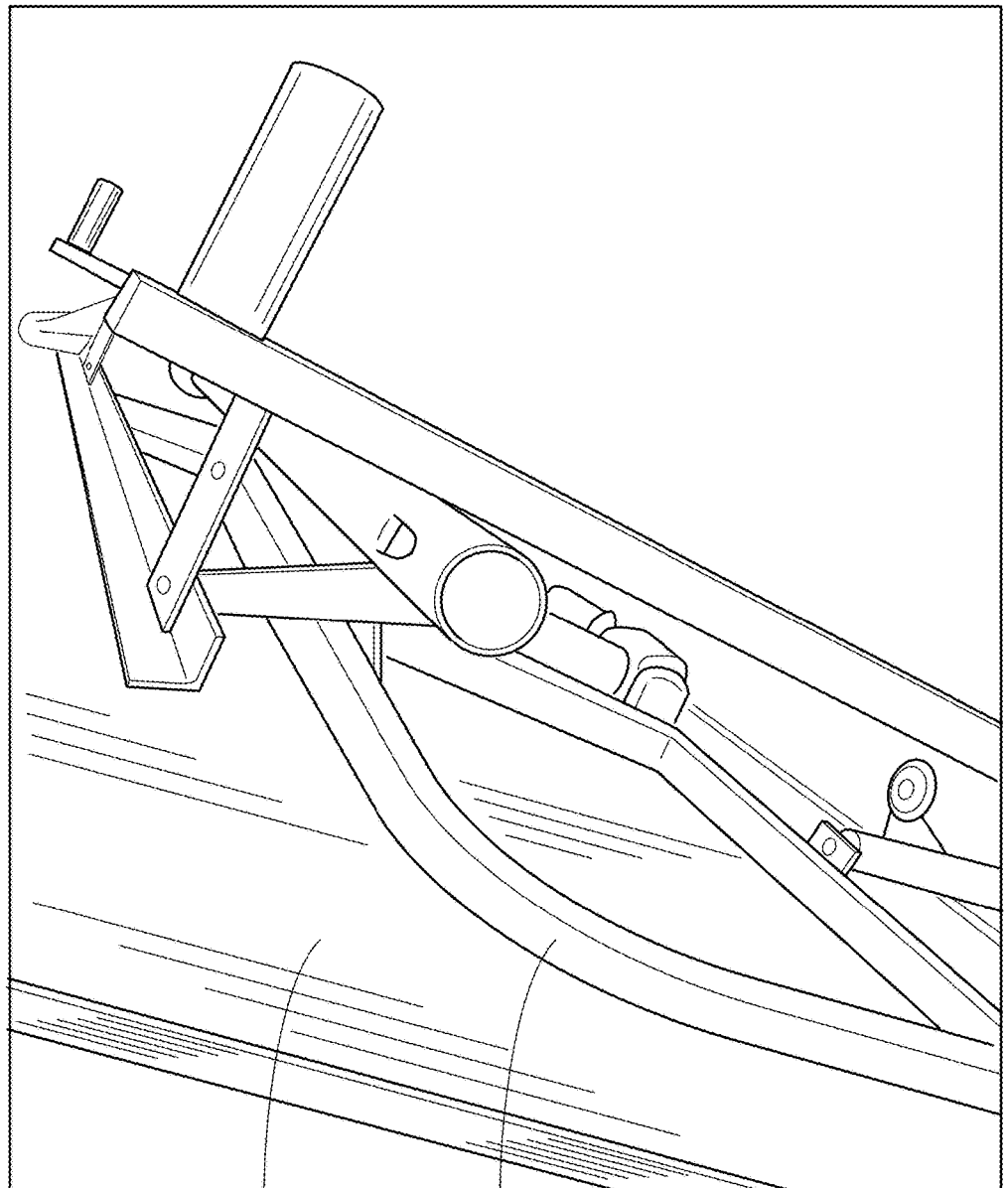
FIG. 35 depicts an embodiment of an adjustable frame for the head.

In an embodiment, the skeleton structure 130 may include more than one section/frame. The sections/frames may be fixed or may be adjustable/movable. Further, the sections/frames may be assembled together to form the skeleton structure 130 in such a way that the sections/frames may be able to move relative to each other to provide the various bed positions required by the user. To achieve this, the sections/frames may be connected together using hinges or like devices that allow a freedom of motion between them. In one embodiment, one frame/section may remain fixed and may act as the foundation for the other movable frames/sections. For example, in an arrangement as shown in FIGS. 10A and 10B, the skeleton structure 130 may have a fixed center frame 1002 and, optionally, adjustable frames for the head 1004, foot 1008, or leg 1010. In this arrangement, the adjustable head frame 1004 and the adjustable leg frame 1010 may be pivotally attached to the center frame 1002. The pivot attachments may enable rotational movement of the head frame 1004 and the leg frame 1010 with respect to the fixed center frame 1002. In a scenario, because of this rotational movement, the head frame 1004 may be raised with the help of the actuators 120 to raise the upper portion of a patient body during meals. Further, the head frame 1004 may be lowered to the normal level after the patient has had his/her meal. In a similar fashion, a person lying on the adjustable bed 102 may raise or lower the head frame 1004 and/or the foot frame 1008 to his/her convenience. In another embodiment, any or none of the frames/sections may be a fixed foundation section in the adjustable bed facility 102. In embodiments, there may be more than one adjustable bed facility 102 configuration depending on the requirements of a user, cost requirements, medical needs, or the like. For example, there may be a configuration where only the head section is adjustable to provide the user with the ability to have an elevated upper body position. This configuration may be a single purpose bed but may also provide the user with a less expensive adjustable bed facility 102 that meets the user's needs. One skilled in the art may understand that there may be many different adjustable bed facility configurations containing fixed and moveable sections. For example, FIG. 35 shows an embodiment of the head frame 1004 including a single piece of material 3502 (e.g., bent steel or the like) as the underlying support as an alternative to two straight pieces of material 1020 as shown in FIG. 10A.

In embodiments, there may be different combinations of movable and fixed sections with one or all of the sections being movable. In an embodiment, the sections may include the skeleton structure 130, mattress 124, springs 122, and the like, and may individually be small mattress structures of the entire adjustable bed facility 102 mattress.

In embodiments, the frames may be made of square tubular steel bars/pipes or any other material capable of providing required strength to the frames. In preferred embodiments, each frame may include two substantially parallel side frame members connected by one or more connector frame members. In order to connect the parallel side frame members, various joining methods such as welding, brazing, riveting, fastening with nuts, and the like can be used. For example, the center frame 1002 may include two substantially parallel side frame members 1012 connected by two substantially parallel connector frame members 1014 and 1018. The two connector frame members 1014 and 1018 may be located within approximately a center one-third of the length of the side frame members 1012. Once the frame members have been connected to each other using any one of the joining methods as discussed above, the center frame 1002 may take a substantially square or rectangular shape. Those skilled in the art would appreciate that the frames may have various other shapes and designs to perform the same functionality and without deviating from the scope of the invention.

In an embodiment, the skeleton structure 114, as part of each adjustable bed facility 102 frame/section, may also provide support and connection members for the components that may be used to move the various adjustable bed facility 102 sections. There may be skeleton structure 130 members that provide connection support to the actuators 120, supports 134, safety brackets 122, vibration motors 118, and the like. These support and connection members may have any shape or configuration required to provide the support and connections needed by the various other components. For example, in addition to the skeleton structure 130 that is used to provide support to the mattress 124 and springs 122 there may be at least one cross member that may provide a connection to the actuator 120 and safety bracket 138.

In an embodiment, the skeleton structure 130 and the sub-frame 128 may interface with each other; the sub-frame 128 may provide structural support and a rigid foundation base to the skeleton structure 130. In an arrangement of this embodiment, only one frame of the skeleton structure 130 may be attached with the sub-frame 128. For example, the center frame 1002 may be rigidly attached to the sub frame 112 in such a manner that the center frame 1002 may not move with respect to the sub frame 128. The sub-frame 128 may provide a base to solidly connect the center frame 1002 to provide a fixed non-moving section. The other moveable frames such as the head frame 1004 and the foot frame 1008 may be moveably connected to the fixed center frame 1002 and additionally supported by the sub-frame 128 using a moveable interface connection.

In an embodiment, the sub-frame 128 may be the rigid structure that is in contact to the floor and may provide a base for any fixed adjustable bed facility 102 sections and an interface for any movable adjustable bed facility 102 sections. In an embodiment, the sub-frame 128 legs may be connected to the sub-frame 128 using a threaded stud into threads of the sub-frame 128. In an embodiment, to prevent the threaded stud from pulling out of the legs during tightening, the head of the threaded stud may be fixed between two or more layers of leg material. This construction may trap the threaded stud head to prevent it from moving away from the end of the leg and may also prevent the threaded stud head from being pulled through the end of the leg during the tightening of the leg to the sub-frame. In addition, the two or more layers of leg material may provide for added strength to the sub-frame 128 legs to prevent distortion at the sub-frame 128 and leg interface. In an embodiment, the sub-frame 128 may have structural members that may run along the length of the adjustable bed facility 102, run along the width of the adjustable bed facility 102, run diagonally across the adjustable bed facility 102, or other orientation in relation to the adjustable bed facility 102 that may be required for support or connection to components.

In an embodiment, the skeleton structure 130 may be used as an RF antenna for receiving communication from the remote control 118. In embodiment, the entire skeleton structure 130 may be used as an antenna; a portion of the skeleton structure 130 may be used as an antenna, or the like.

In one embodiment, the sub-frame 128 may provide solid connections for any fixed section and skeleton structure 130 by rigidly connecting the skeleton structure 130 directly to the sub-frame 128. In this manner, any fixed section and skeleton structure 130 may be rigidly connected to the sub-frame 128, and through the sub-frame 128, rigidly connected to the floor.

Figure 11:
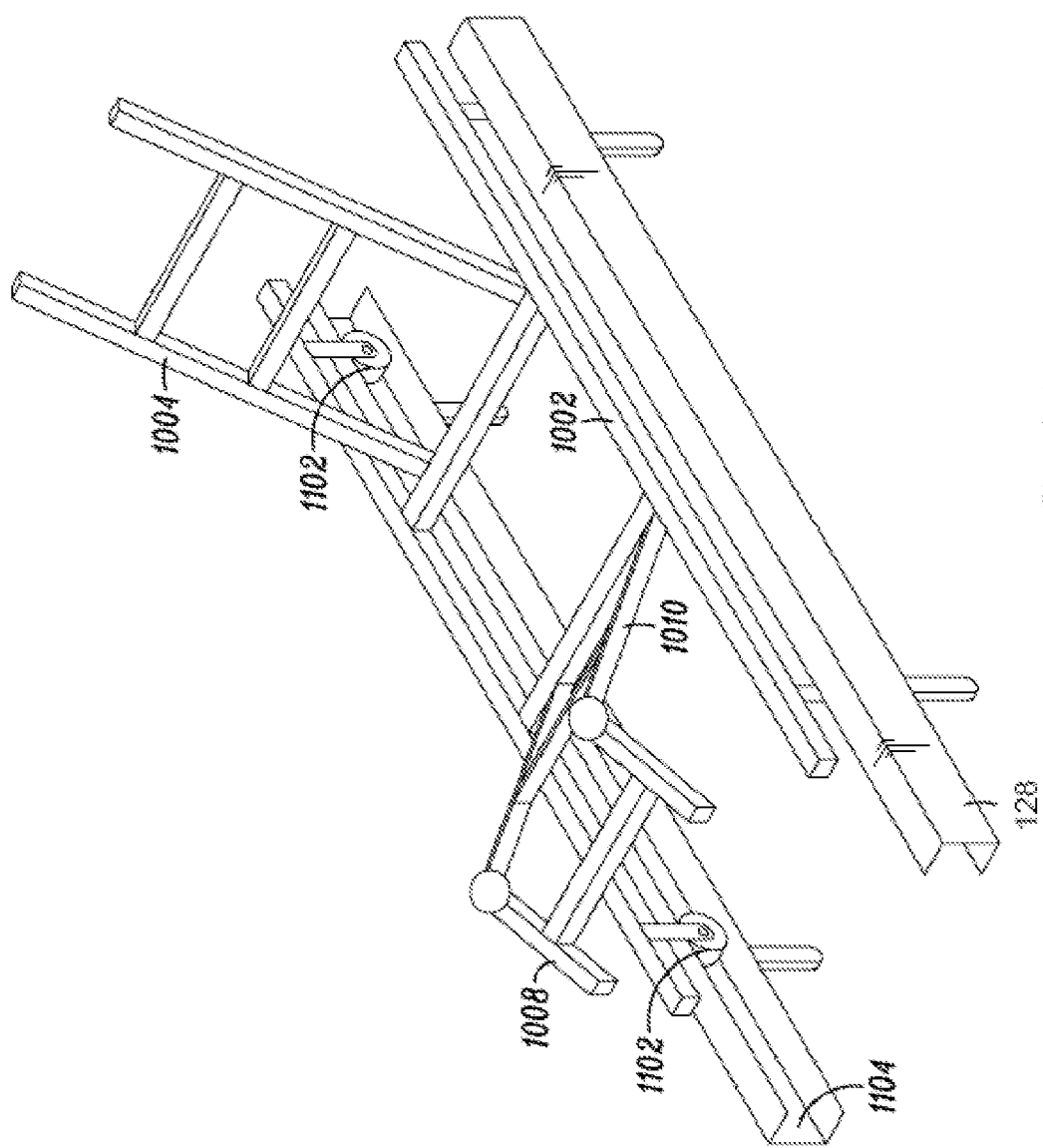
FIG. 11 shows operation of an adjustable bed facility according to an embodiment of the present invention.

In another embodiment, the sub-frame 128 may provide an interface for the fixed adjustable bed facility 102 section and skeleton structure 130 where the fixed section may be able to move or slide in relation to the sub-frame 128. By providing a non-rigid interface connection between the sub-frame 128 and the skeleton structure 114, the fixed adjustable bed facility 102 section may have a freedom of motion but still may be supported by the sub-frame in a solid foundation manner. For example, as shown in FIG. 11, the center frame 1002 may have wheels 1102 that run in a track 1104 and may be able to move horizontally during the motion of one or more of the movable frames. The track 1104 may be in form of a groove, a "C" channel, or the like. Alternatively, the track 1104 may be in the form of a tube and the wheels 1102 may include a concave surface that meets the track 1104, allowing the wheels 110 to run over the track 1104. In an embodiment, the horizontal freedom of motion may provide for a "wall hugger" feature where, as the head frame 1004 is adjusted up, the center frame 1002 may move, along with the head frame 1004, horizontally backward and towards an adjacent wall to maintain a fixed distance between the head frame 1004 and the wall, therefore "hugging" the wall. Similarly, when the head frame 1004 is adjusted down, the center frame 1002 may move horizontally forward and away from the wall to maintain the fixed distance. It may be understood by one skilled in the art that the moveable interface between the skeleton structure 130 and sub-frames 128 may be any type of interface, such as a rack and a pinion arrangement that may allow freedom of motion between the sub-frame 128 and skeleton structure 114.

Figure 12:
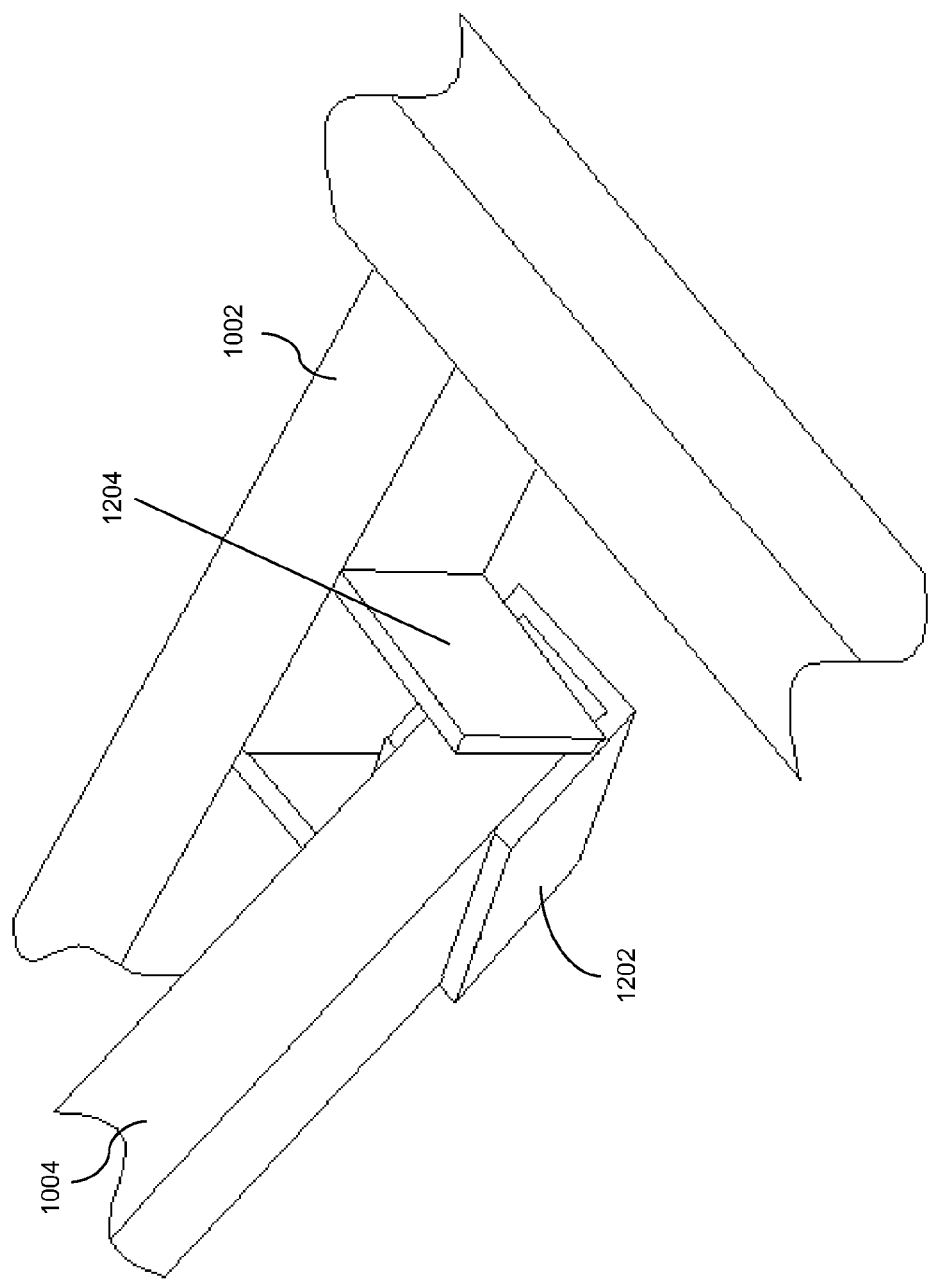
FIG. 12 shows a hinge joint between the frames/sections of an adjustable bed facility.

In an embodiment, any adjustable section/frame may have two connections, a first connection may be provided by a hinge type connection and a second connection may be the connection with the actuator 120 and safety bracket 138 that may provide the force to rotate the adjustable bed facility 102 section up or down. In an embodiment, the hinge type connection between the skeleton structure 130 of a first section and a second section may provide the point of rotation for the section motion. In an embodiment, the adjustable bed facility 102 may contain more than one section and any or all of the sections may be connected by a hinge type connection. For example, as shown in FIG. 12, the head frame 1004 may be connected to the center frame 1002 by two hinge joints. Here, the parallel side frame members of the head frame 1004 may be pivotally connected to a forward connector frame member 1014 of the center frame 1002. The hinged joints between each of the parallel side frame members of the head frame 1004 and the forward connector frame member 1014 may enable the rotational motion between the center frame 1002 and the head frame 1004. In an arrangement of this embodiment, the hinge joints may be reinforced by providing a "U" shaped end bracket 1202 at the end of the parallel side frame members. The "U" shaped end bracket 1202 may be of any thickness that increases the strength of the hinge joint to prevent bending. The thickness of the "U" shaped end bracket 1202 may be determined by the amount of force and torque that may need to be resisted during the movement. Embodiments of the hinge type connection may include door hinges or the like.

Figure 13:
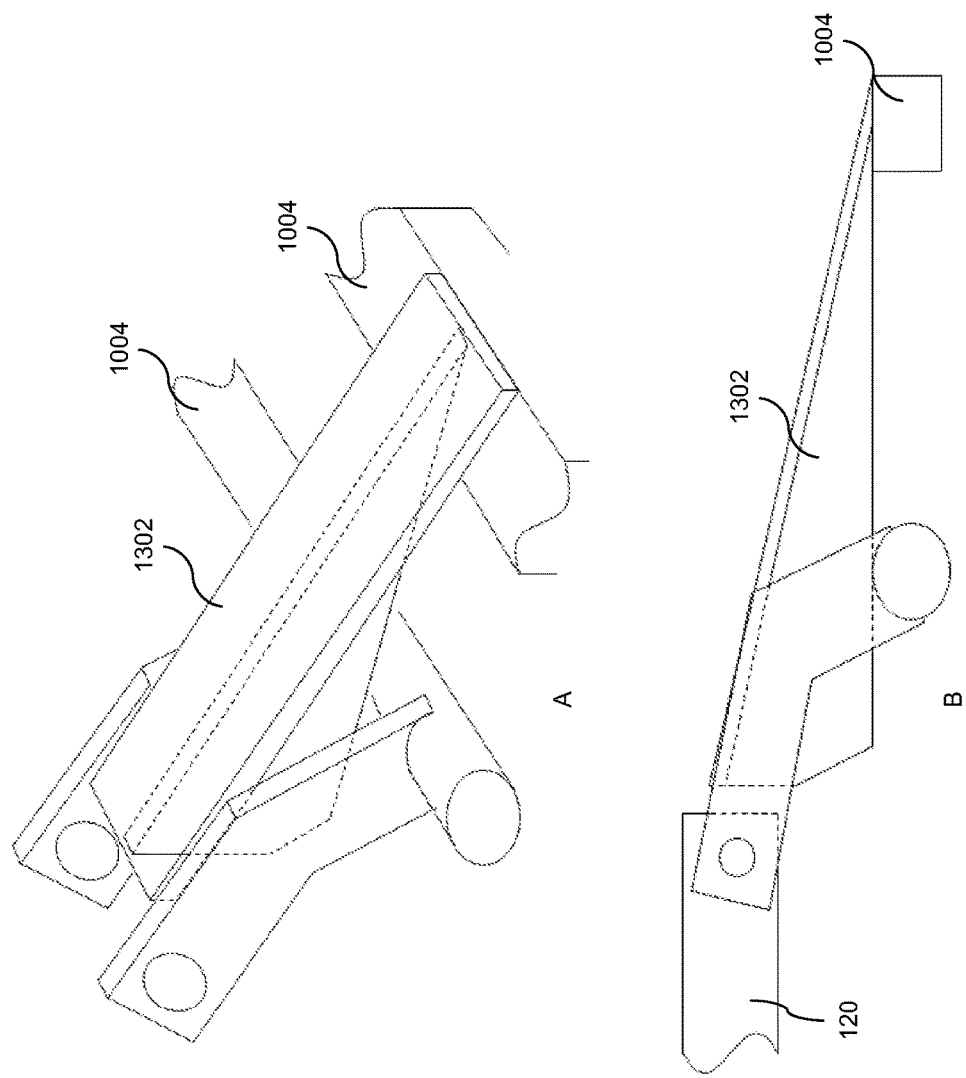
FIG. 13 shows a gusset in accordance with an embodiment of the present invention.

With the adjustable bed facility 102 sections interconnected using hinge type connections there may be at least one actuator 120 that may provide a connection between a fixed adjustable bed facility 102 section and a moveable section. In an embodiment, the hinge connection between the adjustable bed facility 102 sections may be a pivot point bracket that may include additional strengthening to resist bending forces. In an embodiment, the actuation 104 connection may be between two of the skeleton structures 114. For example, a first end of the actuator 120 may be connected to the rear connector frame member 1018 of the center frame 1002 and a second end of the actuator 120 may be connected to the frame that is to be moved (e.g. head frame 1004, leg frame 1010, or foot frame 1008). In an arrangement, as shown in FIG. 13, a downwardly facing extension frame member/a gusset 1302 may be attached to the head frame 1004 or any other frame to be moved. Further, the actuator 120 may be connected to the head frame 1004 to be moved using the downwardly facing extension frame member.

In an embodiment, as shown in FIG. 13, there may be the gusset 1302 for connection between the actuator 120 and the adjustable bed facility 102 section/frame. In embodiments, the gusset 1302 may be an I beam, a T beam, an L beam, a box beam, or any other beam design that may provide the strength to lift the combined weight of the adjustable bed facility 102 section and the user without bending. In an embodiment, to resist bending forces at the connections to the actuator 120 and the adjustable bed facility 102 section, the ends of the gusset may be reinforced. In embodiments, the reinforcement may be an additional bracket added to the ends of the gusset, such as a U bracket or other bracket shape, to provide for increased material thickness and strength of the gusset ends. The thickness of the additional bracket may be determined by the amount of force and torque that may need to be resisted during the adjustable bed facility 102 section movement.

In an embodiment, the controller 150 may coordinate the electronic requirements of the electronic facility 140. In an embodiment, the controller 150 may interface with the communications module 144, remote control 118, air purification facility 160, zone climate control 162, power outlets 154, power connection 158, power supply 152, modular controls 148, wire harness 142, and the like. In an embodiment, the controller 150, communications module 144, and power supply 152 may be mounted directly to the skeleton structure 114. The controller 150, communications module 144, and the power supply 152 may be mounted on the center frame 1002. In order to provide a proper mounting space to the controller 150, the communications module 144, and the power supply 152, an additional frame member 1402 may be added. The additional frame member 1402 may be made of a tubular construction. The additional frame member 1402 is designed in such a manner that it can bear the load of the components mounted on it. In another embodiment, the controller 150, the communications module 144, and the power supply 152 may be mounted on any other frame member of the center frame 1002.

FIG. 15 illustrates an accelerometer 1504 for an adjustable bed 1510 in accordance with an embodiment of the present invention. To describe FIG. 15, reference will be made to FIGS. 10A, 10B, and 11, although it is understood that the accelerometer 1504 can be practiced in different embodiments. Those skilled in the art would appreciate that the accelerometer 1504 may have more or less system elements.

As shown in FIG. 15, the adjustable bed 1510 may include a controller 1502 and a processor 1508. The controller 1502, which may be fixed to the moving frame of the adjustable bed 1510, may include the accelerometer 1504. In embodiments, the accelerometer 1504 may be wired to an electronic circuit inside the controller 1502. Further, the accelerometer 1504 may generate one or more signals in response to the change in the speed of movement of the adjustable bed 1510.

In the present embodiment, the signals generated by the accelerometer 1504 may represent the acceleration or deceleration in the movement of the adjustable bed 1510. These signals may be transmitted to the processor 1508 for processing. The processor 1508 may encrypt the received signals and may generate instructions in response to the received signals. For example, the instructions may correspond to stopping the movement of the adjustable bed 1510. Following this, the processor 1508 may communicate the instructions to the controller 1502 of the adjustable bed 1510. In embodiments, a controller in the controller 1502 may control the adjustable parameter(s) of the adjustable bed 1510 in response to the received instructions. For example, the accelerometer 1504 may generate one or more signals corresponding to the deceleration in the movement of the adjustable bed 1510 caused by an added significant weight. The accelerometer 1504 may transmit these signals to the processor 1508. The processor 1508 may instruct the controller 1502 to cease the movement of the adjustable bed 1510. This may ensure the safety of a user. Also, the accelerometer 1504 may detect changes in the speed of the movement of the adjustable bed 1510, where the movement is hindered by an object trapped inside the adjustable bed 1510.

In embodiments, the processor 1508 may encrypt the received signals and may convert to signal values. These received signal values may be compared with a pre-determined threshold value. These threshold values may be stored in the controller 1502 and may be set/reset by an administrator. In an exemplary scenario, the processor 1508 may instruct the controller 1502 to cease the movement of the adjustable bed 1510 when the received value exceeds the pre-determined threshold value.

In another exemplary scenario, the accelerometer 1504 may detect the blocked movement of the adjustable bed 1510 and transmit these signals to the processor 1508. In response to the transmitted signals, the processor 1508 may instruct the controller 1502 to cease the movement of the adjustable bed 1510. Also, the controller 1502 may move the adjustable bed 1510 slightly. Such movements may ensure the safety of the user. For example, a user may get on/off the adjustable bed 1510 or jump on/off the bed or in similar situations, the movement of the adjustable bed 1510 may be stopped. Therefore, a movable frame of the adjustable bed 1510 may be programmed to cease its operation whenever the user makes a significant motion.

In one embodiment, the controller 1502, with an accelerometer 1504, may be mounted on the center frame 1002 of the adjustable bed 1510. As described previously, the horizontal freedom of motion of the adjustable bed 1510 may provide a "wall hugger" feature to the adjustable bed 1510. In this embodiment, as the head frame 1004 is adjusted up, the center frame 1002 may move, along with the head frame 1004; i.e., the center frame 1002 may move horizontally backward and towards an adjacent wall to maintain a fixed distance between the head frame 1004 and the wall, therefore "hugging" the wall. In such an arrangement, the accelerometer 1504 may detect the fast and/or slow movement of the adjustable bed 1510 towards or away from the wall. These signals may then be transmitted to the processor 1508. The processor 1508 may instruct the controller 1502 to cease the movement of the adjustable bed 1510.

In another embodiment, the horizontal freedom of motion of the adjustable bed 1510 may be limited. Such adjustable beds 1510 may be referred to as "non-wall hugger" types. In this embodiment, the restricted horizontal movement of the center frame 1002 may limit the backward and forward movement towards or away from an adjacent wall. Therefore, the adjustable bed 1510 may not hug the wall. In the present arrangement, the controller 1502 may be placed along the head frame 1004 of the adjustable bed. As the head frame 1004 is adjusted up or down, the controller 1502 may move along with the head frame 1004 moving up and down. In response, the accelerometer 1504 may transmit the signals representing the change in the movement of the head frame 1004 of the adjustable bed to the processor 1508. The processor 1508 may instruct the controller 1502 to cease the movement of the adjustable bed 1510 in response to the signals received from the accelerometer 1504. For instance, the blocked movement of the adjustable bed 1510 may reduce the movement of the adjustable bed 1510. As a result, the processor 1508 may address the controller 1502, and the movement of the adjustable bed 1510 may be stopped.

In another embodiment, the accelerometer 1504 may be placed in the drive motor of the adjustable bed 1510. In embodiments, the accelerometer 1504 may be wired to the PCB of the motor. In such an arrangement, the accelerometer 1504 may be coupled to at least one portion of the motor that may not retract against a force. In the present embodiment, the accelerometer 1504 may generate and transmit signals representing blocked movement of the frame or the motor. The movement may be blocked by an object or a person. The transmitted signals may be compared with the pre-determined threshold value. Accordingly the movement of the adjustable bed 1510 may be stopped. The transmitted signals may vary according to the use of the adjustable bed facility.

In embodiments, the accelerometer 1504 and the processor 1508 may transmit the signals wirelessly. The wireless communication may be by radio frequency (RF), UHF, HF, infrared (IR), BLUETOOTH, or the like. In embodiments, the controller 1502 may have an antenna to receive the control signals from the processor 1508. In an embodiment, the wireless technology may include BLUETOOTH, ultra-wideband (UWB), wireless USB (WUSB), IEEE 802.11, cellular, or the like.

The remote control 118 may include one or more motion detection devices, such as accelerometers, magnetic field detectors, and the like. The remote control 118 may detect a motion of the remote control 118 through these devices and communicate a representation of that motion to the controller 150 to enable control of a feature of the adjustable bed. In an example, a user may make a lifting motion with the remote control 118 and the controller 150 may begin to raise an adjustable portion of the bed until the user makes another motion, such as a back and forth motion indicating to the controller 150 to stop raising the adjustable bed portion. Various other gestures may be made by with the controller to perform other functions including lifting a leg portion of the bed, lowering a back portion of the bed, and the like. Similarly, the gestures could be used to control one or more of the auxiliary devices, to play games on a display controlled by the remote control 118 similarly to a hand held game console device, and the like.

In embodiments, the remote control 118 may include slider controls 1604 that enable the user to control aspects of the adjustable bed facility 102, such as shown in FIG. 16. The slider control 1604 may function when a user slides their finger along the slider control 1604 in adjustment of some aspect of the adjustable bed facility 102, such as the adjustment of a position motor, the power level of a vibration motor, and the like. In addition, the slider control 1604 may control an adjustable feature within the modular controls 148 of the adjustable bed facility 102, such as the volume level of an audio device, the volume level of an audio-visual device, the lighting level of a lamp, a setting of the air purification system 144, the setting of a height of a motorized set of blinds, the speaker volume level of a phone, and the like. The slider control 1604 may be in a plurality of shapes, such as circular 1604A, linear 1604B, semi-circular, and the like. In embodiments, the slider control 1604 may be configured in a two dimensional area, where control is provided in multiple dimensions, such as on the touchpad of a laptop computer. In embodiments, the slider may be implemented with a plurality of technologies, such as the use of a mechanical slider that moves along a track as the user moves their finger, a capacitive coupled touch surface that utilizes changes in capacitance resulting from a user touching or pressing against the slider control 1604 surface, a piezoelectric coupled touch-screen that utilizes changes in electrical potential resulting from a user touching or pressing against the slider control 1604 surface, a thin film transistor (TFT) touch-screen LCD display, and the like. In embodiments, the touch-screen technologies may have the look and operate in a similar fashion to more conventional mechanical slider and wheel configurations. In addition, the touch-screen technologies may be configured in a layout depicting the physical layout of some mechanical device or control, such as a button, a wheel, a slider, or the like, or a pictorial representation of the adjustable bed, with lift motor buttons, vibration motor buttons, sliders for moving the positions of adjustable portions of the bed, and the like. In embodiments, the use of slider controls 1604, implemented any one of a plurality of technologies, may provide the user of the adjustable bed facility 102 with greater flexibility and/or greater ease of use in implementing a controllable aspect of the adjustable bed facility 102.

In embodiments, the remote control 118 may utilize a combination of push button controls 1602 and slider controls 1604. Push buttons may not only perform discrete functions, such as push to active/deactivate an adjustable bed facility 102 function, but may be used in combination with the slider control to select a function of the slider control 1602 or change some aspect of the slider control 1602. For example, a push button control 1602 may sequence through a choice of functions that the slider 1604 controls, such as clicking a button 1602 once for head motor position control, twice for foot motor control, three times for head vibration power level, and the like. In addition, the selected function may be indicated visually though some display capability of the remote control 118, such as through LEDs, an LCD display, or the like. In embodiments, the buttons 1602 may be used in combination with the slider control 1604 to adjust the sensitivity of the slider control 1604, such as pressing a button 1602 a plurality of times to make control of a position motor through the slider control 1604 more or less sensitive, slower or faster, and the like. In embodiments, buttons may provide a plurality of other slider control 1604 related features, such as calibration, default position setting, reset control, and the like. In embodiments, the slider control 1604, when depressed with increased pressure, may perform as a button control, where functions as discussed herein are executed with the use of the slider control 1604 acting as a button control 1602.

In embodiments, there may be a display indication on the remote control 118 associated with the position of articulated portions of the adjustable bed facility 102, such as providing a numeric indication, a visual indication, a bar graph indication, an illuminated slider indication, and angle indication, or the like. For instance, the position of the articulated head portion of the adjustable bed facility 102 may be adjustable from a flat position to a position of maximum elevation, say up at 70 degrees. The remote control 118 may control the positioning of the head portion, and the current position may be indicated by, for example, a number from 0 to 100, where 0 represents the flat position, and 100 represents the most elevated position. In this example, the display of the remote control 118 may indicate the numerical equivalent to the current position, where the numerical indication changes as the head portion of the adjustable bed facility 102 moves. In embodiments, the remote control 118 implementation may utilize any of a plurality of numeric schemes, as the number may only be a representation of the position of the bed. In addition, the user may be able to input the numerical equivalent into the remote control 118 device, for example, by inputting a number such as 50, and having the head portion of the adjustable bed facility 102 rise to a halfway position. The user may be able to store the numerical equivalent of their favorite positions, such as a user inputting and storing the number 25, and being able to recall the stored position in any of a plurality of ways associated with the controls of the remote control 118, such as depressing a memory recall button or the like. The user may also use the remote's sliders 1604 to easily find a position number they desire, even if not saved in memory, select it and then have the frame go to it immediately. This may let the user select, push, and relax rather than having to hold a button and pay attention to the location of the adjustable bed facility 102 as it moves near the desired position. These examples are meant to be illustrative of how a numeric or alphanumeric characters may be used to monitor, store, and recall articulated bed facility 102 positions, and is not meant to be limiting. One skilled in the art would recognize the plurality of similar schemes to achieve similar results. In embodiments these methods may be applied to any remote control 118 parameter, including head motors, foot motors, vibration motors, and the like, as well as modular controls 148 such as audio, video, lamps, air purification, outlets, and the like.

In embodiments, the display indication on the remote control 118 may be associated with a memory function resident on the remote control 118, or in association with the table data 202, 222 stored in the controller 150, as described herein. In embodiments, the implementation of the display indication may be associated with both a memory function in the remote control 118 and the table 202, 222 in the controller 150. This implementation may utilize two-way communications between the remote control and the controller 150, so as to produce a closed-loop command and verification scheme. For instance, in a scheme where commands are only transmitted to the controller 150, the display on the remote control 118 may only indicate the commanded intention of the user, and may under some circumstances, such as when a command is not received by the controller 150, reflect the current state of the adjustable bed facility 102. With two-way communications however, the remote control 118 may always reflect the state of the adjustable bed facility 102 as verified by a return confirmation, or in returned telemetry, from the controller 150. The returned confirmation may reflect the state of the adjustable bed facility 102 as provided in the controller's data table 202, 222, such as the current pointer position in the table 202, 222, a memory location stored in the table 202, 222, a memory location not stored in the table 202, 222, the total range depicted in the table 202, 222, and the like. As a result, the two-way communications scheme may provide a more reliable system implementation. In embodiments however, a one-way command scheme may provide an effective system implementation at a reduced cost. In embodiments, a one-way scheme may utilize a state synchronization event, such as a reset whenever the adjustable bed facility 102 is set back to the flat position, to help ensure that the positions indicated by the remote control 118 are periodically synchronized to the data stored in the adjustable bed's controller 150.

In embodiments, groupings of push buttons 1602 may be provided with adjacent button 1602 suppression. Adjacent button 1602 suppression may work to prevent multiple buttons 1602 or sliders 1604 from responding to a single touch, which may occur with closely spaced buttons 1602 or sliders 1604, such as on a remote control 118. This may be especially the case for users of an adjustable bed facility 102 that are experiencing reduced motor control due to illness or advanced age. Adjacent button 1602 suppression may operate by comparing signal strengths from buttons 1602 within a group of buttons 1602 to suppress touch detections from those that have a weaker signal change than the dominant one. When enabled, the adjacent button 1602 suppression may allow only one independent button 1602, or slide control 1604 function, to indicate one touch at a time. In embodiments, adjacent button 1602 suppression may be enabled or disabled, either globally for all buttons 1602, or for a subset of buttons 1602, leaving other buttons 1602 to be used in combination.

In embodiments, the remote control 118 may provide for proximity sensing, such that a user may execute a function by bringing their hand close to the remote control 118. For instance, the remote control 118 may change power modes as a result of a user moving their hand in close proximity to the remote control 118, such as from a low power mode to a fully active mode. This proximity effect may be implemented through use of a capacitively coupled sensor, utilizing a large electrode within the remote control 118, where the change in capacitance due to the close proximity of the user's hand is sufficient to activate the sensor, and thereby executing the function. In embodiments, the function activated may be any function under remote control, as well as functions such as power modes. Power modes may include a plurality of modes, such as a free-run mode, a low power mode, a sleep mode, and the like. The power mode may be activated either manually, for instance via some button control 1602, or automatically, but such activation indicators as the proximity sensor, a timer function, light source presence, and the like.

In an embodiment, a motion sensor may be provided, either associated directly with the adjustable bed facility 102, on the remote control, or in the environment, such that any movement in the bed may be detected. For example, if a child is sleeping and gets up due to hunger, distress or the like and leaves the adjustable bed 102, the motion sensor may be activated and may signal an alarm indicating the child is awake. In a similar manner, the remote control may provide a sound sensor, such that any noise made in the room may be detected. For example, a child crying, any intruder in the room, any abnormal disturbances like earthquake and the like, may activate the sound sensor. The sound sensor may transmit the signals and an alarm may ring indicating additional noise or disturbance in the room. More generally, any of the types of sensors described herein, such as motion sensors, sound sensors, weight sensors, chemical sensors, smoke detectors, temperature sensors, pressure sensors, or the like may be used to sense a condition of the environment associated with the adjustable furniture facility or a user of the control facility to sense a condition or determine a state or event that may, under control of the control facilities for the adjustable furniture facility, be used to trigger actuation of a component of the adjustable bed facility or one or more of the other systems associated with the adjustable bed facility. The sensor may be included in a feedback loop whereby the sensor continuously updates the control facilities as components or systems are controlled to arrive at an optimal control state for the adjustable furniture facility or for another system associated with the adjustable furniture facility. In addition, the control facilities may obtain information about the state of a user, a state of the adjustable furniture facility, or the state of another system associated with the adjustable furniture facility through a computer or information technology facility, such as by network communication of state information from the adjustable furniture facility or another system. The state information may be used to control or actuate a component of the adjustable furniture facility or of another system associated with the adjustable furniture facility. In embodiments, state information may be integrated at the control facility using a data integration facility. In embodiments state information may be obtained at the control facility by pinging or pulling information from other systems, or by having state information pushed to the control facility by the other systems. In embodiments one or more services (such as software-based services), may be used to communicate state information between or among the control facility for the adjustable bed facility and one or more other systems, such as in a services-oriented software architecture. Devices may thus communicate their state information to the control facility for the adjustable bed facility 102, such as state information about on/off condition, operational levels such as volume control, temperature control, and the like, state information about users, state information about the environment, state information about content (such as information about music, video, television, computer gaming or other content), state information about safety, and any other state, condition or attribute described throughout this disclosure. State information, whether obtained from sensors or by communication among devices, may be used to determine an event or attribute that can in turn trigger actuation of control; thus, the control system for the adjustable furniture facility may actuate a wide range of actions, on the adjustable furniture facility or on another system associated with it, based on state information. Examples include actuating an alert in response to a safety condition (such as crying child, a child out of bed, stillness of an elderly patient, or the like), adjusting entertainment content in response to a state (turning off the system or turning down volume upon detecting snoring, turning down the lights on detecting sleep, selecting preferred content upon detecting presence of a particular user), adjusting comfort-based factors based on state detection (adjusting position, vibration, temperature, volume, content or the like based on detection of user's presence; adjusting some component based on time of day), and many others.

In embodiments, the remote control 118 may provide for reduced susceptibility to RF noise, possibly due to the electro-magnetic environment the adjustable bed facility 102 is exposed to. For example, the remote control may provide RF transmissions that operate in a burst mode, where bursts are transmitted utilizing spread-spectrum techniques. Such a technique may provide transmission over a spread of frequencies, so that external fields may have a reduced effect on the operation of the remote control 118.

In embodiments, the remote control 118 may provide for a data and power cable interface to provide recharging and data exchange capabilities with the remote control 118. The data portion of the cable interface may interface with a computing facility, such as personal computer, mobile computing device, PDA, mobile phone, another remote control 118, a troubleshooting facility, and the like. The power portion of the cable interface may provide for the recharging of the remote control's 118 batteries, and in embodiments, may be similar to that of a cell phone charging cable. In embodiments, the data and power interface may utilize a standard data and power interface, such as USB and the like. In embodiments, at least one of the remote control 118 and data and power cable interface may have indicator lights, such as for charging status, charging on, charging complete, low battery, critical battery, data transfer status, data transfer on-going, data transfer complete, and the like. In embodiments, indicator status may also be displayed, such as on the remote control's 118 LCD display. In embodiments, the data and power cable may be implemented in a plurality of configurations, such as data and power in a single cable, data in one cable and power in a second cable, common cable connectors for data and power, separate cable connectors for data and power, common remote control 118 interface connectors for data and power, separate connectors for data and power, and the like. In addition, the power portion of the data and power cable may be shielded to avoid interference from coupling into the data lines of the data portion of the data and power cable interface. In embodiments, the connection between the remote control 118 may or may not be associated with a cradle for holding the remote control 118 during recharging and/or data exchange. In embodiments, the remote control's 118 data and power cable may make it more convenient to plug the remote control 118 into a power outlet for charging by not requiring the remote control 118 to be inserted into a cradle.

In embodiments, the remote control 118 may provide the data interface to enable internet browsing and program processing capabilities within the remote control 118. The data interface may interface with a computing facility, such as personal computer, mobile computing device, PDA, mobile phone, and the like. The data interface may provide access to programs such as calculator, word processor, image processor, internet browsers, and the like. In embodiments, the program status and content accessed may be displayed, such as on the remote control's 118 LCD display. The status and the content of the program may include the network connection status, internet usage time, available updates over the network, and the like. In embodiments, the data interface may be implemented in a plurality of configurations, such as data cable, wireless communication, and the like. In an embodiment, the data cable may include the standard data interface, the USB, or the like. In an embodiment, the wireless technology may include BLUETOOTH, ultra-wideband (UWB), wireless USB (WUSB), IEEE 802.11, cellular, or the like.

In embodiments, the data interface portion of the cable interface may enable data exchange between the remote control 118 and the computing facility such as for a programming the remote control 118, a full reprogramming of the remote control 118, a partial reprogramming of the remote control 118, the reprogramming of an individual function in the remote control 118, trouble shooting the remote control 118, an exchange of information between the remote control 118 and the computing facility, the downloading of the contents of the remote control 118 onto the computing facility, the downloading of the remote control's 118 programming to the computing facility, the transferring of user preferences to or from the computing facility including to another bed's remote control 118, the upgrading of new features to the remote control 118, download the usage history of the remote control 118, and the like. In embodiments, the data interface portion of the data interface may provide for a programming interface to setup or change the functions of the remote control 118, such as to reassign a button 2002 function, reassign a slider control 2004 function, provide new sequences available for slider control 2004, provide changes to power mode settings, change power up default settings, and the like.

An aspect of the present invention relates to error reporting through a two-way remote control system associated with an adjustable bed. The two-way communications protocols may allow for a hand held remote control (as describe herein) to communicate commands to an adjustable bed (as described herein) to control the adjustable bed. The bed may communicate back to the hand held remote control information relating to the functioning of the bed. The controller of the bed may, for example, communicate errors to the remote control to facilitate maintenance and repair of the adjustable bed systems. The error reporting may be provided through codes such that a technician can understand them (i.e. with reference to a manual) or the reporting may involve presenting language based error reports for easier diagnosis. In embodiments, the error reporting is presented on a display screen on the hand held remote control unit.

In embodiments, the remote control 118 may provide for error reporting, such as to identify failures or errors within the adjustable bed facility 102, including within the remote control 118 itself. Reported Errors may be characterized as fatal errors, such as when some function within the adjustable bed facility 102 no longer working (e.g. a motor failure, controller failure, sensor failure, etc.). Reported errors may be characterized as; non-fatal errors, such as some function within the adjustable bed facility 102 not performing within required limits (e.g., diagnostic information used in assessing the health of the adjustable bed facility 102, such as how well a hall sensor is working, how much current the motors are drawing, etc.); and the like. Information associated with error reporting may be sent to the remote control 118 upon various events. For example, the systems may be arranged such that error reporting is done on an on-demand basis. That is, a user may activate an error reporting mode by either interacting with a user interface on the bed or on the remote. Once placed in error reporting mode, errors may be communicated to the remote. Once the error information is communicated to the remote, information relating to the error(s) may be displayed on the remote. In other embodiments, errors may be sent when as they occur. The systems may be placed in a mode where errors (either fatal or non-fatal or both) may be communicated to the remote on an on-going or periodic basis. In yet other embodiments, the systems may be arranged where information relating to the errors may be sent in an on-going basis and in an on-demand mode, or may be sent in some combination of on-demand and as errors occur. For example, fatal errors may be reported to the remote control 118 automatically as errors occur, but other non-fatal errors or diagnostic information may be delivered on-demand as they are requested.

In embodiments, fatal errors may include error messages associated with a motor that stops working, a controller communication failure, a remote control 118 communication failure, a power supply 152 that stops working, critical software errors, printed circuit board hardware errors, a blown MOSFET, a shorted regulator, and the like. In embodiments, non-fatal errors may include error messages associated with a power supply 152 that may be sourcing too much current, intermittent two-way RF communication, intermittent hall sensor reception, too much heat near or around the printed circuit board, general software errors, motors that may be drawing too much current, motors that may have been used excessively, beyond their duty cycle limits, and the like. In addition, non-fatal error or diagnostic information reporting may include general usage history information that may be useful in investigating the cause of problems, such as recalling the last ten or twenty actions of the adjustable bed facility 102, fatal error information reporting that may include use history that may help determine the cause of the fatal error, and the like.

In embodiments, the adjustable bed facility 102 may provide a steady stream of measurement data, such as in telemetry stream of engineering diagnostic information, to the remote control 118 or to a central information gathering facility to be used in the diagnosis of errors. In embodiments, information associated with error reporting may be stored for later retrieval, either within the adjustable bed facility or external to the adjustable bed, such as in the remote control 118 or associated with the central information gathering facility.

Figure 17A:
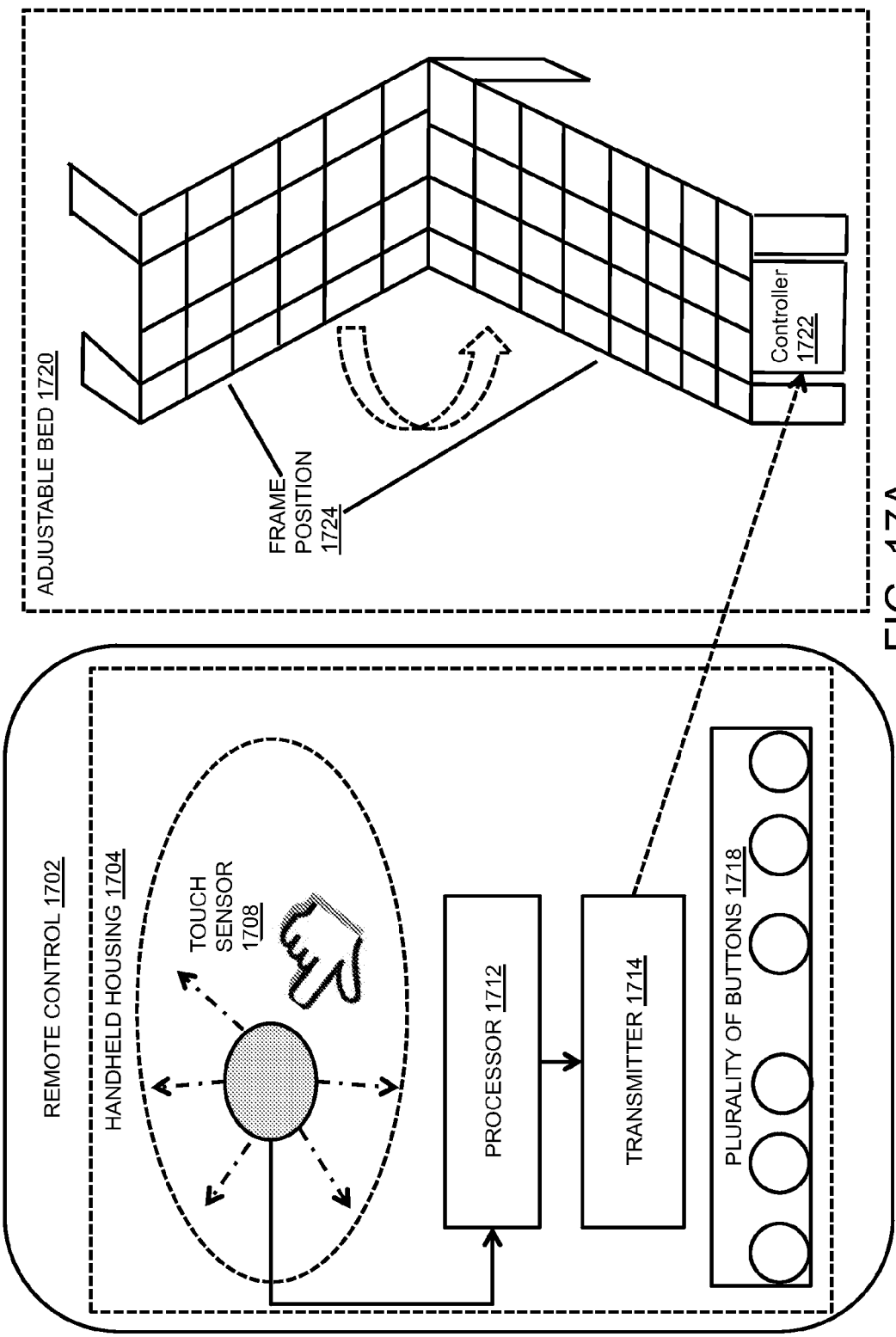
FIG. 17A depicts a remote control to control a frame position of an adjustable bed.

FIG. 17A depicts a remote control 1702 (e.g. remote control 118) to control a frame position 1724 of an adjustable bed 1720 (e.g. as described herein) in accordance with an embodiment of the present invention. The remote control 1702 is shown to have a front face of a hand-held housing 1704. The hand held housing 1704 of the remote control may include a touch sensor 1708 (e.g. touch sensors as described in connection with user input devices 1602 and 1604), a processor 1712, a transmitter 1714 and a plurality of buttons and/or switches 1718. In embodiments, the touch sensor 1708 may be adapted to facilitate a user in adjusting the frame position 1724 of the adjustable bed 1720. The touch sensor 1708 may be presented in a slider form. In embodiments, the slider may be in the form of a dial, a linear strip, a curvilinear strip, a curve, or some other similar shape. In embodiments, the touch sensor 1108 may be a capacitive touch sensor.

The touch sensor 1708 described herein may be constructed using a touch screen technology such as a capacitive touch screen, resistive touch screen, surface acoustic wave touch screen, strain gauge touch screen, optical imaging touch screen, dispersive signal technology touch screen, acoustic pulse recognition touch screen, or other touch sensor technology. The touch sensor 1708 described herein may be presented on the remote control in a variety of shapes and sizes, including, but not limited to: square, rectangular, linear, curvilinear, circular, round, etc. The shapes may be a pattern using a combination of shapes, such as an "X", "Y", "T", etc. The slider form of the touch sensor may facilitate changing a parameter of the bed or auxiliary equipment when a user slides, taps, touches, or otherwise interacts with the touch sensor.

In an exemplary scenario, a user of the adjustable bed 1720 may like to change the frame position 1724 of the adjustable bed 1720. The user may like to adjust the frame position from time to time to feel comfortable. In this case, the user may use the touch sensor 1708 of the remote control 1702 to adjust the frame position 1724 to a new frame position.

The touch sensor 1708 may be coupled with the processor 1712 and the transmitter 1714. The transmitter 1714 may receive inputs from the touch sensor 1708 via the processor 1710. The inputs may correspond to the interaction of the user with the touch sensor 1708. In embodiments, the interaction of the user with the touch sensor 1708 may generate instructions/control signals to control the frame position 1724. These instructions/control signals may be processed in the processor 1712. The processor 1712 may encrypt these instructions and provide to the transmitter 1714. The processor may also, or instead, address the instructions to be communicated to the bed such that only a bed associated with the address responds to the information. The transmitter 1714 may communicate these instructions/control signals to a control box 1722 of the adjustable bed 1720 and a controller in the control box may then control the adjustable parameter(s) of the bed in response to the received instructions.

In an embodiment, the transmitter 1714 may transmit the control signal/instructions wirelessly. The wireless communication may be by radio frequency (RF), UFH, HF, infrared (IR), BLUETOOTH, or the like. In embodiments, the control box 1722 may have an antenna to receive the control signals from the transmitter 1714. In an embodiment, the wireless technology may include BLUETOOTH, ultra-wideband (UWB), wireless USB (WUSB), IEEE 802.11, cellular, or the like.

On receiving the instructions/control signals, the control box 1722 may adjust the frame position 1724 of the adjustable bed 1720. For example, the user may like to tilt the various sub frames of the adjustable bed 1720 to sleep. The control box of the adjustable bed 1120 may tilt the position of the sub frames of the adjustable bed 1720. In embodiments, the adjustable bed 1720 may have a skeleton structure that may include more than one section/frame. The sections/frames may be fixed or may be adjustable/movable. Further, the sections/frames may be assembled together in such a way that the sections/frames may be able to move relative to each other to provide the various bed positions required by the user. To achieve this, the sections/frames may be connected together using hinges or like devices that allow a freedom of motion between them. Theses hinges/connections may be controlled by a Programmable Logic Circuit installed in the control box 1722.

In embodiments, the controller 150 may include a microcomputer, a microprocessor, volatile memory, non-volatile memory, IO connection to components, or the like. The controller 150 may provide an interface to permit software application updates to the controller 150 memory; the controller 150 memory may be over written. In other embodiments, the bed controller may be another form of controller, such as a set of specifically designed circuits designed to operate the adjustable bed 1720.

In another example, the control box 1722 may adjust the frame position 1724 in a configuration where only the head section may be adjusted to provide the user an elevated upper body position.

One skilled in the art may understand that there may be many different adjustable bed 1720 frame positions, which the user may change based on his requirements. It should be noted that the remote control 1702 may be shown to adjust the adjustable bed 1720, but those skilled in the art may appreciate that the remote control may control the parameters associated with adjustable chairs, adjustable couches, and the like to provide comfortable positions when the user may have limited mobility. For example, a user with hip replacement surgery may not be confined to the bed but may require a chair or couch to be adjustable to provide a comfortable sitting position while providing control of other devices within the room to limit the number of times the user must get up and adjust the devices. In an embodiment, while recovering from a surgery, an injury, an illness, or the like, the user may use more than one type of rest facility. The user may require confinement to an adjustable bed for a time and then, with health improvement, be able to move to either an adjustable chair or adjustable couch.

Figure 17B:
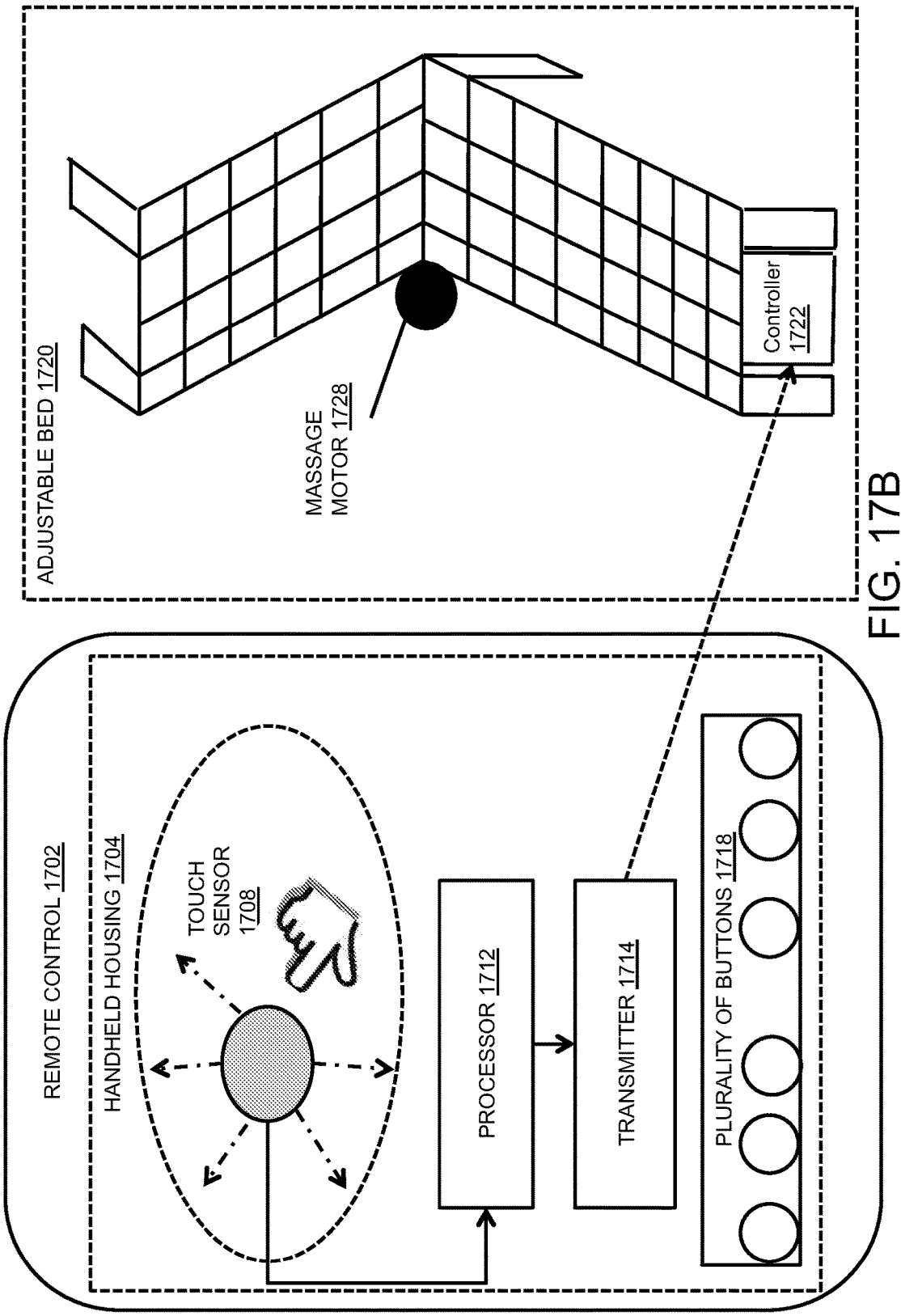
FIG. 17B depicts a remote control to control a massage motor setting of an adjustable bed.

In embodiments, as shown in FIG. 17B, the user may interact with the touch sensor 1708 to adjust the settings of a massage motor 1728 of the adjustable bed 1720. For example, the user may like to adjust the frequency, intensity, or other parameter of the massage motor 1728. The user may interact with the touch sensor 1708 and may provide the instructions to increase/decrease the frequency of the massage motor 1728. As described in the description for FIG. 17A, the touch sensor 1708 may provide the instructions to the transmitter 1714 through the processor 1712. The transmitter 1714 may communicate the instructions to the control box 1722 to change the frequency of the massage motor 1728.

In an embodiment, there may be at least one massage motor 1728 that may provide vibration and massage functions to the adjustable bed 1720. In an embodiment, there may be more than one massage motors in the adjustable bed 1720. In this embodiment, using the remote control 1702, the user may be able to control the vibration mode of the multiple massage motors; the mode may include the vibration setting for a particular bed section, the vibration frequency of at least one of the massage motors, stopping the vibration of at least one of the vibration motors, or the like. In an embodiment, the multiple massage motors may be operated independently or in combination. In an embodiment, the vibration and massage functions may function as a gentle-wake alarm, being activated in response to an alarm clock signal, which may be generated by the electronic facility 140 (e.g., by an alarm clock running in the controller 150 or the like) or may be received as a signal from an external source (e.g., from the remote control 118 or the like), and so on.

FIG. 17C depicts a remote control 1702 to control a plurality of parameters 1730 of an adjustable bed 1720 in accordance with an embodiment of the present invention. The plurality of parameters 1730 may include the parameters associated with the actuators, springs, mattresses, a sub-frame, a skeleton structure, vibration motors, supports, safety brackets, or any other parameter associated with any other facility of the adjustable bed 1720. For example, the user may wish to control the frame position as well as the air pressure/firmness of the mattress of the adjustable bed 1720. Firstly, the user may set the touch sensor 1708 of the remote control 1702 for the mattress parameters by using a button of the plurality of buttons 1718. Once the touch sensor has been set for the mattress parameters, the user may interact with the touch sensor 1708 to generate the control signals to adjust the mattress parameters. After that, the user may switch the mode of the touch sensor 1708 of the remote control 1702 for the frame control parameters. Accordingly, the user may interact with the touch sensor 1708 to generate the control signals to adjust the frame position 1724.

Figure 18A:
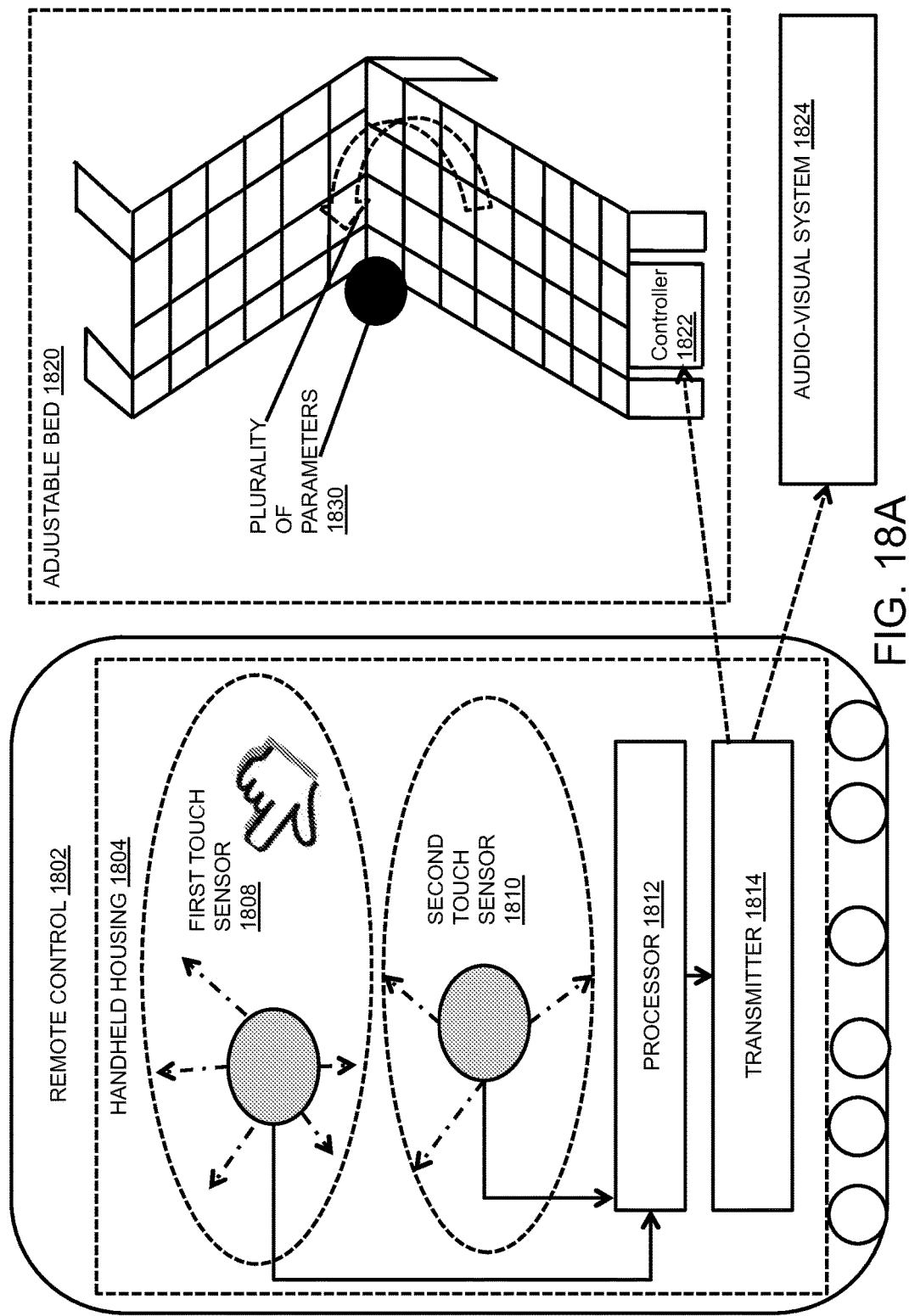
FIG. 18A depicts a remote control for controlling an adjustable bed and an audiovisual system.
Figure 18C:
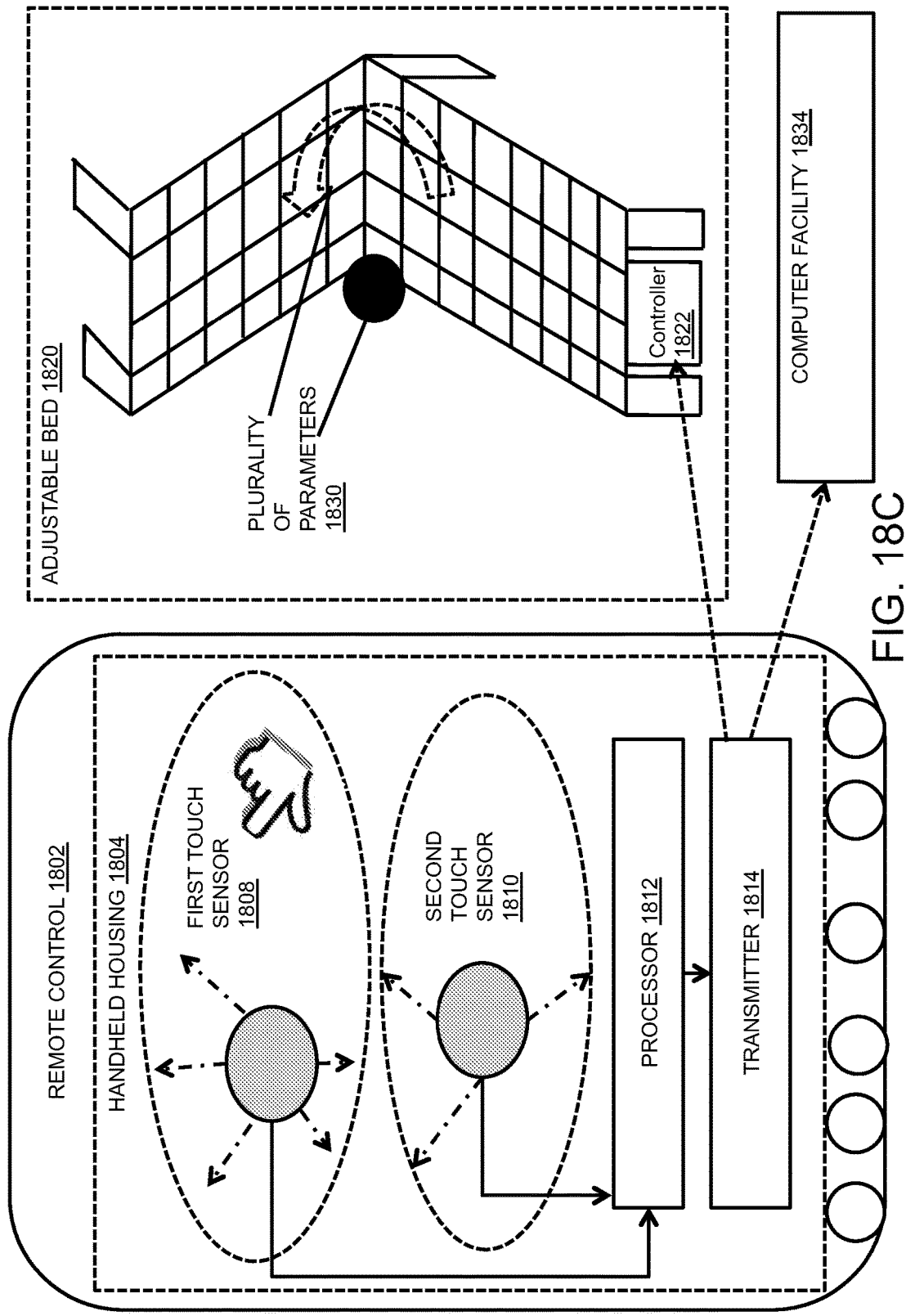
FIG. 18C depicts a remote control for controlling an adjustable bed and a computer facility.
Figure 18D:
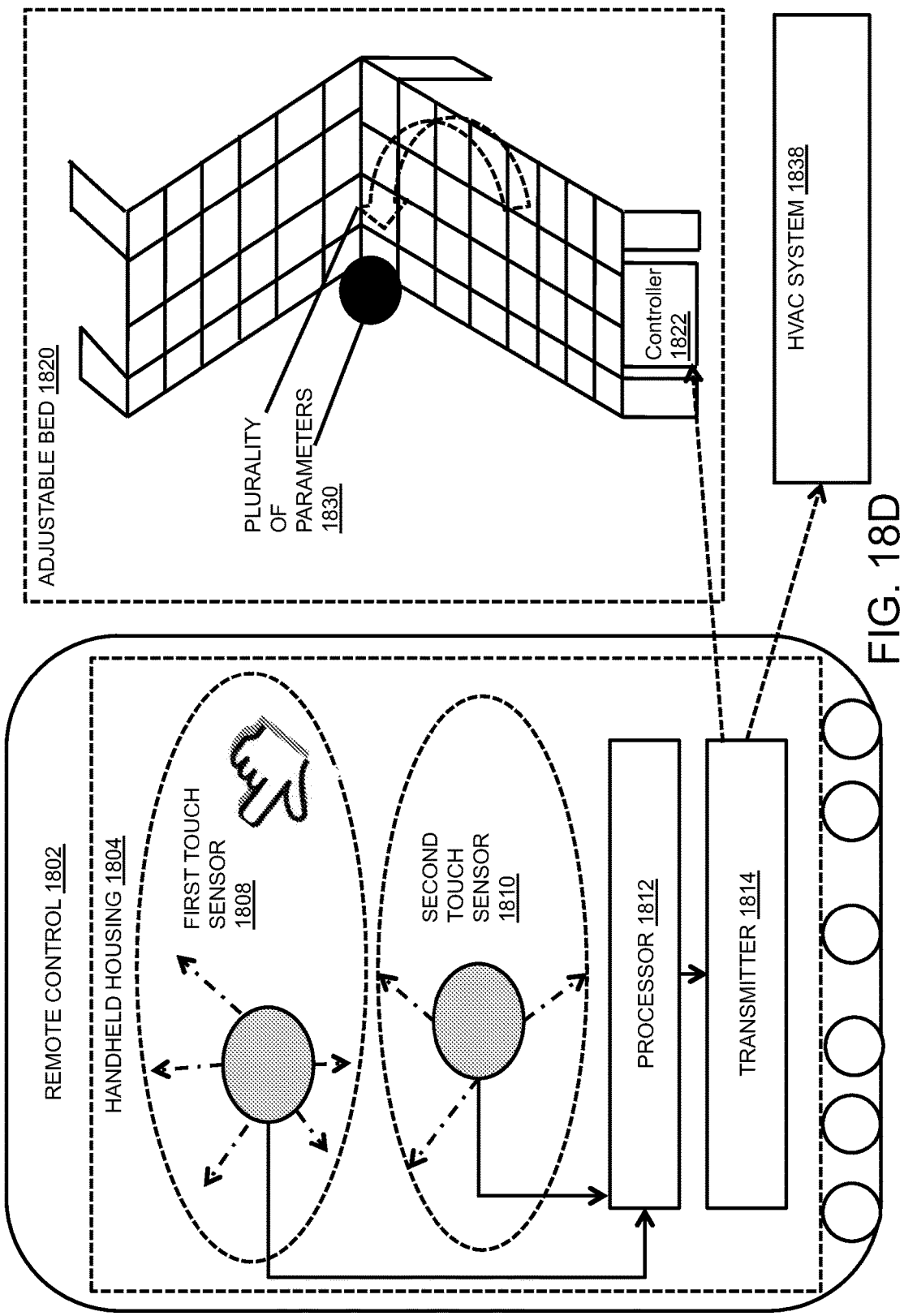
FIG. 18D depicts a remote control for controlling an adjustable bed and a HVAC system.
Figure 18E:
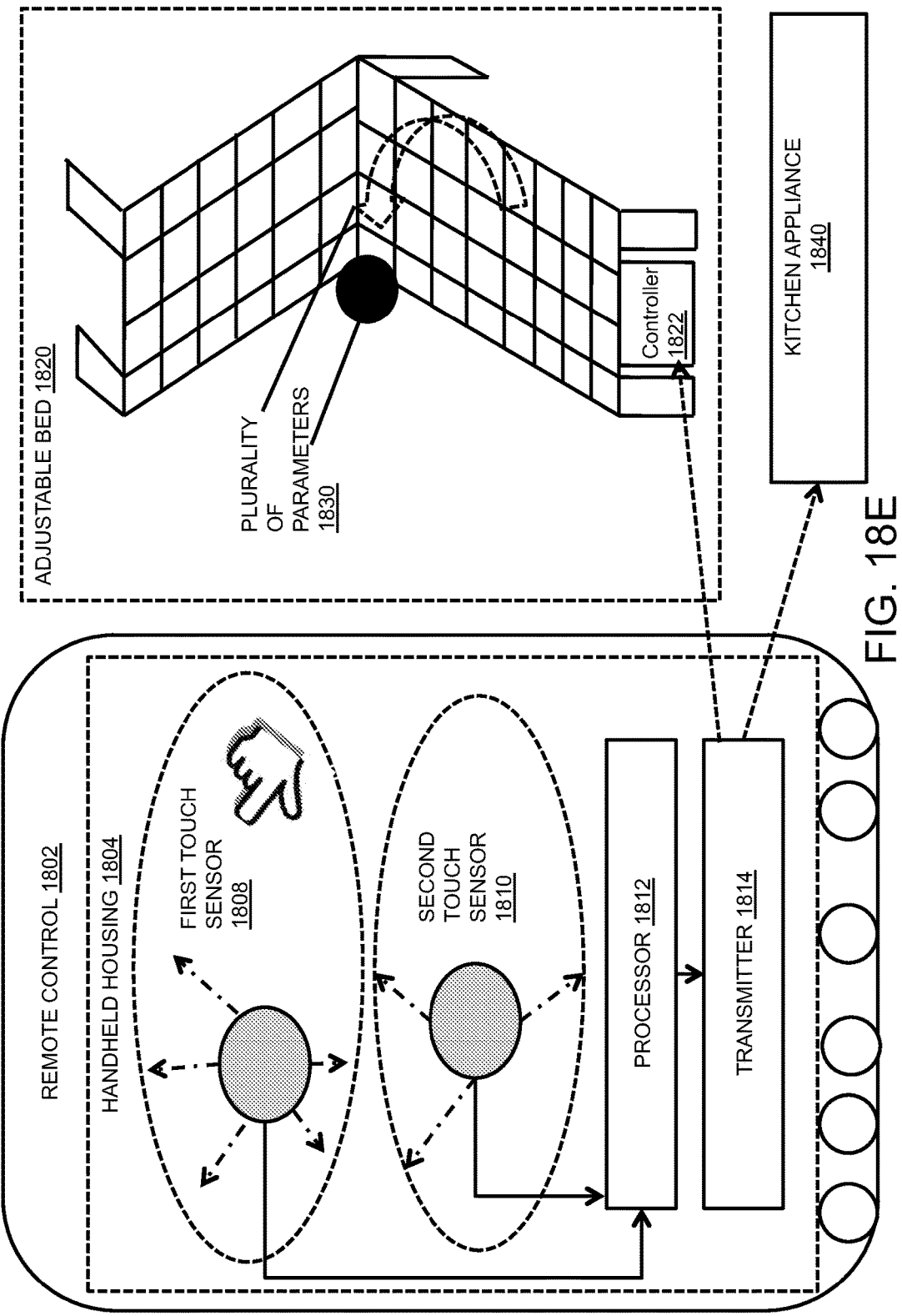
FIG. 18E depicts a remote control for controlling an adjustable bed and a kitchen appliance.
Figure 18F:
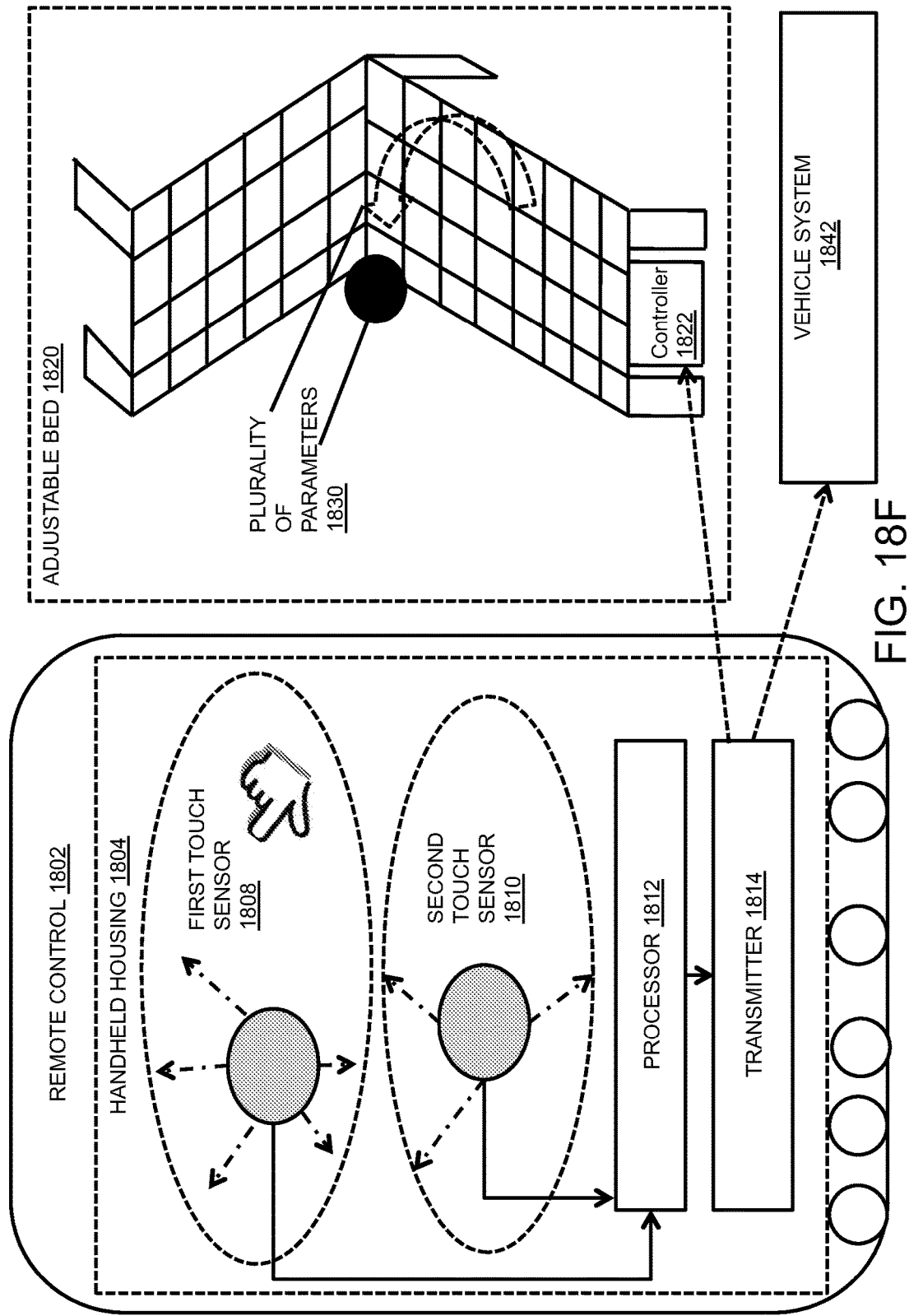
FIG. 18F depicts a remote control for controlling an adjustable bed and a vehicle system.
Figure 18G:
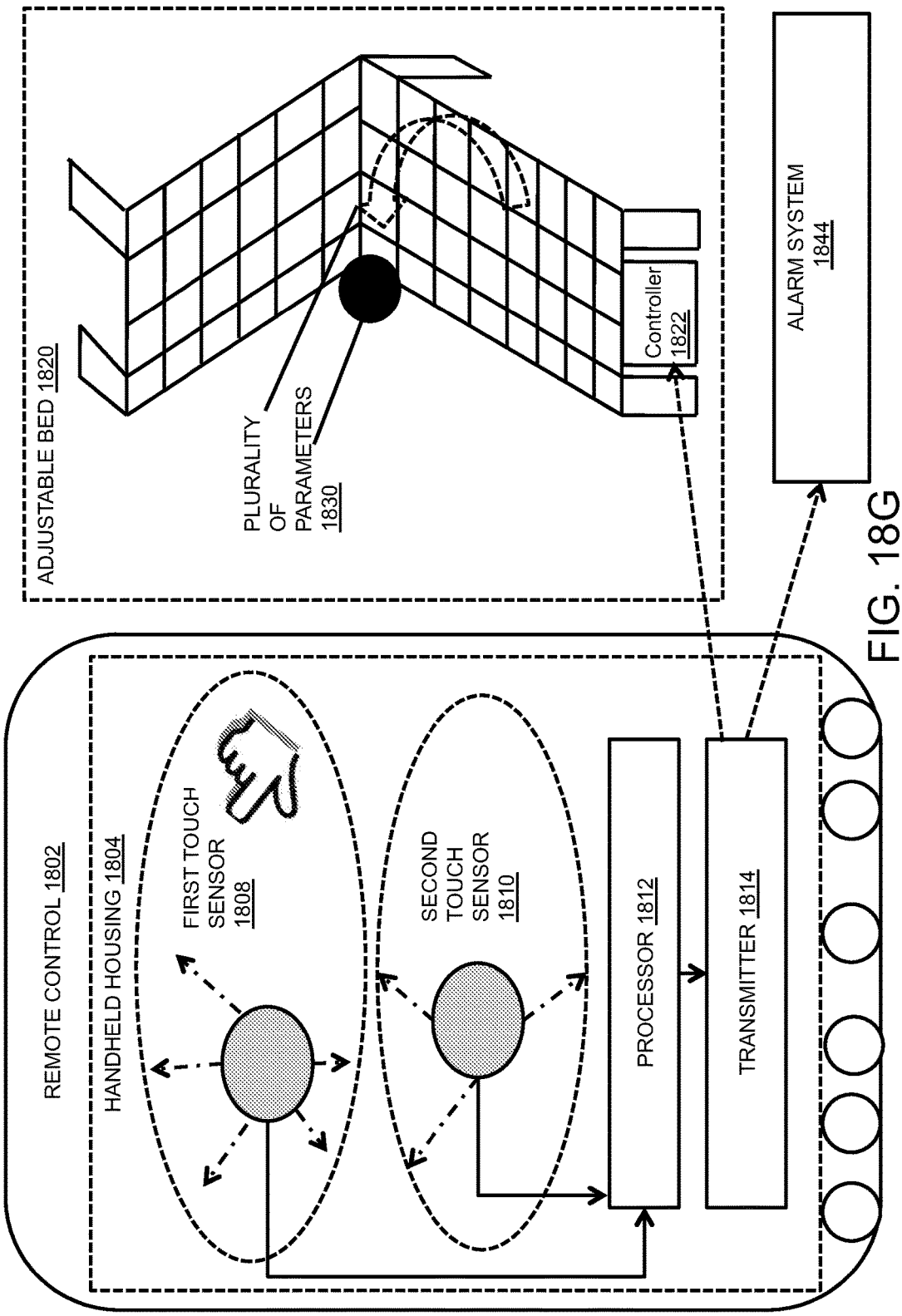
FIG. 18G depicts a remote control for controlling an adjustable bed and an alarm system.

FIG. 18A depicts a remote control 1802 (e.g. remote control 118) for controlling an adjustable bed 1820 and an audio visual system 1824 in accordance with an embodiment of the present invention. To describe FIG. 18A, reference will be made to FIG. 17, although it is understood that the remote control 1802 can be practiced in different embodiments. Those skilled in the art would appreciate that the remote control 1802 may have more or less system elements.

As shown, a hand held housing 1804 of the remote control 1802 may have a first touch sensor 1808, a second touch sensor 1810, a processor 1812, and a transmitter 1814. The first touch sensor 1808 and the second touch sensor 1810 may be presented in a slider form. In embodiments, the slider may be in the form of a dial, a linear strip, a curvilinear strip, a curve, or some other similar shape. In embodiments, the first touch sensor 1808 and the second touch sensor 1810 may be a capacitive touch sensor.

In an exemplary scenario, the user may like to sleep and want to do so while watching TV. He may like to change the frame position and may like to switch-off an audio visual system 1824 present in the room. The user may use the first touch sensor 1808 and may provide the input to the processor 1812 by sliding the first touch sensor 1808 for changing a parameter of the plurality of parameters 1830. The plurality of parameters 1830 may include the parameters associated with the actuators, springs, mattresses, a sub-frame, a skeleton structure, vibration motors, supports, safety brackets, or any other parameter associated with any other facility of the adjustable bed 1820.

As explained in the description for FIG. 17A, the transmitter 1814 may communicate the control signals to the control box 1822 of the adjustable bed 1820. The control box 1822 may adjust the parameter associated with the adjustable bed 1820. Similarly, the user may interact with the second touch sensor 1810 to control the audio-visual system 1824 present in the room. The transmitter 1814 of the remote control 1802 may communicate the control signals pertaining to the second touch sensor 1810 to the audio visual system. In the example, the user may provide the input by using the second touch sensor 1810 to lower the volume of the audio-visual system 1824. In an alternate embodiment, the control signals for the audio-visual system 1822, or other secondary system as described herein, may be sent to the on bed control box 1822 and the control box 1822 may then send the control signals to the audio-visual system 1832, or other secondary system.

In embodiments, as shown in FIG. 18B, the second touch sensor may 1810 may provide the input to control an audio system 1830 present in the room. For example, in addition to changing a parameter associated with the adjustable bed 1820, the user may like to change the volume or channel of the audio system 1832 present in the room. The transmitter 1814 may also transmit the control signals pertaining to the second touch sensor 1810 to control the audio system 1832.

Similarly, the second touch sensor may 1810 may provide the input to control a computer facility 1834, HVAC system 1838, a kitchen appliance 1840, a vehicle system (e.g. a remote starter for the vehicle) 1842, an alarm system 1844, or other secondary or auxiliary system as shown in FIG. 18C, FIG. 18D, FIG. 18E, FIG. 18F, FIG. 18G respectively.

In embodiments, second touch sensor 1810 may provide an interface for temperature sensing, such that the room temperature may be displayed on the remote control at a user's request. Also, the user may be intimated of, for example, the current room temperature, increase/decrease in the room temperature, and the like. The second touch sensor 1810 may provide the rate of rise/drop in the temperature of the surroundings. For example, in case of an emergency such as a fire, the increased room temperature may be detected enabling the user to take the necessary security measures. Also, in case of extremely low room temperatures, for example, during winters, the sensor may detect the decrease in the temperature of the surroundings. On such an indication, the user may switch on a heating device for maintaining the normal room temperature. The transmitter 1814 may transmit the control signals pertaining to the second touch sensor 1810 to control the zoned climate control system 164 or a heating device. Those skilled in the art would appreciate that the temperature sensing may have more or less system elements.

Figure 18H:
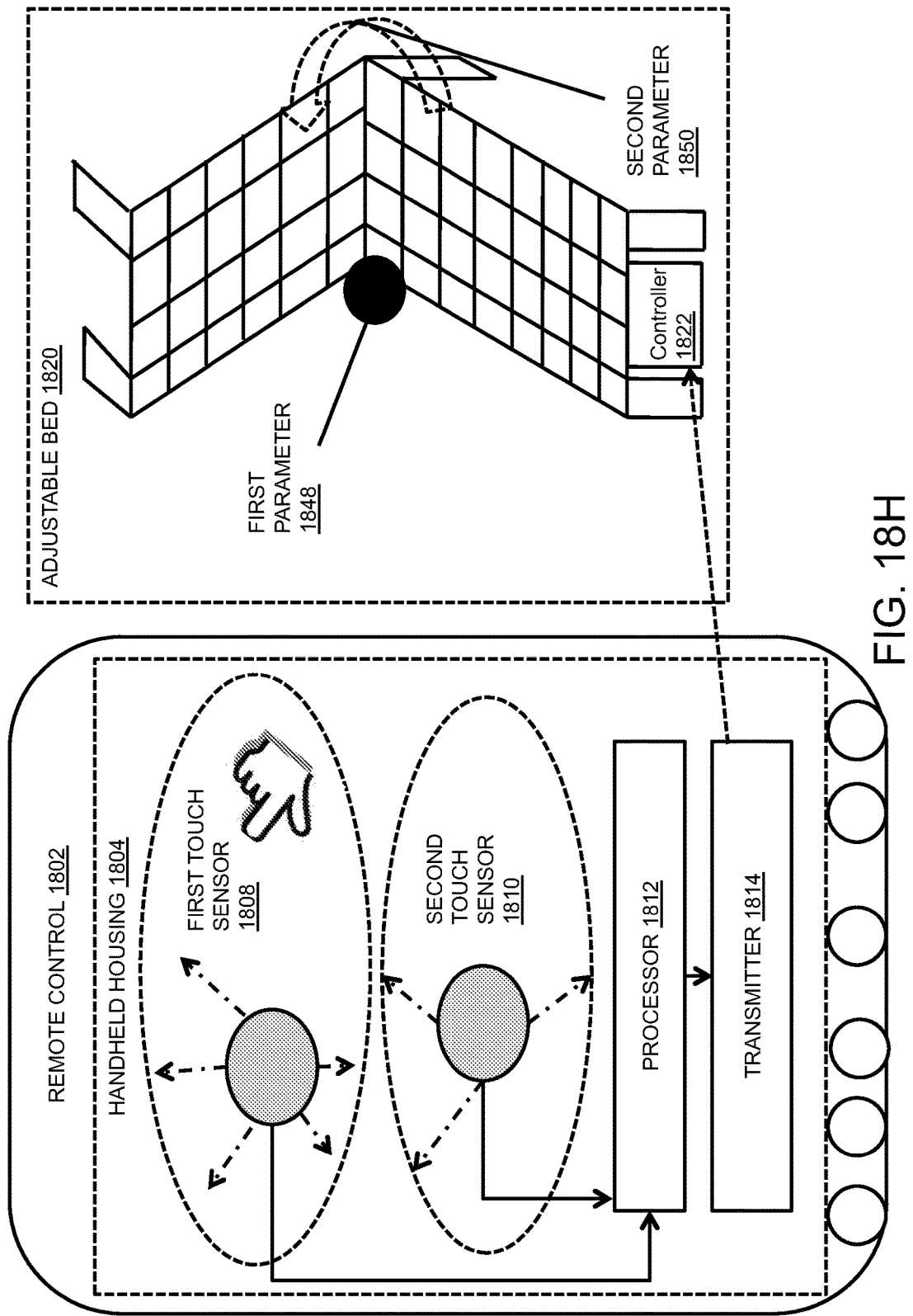
FIG. 18H depicts a remote control for controlling first and second parameters of an adjustable bed.

In embodiments, as shown in FIG. 18H, the first touch sensor 1808 may provide the control signals to control a first parameter 1844 of the adjustable bed 1820. In addition, the second touch sensor 1810 may provide the control signals to control a second parameter 1824 of the adjustable bed 1820. The first parameter 1844 and the second parameter 1848 is shown to be massage motor and the frame position respectively, however those skilled in the art would appreciate that the first and the second parameter may be associated with the actuators, springs, mattresses, a sub-frame, a skeleton structure, vibration motors, supports, safety brackets, or any other facility of the adjustable bed 1820.

Figure 19:
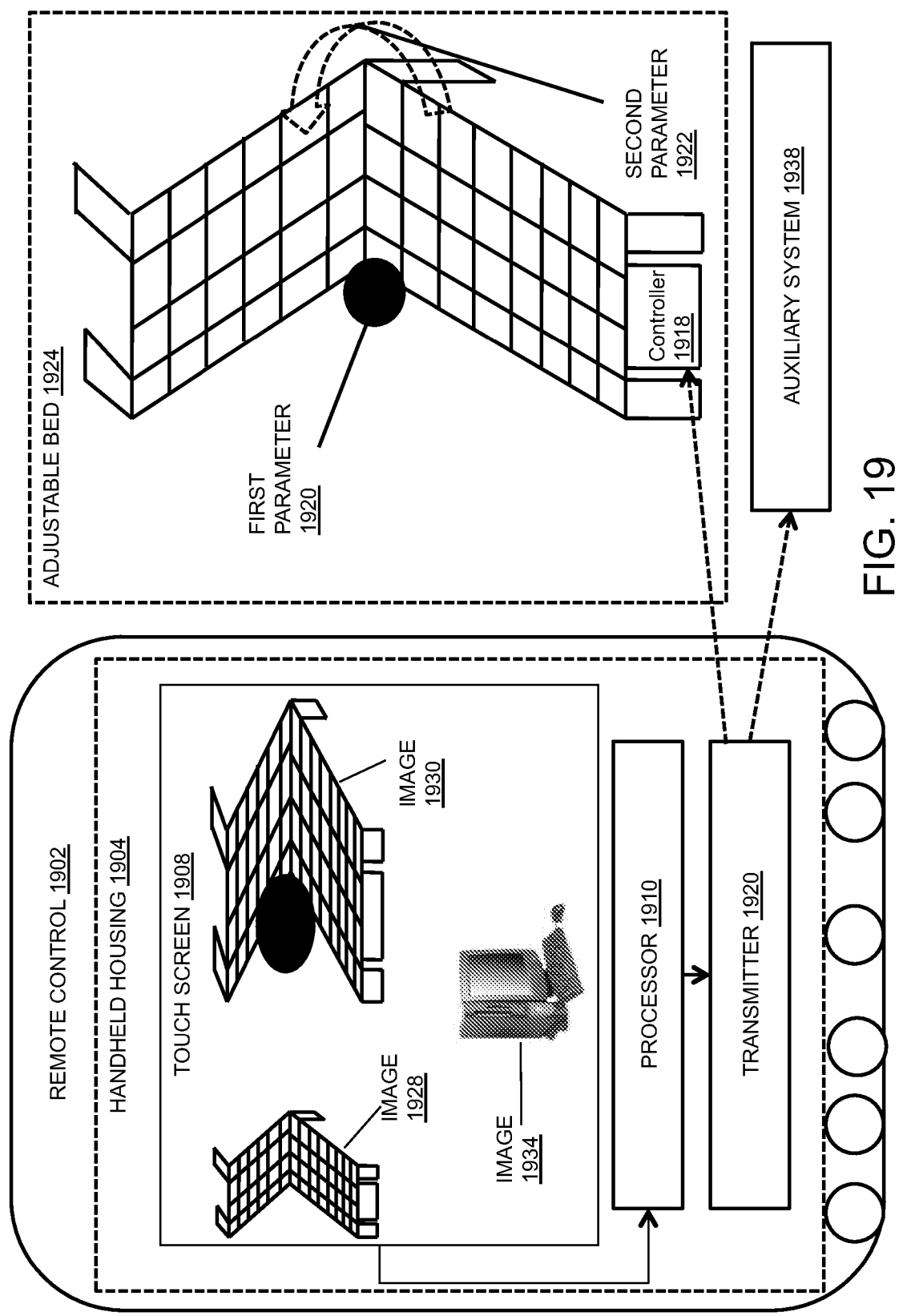
FIG. 19 depicts a remote control for controlling the parameters of an adjustable bed.

FIG. 19 depicts a remote control 1902 (e.g. remote control 118) for controlling the parameters of an adjustable bed 1924 in accordance with an embodiment of the present invention. To describe FIG. 19, reference will be made to FIG. 17 and FIG. 18, although it is understood that the remote control 1902 can be practiced in different embodiments. Those skilled in the art would appreciate that the remote control 1902 may have more or less system elements.

As shown, a hand held housing 1904 of the remote control 1902 may have a touch screen 1908, a processor 1910, and a transmitter 1912. The touch screen 1908 may enable the viewing of a plurality of images. Each of the plurality of images may be a representative of a different function associated with an adjustable bed 1924. As shown in the FIG. 19, the image 1928 may represent the function corresponding to the frame position. Similarly, the image 1930 may represent the function correspond to the massage motor. The touch screen 1908 may be shown to have the image 1928 and image 1930; however those skilled in the art may appreciate that the touch screen 1908 may have multiple images. Each image may be representative of a different function associated with the adjustable bed 1924. Each of the plurality of images may be coded to generate a control signal in response to an interaction with the image. For example, a user may touch the image 1928 to adjust the frame position of the adjustable bed 1924. On touching the image 1928, a control signal may be generated to control the frame position. The control signals may be processed with in a processor 1910 and then sent to the control box 1918 of the adjustable bed 1924 by the transmitter of the remote control 1902.

In an embodiment, an array of vibratory motors may be mounted on the bed frame, in the mattress or otherwise located to impart massage action onto the mattress. The array of vibratory motors may include two or more, and maybe many more, vibratory motors. The array may be controlled as a singular unit, as individual units, as groups and/or sub groups of units or otherwise. In an embodiment, the remote control may display a graphical image of the array to allow a user to set parameters associated with the array. The user may be able to interact with the remote (e.g. through an interactive image on the remote) to control the array as a singular unit, as individual units, as groups and/or sub groups of units or otherwise.

The control box 1918 may adjust the parameters associated with the image 1928 based on the received control signals. In the example, the parameters corresponding to the frame position may be adjusted. Similarly, the image 1930 may represent a function of the adjustable bed 1924. For example, it may represent the settings for the massage motor. The user may touch the image 1930 by using his finger tip 1932. The control signals corresponding to the image 1930 may be generated and transmitted to the control box 1918 of the adjustable bed 1924. In the example, the parameters associated with the massage motor may be adjusted.

In embodiments, at least one of the images may be adapted to produce an additional control signal when touched for a predetermined period of time. For example, the image 1928, when touched for a predefined time, say five seconds, may produce an additional control signal. This additional control signal may change a parameter associated with the adjustable bed 1924. In embodiments, the predefined period of time may be set by the user of the remote control 1902. In embodiments, the predefined period of time may be set by the manufacturer of the remote control 1902.

In embodiments, the touch screen 1904 may include a facility to display an auxiliary image 1934. The auxiliary image 1934 may correspond to an auxiliary system 1938. Examples of the auxiliary system 1938 may include but may not be limited to an audio system, computer system, security system, home security system, HVAC system, kitchen appliance, alarm system, vehicle system (e.g. remote starter for the vehicle), medical device unit etc. When a user touches the auxiliary image 1934, control signal may be generated to control the parameters of the respective auxiliary system. For example, the auxiliary image 1934 may be the image of the audio-visual system. The user may touch the image corresponding to the audio-visual system on the touch screen 1908 to control the volume of the audio-visual system. The control signals may be generated and transmitted by the transmitter 1912 to the audio visual system.

In one exemplary scenario, the auxiliary image 1934 may be the image of the blood pressure system. The user may touch the images corresponding to the blood pressure system on the touch screen 1908 to measure the blood pressure. The signals may be generated and transmitted by the transmitter 1912 to the blood pressure meter. The blood pressure may be activated to measure the blood pressure and heart rate of the user. The user may also activate and monitor its health conditions using a plurality of medical devices, for example, Electrocardiogram, glucose meter, pulse oximeter, and the like.

The images may act as portals to other pages where further related control parameters are offered. For example, the user may be presented with an icon representing an adjustable bed. Once the user interacts with the icon on the touch screen, or through a soft or hard style button, a new page of information may be presented to the user for further selection/interaction.

Figure 20A:
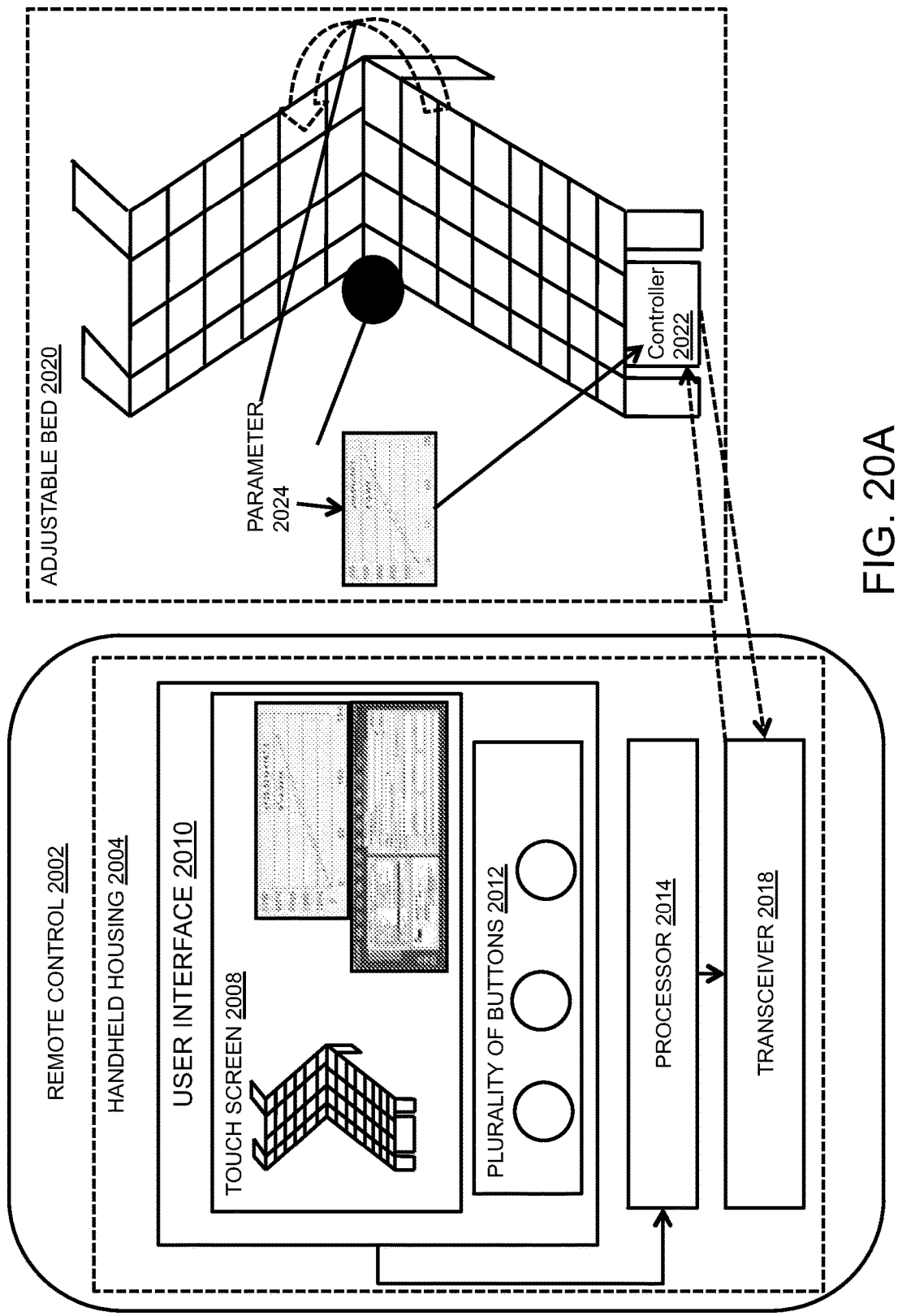

FIG. 20A depicts a remote control 2002 (e.g. remote control 118) for controlling the parameters of an adjustable bed 2024 in accordance with an embodiment of the present invention. To describe FIG. 20, reference will be made to FIG. 17, FIG. 18, and FIG. 19 although it is understood that the remote control 2002 can be practiced in different embodiments. Those skilled in the art would appreciate that the remote control 2002 may have more or less system elements.

As shown, a hand held housing 2004 of the remote control 2002 may have a user interface 2008. The user interface 2008 may include a touch screen 2010, a plurality of buttons 2012. The user interface 2008 may be adapted to facilitate the user in adjusting a parameter 2024 of an adjustable bed 2020. The parameter 2024 may be one of the pluralities of parameters 1730. The instructions corresponding to the parameter 2024 may be provided by the user through the user interface 2010. These instructions may be sent to the processor 2014. On processing these instructions, control signals may be generated by a transceiver 2018. In embodiments, the transceiver 2018 may operate a BLUETOOTH protocol. In embodiments, the transceiver may be an RF transceiver.

These signals may be transmitted to a control box 2022 of the adjustable bed 2020. Once the parameter 2024 has been adjusted, the value of the adjusted parameter 2024 may be sent to the transceiver 2018 of the remote control 2002. In embodiments, the adjusted parameter 1924 may be transmitted to the user interface 2010.

Figure 20B:
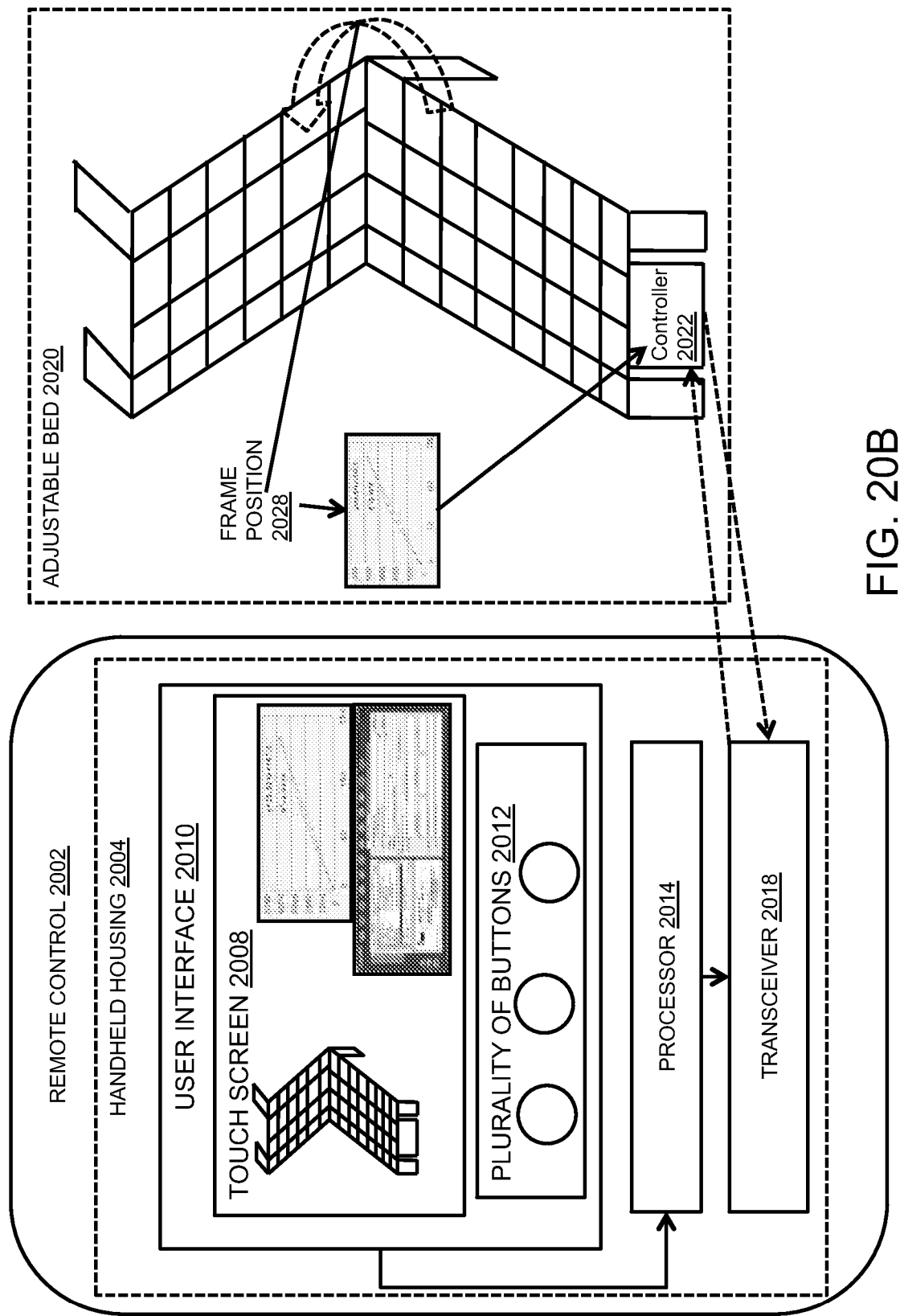

In embodiments, the parameter may be a frame position 2028. As shown in FIG. 20B, the frame position 2028 may be adjusted by using the user interface 2010. For example, the user may like to tilt the frame of the adjustable bed 2020 to feel comfortable. The angle through which its frame can be tilted may be present on the user interface 2010. The user may select the angle to tilt the frame of the adjustable bed 2024 by using the touch screen 2008. The new frame position 2028 may be sent to the transceiver 2018. In the example, the frame of the adjustable bed 2020 may be tilted to 150 degrees from 100 degrees. Once the frame position 2028 may be adjusted, the data indicative of the adjusted frame position 2028 may be communicated to the transceiver 2018 by the control box 2022. In the example, a data indicating that the frame position 2028 is adjusted to 150 degrees may be transmitted to the transceiver 2018. In embodiments, the adjusted frame position 2028 may be provided to the user interface 2010 by the transceiver 2018.

Figure 20C:
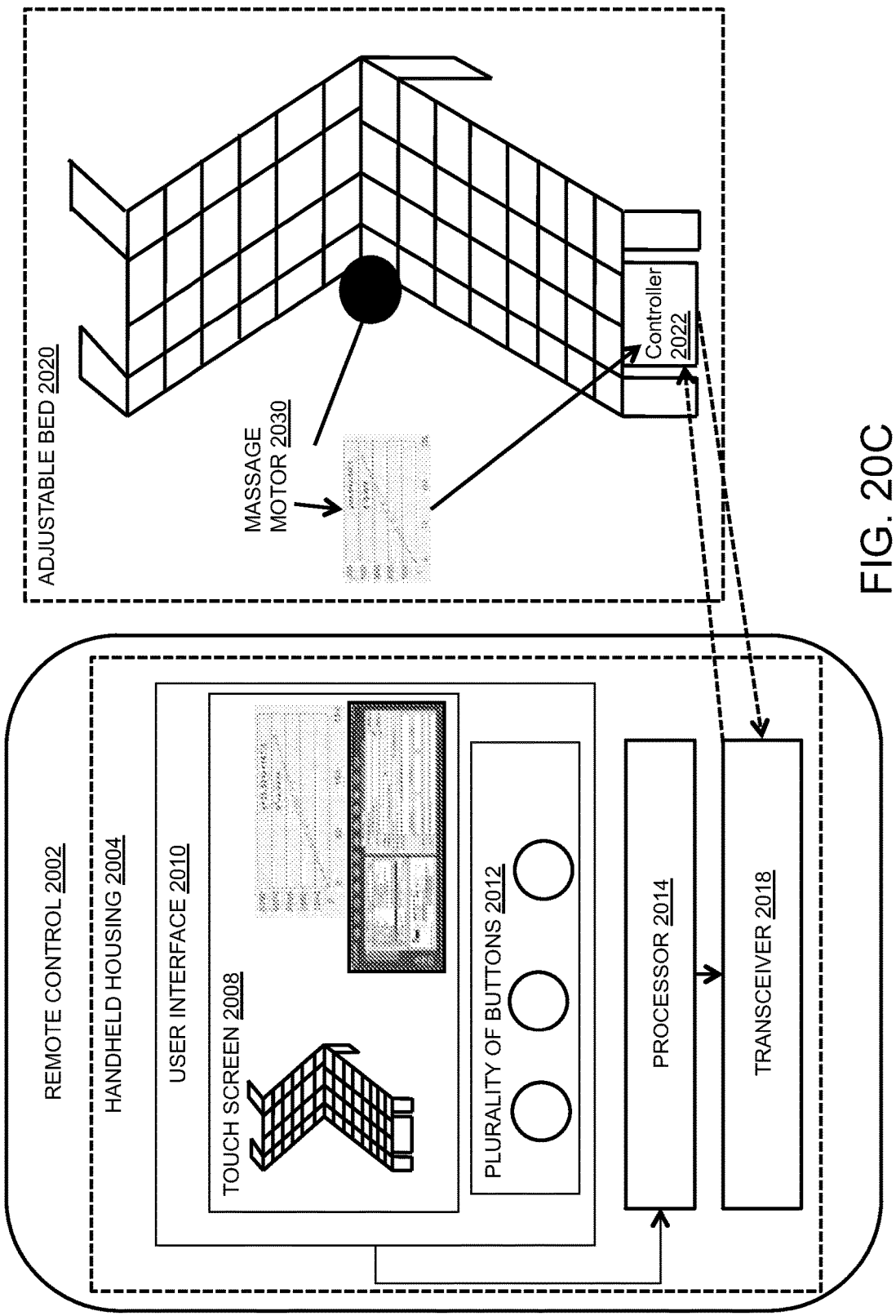

In embodiments, the parameter may be associated with a massage motor 2030. As shown in FIG. 20C, the settings of the massage motor 2030 may be adjusted by using the user interface 2008. The new massage motor settings may be sent to the transceiver 2018. For example, the user may like to increase the frequency of the massage. The user may adjust the speed of the massage by the user interface 2010. The transceiver 2018 may collect the instructions from the user interface 2010 and may communicate to the control box 2022. The control box 2022 may increase the frequency of the massage motor 2030. The new frequency of the massage motor 2030 may be provided to the transceiver 2018. In embodiments, the new frequency of the massage motor 2030 may be provided to the user interface 2008 by the transceiver 2018.

Figure 20D:
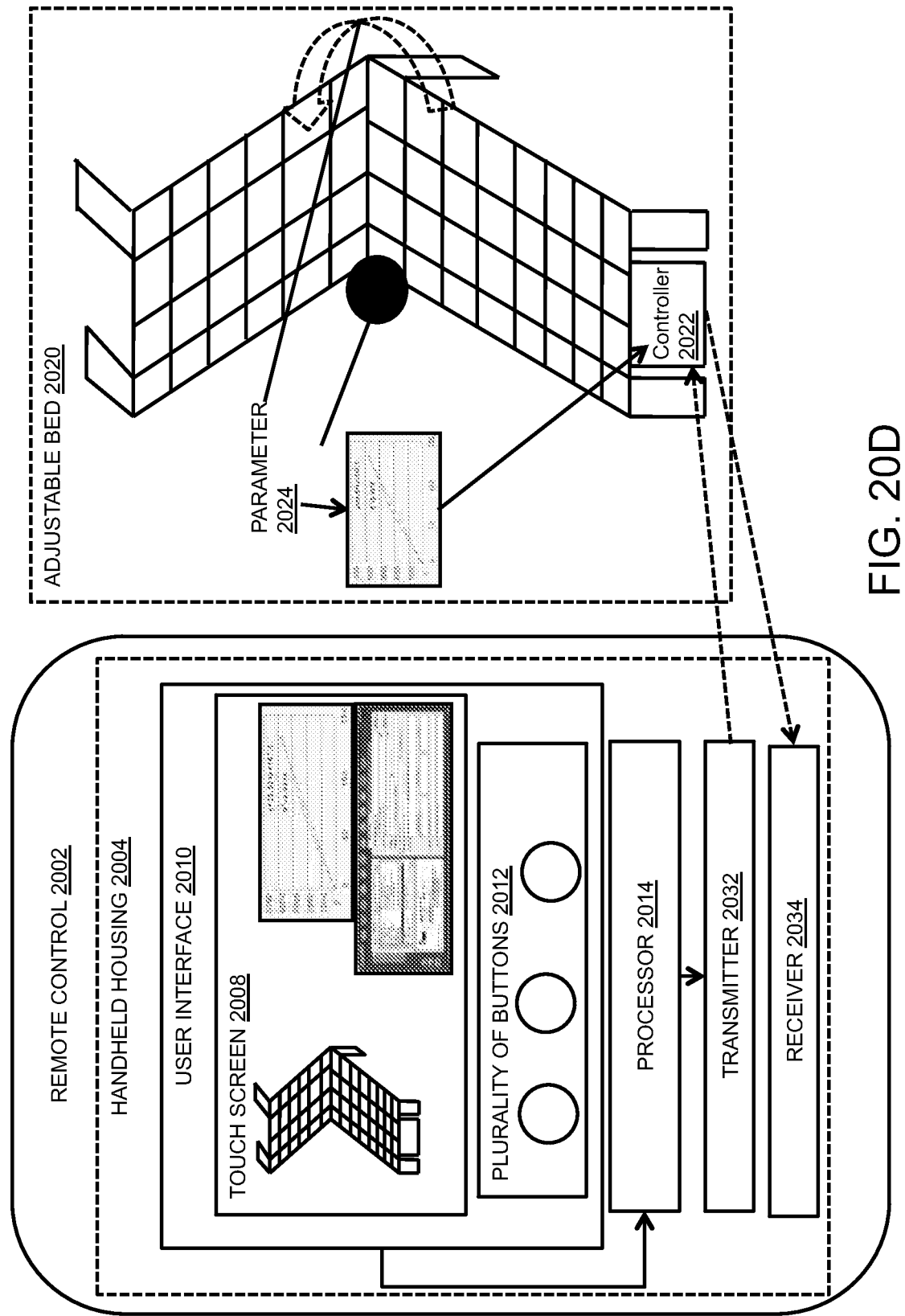

In embodiments, as shown in FIG. 20D, the control signals may be transmitted by a transmitter 2028 to adjust a parameter. For example, the user may provide the instructions to control a parameter 2024 using the user interface 2008. The user interface 2008 may provide the instructions to a transmitter 2032 of the remote control 2002. The transmitter 2032 may provide the instructions to the control box 2022. The control box 2022 may adjust the parameter 2024 and provide the adjusted parameter 2024 to the receiver 2034 of the adjustable bed 2020. In embodiments, the transmitter 2032 and the receiver 2034 may operate at different frequencies. For example, the transmitter 2032 may operate at 2.4 gigahertz and the receiver 2034 may operate at 433.92 gigahertz. In embodiments, the use of different frequencies between transmitting and receiving may be used to avoid signal interference.

Certain embodiments have been depicted as having a transceiver and others as having a transmitter and receiver pair. It should be understood that in certain embodiments, the transceiver may represent multiple components and/or systems and in other embodiments it represents a consolidated set of components and/or systems. If should further be understood that in certain embodiments, the transmitter and receiver pairs may represent separate components and/or systems and in other embodiments they represent a consolidated set of components and/or systems.

Figure 20E:
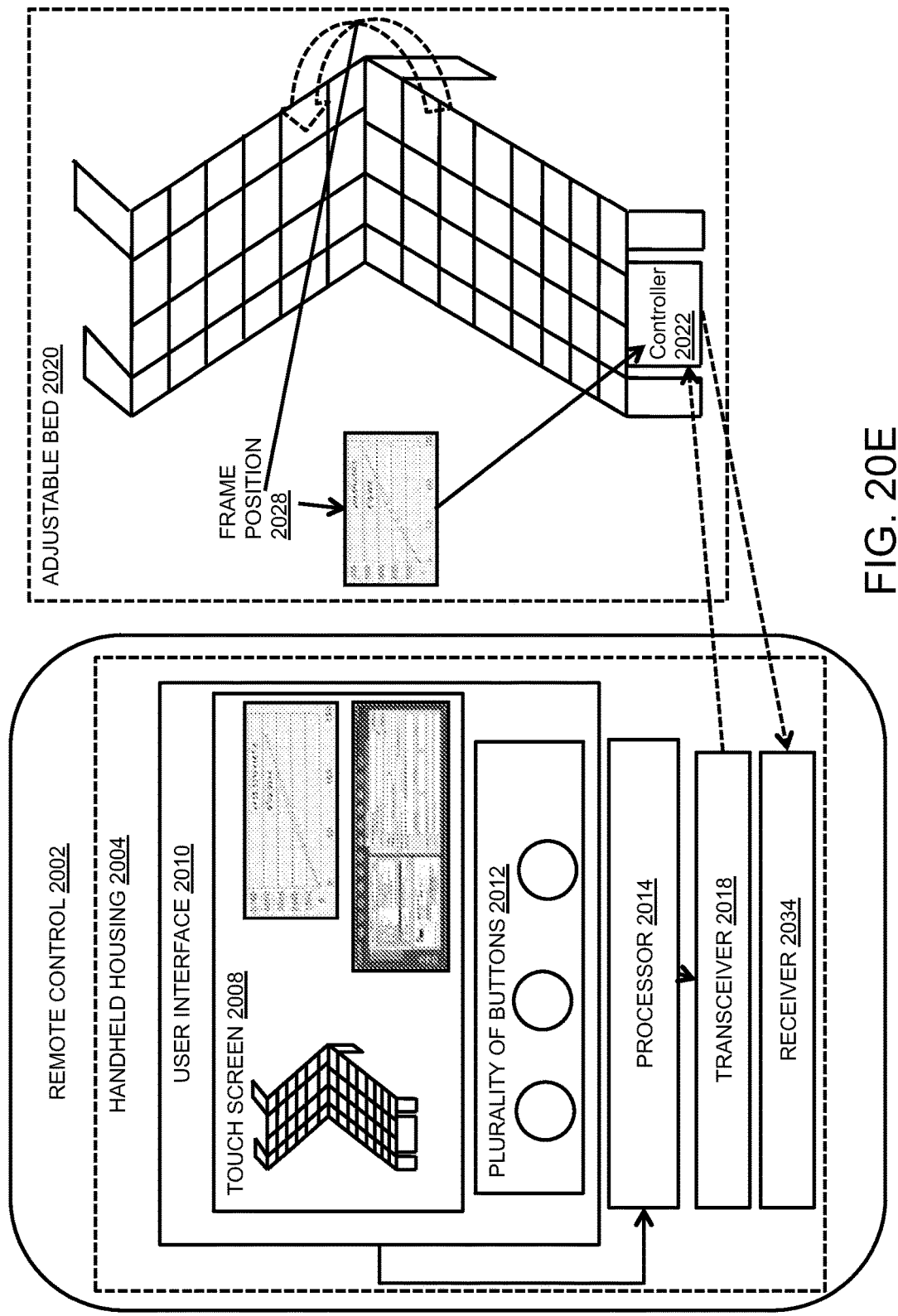

In embodiments, as shown in FIG. 20E, the control signals may be transmitted by the transceiver 2018 to adjust the frame position 2028. In embodiments, as shown in FIG. 20E, the control signals may be transmitted by the transmitter 2032 to adjust the frame position 2028. In addition, the data indicative of a receipt of the adjusted frame position 2028 from the adjustable bed 2024 may be received by the receiver 2034. In the example, the data indicating that the frame has been tilted to 150 degrees may be provided to the receiver 2034. In embodiment, the adjusted parameter pertaining to the frame position 2028 may be provided to the receiver 2034.

Figure 20F:
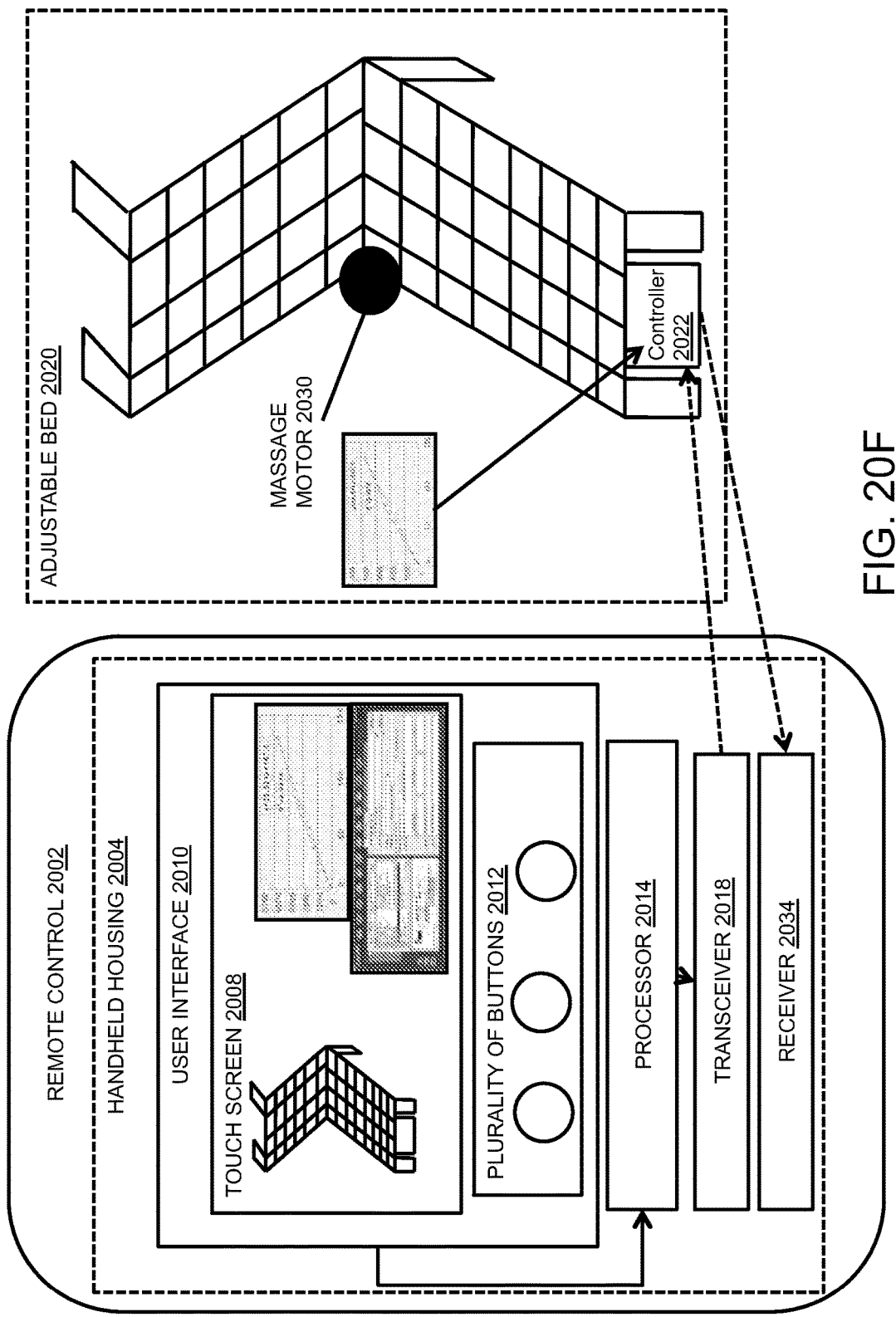

In embodiments, as shown in FIG. 20F, the control signals may be transmitted by the transceiver 2018 to adjust the settings of the massage motor 2030. In addition, the data indicative of a receipt of the adjusted setting of the massage motor 2030 from the adjustable bed 2024 may be received by the receiver 2034.

Figure 20G:
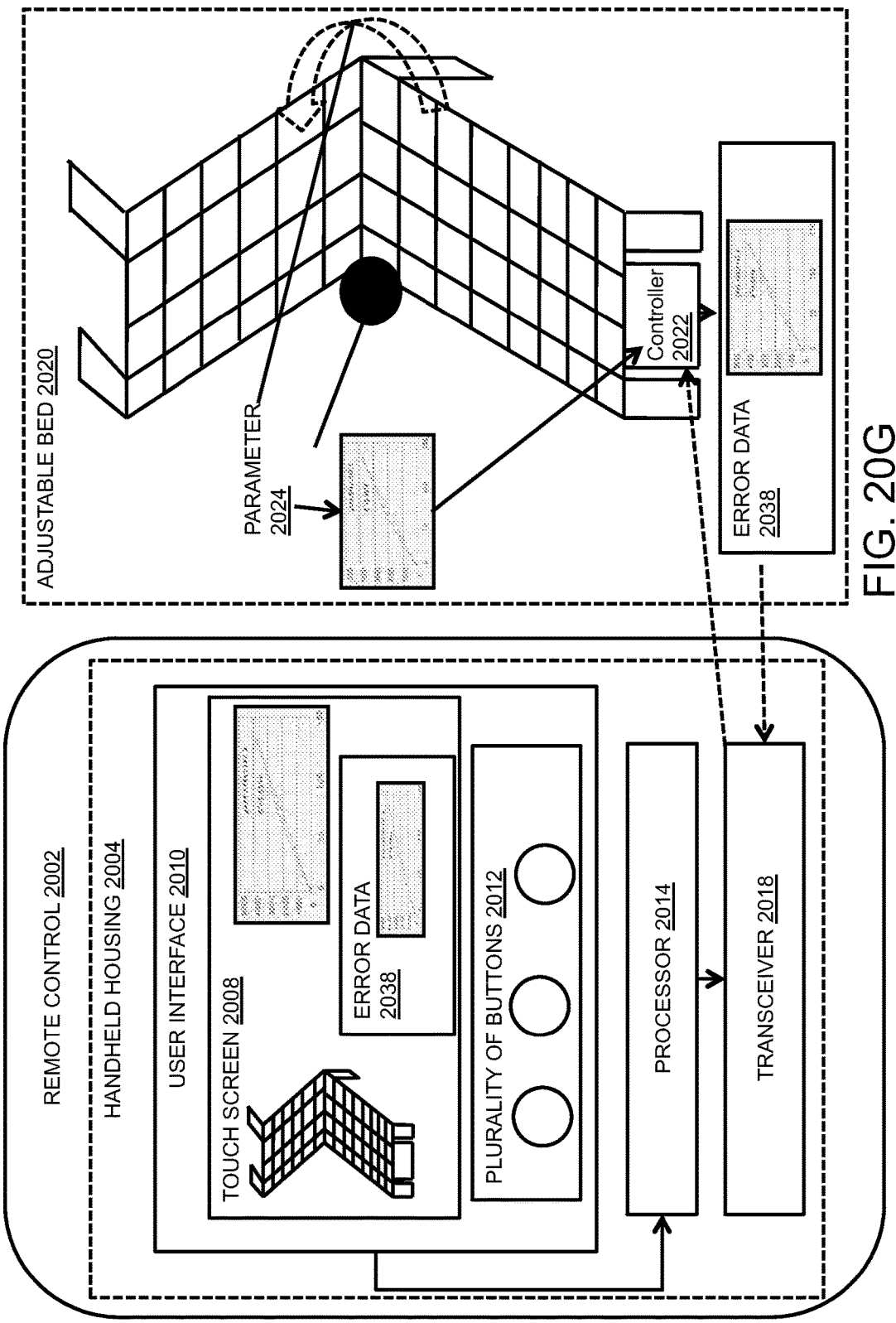

In embodiments, as shown in FIG. 20G, an error data 2032 may be transmitted to the transceiver 2032. For example, the user may have liked to tilt the frame to 70 degrees from 45 degrees. However, the control box 2022 may have adjusted it to 148 degrees due to frame position limitation. In this scenario, an error data 2038 showing that the frame may have been adjusted to 65 degrees instead of 70 degrees may be communicated to the transceiver 2018. In embodiments, this error data 2038 may be transmitted to the user interface 2008. In embodiments, the error data 2038 may indicate the failure of the control box 2022 to adjust the parameters.

Figure 20H:
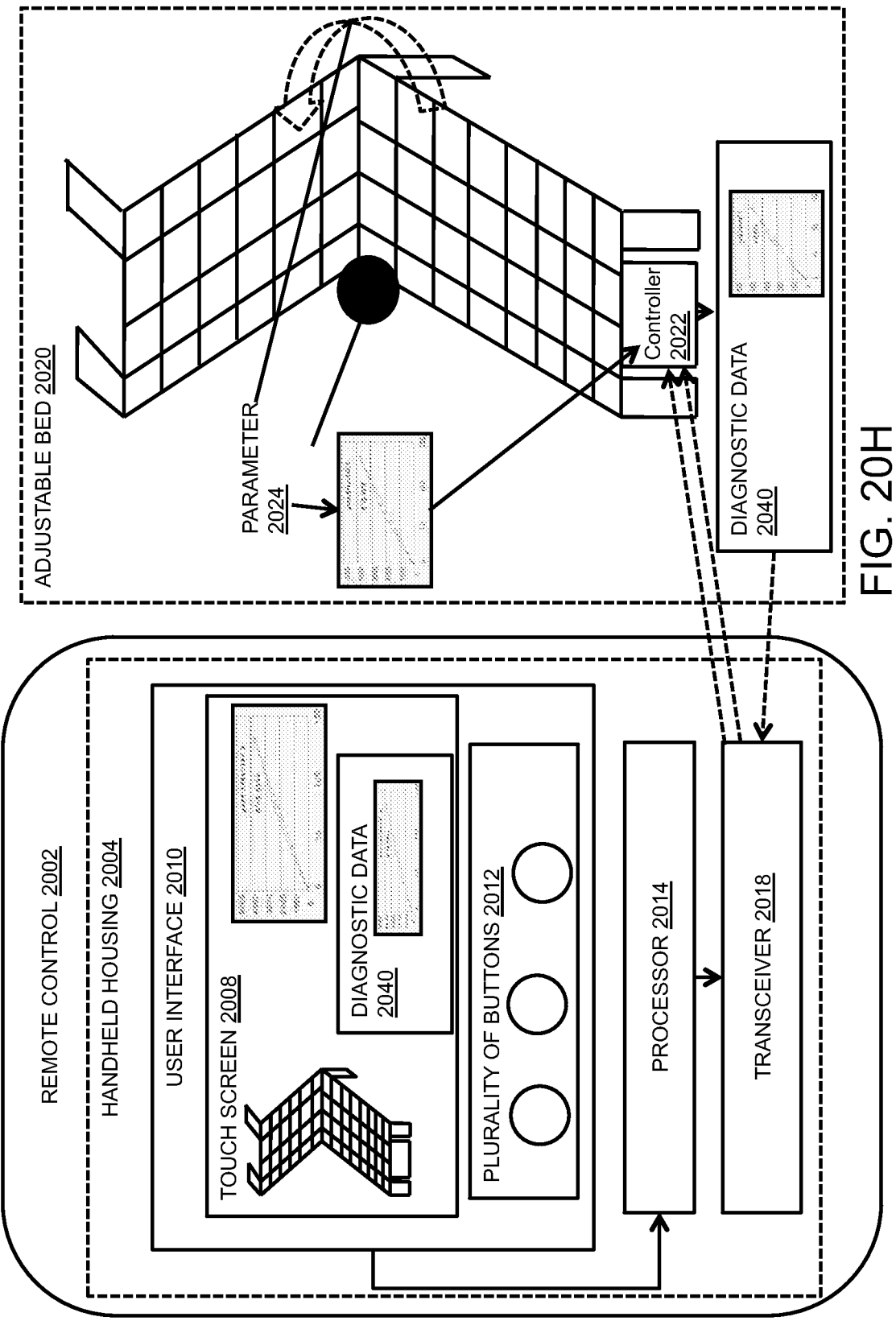

In embodiments, as shown in FIG. 20H, in addition to the control signs to adjust a parameter 2024, the transceiver 2018 may send the diagnostic signals to the control box 2022. The diagnostic signals may cause the adjustable bed to switch to a diagnostic mode. A diagnostic data 2034 may also be transmitted to the transceiver 2018.

In embodiments, as shown in FIG. 20I, a new position indication 2044 of the adjustable bed 2024 may be transmitted to the transceiver 2018. Accordingly, the transceiver 2018 may provide the new position indication 2044 to the user interface 2010. The new position indication 2040 may be indicated digitally. For example, the 150 degree angle at which the frame may be tilted is communicated to the transceiver 2018 by the control box 2022. In embodiments, the frame position 2028 may be calibrated. For example, frame position 2028 from angle 90 degree to 120 degree may be referred as first frame position. Similarly, the frame position 2028 from angle 120 degree to 150 degree may be referred as second frame position. This first frame position or the second frame position may be provided to the transceiver 2018. In embodiments, the data indicating that the parameter has been adjusted may be provided to the transceiver 2018. The new position indication 2044 may be displayed on the user interface 2010. In embodiments, a number corresponding to the frame position 2028 may be displayed. Although, the new position indication 2044 is explained by the frame position 2028, the new position indication may represent a new setting of the massage motor 2030 or any other parameter.

Figure 20J:
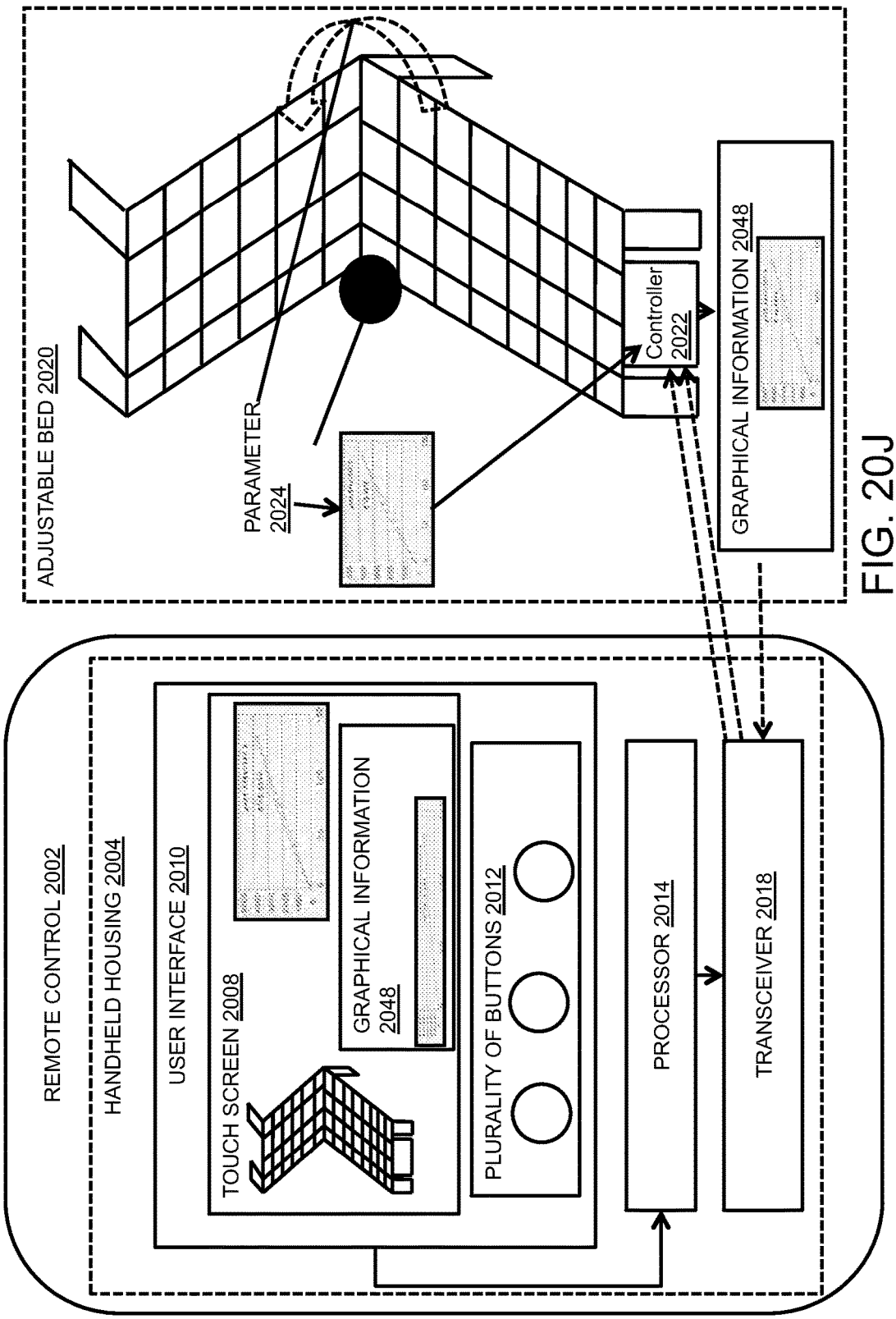

In embodiments, as shown in FIG. 20J, graphical information 2048 of the adjusted parameter 2024 may be provided by the adjustable bed 2020 to the transceiver 2018. The graphical information 2048 may indicate the new setting of the adjustable bed 2020. For example, the graphical information 2048 of the frame position 2028 may be provided to the transceiver 2018. For example, if the upper portion of the bed frame is readjusted to forty five degrees from horizontal, a graphical image depicting the angle may be presented on the screen 2008. Accordingly, the transceiver 2018 may provide the graphical information 2048 to the user interface 2010.

Figure 20K:
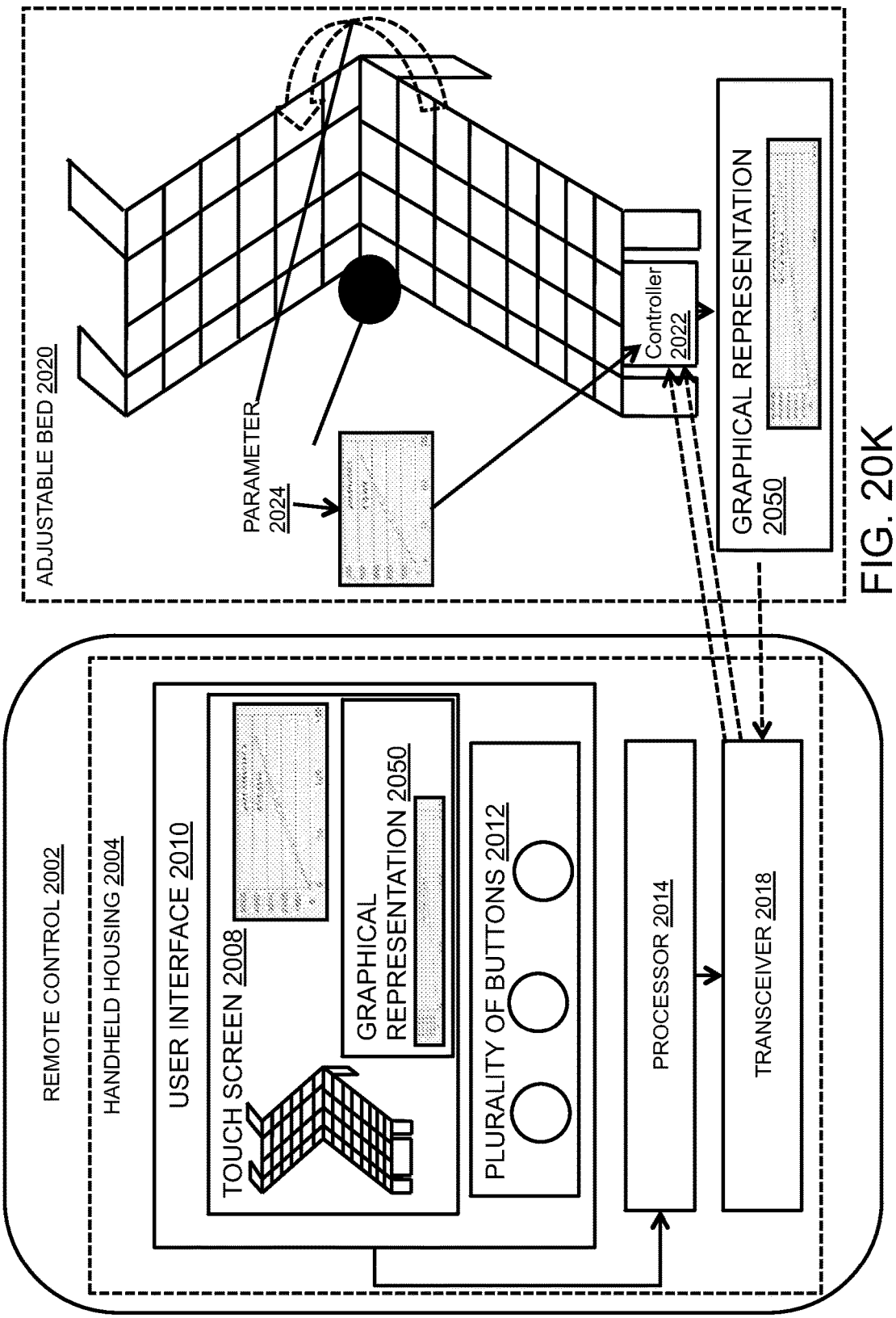

In embodiments, as shown in FIG. 20K, graphical representation 2050 of the adjustable bed parameter may be provided by the adjustable bed 2020 to the transceiver 2018. Accordingly, the graphical representation 2050 may be provided to the user interface 2010. In embodiments, the graphical representation 2050 of the adjustable bed parameter may indicate a current status of the parameter as indicated by the adjustable bed 2020. For example, a graphical representation of the adjusted frame position 2028 may be provided to the user interface 2010. In embodiments, a graphical representation of the adjusted frame position 2028 may be provided to the receiver 2034 of the remote control 2002.

Figure 20L:
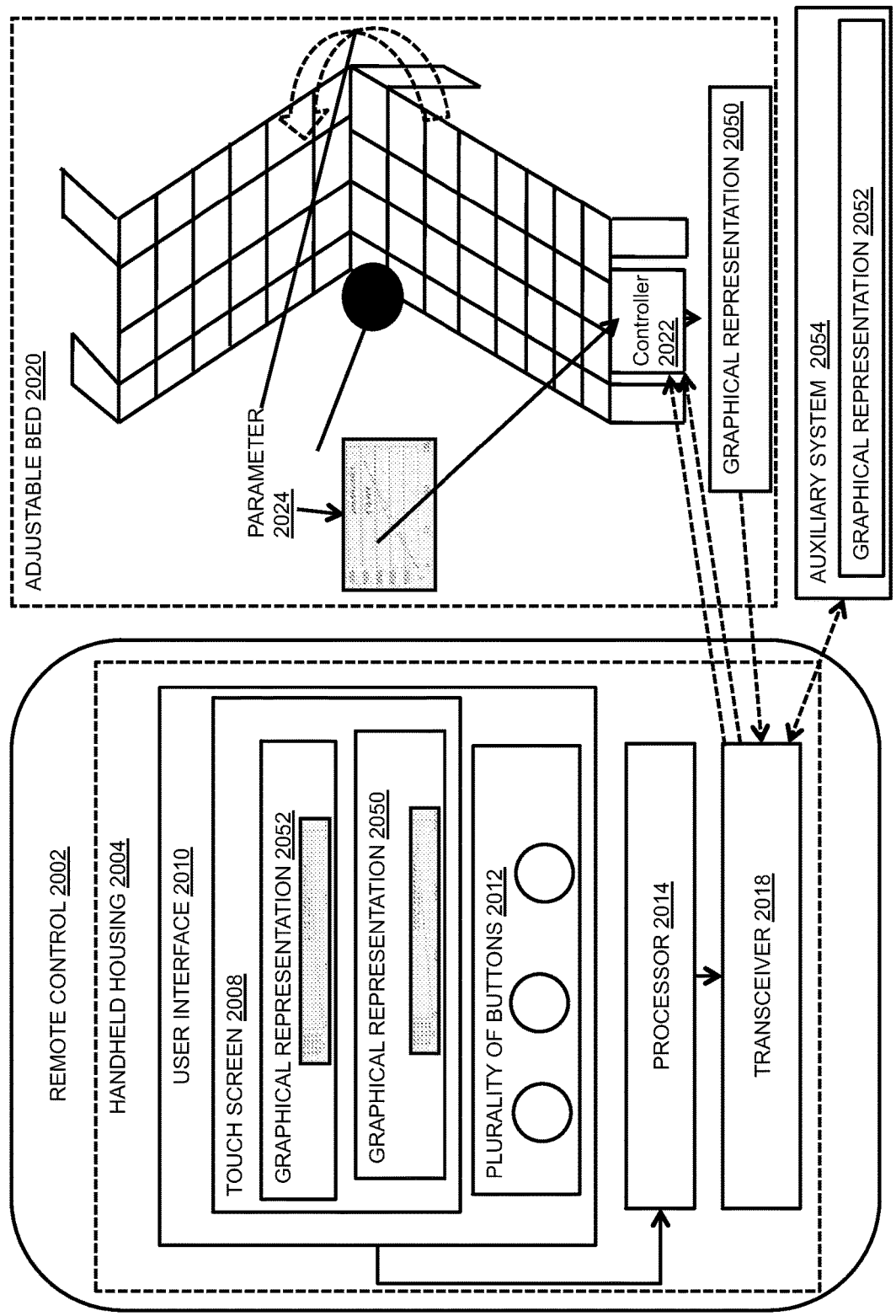

In embodiments, as shown in FIG. 20L, in addition to the graphical representation 2050 of the adjustable bed parameter, graphical representation 2052 of the parameter associated with the auxiliary system 2054 may be provided to the user interface 2010. For example, a graphical representation of the adjusted parameters associated with the auxiliary system 2054 may be provided to the user interface 2010. Examples of the auxiliary system 2054 may include but are not limited to an audio system, a computer system, an HVAC system, a kitchen appliance, an alarm system, and a vehicle system. In embodiments, a graphical representation of the adjusted parameters of the auxiliary system 2054 may be provided to the receiver 2034 of the remote control 2002.

Figure 21A:
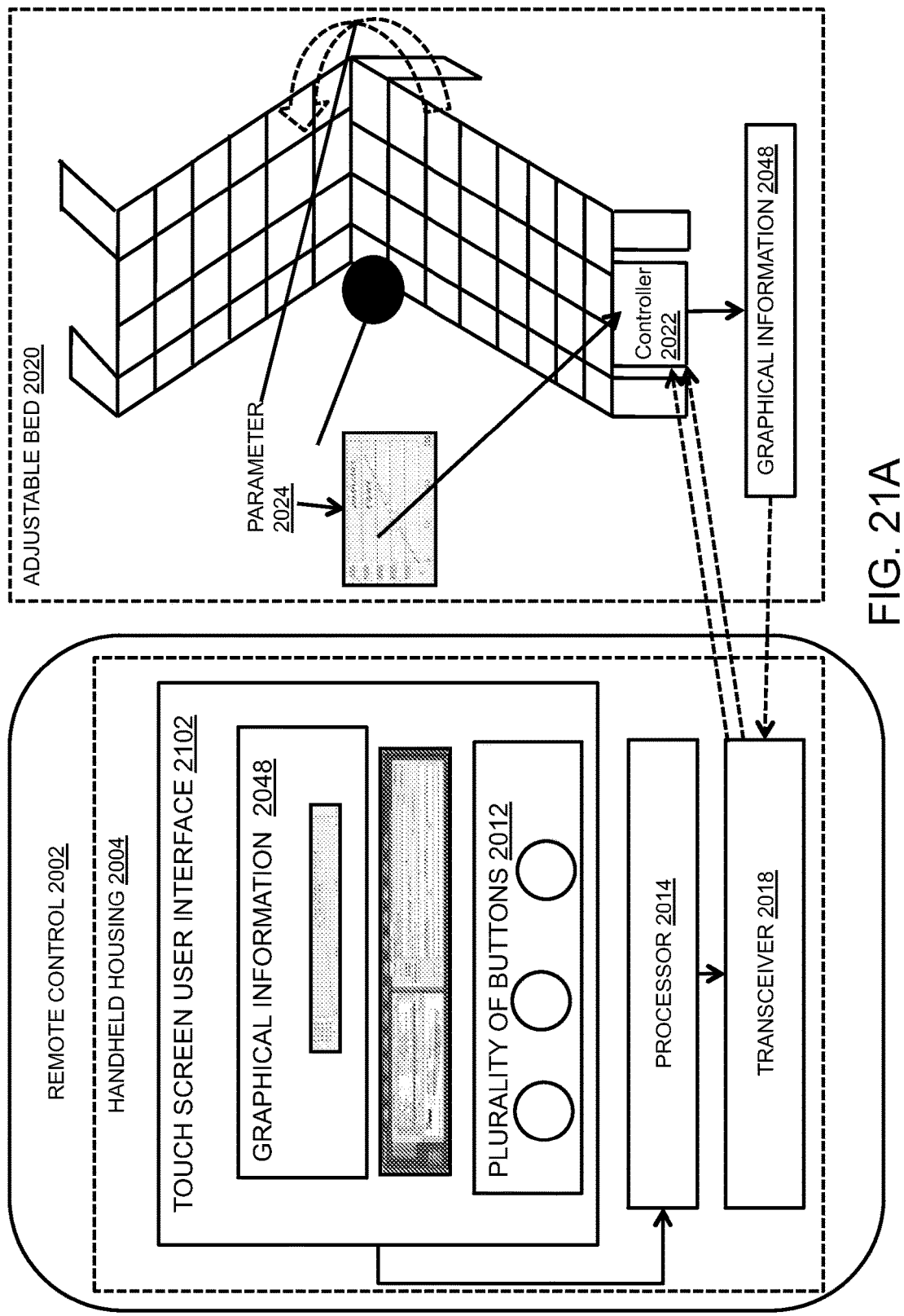
FIGS. 21A and 21B depict a remote control with a touch screen user interface in accordance with various embodiments of the present invention.
Figure 21B:
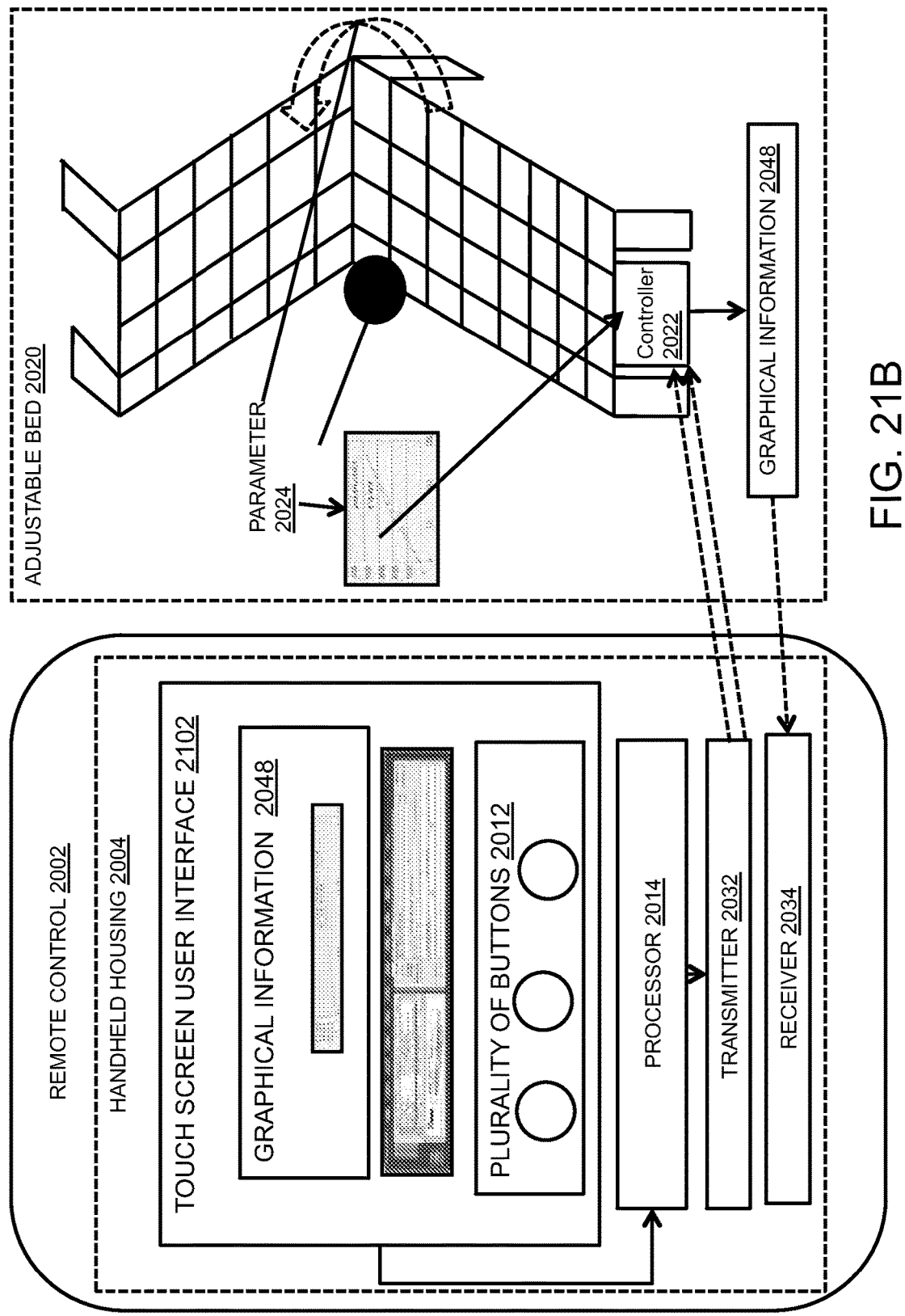

In embodiments, as shown in FIG. 21A, the user interface may be a touch screen user interface 2102. The user may interact with the touch screen user interface 2102. The instructions from the user may be provided to the control box 2022 by the transceiver 2018. The control box 2022 may communicate the graphical information 2048 of the adjusted parameters associated with the adjustable bed 2020 to the transceiver 2018. In embodiments, as shown in FIG. 21B, the control box 2022 may communicate the graphical information 2048 of the adjusted parameter associated with the adjustable bed 2020 to the receiver 2034. The transceiver 2018 may provide the graphical information 2048 to the touch screen user interface 2102. Now, the user may interact with the graphical information 2048 on the touch screen user interface 2102 to adjust the parameter 2024. For example, the graphical information corresponding to the frame position 2028 may be provided to the touch screen user interface 2102. The user may interact with the graphical information corresponding to the frame position 2028 and may increase the angles between the frames.

FIG. 22 depicts a flow chart 2200 for changing an adjustable parameter associated with an adjustable bed 1720 in accordance with an embodiment of the present invention. To describe FIG. 22, reference will be made to FIG. 17, FIG.

18, FIG. 19, FIG. 20, and FIG. 21, although it may be understood that the method for changing an adjustable parameter can be practiced in different embodiments. Those skilled in the art would appreciate that the flow chart 2200 may have more or less number of steps.

At step 2202, a control signal to change an adjustable parameter of the adjustable bed 1720 may be sent to the adjustable bed 1720 by the remote control 1702. As explained in the descriptions for FIG. 17, FIG. 18, FIG. 19, FIG. 20, and FIG. 21, the control signal may be generated by the user interaction with the touch sensor 1708, a user interface 2010, a touch screen user interface 2102, or any other similar facility. The adjustable parameter may include the parameter associated with the actuators, springs, mattresses, a sub-frame, a skeleton structure, vibration motors, supports, safety brackets, or any other parameter associated with any other facility of the adjustable bed 1720. In embodiments, the control signal may be provided to the control box 1722 by the transmitter 1714, transceiver 2018, or any other similar facility of the remote control 1702. For example, a control signal may be sent indicating change in the angle of the frame of the adjustable bed 1720 from 120 degrees to 150 degrees. At step 2204, the adjustable bed 1720 may change the adjustable parameter in accordance with the control signal. For example, the frame of the adjustable bed 1720 may be adjusted to 150 degrees. At step 2208, the adjustable bed 1720 may send data that may indicate a new setting of the changed adjustable parameter. For example, the information that the frame of the adjustable bed 1720 has been tilted to 150 degrees may be relayed. At step 2210, a number indicative of the data may be displayed on the remote control 1702. For example, the frame angle (150 degrees) may be displayed on the user interface 2010, a touch screen user interface 2102, or any other facility of the remote control 1702.

Figure 23:
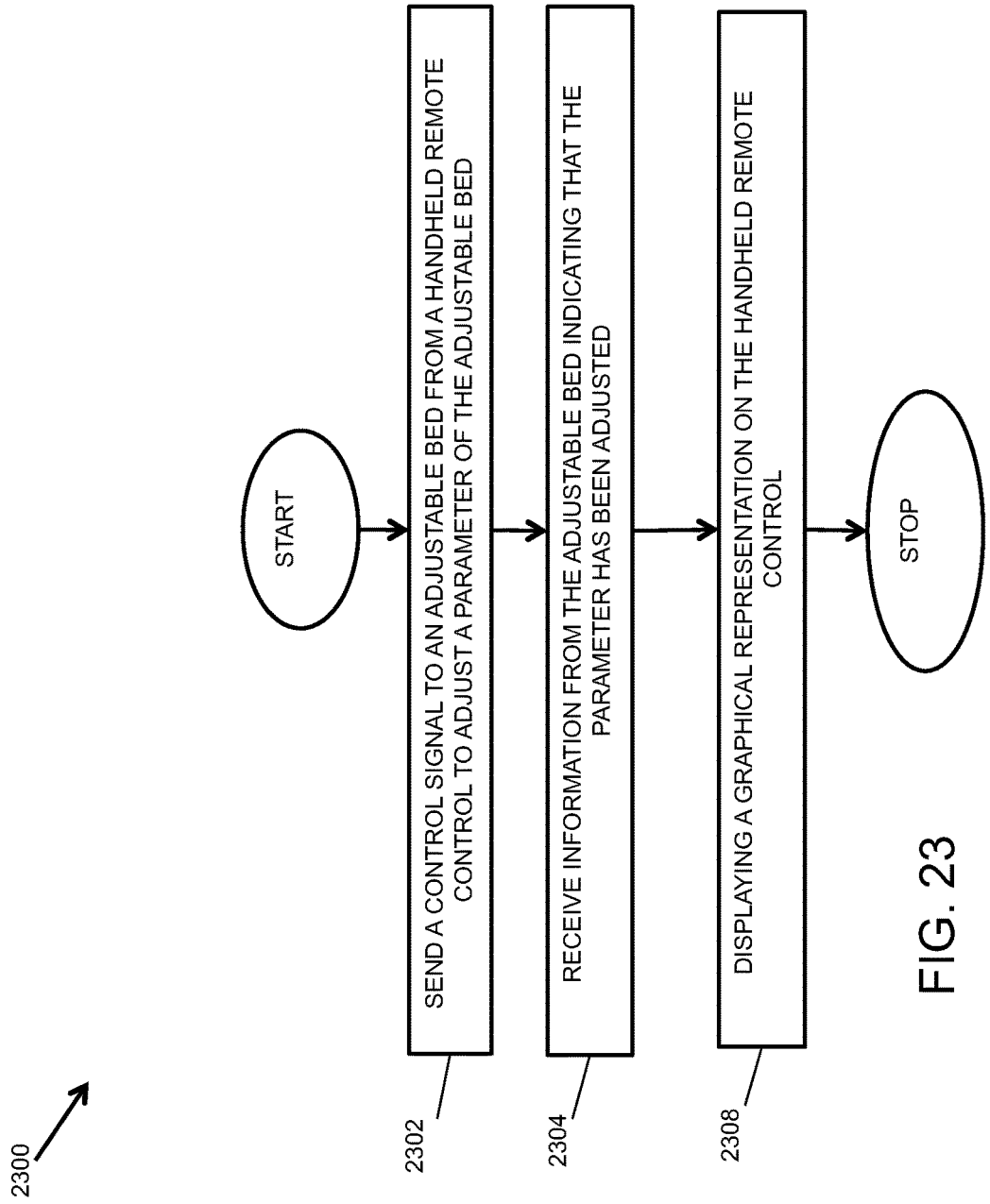
FIGS. 23 and 24 depicts a flow chart for displaying a graphical representation of an adjustable parameter associated with an adjustable bed in accordance with various embodiments of the present invention.

FIG. 23 depicts a flow chart 2300 for displaying a graphical representation of the adjustable parameter associated with an adjustable bed 1720 in accordance with an embodiment of the present invention. To describe FIG. 23, reference will be made to FIG. 17, FIG. 18, FIG. 19, FIG. 20, FIG. 21, and FIG. 22 although it is understood that the method for displaying a graphical representation of the adjustable parameter associated with an adjustable bed 1720 can be practiced in different embodiments. Those skilled in the art would appreciate that the flow chart 2300 may have more or less number of steps.

At step 2302, a control signal to change an adjustable parameter of the adjustable bed 1720 may be sent through the remote control 1702. As the descriptions for FIG. 17, FIG. 18, FIG. 19, FIG. 20, and FIG. 21 indicate, the control signal may be generated by the user interaction with the touch sensor 1708, a user interface 2010, a touch screen user interface 2102, or any other similar facility. For example, a control signal for changing the 120 degree angle of the frame of the adjustable bed 1720 to a 150 degree angle may be sent. At step 2304, the information indicating that the parameter associated with the adjustable bed 1720 may be received by the remote control 1702 from the adjustable bed 1720. For example, the information that the frame of the adjustable bed 1720 has been tilted to 150 degrees may be received by the remote control 1702. At step 2308, a graphical representation of the adjusted parameter may be displayed on the remote control 1702. For example, as shown in FIG. 20L, the various angles associated with the frame and the current angle of the frame of the adjustable bed 1720 may be displayed on the touch screen 2008 of the user interface 2010. In embodiments, the user may interact with the graphical representation to change an adjustable parameter of the adjustable bed 1720.

Figure 24:
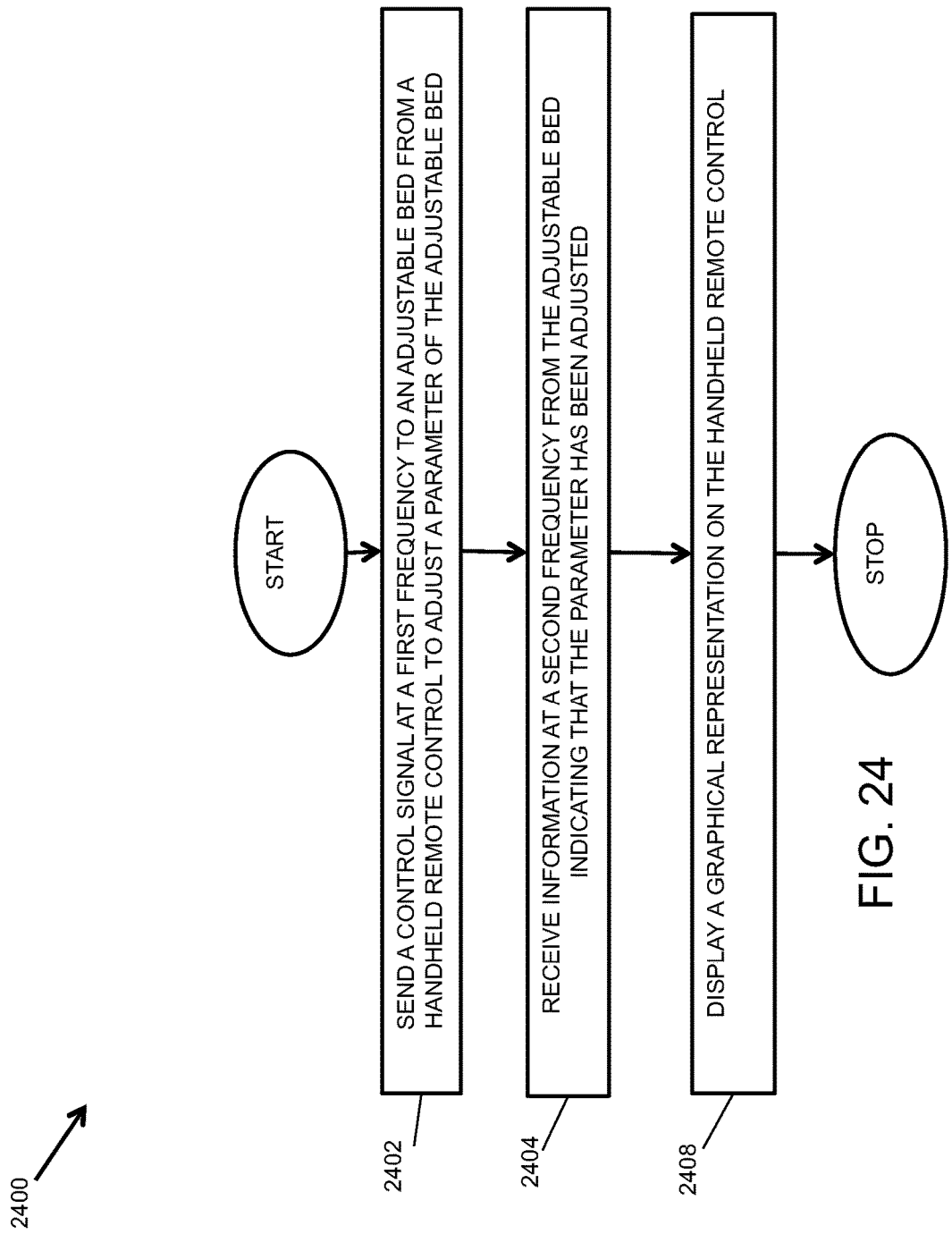

FIG. 24 depicts a flow chart 2400 for displaying a graphical representation of the adjustable parameter associated with an adjustable bed 1720 in accordance with an embodiment of the present invention. To describe FIG. 24, reference will be made to FIG. 17, FIG. 18, FIG. 19, FIG. 20, FIG. 21, FIG. 22, and FIG. 23, although it is understood that the method for displaying a graphical representation of the adjustable parameter associated with an adjustable bed 1720 can be practiced in different embodiments. Those skilled in the art would appreciate that the flow chart 2400 may have more or less number of steps.

At step 2402, a control signal to change an adjustable parameter of the adjustable bed 1720 may be sent at a first frequency by the remote control 1702. For example, a control signal for changing the angle of the frame of the adjustable bed 1720 from 120 degrees to 150 degrees may be sent at 18.83 gigahertz frequency. At step 2404, the information indicating that the parameter associated with the adjustable bed 1720 may be received at a second frequency by the remote control 1702 from the adjustable bed 1720. For example, the information that the frame of the adjustable bed 1720 has been tilted to 150 degrees may be received at 4.46 gigahertz frequency. In embodiments, the first and the second frequency may be different. At step 2408, a graphical representation of the adjusted parameter may be displayed on the remote control 1702. For example, as shown in FIG. 20L, the various angles associated with the frame and the current angle of the frame of the adjustable bed 1720 may be displayed on the touch screen 2008 of the user interface 2010.

Figure 25:
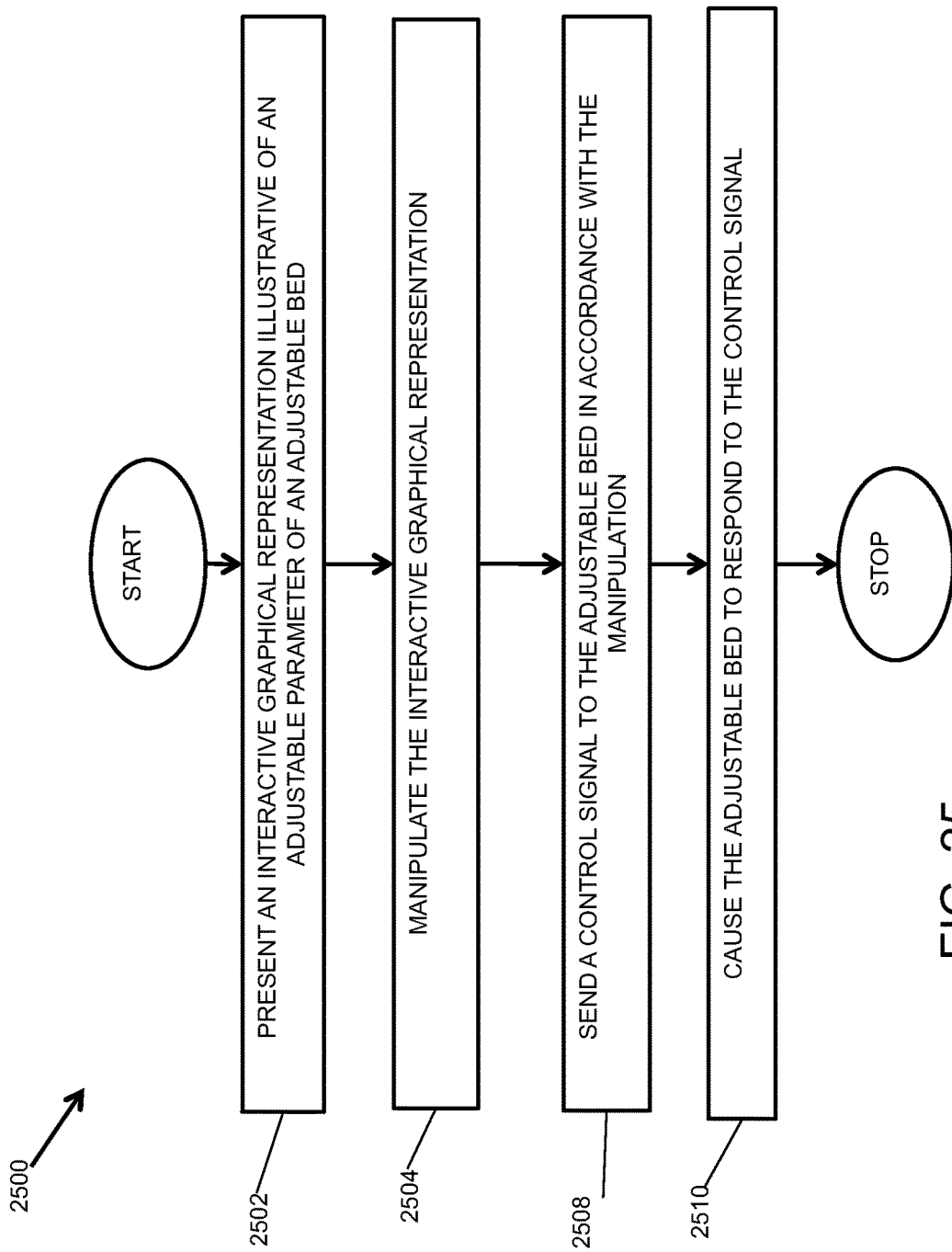
FIGS. 25 and 26 depict a flow chart for adjusting an adjustable parameter associated with an adjustable bed in accordance with various embodiments of the present invention.
Figure 26:
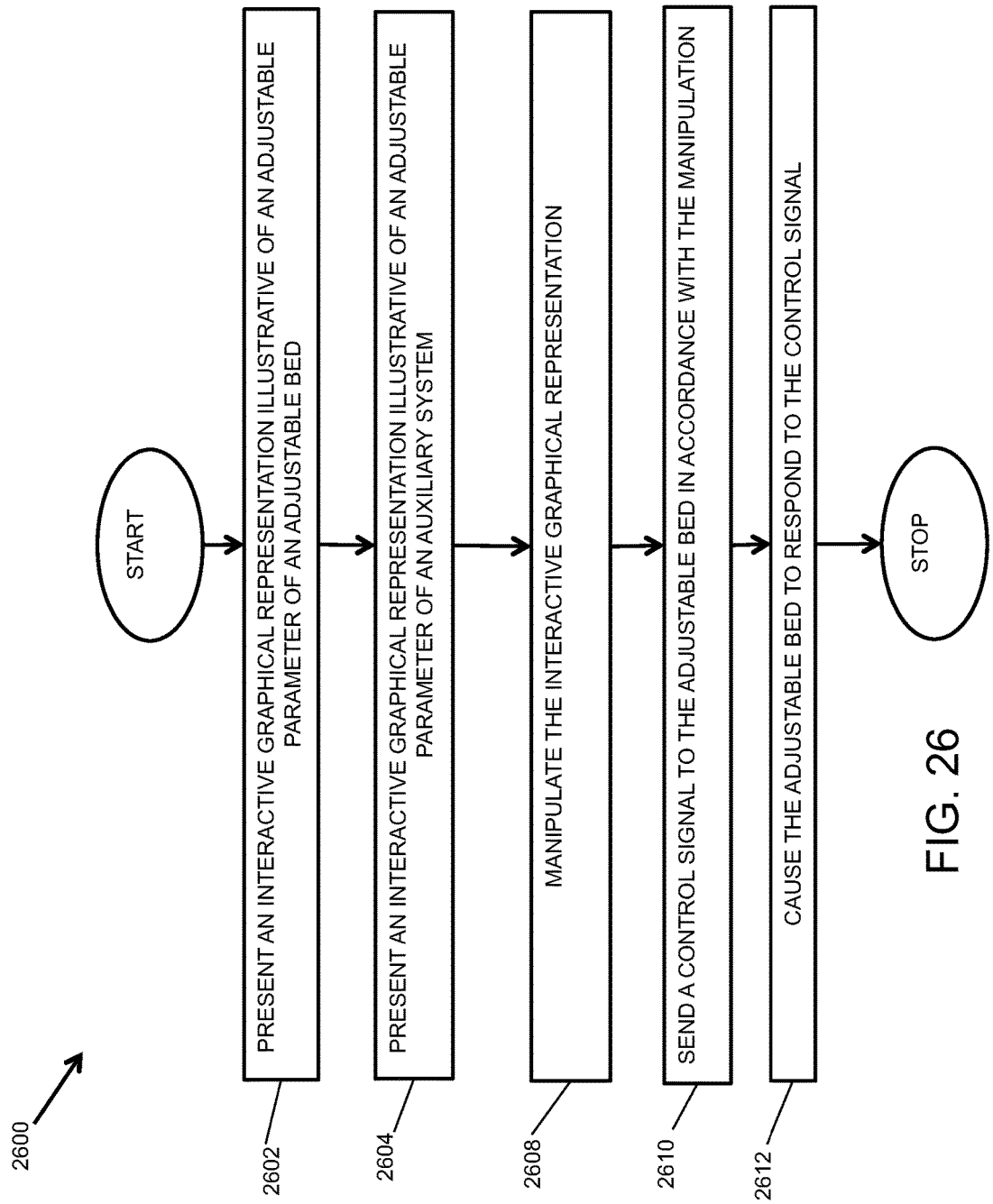

FIG. 25 depicts a flow chart 2500 for adjusting an adjustable parameter associated with an adjustable bed 1720 in accordance with an embodiment of the present invention. To describe FIG. 25, reference will be made to FIG. 17, FIG. 18, FIG. 19, FIG. 20, FIG. 21, FIG. 22, FIG. 23, and FIG. 24, although it is understood that the method for adjusting an adjustable parameter associated with an adjustable bed 1720 can be practiced in different embodiments. Those skilled in the art would appreciate that the flow chart 2500 may have more or less steps.

At step 2502, an interactive graphical representation illustrative of an adjustable parameter of an adjustable bed 1720 may be presented on the remote control 2002. For example, a graphical icon, illustrating the various angles by which a frame of an adjustable bed 1720 may be tilted, may be presented on the touch screen user interface 2102. The user may manipulate the graphical representation to adjust the parameter of the adjustable bed 2024 at step 2504. For example, the user may click and select an angle of 150 degrees on the interactive graphical representation of the frame position present on the touch screen user interface 2102. A control signal may be sent at step 2508 by the remote control 1702 to adjust the adjustable parameter based on the user manipulation at step 2504. For example, the control signals having the instructions to change the frame angle to 150 degree may be sent to the adjustable bed 1720 by the remote control 1702. At step 2510, the adjustable parameter of the adjustable bed 1720 may be changed. For example, the frame angle of the adjustable bed 1720 may be changed to 150 degrees.

FIG. 25 depicts a flow chart 2500 for adjusting an adjustable parameter associated with an adjustable bed 1720 in accordance with an embodiment of the present invention. To describe FIG. 25, reference will be made to FIG. 16, FIG. 17, FIG. 18, FIG. 19, FIG. 20, FIG. 21, FIG. 22, FIG. 23, and FIG. 24, although it is understood that the method for adjusting an adjustable parameter associated with an adjustable bed 1720 can be practiced in different embodiments. Those skilled in the art would appreciate that the flow chart 2500 may have more or less steps.

At step 2602, an interactive graphical representation illustrative of an adjustable parameter of an adjustable bed 1720 and an adjustable parameter of the auxiliary system 2052 may be presented on the remote control 1702. For example, a graphical icon, illustrating the various angles by which a frame of an adjustable bed 1720 may be tilted, may be presented on the touch screen user interface 2102. In addition, a graphical representation of the various values of the volume of a TV may be presented on the touch screen user interface 2102. The user may manipulate the graphical representation to adjust the parameter of the adjustable bed 2024 at step 2604. For example, the user may click and select a 150-degree angle on the interactive graphical representation of the frame position present on the touch screen user interface 2102. In addition, the user may select a TV volume value from the graphical representation of the auxiliary system 2052 at step 2608. At step 2610, a control signal may be sent to the auxiliary system 2052 and to the adjustable bed 1720. The control signal may be sent by the remote control 1702 to adjust the adjustable parameter based on the user manipulation at step 2604 and at step 2608. For example, the control signals having the instructions to change the frame angle to 150 degrees may be sent to the adjustable bed 1720 by the remote control 1702. In addition, the control signal to lower the volume of the TV may be sent to the TV. At step 2612, the adjustable parameter of the adjustable bed 1720 and the auxiliary system 2052 may be changed. For example, the frame angle of the adjustable bed 1720 may be changed to 150 degrees.

Figure 27:
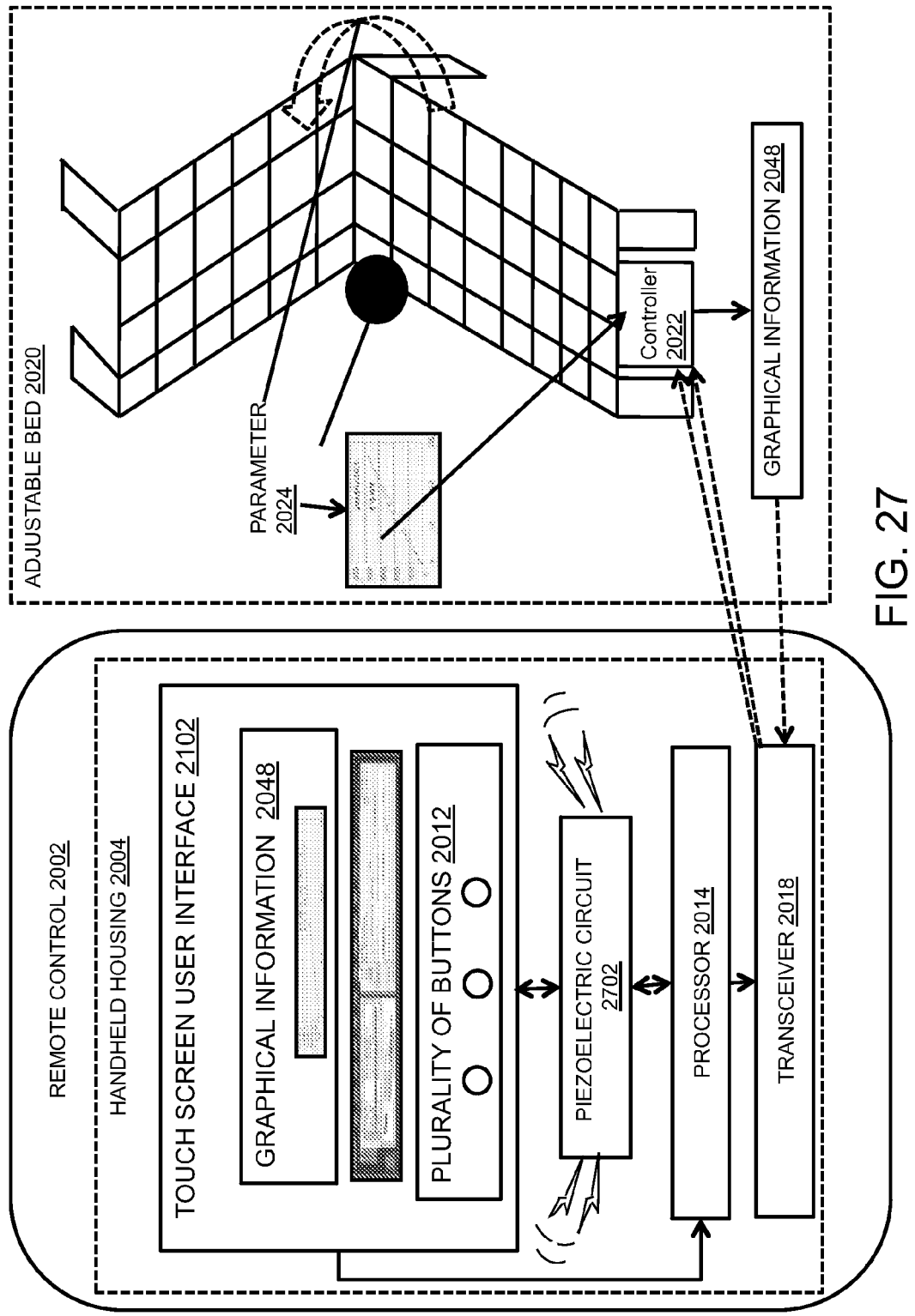
FIG. 27 depicts a remote control with a piezoelectric circuit of an adjustable bed in accordance with various embodiments of the present invention.

FIG. 27 depicts a remote control 2002, including a piezoelectric circuit 2702 of an adjustable bed 2020, in accordance with various embodiments of the present invention. The remote control may include a handheld housing 2004, a touch screen user interface 2102, a processor 2014, a wireless transceiver 2018, and a piezoelectric circuit 2702. The touch screen user interface 2102 may be provided with a plurality of buttons 2012 and graphical information 2048. The plurality of buttons 2012 may be utilized to adjust various operational settings and user preferences such as adjustment of bed angle, adjustment in massage motor speed, and the like. The graphical information 2048 may indicate the new operational settings of the adjustable bed 2020. For example, if an upper portion of the bed frame is adjusted to forty-five degrees from a horizontal plane, a graphical image depicting the angle may be presented on the remote control 2002.

The touch screen user interface 2102 may be adapted to facilitate the user in adjusting a parameter 2024 of the adjustable bed 2020. The instructions corresponding to the parameter 2024 may be provided by the user through the user interface 2102. These instructions may be sent to the processor 2014. On processing these instructions, control signals may be generated by a transceiver 2018. In embodiments, the transceiver 2018 may communicate via a BLUETOOTH protocol. In embodiments, the transceiver may be an RF transceiver.

The piezoelectric circuit 2702 may be coupled to the remote control 2002 touch-screen. The piezoelectric circuit 2702 may be utilized to enable the remote control 2002 to vibrate. Changes in electrical potential resulting from a user touching or pressing against the touch screen may cause the remote control to vibrate. Vibration may be used to indicate that certain operational settings and user preferences have been accomplished/achieved. In an exemplary case, vibration of the remote control 2002 may be utilized to indicate that the required massage motor speed has been achieved by the adjustable bed 2020. In another exemplary case, vibration of the remote control 2002 may be utilized to indicate that the required frame position has been achieved by the adjustable bed 2020. In yet another exemplary case, vibration of the remote control 2002 may be utilized to indicate that the controller of the adjustable bed 2020 has reached a diagnostic mode. In still another embodiment, vibration of the remote control 2002 may be utilized to indicate off and on states of the timer. For example, vibration of the remote control 2002 may indicate that the timer is about to go off in a predefined time. The predefined time may be ten seconds, one minute, an hour or the like. Similarly, vibration of the remote control 2002 may be utilized to indicate user preferences associated with a second system. The second system is any of the devices or systems associated with the adjustable bed 2020, such as a lighting system, an air purification system, an audio system, a CD player, an MP3 player, a DVD player, a lamp, an alarm clock, a music player, a telephone, a video system, or an entertainment technology system, computer system, information technology system, networking system, and the like.

In some embodiments, feedback from an accelerometer 1504 wired to the adjustable bed 1510 may be sent back to the processor 1508 for processing and relay to the piezoelectric circuit 2702. For example, the accelerometer 1504 may generate one or more signals corresponding to the deceleration in the movement of the adjustable bed 1510 caused by an added significant weight. The accelerometer 1504 may transmit these signals to the processor 1508. The processor 1508 may instruct the controller 2002 to cease the movement of the adjustable bed 1510 and generate a vibration of the remote control 2002 via the piezoelectric circuit 2702.

Figure 28:
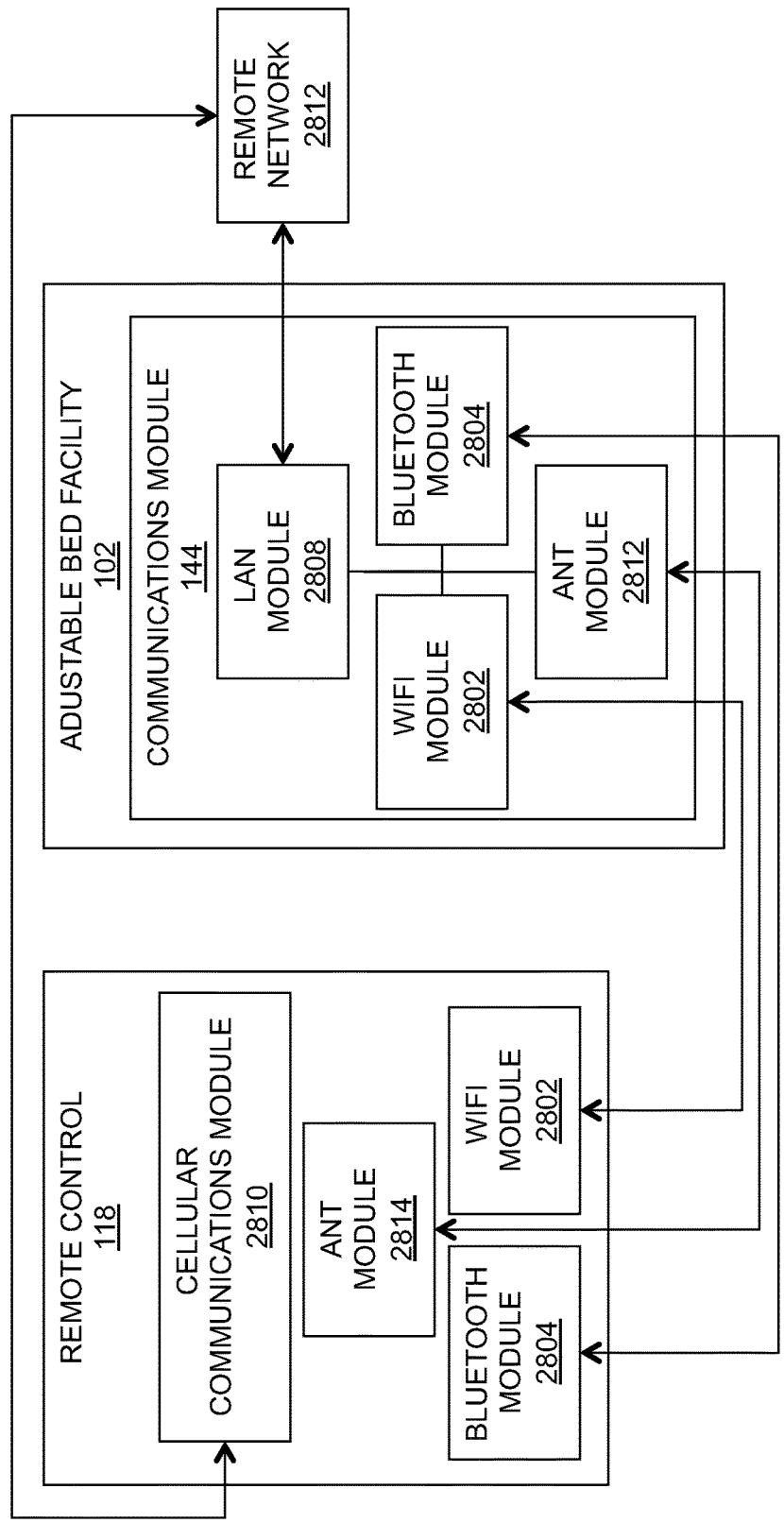
FIG. 28 depicts a remote control and communication module of an adjustable bed facility.

Referring to FIG. 28, both the remote control 118 and the communications module 144 may include a WIFI communication module 2802, a BLUETOOTH communication module 2804, an ANT communication module 2814, or the like. The WIFI communication modules 2802 may be capable of pairing to and wirelessly communicating with each other, as may the BLUETOOTH communication modules 2804 with each other and the ANT communication modules 2814 with each other.

The communications module 144 may include a local area network module 2808 capable of operatively coupling to a local area network, providing network communications between the adjustable bed facility 102 and a remote network 2812. The local area network module 2808 may function as a router, gateway, proxy, or the like, providing network communications between the remote control 118 and the remote network 2812. Embodiments of these network communications may include wireless communications (e.g., WIFI, BLUETOOTH, ANT, etc.) between the remote control 118 and the communications module 144 and network communications (of any kind) between the communications module 144 and the remote network 2812.

Embodiments of the remote control 118 may include a smart phone or the like and thus may additionally include a cellular communications module 2810 (e.g., for CDMA, GSM, or other such communications). The cellular communications module 2810 may provide a path for network communications that perhaps does not involve the adjustable bed facility 102 (e.g., communication directly between the remote control 118 and a cellular network, etc.). Conversely, embodiments of the remote control 118 may communicate with the remote network 2812 via only wireless communications to/from the communications module 144, without utilizing the cellular communications module 2810. For example, a user of the remote control 118 could access resources on the remote network 2812 (e.g., websites, etc.) even in environments (e.g., hospitals, etc.) where cellular communications are prohibited, unavailable, impractical, or the like.

Figure 29:
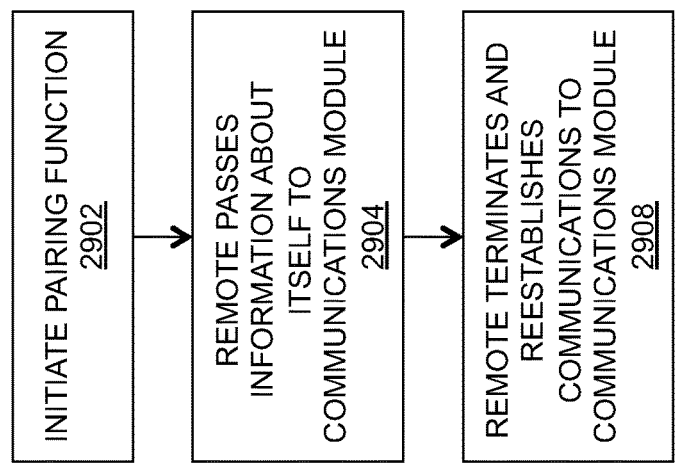
FIG. 29 depicts a flow chart for communicating with and through an adjustable bed facility.

Referring to FIG. 29, a user initiates a pairing function of the remote control 118 (step 2902), for example by pressing a button, touching an icon, entering a password or other code into the remote control 118, and so on. In embodiments where both the remote control 118 and the communications module 144 support at least two of WIFI, BLUETOOTH, and ANT communications, the user may select which of these communications technologies to use for performing the pairing function. Alternatively, when at least two communications technologies are available, the remote control 118 may default to attempting to perform the pairing function via one communication technology first and then, if that fails, to attempting to perform the pairing function via another. For example, the remote control 118 may use BLUETOOTH in the first attempt to perform the pairing function, WIFI in the second attempt, and so on.

In any case, initiating the pairing function may include discovering, at the remote control 118, which adjustable bed facilities 102 are available for pairing (e.g., there may be more than one adjustable bed facility 102 within communication range of the remote control 118) and then selecting one of those adjustable bed facilities 102 for pairing with the remote control 118. In embodiments, for example, a user may be led through the steps of discovery/selection via prompts on a screen of the remote control 118 and may provide relevant feedback (e.g., an indication as to which adjustable bed facility 102 to select, etc.) via inputs of the remote control 118.

Initiating the pairing function may also include establishing communications between the remote control 118 and the communications facility 144 of the adjustable bed facility 102. Methods of establishing WIFI, BLUETOOTH, ANT, etc. communications between two devices are known in the art and may include entering a password or the like at the remote control 118.

Once communications are established between the remote control 118 and the communications module 144 of the adjustable bed facility 102, the remote control 118 may pass information about itself (e.g., phone number, MAC address, software version, user preferences stored in the remote control 118, etc.) to the communications module 144 (step 2904), which may store them for later use.

Later, communications between the remote control 118 and the communications module 144 may be terminated and then reestablished (step 2908). In embodiments, the initial pairing and communications (see steps 2902 and 2904, described above) may occur via one communication module (e.g., BLUETOOTH communication module 2804) and then subsequent communications may occur via another (e.g., WIFI communication module 2802). Thus, the communication modules may employ incompatible interfaces to physical transmission media (e.g., BLUETOOTH and WIFI are incompatible because they rely on different physical specifications that do not support signal and binary transmission between the two).

Generally, communications modules are incompatible when signal and binary transmission between the modules is impossible due to a difference in the media layers (physical layer, data link layer, and network layer) of the communications modules. For example, at the physical level such differences between communications modules may manifest as dependence on different communications media (e.g., copper wire vs. optical cable vs. air); dependence on different configurations of a communications media (e.g., copper configured as 10BASE2 vs. copper configured as 100BASE-TX; air used with FSK modulation vs. air used with ASK modulation; and so on); etc. A variety of incompatible differences between media layers will be appreciated and, thus, a variety of incompatibilities between communications modules will likewise be appreciated.

In embodiments, the communications module 144 may use the information that it has about the remote control 118 (e.g., the information it received in step 2904, described above) to establish an ad hoc WIFI network between itself and the remote control 118. For example, the communications module 144 may configure its WIFI communication module 2802 to accept an ad hoc connection from a device having the MAC address of the remote control 118 (i.e., the remote control 118 itself). In cases where the initial pairing and communications occurred via BLUETOOTH, this may alleviate the need to ever enter a WIFI network access password or the like into the remote control 118. In particular, the WIFI communications module 2802 of the communications module 144 may be configured (e.g., by way of the information about the remote control 118 received via BLUETOOTH communications) to accept connections/communications from the remote control 118. Alternatively, however, the WIFI communications module 2802 may be configured to accept connections/communications from any WIFI-enabled device that provides the correct password.

In embodiments, establishing communications may be as simple as transmitting a message at some time without acknowledgement of receipt. Establishing communications may also include transmitting a message and then retransmitting the message upon failure to receive an acknowledgement of receipt of the message. Establishing communications may also include establishing a connection via a connection-based protocol (such as and without limitation TCP/IP). Establishing communications may include selecting a frequency division, time division, code division, modulation, etc. that is suitable for transmitting and receiving data between communications modules. A variety of techniques for establishing communications will be appreciated.

Figure 30:
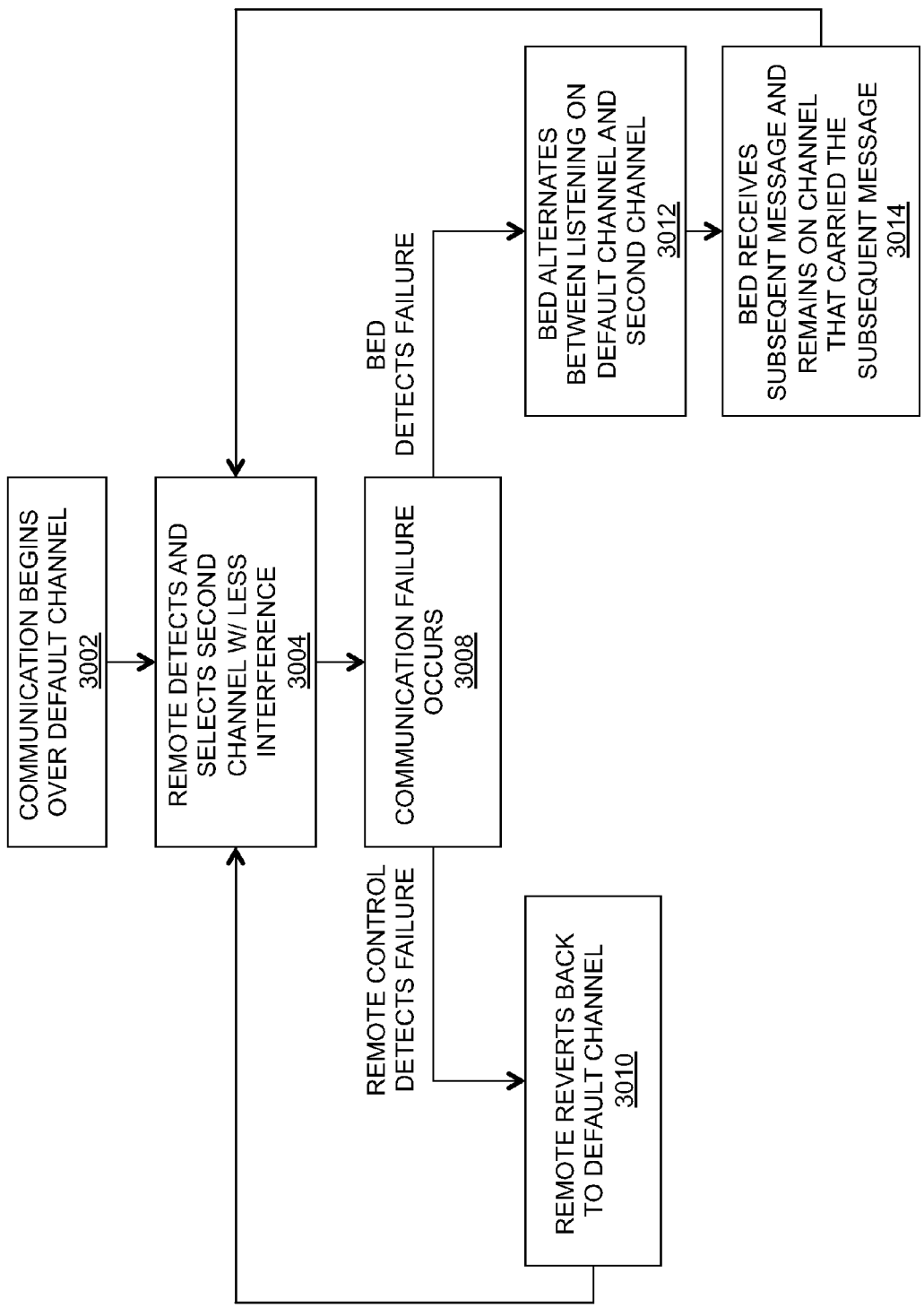
FIG. 30 depicts an interaction diagram for communications between a remote control and a number of adjustable bed facilities.

Referring to FIG. 30, the remote control 118 may communicate with a number of adjustable bed facilities 102. As described below, the communication includes acknowledgements and may occur over multiple channels, allowing substantially reliable communication between the remote control 118 and the adjustable bed facilities 102 even in the presence of interference, for example as might occur in an environment with other remote controls communicating with other adjustable bed facilities.

A plurality of wireless communication channels (embodied, e.g., as frequency-division multiplexed channels, time-division multiplexed channels, code-division multiplexed channels, etc.) may be available between the remote control 118 and the adjustable bed facility 102. For example, these wireless channels may be embodied as BLUETOOTH channels between BLUETOOTH modules 2804, WIFI channels between the WIFI modules 2802, and so on. Communication between the remote control 118 and the adjustable bed facility 102 begins over a default channel selected from the plurality of wireless communication channels (step 3002). Upon detecting a second wireless communication channel with less interference than the default channel, the remote control 118 may select the second wireless communication channel for future communication with the adjustable bed facility 102 (step 3004). The remote control 118 may instruct the adjustable bed facility 102 to communicate using the second wireless communication channel. Thereafter, communications continue over the second wireless communication channel until a communications failure occurs (step 3008). In embodiments, the remote control 118 transmits a command to the adjustable bed facility 102 instructing the adjustable bed facility 102 to switch to the new channel.

Communications between the remote control 118 and the adjustable bed facilities 102 may include commands from the remote control 118 and acknowledgements from the adjustable bed facilities 102. A communications failure occurs when an expected command or acknowledgement fails to arrive prior to expiration of a timeout period. In particular, after sending a command to the adjustable bed facility 102, the remote control 118 expects to receive, prior to expiration of a timeout period, an acknowledgement from the adjustable bed facility 102; after receiving a command from the remote control 118, the adjustable bed facility 102 transmits an acknowledgement and expects to receive, prior to expiration of a timeout period, a subsequent command from the remote control 118.

If the remote control 118 detects the communications failure (i.e., timeout prior to receiving expected acknowledgement), the remote control 118 reverts back to communicating over the default channel (step 3010). Eventually, the remote control 118 may again find another channel with less interference, at which point the remote control 118 may select that channel for future communication (step 3004).

If the adjustable bed facility 102 detects the communications failure (i.e., timeout prior to receiving expected subsequent command), the adjustable bed facility 102 begins alternating between the second channel and the default channel, listening for a the subsequent command from the remote control 118 on both channels, sequentially, (step 3012) until it receives the subsequent command. Having received the subsequent command, the adjustable bed facility 102 stops scanning and instead continues listening on the channel that carried the subsequent message received (step 3014).

Figure 31:
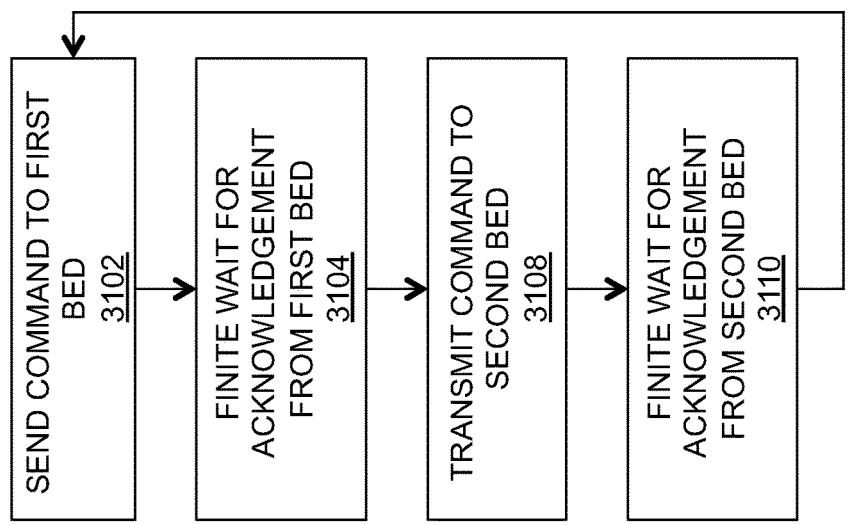
FIG. 31 depicts a flow chart for controlling more than one adjustable bed facility using a single remote control.

Referring to FIG. 31, embodiments of the remote control 118 may command more than one adjustable bed facility 102 at a time. The remote control 118 may send a command to a first adjustable bed facility 102 (step 3102); wait for a finite timeout period to receive an acknowledgement from the first adjustable bed facility 102 (step 3104); upon receiving the acknowledgement or upon expiration of the timeout period, transmit the command to a second adjustable bed facility 102 (step 3108); wait for the finite timeout period to receive an acknowledgement from the second adjustable bed facility 102 (step 3110); and so on. Subsequent commands may be sent, for example, in response to user input to the remote control 118. These subsequent commands may include retransmissions of earlier commands for which acknowledgement was not received prior to expiration of the timeout period. For example and without limitation, the remote control 118 may send a command to a first bed, fail to receive acknowledgement from the first bed prior to expiration of a timeout period, send the command to a second bed, successfully or unsuccessfully receive acknowledgement from the second bed prior to expiration of a timeout period, and then retransmit the command to the first bed.

Figure 32:
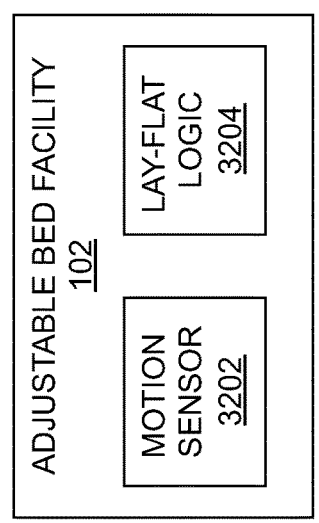
FIG. 32 depicts an adjustable bed facility outfitted with a motion sensor and related logic.

Referring to FIG. 32, the adjustable bed facility 102 may be outfitted with a motion sensor 3202 operatively coupled to lay-flat logic 3204 for transitioning the adjustable bed facility 102 to a laying-flat position. The motion sensor 3202 is configured to detect motion of an actuator 120. In embodiments the motion sensor 3202 may include a Hall effect sensor, an optical source/detector pair separated by a material that is alternately transparent and opaque as it translates between the source/detector pair, and so on. In embodiments, the lay-flay logic 3204 may be implemented in hardware, software, or the like.

Figure 33:
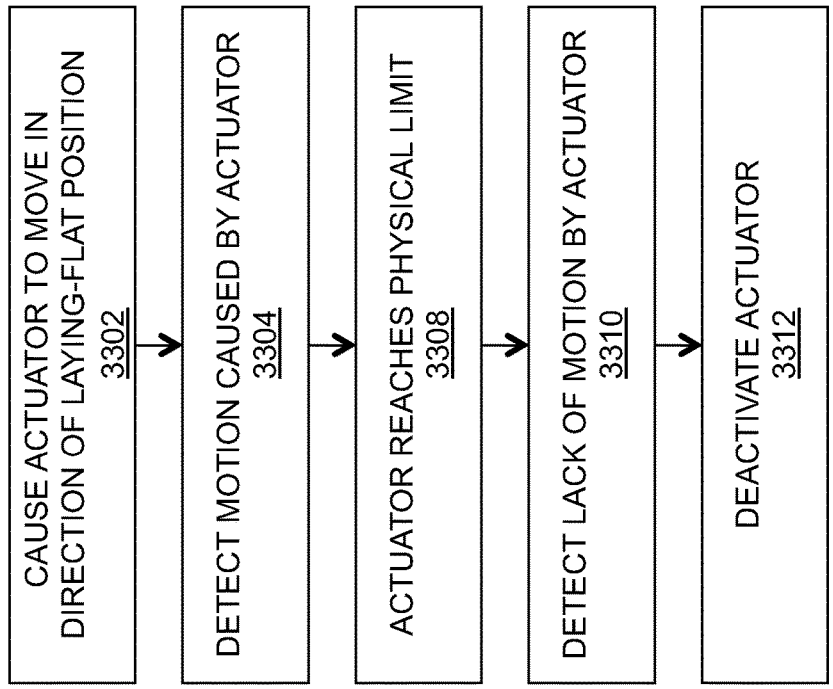
FIG. 33 depicts a flow chart for laying an adjustable bed facility flat.

Referring to FIG. 33, in response to a command to lay the adjustable bed facility 102 flat, the lay-flat logic 3204 causes or activates an actuator 120 to move in a direction bringing the adjustable bed facility 102 to a laying-flat position (step 3302). As the adjustable bed facility 102 moves, the motion sensor 3202 detects the motion (step 3304). The actuator 120 reaches a physical limit when the bed is laid flat, preventing further motion by the actuator 120, even though the lay-flat logic 3204 continues to urge the actuator 120 to move in the direction that brought the adjustable bed facility 102 to the laying-flat position (step 3308). The motion sensor 3202 detects the lack of motion (step 3310). The lay-flat logic 3204 responds to the lack of motion (either immediately or after a period of time) by deactivating the actuator 120 (step 3312). By detecting the lack of motion and deactivating the actuator 120, the lay-flat logic 3204 conserves energy/frees up power to be used by other aspects of the adjustable bed facility 102. In addition, it should be appreciated that the lay-flat logic 3204 does not depend upon the magnitude of the speed of the bed's motion, only the state of motion (i.e., moving vs. not moving). Thus, any configuration in which the actuator 120 can move at all in response to the lay-flat logic 3204 (e.g., actuators of different speeds/strengths, things of different weights laying on the bed, etc.) can operate according to this method.

As described above for example with reference to FIG. 2, the electronic facility 140 includes a controller 150 and a communications module 144.

Figure 34:
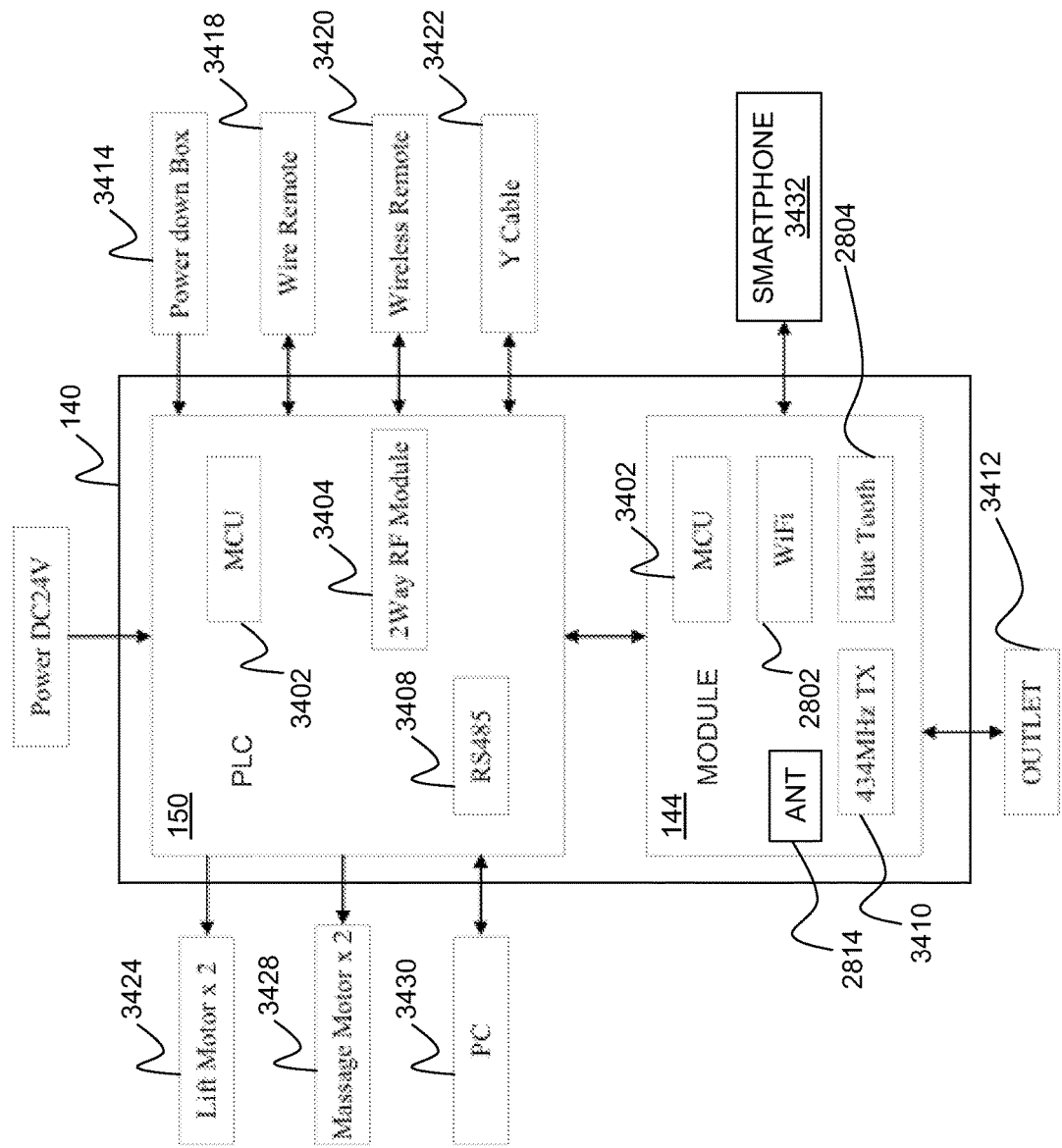
FIG. 34 depicts an embodiment of a controller and a communications module.

Referring now to FIG. 34, an embodiment of the controller 150 may include a programmable logic controller (PLC) or the like, including a MicroController Unit (MCU) 3402, a 2-way RF communication module 3404, and a data port 3408 (e.g., serial data port RS485 or the like). An embodiment of the communications module 144 may include an MCU 3402, the WIFI communication module 2802, the BLUETOOTH communication module 2804, the ANT communication module 2814, and a low-power or short-range radio interface 3410 (e.g., 434 MHz radio interface of the like). The communications module 144 may be in operative communication with a data outlet 3412 through which an IPHONE or smartphone, computer, network, or the like communicates with the communications module 144. Additionally or alternatively, an IPHONE, DROID phone, or smartphone 3432 (or computer, network, or the like) may wirelessly communicate with the communications module 144.

The WIFI communication module 2802 implements and communicates via one of the family of IEEE 802.11 standards. The BLUETOOTH communications module 2804 implements and communicates via to one of the family of BLUETOOTH standards (e.g., Bluetooth v1.0, v1.0B, v1.1, v1.2, v2.0+EDR, v2.1+EDR, v3.0+HS, v3.0+EDR, etc.). The ANT communication module 2814 implements and communicates according to one of the family of ANT standards (e.g., ANT, ANT+, etc.). In embodiments, the ANT communication module 2814 supports communications of at least 1 Mbps in a broadcast network, a peer-to-peer network (acknowledged or bidirectional), a secure authenticated network, a star network, a shared uni-directional network, a shared bi-directional network, an ad-hoc automatically shared network, a scanning mode network (e.g., a single hub node receiving communications from a plurality of other nodes), a practical mesh network (e.g., multiple star networks connected by shared relay nodes), a shared cluster network (e.g., networks with shared hub nodes in bidirectional communication), and so on.

The electronic facility 140 may be operatively coupled to a power down box 3414, a wire remote 3418 (e.g., an embodiment of the remote control 118), a wireless remote 3420 (e.g., an embodiment of the remote control 118), a Y cable 3422, a lift motor 3424 (e.g., an embodiment of the actuator 120), a massage motor 3428 (e.g., an embodiment of the vibration facility 132), a personal computer 3430, and so on.

The power down box 3414 may include a housing containing a battery and a button or the like to initiate a power down sequence. The power down sequence may command the controller 150 to lay the adjustable bed facility 102 flat. Without limitation, this may include invoking, in response to a press of the button, the method described hereinabove with reference to FIG. 33.

The Y cable 3422 may make a shared, wired communications path available between controller 150 and a number of other devices.

In accordance with various embodiments of the present invention, vibration of the remote control 2002 may be initiated automatically as soon as the user preferences are adjusted. In such a scenario, a user may perform a task to govern the vibration mode. In an embodiment, vibration may be initiated based on user interaction with the remote control 2002 through touch-based methods. For example, vibration may be initiated through a single touch on the touch screen user interface 2102. In another example, vibration of the remote control 2002 may be initiated through a continual touch on the touch screen user interface 2102. In another exemplary scenario, vibration of the remote control 2002 may be initiated through a persistent touch on the touch screen user interface 2102. In yet another scenario, vibration of the remote control 2002 may be initiated through a swipe or any other similar mechanism without limitations. In certain embodiments of the present invention, human biometric and behaviometric techniques may be employed to initiate the vibrations for various operational characteristics.

In accordance with various embodiments of the present invention, the touch screen user interface 2102 may also allow the user to adjust various operational settings and user preferences using various methods including, without limitations, single touch, persistent touch, continual touch, and the like.

Figure 36:
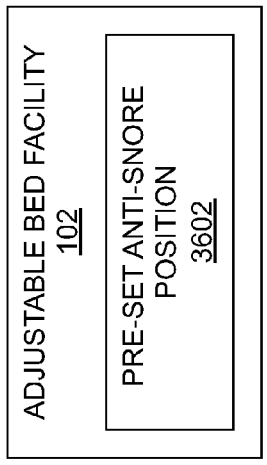
FIG. 36 depicts an adjustable bed facility.

Referring to FIG. 36, the adjustable bed facility 102 may include a pre-set anti-snore position 3602 for quieting a snoring occupant of the adjustable bed facility 102. The anti-snore position 3602 may be a head elevation position, such as 7-degrees above flat, 15-degrees above flat, something between 7- and 15-degrees above flat, and so on. In embodiments the adjustable bed facility 102 may assume the anti-snore position 3602 (e.g., by adjusting the position of the head frame 1004) in response to a user input. Without limitation, the user input may include a direct input to the adjustable bed facility 102 such as a press of a button or touch screen on the adjustable bed facility 102, a voice-command input, a signal transmitted by the remote control 118 (or the like) in response to the user input, and so on. In embodiments the adjustable bed facility 102 may assume the anti-snore position 3602 in response to a sensor input indicating that the occupant of the adjustable bed facility 102 is or may be snoring. For example and without limitation the sensor may include an acoustic sensor responsive to the sound of snoring; an air-flow sensor responsive to inhibited breathing such as due to snoring or sleep apnea, and so on; a vibration sensor that detects a characteristic vibration of the user associated with snoring; or the like.

Figure 37:
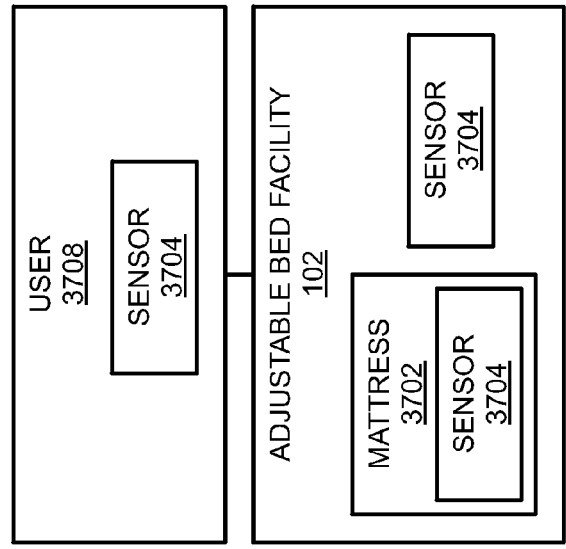
FIG. 37 depicts a user, adjustable bed facility, and mattress instrumented with sensors.

Referring to FIG. 37, a user 3708 may lay upon a mattress 3702 of the adjustable bed facility 102. The user 3708, the mattress 3702, and the adjustable bed facility 102 may be instrumented with sensors 3704. The sensors 3704 may detect various indicia of sleep quality and report the indicia (e.g., via wired or wireless communication) to other elements of the adjustable bed facility 102, the remote control 118, the auxiliary systems 114, and so on. This allows for both real-time adjustment of the adjustable bed facility 102 to improve the sleep quality and reporting of the indicia and the sleep quality. Without limitation the reporting may occur via the remote control 118 or any other device in communication with the sensors 3704 or the adjustable bed facility 102. In addition to any and all such devices described herein and elsewhere, the other device in communication with the sensors 3704 may include a bed-side display device.

The real-time adjustment of the adjustable bed facility 102 may occur at a natural waking point as determined by reference to an indication of sleep quality. The indication of sleep quality may indicate that a user 3708 is lightly asleep, deeply asleep, in Rapid Eye Movement (REM) sleep, and so on. For example and without limitation, the sensors 3704 may include a headband that senses indicia of sleep quality such as and without limitation to electrical signals produced by the user's 3708 brain; the sensors 3704 may include a motion sensor that detects motion of the user 3708 (e.g., rolling, kicking, arms moving, etc.); the sensors 3704 may include a pressure sensor that detects a sleep position of the user 3708; the sensors 3704 may include an acoustic sensor that detects a noise of the user 3708 (e.g., snoring, sleep talking, etc.); the accelerometer 1504; and so on.

Figure 38:
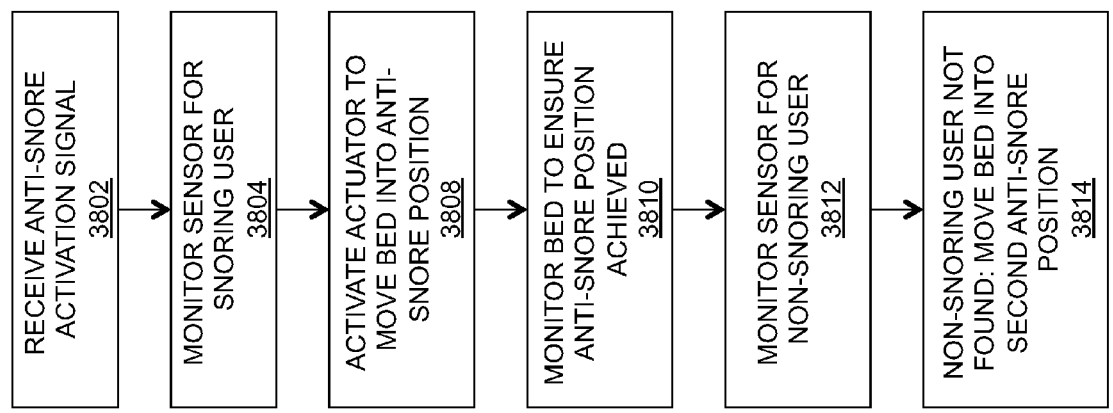
FIG. 38 depicts a flow chart for adjusting an adjustable bed facility.

Referring to FIG. 38, a controller may receive 3802 an anti-snore activation signal from a remote control; monitor 3804 a sensor 3704 for a first reading indicative of a snoring user; activate 3808 an actuator 120 to move an adjustable bed facility 102 into an anti-snore position 3602; monitor 3810 the adjustable bed facility 102 to confirm that the adjustable bed facility 102 achieves the anti-snore position 3602; monitor 3812 the sensor 3704 for a second reading; and, after failing to receive the second reading, activating 3814 the actuator 120 to move the adjustable bed facility 102 into a second anti-snore position.

Figure 39:
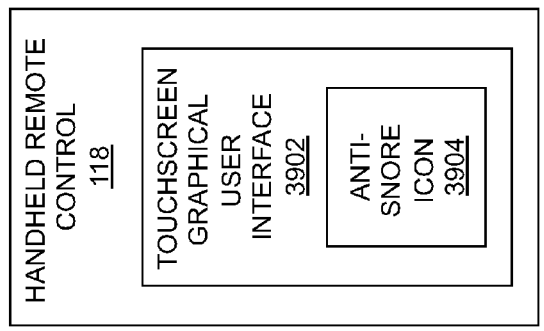
FIG. 39 depicts a remote control.

Referring to FIG. 39, the remote control 118 may include a touchscreen graphical user interface 3902 adapted to display an anti-snore icon 3904, receive a touch input indicating user-selection of the anti-snore icon 3904, and transmit an anti-snore activation signal in response to the touch input.

In an embodiment of the present invention, the user may define different types of vibrations for indicating various operational settings and user preferences. In another embodiment, sound effects may also be associated in conjunction with the vibrations to indicate various operational settings and user preferences.

In accordance with various embodiments of the present invention, vibrations may be initiated in ways other than through touch-based modes. In an exemplary scenario, vibrations may be initiated using buttons provided on the remote control 2002. For example, several buttons may be provided that may designate a specific user preference.

When a user presses a specific button, the user preference associated with that button may be identified and the remote control 2002 may be enabled to vibrate as soon as the specific user preference resets. In another embodiment, a single button may be provided to perform operations associated with various user preferences.

In accordance with various embodiments, icons may be provided on the remote control 2002 to control various operational settings and user preferences. These icons may be related to a timer, a clock, massage motor speed, horizontal bed angle setting, vertical bed angle setting, bed height, bed width, bed length, and the like. Similarly, various icons related to the second system may also be provided on the remote control 2002. Interaction with any of these icons may result in vibration of the remote control as described herein.

In accordance with various embodiments of the present invention, the remote control 2002 may be utilized to perform several operations such as controlling the adjustable bed 2020 based on user preferences, identifying resetting of user preferences associated with the adjustable bed 2020, controlling operations of the second system based on user preferences, identifying resetting of user preferences associated with the second system, and the like without limitations.

The elements depicted in flow charts and block diagrams throughout the figures imply logical boundaries between the elements. However, according to software or hardware engineering practices, the depicted elements and the functions thereof may be implemented as parts of a monolithic software structure, as standalone software modules, or as modules that employ external routines, code, services, and so forth, or any combination of these; and all such implementations are within the scope of the present disclosure. Thus, while the foregoing drawings and descriptions set forth functional aspects of the disclosed systems, no particular arrangement of software for implementing these functional aspects should be inferred from these descriptions unless explicitly stated or otherwise clear from the context.

Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods or processes described above, and steps thereof, may be realized in hardware, software, or any combination of these suitable for a particular application. The hardware may include a general-purpose computer and/or dedicated computing device. The processes may be realized in one or more microprocessors, microcontrollers, embedded microcontrollers, programmable digital signal processors, or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as computer executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

All documents referenced herein are hereby incorporated by reference.

What is claimed is:

1. An adjustable bed system comprising:
 a first adjustable bed facility comprising a first adjustable bed controller mounted thereto, the first adjustable bed controller being adapted to (i) receive a repositioning command from a first remote control, (ii) adjust a position of a first adjustable bed facility bed segment according to the repositioning command, and (iii) transmit the repositioning command to a second adjustable bed controller of a second adjustable bed facility; and
 a second adjustable bed facility comprising a second adjustable bed controller mounted thereto, the second adjustable bed controller being adapted to (i) receive the repositioning command from the first adjustable bed controller and (ii) adjust a position of a second adjustable bed facility bed segment according to the repositioning command;
 wherein:
  the first adjustable bed facility and the second adjustable bed facility are arranged in an adjacent, side-by-side arrangement; and
  the first adjustable bed controller and the second adjustable bed controller are adapted to communicate information to each other related to synchronizing motion of the first adjustable bed facility bed segment and the second adjustable bed facility bed segment according to the repositioning command.

2. The adjustable bed system of claim 1, wherein the first adjustable bed facility and second adjustable bed facility are twin size adjustable bed facilities that are adjacent to one another to form a king size adjustable bed facility.

3. The adjustable bed system of claim 1, wherein the first adjustable bed controller and the second adjustable bed controller are adapted to communicate information wirelessly to each other.

4. The adjustable bed system of claim 1, wherein the first adjustable bed controller and the second adjustable bed controller are adapted to communicate information wirelessly to each other by a wireless communication protocol comprising at least one of a radio frequency (RF) protocol, an infrared (IR) protocol, a BLUETOOTH protocol, and a WIFI protocol.

5. The adjustable bed system of claim 1, wherein the first adjustable bed controller and the second adjustable bed controller are adapted to communicate information to each other via a wired connection.

6. The adjustable bed system of claim 1, wherein the first adjustable bed controller and the second adjustable bed controller are further adapted to communicate information to each other related to at least one of implementing a safety feature, communicating an error, communicating a software update, communicating a preference, communicating a setting, and communicating a report.

7. The adjustable bed system of claim 1, wherein the second adjustable bed controller is further adapted to (i) receive a second repositioning command from a second remote control, and (ii) adjust a position of a bed segment of the second adjustable bed facility following receipt of the second repositioning command and independently from motion of the first adjustable bed facility.

8. A method for repositioning an adjustable bed system, the method comprising:
transmitting a repositioning command from a first remote control to the first adjustable bed controller of the adjustable bed system of claim 1;
adjusting the position of the first adjustable bed facility bed segment according to the repositioning command;
transmitting the repositioning command from the first adjustable bed controller to the second adjustable bed controller; and
adjusting the position of the second adjustable bed facility bed segment according to the repositioning command and synchronously with adjustment of the position of the first adjustable bed facility.

9. The method of claim 8, wherein the first adjustable bed controller and the first remote control communicate wirelessly to each other.

10. The method of claim 8, wherein the first adjustable bed controller and the first remote control communicate information to each other via a wired connection.

11. The method of claim 8, wherein the first remote control comprises a touch screen display receiving user input for the repositioning command.

12. The method of claim 8, wherein the first remote control is a cell phone or a smart phone.

13. The method of claim 8, wherein the first adjustable bed facility and second adjustable bed facility are twin size adjustable bed facilities that are adjacent to one another to form a king size adjustable bed facility.

14. The method of claim 8, wherein the first adjustable bed controller and the second adjustable bed controller communicate information wirelessly to each other.

15. The method of claim 8, wherein the first adjustable bed controller and the second adjustable bed controller communicate information to each other via a wired connection.

16. The method of claim 8, wherein the first adjustable bed controller and the second adjustable bed controller communicate information wirelessly to each other by a wireless communication protocol comprising at least one of a radio frequency (RF) protocol, an infrared (IR) protocol, a BLUETOOTH protocol, and a WIFI protocol.

17. The method of claim 8, wherein the first adjustable bed controller and the second adjustable bed controller further communicate information to each other related to at least one of implementing a safety feature, communicating an error, communicating a software update, communicating a preference, communicating a setting, and communicating a report.

* * * * *